United States Patent
Kiakos et al.

(10) Patent No.: US 11,964,943 B2
(45) Date of Patent: Apr. 23, 2024

(54) 3,5-DIARYLIDENYL-N-SUBSTITUTED-PIPERID-4-ONE-DERIVED INHIBITORS OF STAT3 PATHWAY ACTIVITY AND USES THEREOF

(71) Applicants: Konstantinos Kiakos, Vienna (AT); John A. Hartley, London (GB); Moses Namfong Lee, Vancouver, WA (US)

(72) Inventors: Konstantinos Kiakos, Vienna (AT); John A. Hartley, London (GB); Moses Namfong Lee, Vancouver, WA (US)

( * ) Notice: Subject to any disclaimer, the term of this patent is extended or adjusted under 35 U.S.C. 154(b) by 204 days.

(21) Appl. No.: 15/929,736

(22) Filed: May 19, 2020

(65) Prior Publication Data
US 2020/0399220 A1 Dec. 24, 2020

Related U.S. Application Data

(63) Continuation of application No. PCT/EP2018/081905, filed on Nov. 20, 2018.

(60) Provisional application No. 62/588,678, filed on Nov. 20, 2017.

(51) Int. Cl.
| | |
|---|---|
| *C07D 211/74* | (2006.01) |
| *A61K 31/282* | (2006.01) |
| *A61K 31/45* | (2006.01) |
| *A61K 31/555* | (2006.01) |
| *A61K 33/243* | (2019.01) |
| *A61K 45/06* | (2006.01) |
| *A61P 35/00* | (2006.01) |
| *C07D 213/68* | (2006.01) |
| *G01N 33/58* | (2006.01) |
| *A61K 31/337* | (2006.01) |

(52) U.S. Cl.
CPC ......... *C07D 213/68* (2013.01); *G01N 33/582* (2013.01); *A61K 31/282* (2013.01); *A61K 31/337* (2013.01); *A61K 33/243* (2019.01); *A61K 45/06* (2013.01)

(58) Field of Classification Search
CPC .. A61K 31/174; A61K 31/194; A61K 31/555; A61K 33/26; A61K 38/42; A61K 31/282; A61K 31/45; A61K 31/337; A61K 33/243; A61K 45/06; A61P 1/16; A61P 9/00; A61P 13/12; A61P 37/06; A61P 11/00; A61P 31/04; A61P 43/00; A61P 35/00; C07H 23/00; A61N 1/0266; C07D 211/74; C07D 213/68; G01N 33/582
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,085,102 A | 4/1978 | Krapcho et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,698,155 A | 12/1997 | Grosswald et al. | |
| 5,733,566 A | 3/1998 | Lewis | |
| 6,136,839 A | 10/2000 | Isakson et al. | |
| 7,355,045 B2 | 4/2008 | Dey et al. | |
| 2005/0148774 A1 | 7/2005 | Dey et al. | |
| 2012/0316203 A1 | 12/2012 | Kuppusamy et al. | |

FOREIGN PATENT DOCUMENTS

| | | |
|---|---|---|
| CN | 103421006 | 12/2013 |
| SE | 1200735 | 4/2013 |
| WO | 2011/005790 | 1/2011 |
| WO | 2014/022660 | 2/2014 |
| WO | 2017/198870 | 11/2017 |

OTHER PUBLICATIONS

Derivative, 2023, https://en.wikipedia.org/wiki/Derivative_(chemistry).*
Cancer-Prevention, 2023, https://www.cancerresearchuk.org/about-cancer/causes-of-cancer/can-cancer-be-prevented-0.*
Kasembeli et al., International Journal of Molecular Sciences, 2018, 19, 2299.*
PulmonaryFibrosis-Prevention, 2023, https://pulmonaryfibrosisnews.com/pulmonary-fibrosis-prevention/#:~:text=There%20are%20currently%20no%20established,to%20undergo%20regular%20medical%20examinations.*
RA-Prevention, 2023, https://www.medicalnewstoday.com/articles/rheumatoid-arthritis-prevention#early-treatment.*
Adams et al., Bioorganic & Medicinal Chemistry; 2004, 12:3871-3883.
Adams et al., Anti-Cancer Drugs; 2005, 16:263-275.

(Continued)

*Primary Examiner* — Sun Jae Yoo
(74) *Attorney, Agent, or Firm* — Grüneberg and Myers PLLC

(57) ABSTRACT

3,5-Diarylidenyl-N-substituted-piperid-4-one analogs, and pharmaceutically acceptable derivatives thereof, are useful in the treatment or prevention of disorders including cancer, autoimmune disorders, inflammatory disorders, and fibrotic disorders. The compounds are included in pharmaceutical compositions, and are useful for treating disorders, such as cancer associated with aberrant Stat3 pathway activity. The compositions further include another therapeutic agent, such as an anticancer drug. Such compounds or compositions thereof are used to treat resistant and/or metastatic cancers. Methods also inhibit Stat3 pathway activity in a cell. Other methods are useful for making the pharmaceutical compounds. Synthetic methods are also useful for making the compounds. The compounds and compositions are useful as a fluorescent probe.

18 Claims, 57 Drawing Sheets

Specification includes a Sequence Listing.

(56) References Cited

OTHER PUBLICATIONS

Almansour et al., Molecules; 2014, 19:10033-10055.
Almansour et al., BioMed Research International; 2015, Article ID:965987, 9 pages.
Almeida et al., DNA Repair; 2006, 5:219-225.
Aly et al., High Performance Polymers; 1992, 4(3):187-195.
Baumann et al., Nature Reviews Cancer; 2008, 8:545-554.
Bharkavi et al., Synlett; 2015, 26:1665-1670.
Bharti et al., Blood; 2004, 103(8):3175-3184.
Bingham et al., Chem. Commun.; 2001, 603-604.
Bowman et al., Oncogene; 2000, 19:2474-2488.
Bromberg et al., Oncogene; 2000, 19:2468-2473.
Caira et al., Journal of Pharmaceutical Sciences; 2004, 93(3):601-611.
Caricato, et al., (ed.), IOps Reference; 2013, 2nd Edition, pp. 1-170.
Cesari et al., Circulation; 2003, 108:2317-2322.
Chen et al., ACS Medicinal Chemistry Letters; 2010, 1:85-89.
Chiba, Tomohiro, EC Cancer; 2016, 1.S1:S1-S8.
Chou, Ting-Chao, Cancer Research; 2010, 70(2):440-446.
Darnell, Jr., James E., Science; 1997, 277(5332), 29 pages.
Das et al., ChemMedChem.; 2009, 4(11), 27 pages.
Das et al., Bioorganic & Medicinal Chemistry Letters; 2016, 26:1319-1321.
Davis et al., Arch. Pharm. Chem. Life Sci.; 2008, 341:440-445.
Dimmock et al., Journal of Medicinal Chemistry; 2001, 44(4):586-593.
Du et al., European Journal of Medicinal Chemistry; 2006, 41:213-218.
During et al., Annals of Neurology; 1989, 25(4):351-356.
El-Kashef et al., J. Chem. Tech. Biotechnol.; 1993, 57:15-19.
El-Subbagh et al., J. Med. Chem; 2000 43(15):2915-2921.
Feldmann et al., Annu. Rev. Immunol.; 1996, 14:397-440.
Furtek et al., ACS Chemical Biology; 2016, 11:308-318.
Geies et al., Bull. Chem. Soc. Jpn.; 1993, 66(12):3716-3723.
Hambardzumyan et al., Cancer Cell; 2006, 10(6):454-456.
Han et al., Journal of Combinatorial Chemistry; 2010, 12(1):16-19.
Harada et al., Autoimmunity; 2007, 40(1):1-8.
Harris et al., The Journal of Immunology; 2007, 179:4313-4317.
Hartley et al., Methods in Molecular Biology, Second Ed.; 2011, 731:309-320.
Hirano et al., Oncogene; 2000, 19:2548-2556.
Hossain et al., Bioorganic & Medicinal Chemistry; 2016, 24:2206-2214.
Howard et al., J. Neurosurg.; 1989, 71:105-112.
Huang et al., Biochem. J.; 1999, 342:231-238.
Huber et al., Monatsh Chem; 2015, 146:973-981.
Hübschle et al., Journal of Applied Crystallography; 2011, 44:1281-1284.
Imran et al., Critical Reviews in Food Science and Nutrition; 2018, 58(8):1271-1293.
Ingólfson et al., ACS Chemical Biology; 2014, 9:1788-1798.
Jha et al., Indian Journal of Chemistry; 2006, 45B:2313-2320.
Johnston et al., Molecular Interventions; 2011, 11(1):18-26.
Karthikeyan et al., Bull. Korean Chem. Soc.; 2009, 30(11):2555-2558.
Kasembeli et al., International Journal of Molecular Sciences; 2018, 19:2299, 30 pages.
Krijnen et al., Journal of the American Chemical Society; 1989, 111(12):4433-4440.
Langer et al., Journal of Macromolecular Science, Part C; 1983, 23(1):61-126.
Langer, Robert, Science; 1990, 249(4976):1527-1533.
Lee et al., Journal of Medicinal Chemistry; 2010, 53(1):325-334.
Levy et al., Science; 1985, 228:190-192.
Libby et al., Circulation; 2002, 105(9):1135-1143.
Lopez-Berestein et al., Arch intern Med; 1989, 149:2533-2536.
Lu et al., Cellular Physiology and Biochemistry; 2008, 21:305-314.
Manolagas, S.C., Bone; 1995, 17(2):63S-37S.
Moodley et al., Am. J. Resp. Cell Mol. Bio.; 2003, 29:490-498.
Naidu et al., Cancer Research; 2015, 75(15):Abstract nr 1720, 4 pages.
Nesterov, Vladimir N., Acta Crystallographica; 2004, C60:0806-0809.
Olive et al., Radiation Research; 2012, 178:AV35-AV42.
Orshal et al., Am J Physiol Regul Integr Comp Physiol; 2004, 286:R1013-R1023.
Pati et al., European Journal of Medicinal Chemistry; 2008, 43(1):1-7.
Pati et al., European Journal of Medicinal Chemistry; 2009, 44(1):54-62.
Pedroza et al., Rheumatology; 2018, 57:1838-1850.
Pignanelli et al., Scientific Reports; 2017, 7(1105), 25 pages.
Rae et al., Breast Cancer Res Treat; 2007, 104:13-19.
Rath et al., Cancer Research; 2014, 74(8):2316-2327.
Rosenbloom et al., Biochimica et Biophysica Acta; 2013, 7:1088-1103.
Saudek et al., The New England Journal of Medicine; 1989, 321(9):574-579.
Selvendiran et al., Cancer Res; 2006, 66(9):4825-4834.
Selvendiran et al., Cell Cycle; 2008, 7(1):81-88.
Selvendiran et al., Molecular Cancer Therapeutics; 2010, 9(5):1169-1179.
Sheldrick, G.M., Acta Crystallographica; 2008, A64:112-122.
Sheldrick, G.M., Acta Crystallographica; 2015, C71:3-8.
Si et al., Exp Biol Med; 2007, 232:427-436.
Spanswick et al., Methods in Molecular Biology; 2010, 613:267-282.
Stephens et al., Molecular Genetics and Metabolism; 2004, 82:180-186.
Tan et al., Journal of Medicinal Chemistry; 2014, 57:5904-5918.
Tierney et al., Cancer Biology & Therapy; 2012, 13(9):766-775.
Treat et al., Ovarian Cancer; 2001, vol. 15, issue 5, 7 pages.
Van Tonder et al., AAPS PharmSciTech; 2004, 5(1) Article 12, 10 pages.
Vatsadze et al., Russian Chemical Bulletin, Int'l Ed .; 2006, 55(7):1184-1194.
Wu et al., Bioorganic & Medicinal Chemistry; 2013, 21:3058-3065.
Xiang et al., Blood; 2016, 128(14):1845-1853.
Yadav et al., Bioorganic & Medicinal Chemistry; 2010, 18:6701-6707.
Yang et al., Mol Cancer Ther; 2008, 7(11):3519-3526.
Youssef et al., Arch. Pharm. Pharm. Med. Chem.; 2004, 337:42-54.
Yu et al., Nature Reviews Cancer; 2004, 4:97-105.
Yuan et al., New Journal of Chemistry; 2008, 32:1924-1934.
Zhang et al., Cancer Medicine; 2016, vol. 5, issue 6:1251-1258.
Zhou et al., Chem. Pharm. Bull.; 2013, 61(11):1149-1155.
International Search Report dated Mar. 13, 2019 in PCT/EP2018/081905.
Written Opinion dated Mar. 13, 2019 in PCT/EP2018/081905.
Bixel et al., Int. J. Cancer: 141, 1856-1866 (2017).
El Naggar et al., Cancer Biology & Therapy; 2016, vol. 17, No. 10, 1107-1115.
Gregory et al., Med Chem Res (2013) 22:5588-5597.
Karuppaiyah et al., Free Radical Biology and Medicine 48 (2010) 1228-1235.
Kumar et al., PLOS ONE; 2014, 9(3):1-10.
European Office Action Communication pursuant to Article 94(3) EPC dated Apr. 22, 2022 in European Application No. 18814494.3, 6 pages.
Kandi, et al., "$C_5$-curcuminoid-4-amioquinoline based molecular hybrids: design, synthesis and mechanistic investigation of anticancer activity", New J. Chem., vol. 39, 2015, pp. 224-234.
Mandalapu, et al., "Synthesis and biological evaluation of some novel triazole hybrids of curcumin mimics and their selective anticancer activity against breast and prostate cancer cell lines", Bioorganic & Medicinal Chemistry Letters, vol. 26, 2016, pp. 4223-4232.
European Communication pursuant to Article 94(3) EPC dated Feb. 17, 2023, in European Application No. 18814494.3, 5 pages.

\* cited by examiner

C

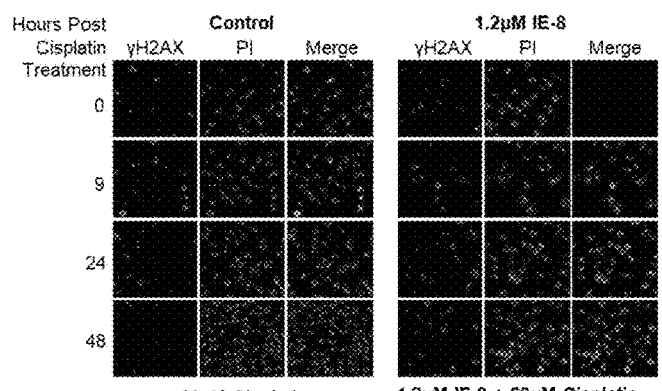
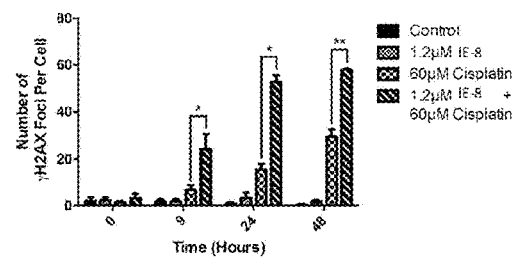
FIG. 21B
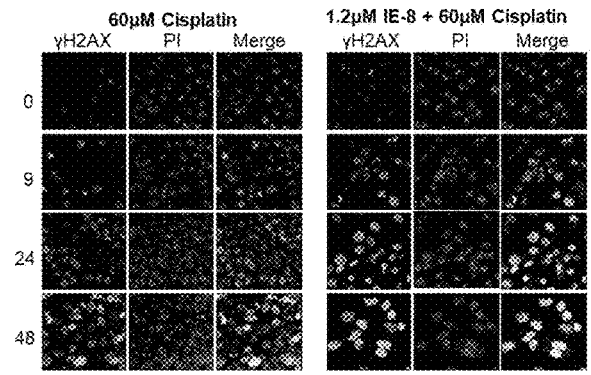
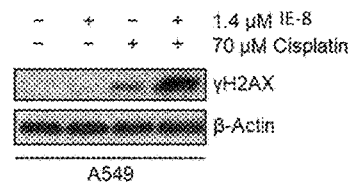
FIG. 21C
FIG. 21A

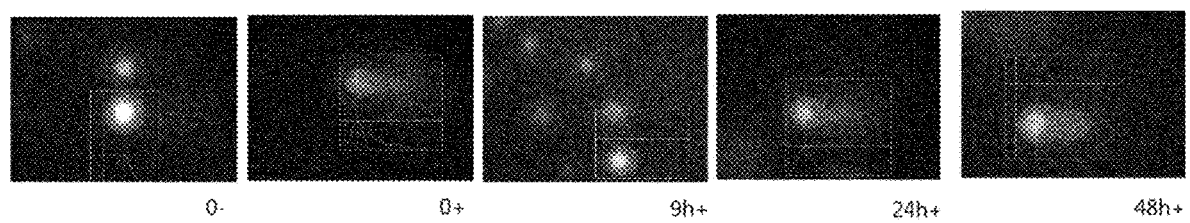
FIG. 23A
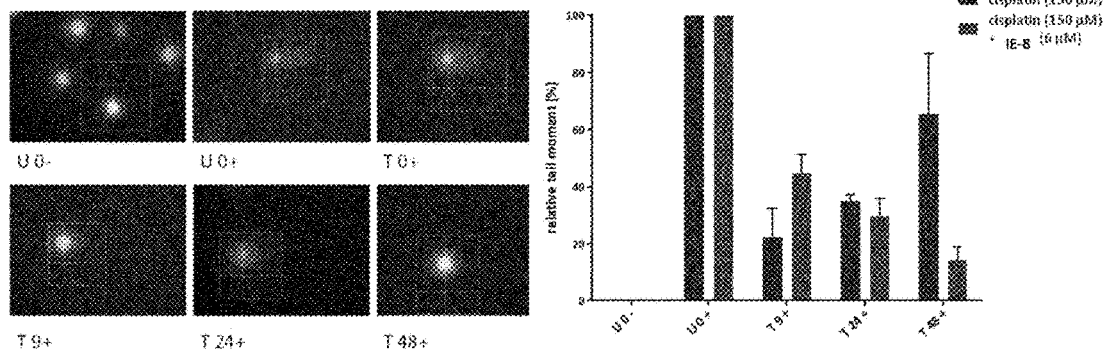
FIG. 23B
FIG. 23C

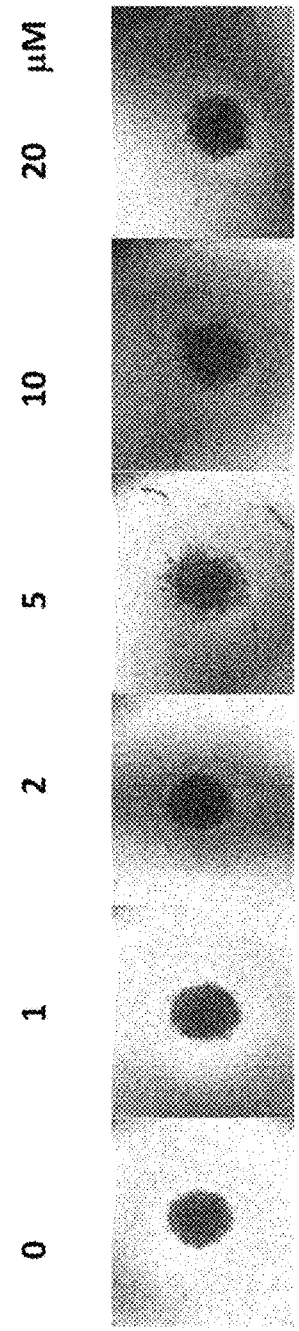
FIG. 24A
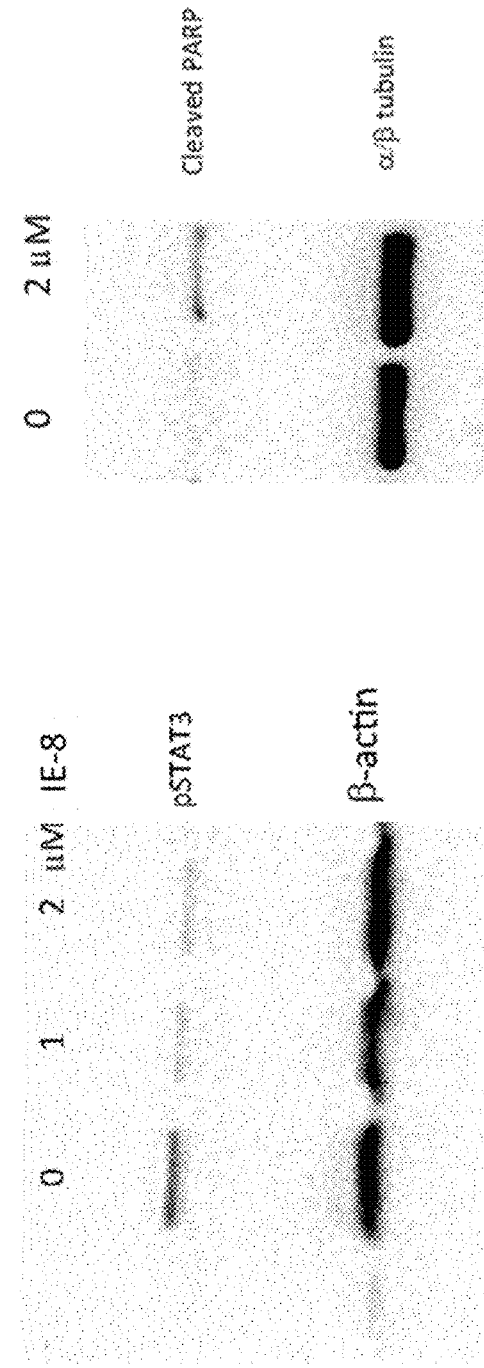
FIG. 24C
FIG. 24B

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide containing the high-affinity
      sis-inducible element (hSIE) probe SIE

<400> SEQUENCE: 1
agcttcattt cccgtaaatc ccta                                          24

<210> SEQ ID NO 2
<211> LENGTH: 19
<212> TYPE: DNA
<213> ORGANISM: Artificial Sequence
<220> FEATURE:
<223> OTHER INFORMATION: Non-specific competitor

<400> SEQUENCE: 2
agcgcctccc cggccgggg                                                19
```

3,5-DIARYLIDENYL-N-SUBSTITUTED-PIPERID-4-ONE-DERIVED INHIBITORS OF STAT3 PATHWAY ACTIVITY AND USES THEREOF

CROSS REFERENCE TO RELATED APPLICATIONS

The present application is a continuation of the International Application PCT/EP2018/081905, filed Nov. 20, 2018, which claims priority of U.S. Provisional Application No. 62/588,678, filed Nov. 20, 2017, the entire contents of both of which are hereby incorporated by reference in their entireties for all purposes.

REFERENCE TO A SEQUENCE LISTING

The present application is accompanied by an ASCII text file as a computer readable form containing the sequence listing, titled "Sequence-Listing-as-filed.txt," created on May 13, 2020 at 1:20 pm, with the file size of 872 bytes, which is incorporated by reference in its entirety. Applicants hereby state that the information recorded in computer readable form is identical to the written (on paper or compact disc) sequence listing.

BACKGROUND OF THE INVENTION

Field of the Invention

The present disclosure relates to Compounds of Formula I, and pharmaceutically acceptable derivatives thereof. Compounds of Formula I, and pharmaceutically acceptable derivatives thereof, can be used a as effective and selective inhibitors of the pStat3 pathway activity. The present disclosure also relates to pharmaceutical compositions comprising a Compound of Formula I, or a pharmaceutically acceptable derivative thereof, alone or in combination with another therapeutic agent, such as an anticancer drug. Further, the present disclosure provides their use in the treatment of cancer, and other pathogenic conditions in which Stat3 activation is implicated.

Discussion of the Background

Stat3 is a member of the Stat (Signal Transducer and Activator of Transcription) protein family which encompasses cytoplasmic transcription factors activated in response to cytokines (e.g. IL-6) and growth factors to stimulate crucial biological processes such as cell proliferation and cell survival, inflammation and immune responses. Stat3 activation and phosphorylation is mediated by growth factor receptor tyrosine kinases (e.g. EGFR and HER2), upstream kinases such as JAKs (Janus kinases; JAK1, JAK2, JAK3 and TYK2), and tyrosine kinases of the Src protein family but not limited thereto. Phosphorylation of Stat3 monomers occurs at Tyrosine705 (pTyr705) leading to Stat3 homodimers through dimerization of an $SH_2$ domain enabling the translocation to the nucleus and the binding to critical DNA-response elements in the promoters of target genes to regulate gene expression.

Stat3 activation has been found in autoimmune diseases (e.g., as a result of generating TH17 T cell responses [Harris, T. J., et al. *J. Immunol* 2007, 179, 4313]) and in a series of inflammation-related diseases, such as atherosclerosis, peripheral vascular disease, coronary artery disease, hypertension, osteoporosis, type 2 diabetes, and dementia.

Activated Stat3 (phosphorylated Stat3) has been demonstrated in a series of autoimmune and inflammatory diseases. [Kasembeli, M. M., et al., *Int. J. Mol. Sci.* 2018, 19, 2299] Notably, Interleukin-6-mediated inflammation is the common causative origin for a series of diseases such as atherosclerosis [Libby, P., et al., *Circulation*, 2002, 105, 1135], type 2 diabetes or peripheral vascular disease [Stephens, J. W., et al., *Mol Genet Metab*, 2004, 8, 180], coronary artery disease [Cesari, M., et al., *Circulation*, 2003, 108, 2317], hypertension [Orshal, J. M. *Am J Physiol Regul Integr Comp Physiol*, 2004, 286, R1013], and osteoporosis [Manolagas, S. C., *Bone*, 1995, 17, 63], wherein Interleukin-6 (IL-6) is crucial in the activation of the gp130/Jak/STAT pathway. Further autoimmune disorders such as rheumatoid arthritis [Feldmann, M., et al., *Annu RevImmunol*, 1996, 14, 397], systemic lupus erythematosus[Harada, T., et al., *Autoimmunity*, 2007, 40, 1] were also related to aberrant Stat3 pathway activity.

The Stat3 pathway has been further associated with various forms of fibrosis, such as renal fibrosis[Huang, J.-S., et al., *Biochem. J* 1999, 342, 231], liver fibrosis[Si, H. F., et al. *Exp Biol Med* 2007, 232, 427], lung fibrosis[Kasembli, M. M., et al., *Int. J. Mol. Sci.* 2018, 19, 2299], and skin fibrosis[Pedroza, M., et al., *Rheumatology*, 2018, 57, 1838]. A potential role for Stat3-mediated signaling in the pathogenesis of fibrotic diseases characterized by excessive fibrosis was observed. [Moodley, Y. P., et al. *Am J Respir Cell Mol Biol* 2003, 29, 490-8]

In particular, aberrant activation of Stat3 has been demonstrated in a plethora of human cancer cells, such as head and neck cancer, myeloma, prostate cancer, breast cancer, colon cancer, and ovarian cancer[Yu, H., et al. *Nat Rev Cancer* 2004, 4, 97; Lu, Y, et al. *Cell Physiol. Biochem.* 2008, 21, 305; Selvendiran, K, et al. *Cell Cycle* 2008, 7, 81; Yang, F, et al. *Mo. Cancer. Ther.* 2008, 7, 3519]. Being a transcription regulator, Stat3 acts multiply as a key cellular-signaling molecule in carcinogenesis by targeting genes and proteins involved in cell cycle, cell survival, oncogenesis, tumor invasion, and metastasis, comprising Bcl-xL, Mcl-1, cyclin D1/D2, c-Myc, VEGF (vascular endothelial growth factor), and HIF1 (hypoxia-inducible factor 1). Activated Stat3 is also involved in malignant phenotypes of cancer cells, the emergence of resistance to both related art chemotherapeutics and molecular targeted therapies, and resistant cancer cells, such as cancer stem cells (also referred to as tumor initiating cells, highly tumorigenic cells, or super malignant cells) that are refractory towards conventional DNA-damaging and molecular targeted therapeutics, and resistant to radiation (i.e. radiotherapy) [Damell, J. E. Jr. *Science* 1997, 277, 1630; Bromberg, J, et al. *Oncogene* 2000, 19, 2468; Bowman, T. et al. *Oncogene* 2000, 19, 2474; Hirano, T., et al. *Oncogene* 2000, 19, 2548; Hambardzumyan, D., et al. *Cancer Cell* 2006, 10, 454; Baumann, M., et al. *Nat Rev Cancer* 2008, 8, 545; Zhang, Y., et al. *Cancer Med.* 2016, 5, 1251]. Persistent activation of Stat3 is therefore significantly linked to poor prognosis in several types of cancer.

A great number of compounds such as stattic, ruxolinitib, atovaquone, napabucasin, curcumin, HO-3867[Rath, K. S., et al., *Cancer Res.* 2014, 74, 2316; Naidu, S., et al., *Cancer Res.* 2015, 75, 1720] have been reported to disrupt Stat3 signaling via different modes of action encompassing the inhibition of Tyr kinases, blocking Stat3 dimerization by targeting the $SH_2$ domain, and inducing dephosphorylation of pStat3 (phosphorylated Stat3)[Chiba, T., *EC Cancer* 2016, L. S1, S1; Furtek, S. L., et al. *ACS Chem. Biol.* 2016, 11, 308; Chen, J., et al. *ACS Med Chem. Lett.* 2010, 1, 85;

Xiang, M., et al. *Blood* 2016, 128, 1845]. Among these, natural product curcumin, isolated from the *Curcumin longa* plant, is known to produce a wide variety of effects that could confer anticancer activity, however failing in clinical trials due to lack of selectivity with regard to molecular target and type of cells next to insufficient bioavailability [Pignanelli, C., et al. *Nature* 2017, 7, 1105; Imran, M., et al. *Crit. Rev. Food Sci. Nutr.* 2018, 58, 1271]. Despite the plethora of investigations on Stat3-targeting drugs, only Napabucasin has been granted orphan drug designation by the FDA for the treatment of gastric cancer including gastroesophageal junction (GEJ) and pancreatic cancer. However, Napabucasin lacks sufficient solubility in physiological media.

Accordingly, there is a need for effective agents in the treatment and prevention of diseases associated with aberrant Stat3 pathway activity. There is also a need for effective and bioavailable agents in the treatment and prevention of diseases associated with aberrant Stat3 activity, such as cancer. There is further the need for effective and selective agents in the treatment of diseases resistant to related art therapies, where Stat3 is a mediator of this resistance. Therefore, there is also a need for agents effectively and selectively inhibiting Stat3 pathway activity.

SUMMARY OF THE INVENTION

In one aspect, the present disclosure provides compounds represented by Formula I, defined below, and pharmaceutically acceptable derivatives thereof, collectively referred to herein as "Compounds of the Invention" or "Compound of Formula I" (each is individually referred to hereinafter as a "Compound of the Invention" or "Compound of Formula I").

In another aspect, the present disclosure provides a Compound for use in the treatment or prevention of a disorder comprising a Compound of Formula I, or a pharmaceutically acceptable derivate thereof, wherein the disorder is selected from the group consisting of cancer, autoimmune disorder, inflammatory disorder, and fibrotic disorder.

In another aspect, the present disclosure provides a pharmaceutical composition comprising a Compound of Formula I, or a pharmaceutically acceptable derivative thereof, and another therapeutic agent.

In another aspect, the present disclosure provides a Compound of Formula I, or a pharmaceutically acceptable derivative thereof, for use as a medicament.

In another aspect, the present disclosure provides a use of a Compound of Formula I, or a pharmaceutically acceptable derivative thereof, for the manufacture of a medicament for the treatment or prevention of a disorder, wherein the disorder is selected from the group consisting of cancer, autoimmune disorder, inflammatory disorder, and fibrotic disorder.

In another aspect, the present disclosure provides a method of preparing the pharmaceutical composition of any one of Formula I, comprising admixing a Compound of Formula I, or a pharmaceutically acceptable derivative thereof, with a pharmaceutically acceptable carrier.

In another aspect, the present disclosure provides a method of treating or preventing a disorder in a subject identified as in need of such treatment or prevention, comprising administering to said subject a Compound of Formula I, or a pharmaceutically acceptable derivative thereof, wherein the disorder is selected from the group consisting of cancer, autoimmune disorder, inflammation disorder, and fibrotic disorder.

In another aspect, the present disclosure provides a method of inhibition of Stat3 pathway activity in a cell, comprising administering to the cell a Compound of Formula I, or a pharmaceutically acceptable derivative thereof.

In another aspect, the present disclosure provides a method for screening for or identifying a Compound of Formula I in a subject, wherein the method comprises administering at least one compound to a subject, illumination of the subject, and assaying for the emission of the illuminated subject.

In another aspect, the present disclosure provides a use of a Compound of Formula I as a fluorescent probe.

In another aspect, the present disclosure provides a process of preparing a Compound of Formula I, or a pharmaceutically acceptable derivative thereof, wherein the process comprises reacting an N-substituted-piperid-4-one with an unsubstituted or substituted benzaldehyde, wherein the N-substituted-piperid-4-one is selected from a group consisting of N-phenyl-piperid-4-one, and N-iso-propyl-piperid-4-one, and wherein the substituted benzaldehyde is selected from the group consisting of 4-methylbenzaldehyde, 4-nitrobenzaldehyde, 4-methoxybenzaldeyde, 3-hydroxy-4-methoxy-benzaldehyde, 4-hydroxy-3-methoxy-benzaldehyde, 3,4-dimethoxybenzaldehyde, and 3,4,5-trimethoxybenzaldehyde, preferably wherein the benzaldehyde is substituted.

The present invention includes the following embodiments:

1. A compound of Formula I:

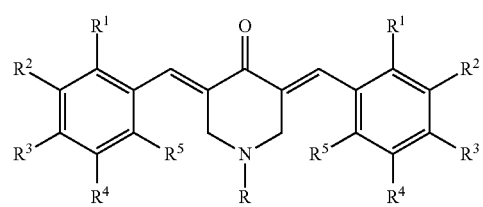

or a pharmaceutically acceptable derivative thereof, wherein:
R is selected from:
(a) —H, —($C_1$-$C_6$)alkyl, —($C_2$-$C_6$)alkenyl, —($C_2$-$C_6$) alkynyl, —($C_3$-$C_8$)cycloalkyl, —($C_6$-$C_{14}$)bicycloalkyl, —($C_8$-$C_{20}$)tricycloalkyl, —($C_5$-$C_8$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, 4 or 5 independently selected $R^6$ groups; and
(b) —($C_6$-$C_{14}$)aryl, —($C_1$-$C_6$)alkyl-($C_6$-$C_{14}$)aryl, -(5- to 10-membered)heteroaryl, and —($C_1$-$C_6$)alkyl-(5- to 10-membered)heteroaryl, each of which is unsubstituted or substituted with 1, 2, 3, 4 or 5 independently selected $R^6$ groups;
$R^6$ is selected from:
(a) —H, —($C_1$-$C_6$)alkyl, —($C_2$-$C_6$)alkenyl, —($C_2$-$C_6$) alkynyl, —($C_1$-$C_6$)alkoxy, and —($C_3$-$C_8$)cycloalkyl; and
(b) -halo, —C(halo)$_3$, —CH(halo)$_2$, —CH$_2$(halo), —CN, —NO, —NO$_2$, —N$_3$, —OH, —SH, —N($R^7$)$_2$, —NH (OH), —C(=O)$R^7$, —C(=O)O$R^7$, —OC(=O)$R^7$, —C(=O)N($R^7$), —N($R^7$)C(=O)$R^7$, —N($R^7$)C(=O) N($R^7$)$_2$, —OC(=O)N($R^7$)$_2$ and —N($R^7$)C(=O)O$R^7$;
$R^1$, $R^2$, $R^3$, $R^4$ and $R^5$ are independently selected from:

(a) —H, —(C$_1$-C$_6$)alkyl, —(C$_2$-C$_6$)alkenyl, —(C$_2$-C$_6$)alkynyl, and —(C$_1$-C$_6$)alkoxy; and (b) -halo, —C(halo)$_3$, —CH(halo)$_2$, —CH$_2$(halo), —CN, —NO, —NO$_2$, —N, —OH —SH, —N(R$^7$)$_2$, —NH(OH), —C(=O)R$^7$, —C(=O)OR, —OC(=O)R$^7$, —C(=O)N(R$^7$)$_2$, —N(R$^7$)C(=O)R$^7$, —N(R$^7$)C(=O)N(R$^7$)$_2$, —OC(=O)N(R$^7$)$_2$, and —N(R$^7$)C(=O)OR$^7$;

each R$^7$ is independently selected from —H, —(C$_1$-C$_6$)alkyl, —(C$_2$-C$_6$)alkenyl, and —(C$_2$-C$_6$)alkynyl;

each halo is independently —F, —C$_1$, —Br, or —I.

2. The compound according to embodiment 1, wherein R is —H.

3. The compound according to embodiment 1, wherein R is —(C$_1$-C$_6$)alkyl, which is unsubstituted or substituted with 1, 2, 3, 4 or 5 independently selected R$^6$ groups.

4. The compound according to embodiment 1 or 3, wherein R is —(C$_1$-C$_6$)alkyl, which is unsubstituted.

5. The compound according to any one of embodiments 1 or 3 to 4, wherein R is —CH$_3$, —CH$_2$—CH$_3$, iso-propyl, or tert-butyl.

6. The compound according to embodiment 1, wherein R is -(5- to 10-membered)heteroaryl or —(C$_1$-C$_6$)alkyl-(5- to 10-membered)heteroaryl, each of which is unsubstituted or substituted with 1, 2, 3, 4 or 5 independently selected R$^6$ groups.

7. The compound according to embodiment 1 or 6, wherein the -(5- to 10-membered)heteroaryl is a -(5- or 6-membered)heteroaryl.

8. The compound according to embodiment 1 or 6, wherein the —(C$_1$-C$_6$)alkyl-(5- to 10-membered)heteroaryl is a —(C$_1$-C$_6$)alkyl-(5- or 6-membered)heteroaryl.

9. The compound according to any one of embodiments 1 and 6 to 8, wherein R is selected from the group consisting of

[chemical structures]

wherein each n is an integer independently selected from 0, 1, 2, 3, 4, or 5.

10. The compound according to embodiment 1, wherein R is —(C$_6$-C$_{14}$)aryl or —(C$_1$-C$_6$)alkyl-(C$_6$-C$_4$)aryl, each of which is unsubstituted or substituted with 1, 2, 3, 4 or 5 independently selected R$^6$ groups.

11. The compound according to embodiment 1 or 10, wherein R is —(C$_6$-C$_{14}$)aryl or —(C$_1$-C$_6$)alkyl-(C$_6$-C$_{14}$)aryl, which is unsubstituted.

12. The compound according to any one of embodiments 1 and 10 to 11, wherein R is -phenyl or -benzyl.

13. The compound according to any one of embodiments 1 and 10 to 12, wherein R is -phenyl.

14. The compound according to any one of embodiments 1 to 13, wherein R$^6$ is independently selected from —H, —(C$_1$-C$_6$)alkyl, —(C$_1$-C$_6$)alkoxy, —NO, —NO$_2$, —N(R$^7$)$_2$, and —NH(OH).

15. The compound according to any one of embodiments 1 to 14, wherein R$^7$ is independently selected from —H or —(C$_1$-C$_6$)alkyl.

16. The compound according to any one of embodiments 1 to 15, wherein R$^1$, R$^2$, R$^3$, R$^4$ and R$^5$ are independently selected from —H, -halo, —(C$_1$-C$_6$)alkyl, —(C$_1$-C$_6$)alkoxy, —NO, —NO$_2$, —N(R$^7$)$_2$, —NH(OH), or —OH.

17. The compound according to any one of embodiments 1 to 16, wherein R$^1$, R$^2$, R$^3$, R$^4$ and R$^5$ are independently selected from —H, —(C$_1$-C$_6$)alkyl, —(C$_1$-C$_6$)alkoxy, —NO$_2$, or —OH.

18. The compound according to any one of embodiments 1 to 17, wherein R$^7$ is —H or —(C$_1$-C$_6$)alkyl.

19. The compound according to any one of embodiments 1 to 18, wherein at least one of the R$^1$, R$^2$, R$^3$, R$^4$ or R$^5$ groups is —H.

20. The compound according to any one of embodiments 1 to 19, wherein at least one of the R$^1$, R$^2$, R$^3$, R$^4$ or R$^5$ groups is —(C$_1$-C$_6$)alkyl.

21. The compound according to any one of embodiments 1 to 20, wherein at least one of the R$^1$, R$^2$, R$^3$, R$^4$ or R$^5$ groups is selected from —CH$_3$, —CH$_2$—CH$_3$, iso-propyl, or tert-butyl.

22. The compound according to any one of embodiments 1 to 21, wherein at least one of the R$^1$, R$^2$, R$^3$, R$^4$ or R$^5$ groups is —(C$_1$-C$_6$)alkoxy.

23. The compound according to any one of embodiments 1 to 22, wherein at least one of the R$^1$, R$^2$, R$^3$, R$^4$ or R$^5$ groups is selected from —OCH$_3$, —OCH$_2$—CH$_3$, —O-iso-propyl, or —O-tert-butyl.

24. The compound according to any one of embodiments 1 to 23, wherein at least one of the R$^1$, R$^2$, R$^3$, R$^4$ or R$^5$ groups is —NO$_2$.

25. The compound according to any one of embodiments 1 to 24, wherein at least one of the R$^1$, R$^2$, R$^3$, R$^4$ or R$^5$ groups is —OH.

26. The compound according to any one of embodiments 1 to 25, wherein the R$^1$, R$^2$, R$^3$, R$^4$ or R$^5$ groups are selected to form the following substituents:

[chemical structures]

-continued

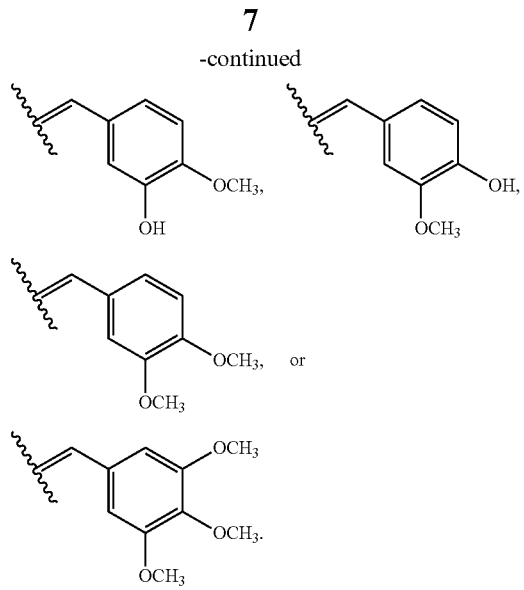

27. The compound of embodiment 1, wherein the compound is selected from the group

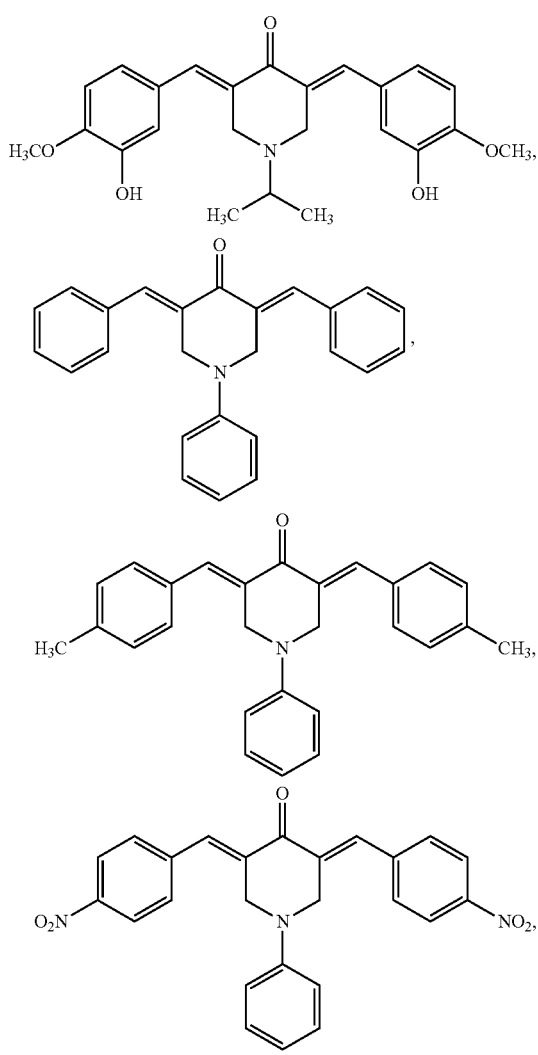

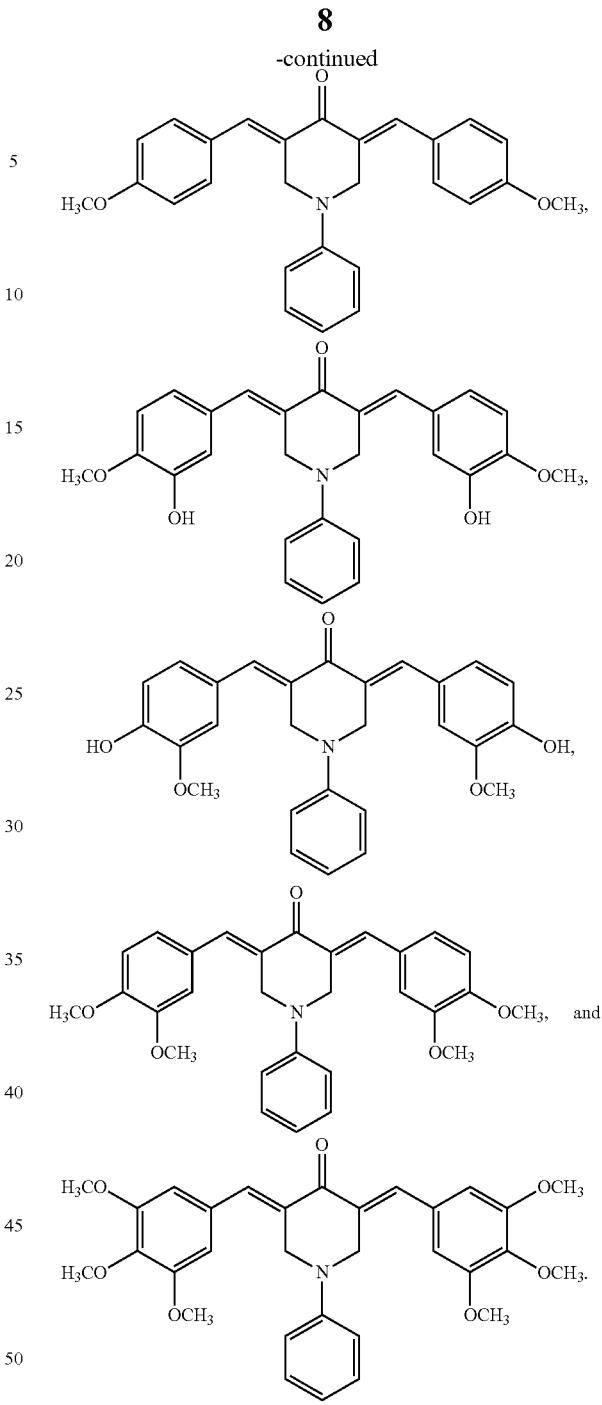

consisting of:

28. The compound of any one of embodiments 1 to 27, wherein the compound is achiral or chiral.

29. The compound according of any one of embodiments 1 to 28, wherein the compound is achiral.

30. The compound of any one of embodiments 1 to 29, wherein the pharmaceutically acceptable derivative is a pharmaceutically acceptable salt.

31. A compound of any one of embodiments 1 to 30, or a pharmaceutically acceptable derivative thereof for use in the treatment or prevention of a disorder, wherein the disorder is selected from the group consisting of cancer, autoimmune disorders, inflammatory disorders, and fibrotic disorders.

32. The compound for use of embodiment 31, wherein the cancer is selected from the group consisting of breast cancer, head and neck cancer, lung cancer, ovarian cancer, pancreatic cancer, colorectal carcinoma, prostate cancer, cervical cancer, renal cancer, skin cancer, hepatocellular carcinoma, liver cancer, esophageal cancer, cervical cancer, glioma, bladder cancer, endometrial cancer, bile duct cancer, bone cancer, retinoblastoma, gallbladder cancer, pituitary cancer, rectal cancer, salivary gland cancer, nasal pharyngeal, sarcoma, brain cancer, gastric cancer, multiple myeloma, leukemia, thyroid cancer, and lymphoma.

33. The compound for use of embodiment 31 or 32, wherein the cancer is selected from the group consisting of skin cancer, leukemia, prostate cancer, colon cancer, lung cancer, and ovarian cancer.

34. The compound for use of any one of embodiments 31 to 33, wherein the cancer is a metastatic cancer.

35. The compound for use of any one of embodiments 31 to 34, wherein the cancer comprises cancer stem cells.

36. The compound for use of any one of embodiments 31 to 35, wherein the cancer is resistant towards a chemotherapy and/or a radiotherapy.

37. The compound for use of embodiment 31, wherein the autoimmune disorder and/or the inflammatory disorder is selected from the group consisting of inflammatory bowel disease, arthritis, autoimmune demyelination disorder, Alzheimer's disease, stroke, ischemia reperfusion injury, cachexia, asthma, and multiple sclerosis.

38. The compound for use of embodiment 31, wherein the fibrotic disorder is selected from the group consisting of vascular fibrosis, pulmonary fibrosis, pancreatic fibrosis, liver fibrosis, renal fibrosis, musculoskeletal fibrosis, cardiac fibrosis, skin fibrosis, eye fibrosis, glaucoma, progressive systemic sclerosis (PSS), chronic graft versus-host disease, scleroderma, Peyronie's disease, post-cystoscopic urethral stenosis, idiopathic and pharmacologically induced retroperitoneal fibrosis, mediastinal fibrosis, progressive massive fibrosis, proliferative fibrosis, and neoplastic fibrosis.

39. A pharmaceutical composition comprising a compound of any one of embodiments 1 to 31, or a pharmaceutically acceptable derivative thereof, and another therapeutic agent.

40. The pharmaceutical composition of embodiment 39, wherein the therapeutic agent is an anticancer drug.

41. The pharmaceutical composition of embodiments 39 or 40, wherein the anticancer drug is selected from the group consisting of taxanes, ruthenium-based compounds, and platinum-based compounds.

42. The pharmaceutical composition of any one of embodiments 39 to 41, wherein the anticancer drug is selected from the group consisting of paclitaxel, oxaliplatin, and cisplatin.

43. The pharmaceutical composition of any one of embodiments 39 to 42, wherein the anticancer activity of the anticancer drug is enhanced.

44. The pharmaceutical composition of any one of embodiments 39 to 43 for use in the treatment or prevention of a disorder, wherein the disorder is selected from the group consisting of cancer, autoimmune disorders, inflammation disorders, and fibrotic disorders.

45. Compound for use of any one of embodiments 31 to 38, or a pharmaceutically acceptable derivative thereof, or the pharmaceutical composition of any one of embodiments 39 to 44, wherein the treatment or prevention further comprises radiotherapy, immunotherapy and/or surgery.

46. A compound of any one of embodiments 1 to 30, or a pharmaceutically acceptable derivative thereof, for use as a medicament.

47. Use of a compound of any one of embodiments 1 to 30, or a pharmaceutically acceptable derivative thereof, for the manufacture of a medicament for the treatment or prevention of a disorder, wherein the disorder is selected from the group consisting of cancer, autoimmune disorders, inflammatory disorders, and fibrotic disorders.

48. The use of embodiment 47, wherein the cancer is selected from the group consisting of breast cancer, head and neck cancer, lung cancer, ovarian cancer, pancreatic cancer, colorectal carcinoma, prostate cancer, cervical cancer, renal cancer, skin cancer, hepatocellular carcinoma, liver cancer, esophageal cancer, cervical cancer, glioma, bladder cancer, endometrial cancer, bile duct cancer, bone cancer, retinoblastoma, gallbladder cancer, pituitary cancer, rectal cancer, salivary gland cancer, nasal pharyngeal, sarcoma, brain cancer, gastric cancer, multiple myeloma, leukemia, thyroid cancer, and lymphoma.

49. The use of embodiment 47 or 48, wherein the cancer is selected from the group consisting of skin cancer, leukemia, prostate cancer, colon cancer, lung cancer, and ovarian cancer.

50. The use of any one of embodiments 47 to 49, wherein the cancer is a metastatic cancer.

51. The use of any one of embodiments 47 to 50, wherein the cancer comprises cancer stem cells.

52. The use of any one of embodiments 47 to 51, wherein the cancer is resistant towards a chemotherapy and/or a radiotherapy.

53. The use of embodiment 47, wherein the autoimmune disorder and/or the inflammatory disorder is selected from the group consisting of inflammatory bowel disease, arthritis, autoimmune demyelination disorder, Alzheimer's disease, stroke, ischemia reperfusion injury, cachexia, asthma, and multiple sclerosis.

54. The use of embodiment 47, wherein the fibrotic disorder is selected from the group consisting of vascular fibrosis, pulmonary fibrosis, pancreatic fibrosis, liver fibrosis, renal fibrosis, musculoskeletal fibrosis, cardiac fibrosis, skin fibrosis, eye fibrosis, glaucoma, progressive systemic sclerosis (PSS), chronic graft versus-host disease, scleroderma, Peyronie's disease, post-cystoscopic urethral stenosis, idiopathic and pharmacologically induced retroperitoneal fibrosis, mediastinal fibrosis, progressive massive fibrosis, proliferative fibrosis, and neoplastic fibrosis.

55. The use of any one of embodiments 47 to 54, wherein the use further comprises another therapeutic agent.

56. The use embodiment 55, wherein the therapeutic agent is an anticancer drug.

57. The use of any one of embodiments 55 or 56, wherein the anticancer drug is selected from the group consisting of taxanes, ruthenium-based compounds, and platinum-based compounds.

58. The use of any one of embodiments 55 to 57, wherein the anticancer drug is selected from the group consisting of paclitaxel, oxaliplatin, and cisplatin.

59. The use of any one of embodiments 55 to 58, wherein the anticancer activity of the anticancer drug is enhanced.

60. A method of preparing the pharmaceutical composition of any one of embodiments 39 to 45, comprising admixing a compound of any one of embodiments 1 to 30, or a pharmaceutically acceptable derivative thereof, with a pharmaceutically acceptable carrier.

61. A method of treating or preventing a disorder in a subject identified as in need of such treatment or prevention, comprising administering to said subject a compound of any one of embodiments 1 to 30 or a pharmaceutically acceptable derivative thereof, wherein the disorder is selected from the group consisting of cancer, autoimmune disorders, inflammation disorders, and fibrotic disorders.

62. The method of embodiment 61, wherein the cancer is selected from the group consisting of breast cancer, head and neck cancer, lung cancer, ovarian cancer, pancreatic cancer, colorectal carcinoma, prostate cancer, cervical cancer, renal cancer, skin cancer, hepatocellular carcinoma, liver cancer, esophageal cancer, cervical cancer, glioma, bladder cancer, endometrial cancer, bile duct cancer, bone cancer, retinoblastoma, gallbladder cancer, pituitary cancer, rectal cancer, salivary gland cancer, nasal pharyngeal cancer, sarcoma, brain cancer, gastric cancer, multiple myeloma, leukemia, thyroid cancer, and lymphoma.

63. The method of embodiment 61 or 62, wherein the cancer is selected from the group consisting of skin cancer, leukemia, prostate cancer, colon cancer, lung cancer, and ovarian cancer.

64. The method of any one of embodiments 61 to 63, wherein the cancer is a metastatic cancer.

65. The method of any one of embodiments 61 to 64, wherein the cancer comprises cancer stem cells.

66. The method of embodiment 61, wherein the autoimmune disorder and/or the inflammatory disorder is selected from the group consisting of inflammatory bowel disease, arthritis, autoimmune demyelination disorder, Alzheimer's disease, stroke, ischemia reperfusion injury, and multiple sclerosis.

67. The method of embodiment 61, wherein the fibrotic disorder is selected from the group consisting of vascular fibrosis, pulmonary fibrosis, pancreatic fibrosis, liver fibrosis, renal fibrosis, musculoskeletal fibrosis, cardiac fibrosis, skin fibrosis, eye fibrosis, glaucoma, progressive systemic sclerosis (PSS), chronic graft versus-host disease, scleroderma. Peyronie's disease, post-cystoscopic urethral stenosis, idiopathic and pharmacologically induced retroperitoneal fibrosis, mediastinal fibrosis, progressive massive fibrosis, proliferative fibrosis, and neoplastic fibrosis.

68. The method of any one of embodiments 61 to 67, wherein the method further comprises another therapeutic agent.

69. The method of embodiment 68, wherein the therapeutic agent is an anticancer drug.

70. The method of embodiment 68 or 69, wherein the anticancer drug is selected from the group consisting of taxanes, ruthenium-based compounds, and platinum-based compounds.

71. The method of any one of embodiments 68 to 70, wherein the anticancer drug is selected from the group consisting of paclitaxel, oxaliplatin, and cisplatin.

72. The method of any one of embodiments 68 to 71, wherein the anticancer activity of the anticancer drug is enhanced.

73. A method of inhibition of Stat3 pathway activity in a cell, comprising administering to the cell a compound of any one of embodiments 1 to 30, or a pharmaceutically acceptable derivative thereof.

74. The method of embodiment 73, wherein the cell is a cancer cell.

75. The method of embodiment 73 or 74, wherein the method is carried out in vitro.

76. The method of embodiment 73 or 74, wherein the method is carried out in vivo.

77. The method of any one of embodiments 73 to 76, wherein the inhibition of Stat3 pathway activity is associated with a reduction of phosphorylated Stat3 (pStat3).

78. The method of any one of embodiments 73 to 77, wherein the inhibition of Stat3 pathway activity is associated with a reduction of Bcl-2, Bcl-xL, and survivin.

79. The method of any one of embodiments 73 to 78, wherein the inhibition of Stat3 pathway activity is associated with cell death mechanisms selected from the group consisting of apoptosis, paraptosis, and methuosis.

80. A compound of any one of embodiments 1 to 30, or a pharmaceutically acceptable derivative thereof, for use as a fluorescent probe.

81. The compound for use of embodiment 80, wherein the fluorescent probe is detected in cells.

82. The compound for use of embodiment 80 or 81, wherein the fluorescent probe is detected in cancer cells.

83. A process of preparing a compound of any one of embodiments 1 to 30, or a pharmaceutically acceptable derivative thereof, wherein the process comprises reacting an N-substituted-piperid-4-one with an unsubstituted or substituted benzaldehyde, wherein the N-substituted-piperid-4-one is selected from a group consisting of N-phenyl-piperid-4-one, and N-iso-propyl-piperid-4-one, and wherein the substituted benzaldehyde is selected from the group consisting of 4-methylbenzaldehyde, 4-nitrobenzaldehyde, 4-methoxybenzaldeyde, 3-hydroxy-4-methoxy-benzaldehyde, 4-hydroxy-3-methoxy-benzadehyde, 3,4-dimethoxybenzaldehyde, and 3,4,5-trimethoxybenzaldehyde, preferably wherein the benzaldehyde is substituted.

84. The process of embodiment 83, wherein the reaction is performed in solution in the presence of an acid or a base.

BRIEF DESCRIPTION OF DRAWINGS

FIG. 21A shows DU145 cells treated with media (control), 1.2 µM IE-8 for 18 h, 60 µM cisplatin for 1 h or a combination of IE-8 and cisplatin, that were fixed and stained for γ-H2AX at 0, 9, 24 and 48 h post cisplatin treatment. γ-H2AX foci are evident in cells treated with cisplatin alone, and are enhanced significantly in the combination treatments.

FIG. 21B shows quantification of three repeats of the above staining that was performed with CellProfiler with a threshold of 0.3. Cells treated with a combination of both IE-8 and cisplatin have significantly more γ-H2AX foci, indicative of greater levels of DNA damage response, due to persistence of DNA adducts which—if left unrepaired—can lead to more DNA strand breaks.

FIG. 21C shows A549 cells that were treated with a combination of IE-8 and cisplatin and harvested for immunoblotting 24 h after drug treatment. An increase in γ-H2AX staining is evident in the combination treated cells.

FIG. 23A shows representative fluorescence microscopy images of A2780 cis-res cells treated with 150 µM cisplatin for 1 h, wherein the treatment was collected over a period of 48 h. U stands or untreated samples and T for treated. +/− further denotes the additional treatment with MMS.

FIG. 23B shows representative fluorescence microscopy images of A2780 cis-res cells treated with 150 µM cisplatin for 1 h and 3 h later with 6 µM IE-8 for 1 h, wherein the treatment was collected over a period of 48 h. U stands or untreated samples and T for treated. +/− further denotes the additional treatment with MMS.

FIG. 23C shows a bar diagram displaying the average relative tail moments (as derived from the Comet Assay IV software, averaged within the group) of two independent combination experiments (averaged between groups). IE-8 impairs the repair (unhooking) of the cisplatin-induced DNA interstrand crosslinks, the lesion detected by the modified comet assay. The A2780-cisplatin resistant cells are proficient at unhooking the DNA ICLs (as evidenced by an increase in the tail moment). However, treatment with IE-8, impairs this process as evidenced by an ever increasing reduction in the tail moment size.

FIG. 24A shows images of HCTI 16-oxaliplatin resistant spheroids (upper panel), derived by cells seeded at a concentration of 1000 cells/well and allowed to form spheroids for four days. On day 4, spheroids were treated with increasing doses of IE-8. Images were taken on day 4 post the initiation of treatment. Images (with the spheroids' dimensions embedded) of the untreated and the 20 µM IE-8 treated spheroids (lower panel).

FIG. 24B shows an immunoblot of HCT16-oxaliplatin resistant spheroid lysates, showing inhibition of pStat3.

FIG. 24C shows an induction of apoptosis as evidenced by the cleavage of PARP in the same spheroids.

APC-Cy7 (780/60 nm), AF-700 (720/40 nm). Data were analyzed using the Flowing Software (University of Turku, Finland). Data are depicted as raw fluorescence intensity values (arbitrary units, au.).

Figure 30A:
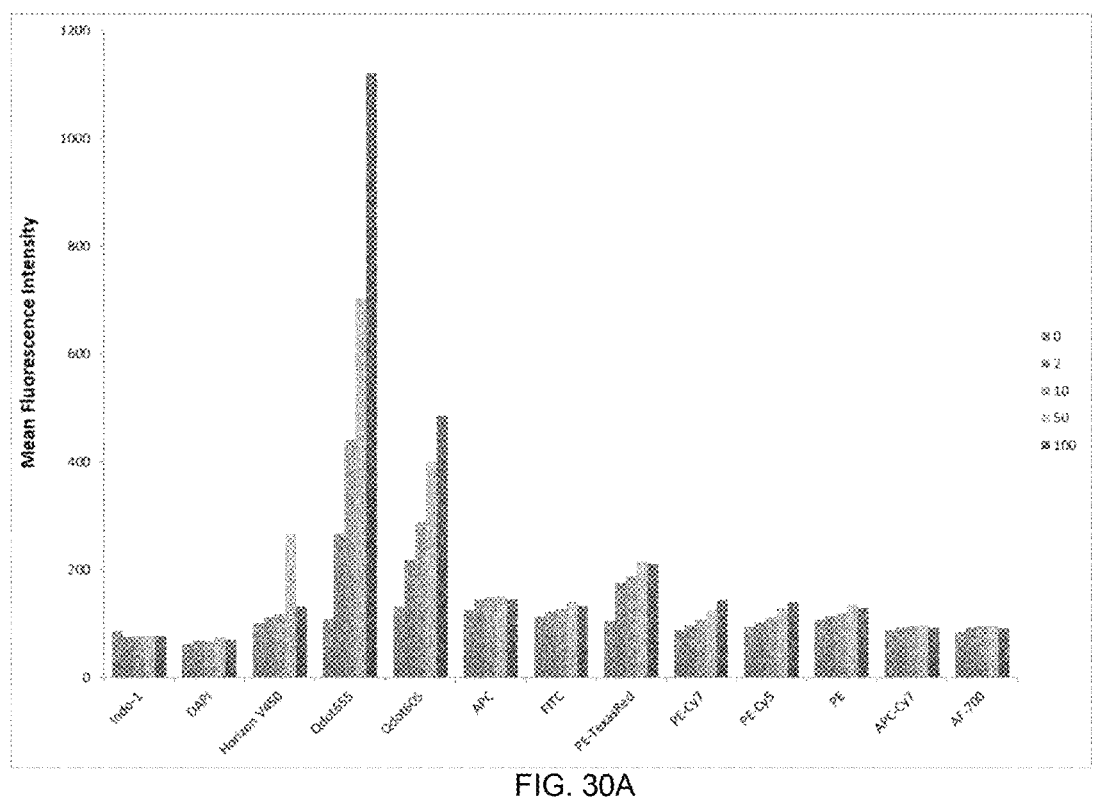
FIG. 30A shows an intracellular drug accumulation measured on an LSRFortessa flow cytometer (BD Biosciences, East Rutherford, NJ, USA) after 1 hr of IE-8 treatment. The cell line tested was A2780. A comparative drug accumulation is shown. The compound's fluorescence was detected using: 355 nm laser excitation wavelength and DAPI (450/40 nm) and Indo-1 (519/40 nm) bandpass emission filter. 405 nm laser excitation wavelength and Qdot605 (610/20 nm), Horizon V450 (450/40 nm) and Qdot655 (660/20 nm) bandpass emission. 488 nm laser excitation wavelength and PE-Cy5 (670/30 nm), PE (575/26 nm), PE-Texas Red (630/30 nm), FITC (530/30 nm), and PE-Cy7 (780/60 nm). 640 nm laser excitation and APC (660/20 nm), APC-Cy7 (780/60 nm), AF-700 (720/40 nm). Data were analyzed using the Flowing Software (University of Turku, Finland). Data are depicted as raw fluorescence intensity values (arbitrary units, a.u.).
Figure 30B:
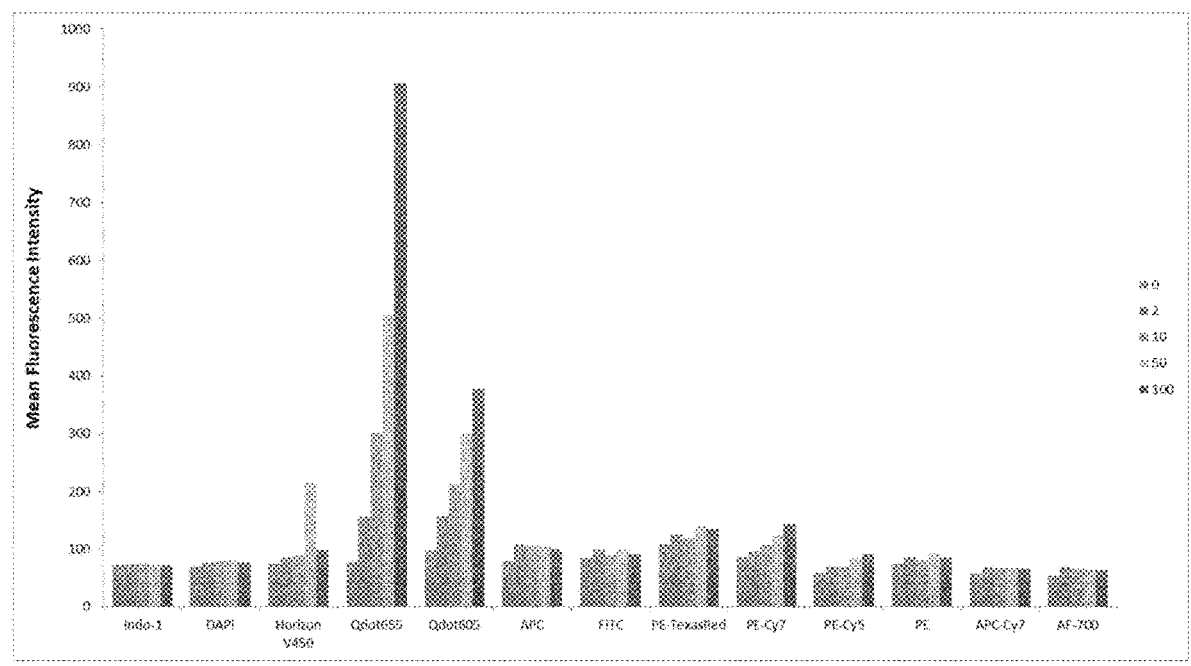
FIG. 30B shows an intracellular drug accumulation measured on an LSRFortessa flow cytometer (BD Biosciences, East Rutherford, NJ, USA) after 1 hr of IE-8 treatment. The cell line tested was A2780-cisplatin resistant. A comparative drug accumulation is shown. The compound's fluorescence was detected using: 355 nm laser excitation wavelength and DAPI (450/40 nm) and Indo-1 (519/40 nm) bandpass emission filter. 405 nm laser excitation wavelength and Qdot605 (610/20 nm), Horizon V450 (450/40 nm) and Qdot655 (660/20 nm) bandpass emission. 488 nm laser excitation wavelength and PE-Cy5 (670/30 nm), PE (575/26 nm), PE-Texas Red (630/30 nm), FITC (530/30 nm), and PE-Cy7 (780/60 nm). 640 nm laser excitation and APC (660/20 nm).
Figure 30C:
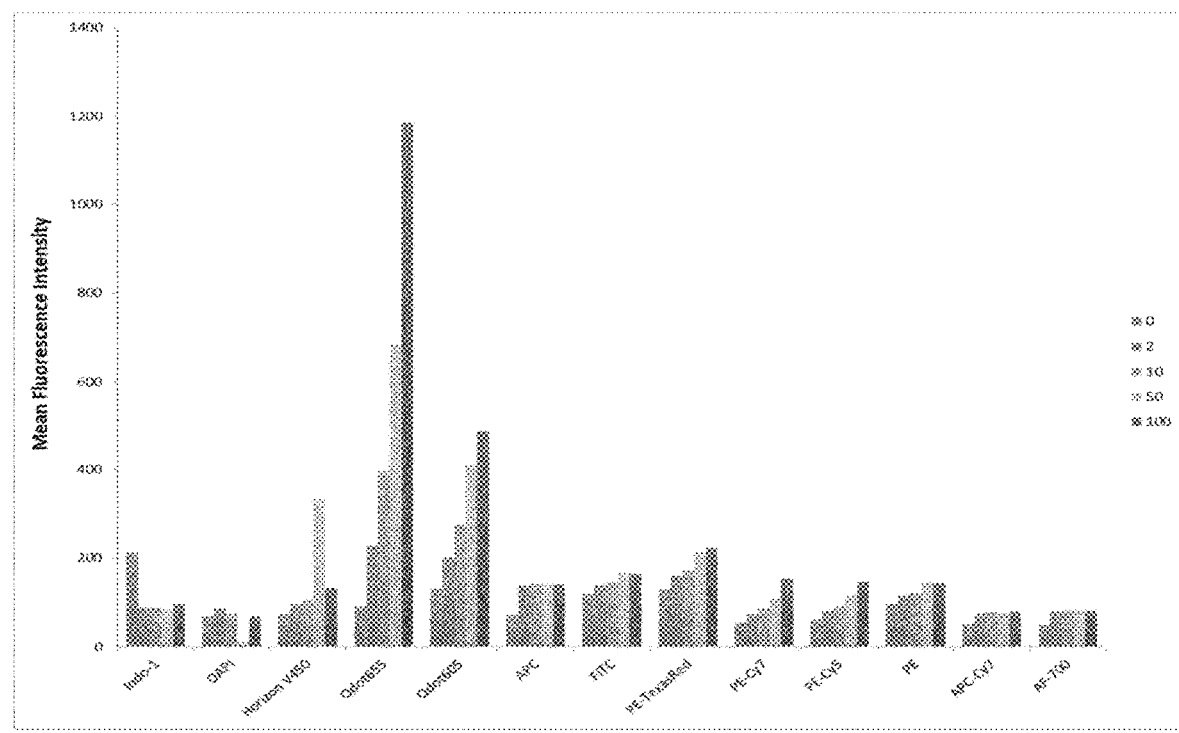

FIG. 30C shows an intracellular drug accumulation measured on an LSRFortessa flow cytometer (BD Biosciences, East Rutherford, NJ, USA) after 1 hr of IE-8 treatment. The cell line tested was HCT116. A comparative drug accumulation is shown. The compound's fluorescence was detected using: 355 nm laser excitation wavelength and DAPI (450/40 nm) and Indo-1 (519/40 nm) bandpass emission filter. 405 nm laser excitation wavelength and Qdot605 (610/20 nm), Horizon V450 (450/40 nm) and Qdot655 (660/20 nm) bandpass emission. 488 nm laser excitation wavelength and PE-Cy5 (670/30 nm), PE (575/26 nm), PE-Texas Red (630/30 nm), FITC (530/30 nm), and PE-Cy7 (780/60 nm). 640 nm laser excitation and APC (660/20 nm), APC-Cy7 (780/60 nm), AF-700 (720/40 nm). Data were analyzed using the Flowing Software (University of Turku, Finland). Data are depicted as raw fluorescence intensity values (arbitrary units, a.u.).

Figure 30D:
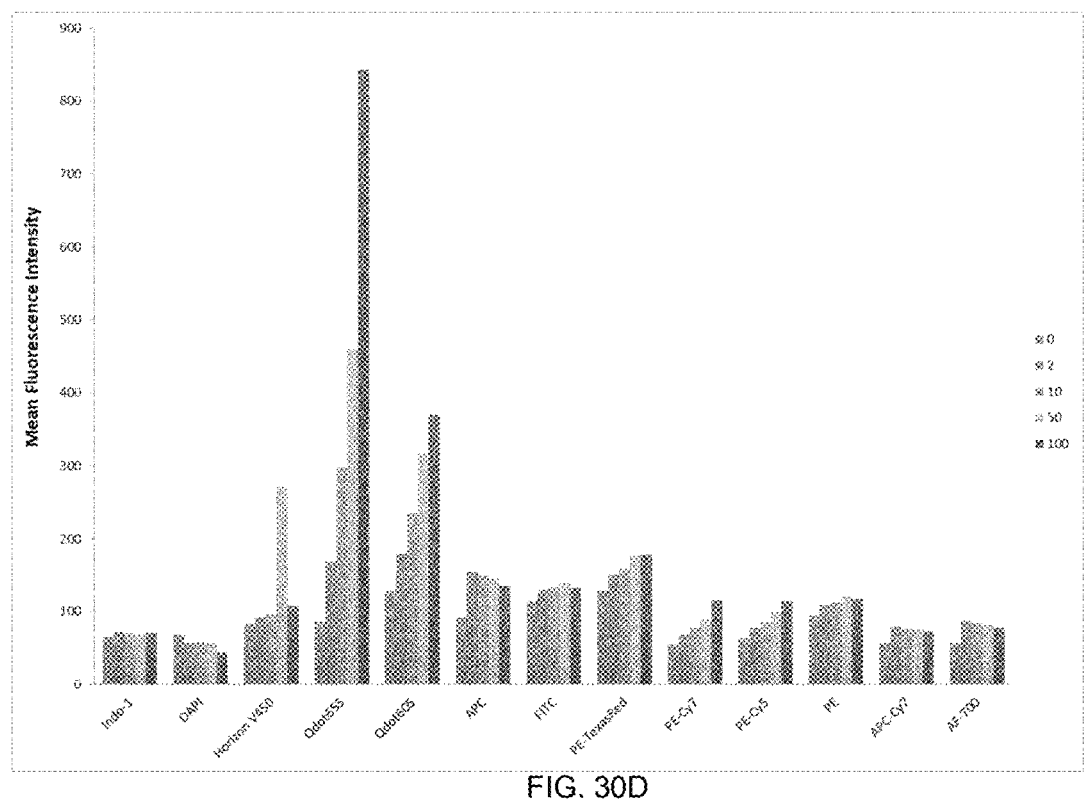

FIG. 30D shows an intracellular drug accumulation measured on an LSRFortessa flow cytometer (BD Biosciences, East Rutherford, NJ, USA) after 1 hr of IE-8 treatment. The cell line tested was HCT116-oxaliplatin resistant. A comparative drug accumulation is shown. The compound's fluorescence was detected using: 355 nm laser excitation wavelength and DAPI (450/40 nm) and Indo-1 (519/40 nm) bandpass emission filter. 405 nm laser excitation wavelength and Qdot605 (610/20 nm), Horizon V450 (450/40 nm) and Qdot655 (660/20 nm) bandpass emission. 488 nm laser excitation wavelength and PE-Cy5 (670/30 nm), PE (575/26 nm). PE-Texas Red (630/30 nm), FITC (530/30 nm), and PE-Cy7 (780/60 nm). 640 nm laser excitation and APC (660/20 nm), APC-Cy7 (780/60 nm), AF-700 (720/40 nm). Data were analyzed using the Flowing Software (University of Turku, Finland). Data are depicted as raw fluorescence intensity values (arbitrary units, a.u.).

Figure 30E:
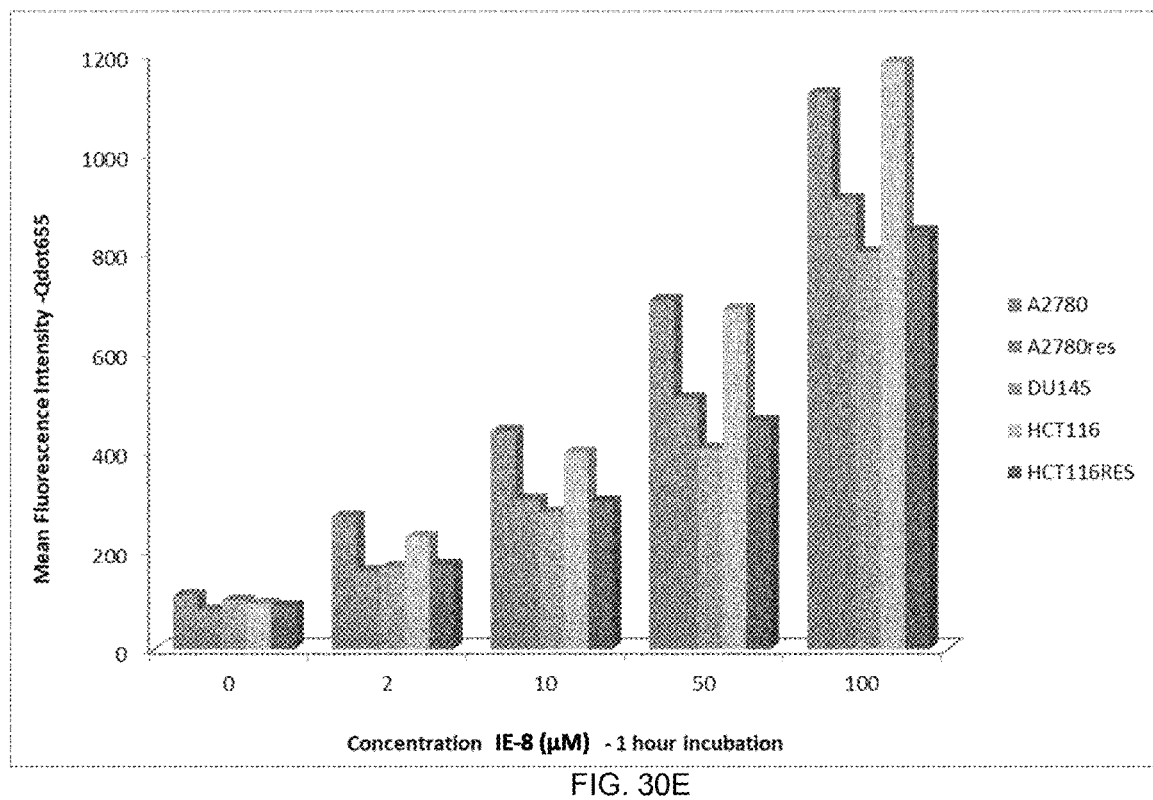

FIG. 30E shows intracellular drug accumulations measured on an LSRFortessa flow cytometer (BD Biosciences, East Rutherford, NJ, USA) after 1 hr of IE-8 treatment. The cell lines tested were: A2780, A2780-cisplatin resistant, HCT116, HCT116-oxaliplatin resistant, and DU145. A comparative drug accumulation is shown. The compound's fluorescence was detected using: 355 nm laser excitation wavelength and DAPI (450/40 nm) and Indo-1 (519/40 nm) bandpass emission filter. 405 nm laser excitation wavelength and Qdot605 (610/20 nm), Horizon V450 (450/40 nm) and Qdot655 (660/20 nm) bandpass emission. 488 nm laser excitation wavelength and PE-Cy5 (670/30 nm). PE (575/26 nm), PE-Texas Red (630/30 nm). FITC (530/30 nm), and PE-Cy7 (780/60 nm). 640 nm laser excitation and APC (660/20 nm), APC-Cy7 (780/60 nm), AF-700 (720/40 nm). Data were analyzed using the Flowing Software (University of Turku, Finland). Data are depicted as raw fluorescence intensity values (arbitrary units, a.u.). Exposure to IE-8 results in a marked dose-dependent increase in intensity in the Qdot655 channel (and to a lesser extent in the Qdot605 channel), upon a 405 nm excitation, in all the cell lines tested.

Figure 31A:
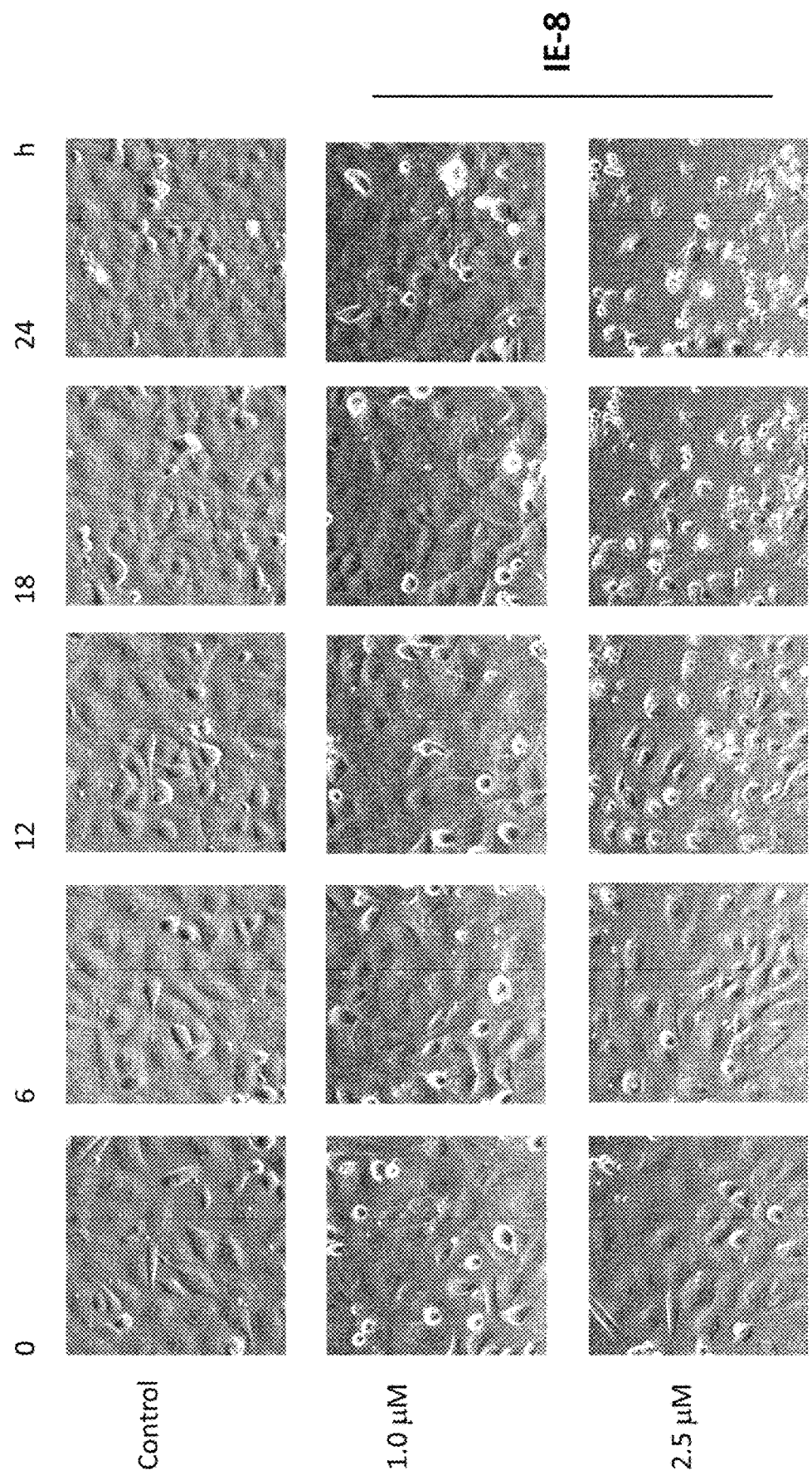

FIG. 31A shows DU145 cells that were treated with increasing concentration of IE-8 (top: 1.0 µM; bottom: 2.5 mM), and images were taken every 6 hours over a period of 24 h on a live cell microscope (Visitron Systems, Puchheim, Germany) using a 40× oil immersion DIC objective and the imaging software VisiView. At increasing doses, the induction of vacuoles emerges at earlier times. This vacuolisation—which ultimately leads to cell lysis—is reminiscent of the morphological signature of methuosis and paraptosis, non-apoptotic cell death mechanisms, which entail the extreme displacement of the cytoplasm with fluid-filled vacuoles.

Figure 31B:
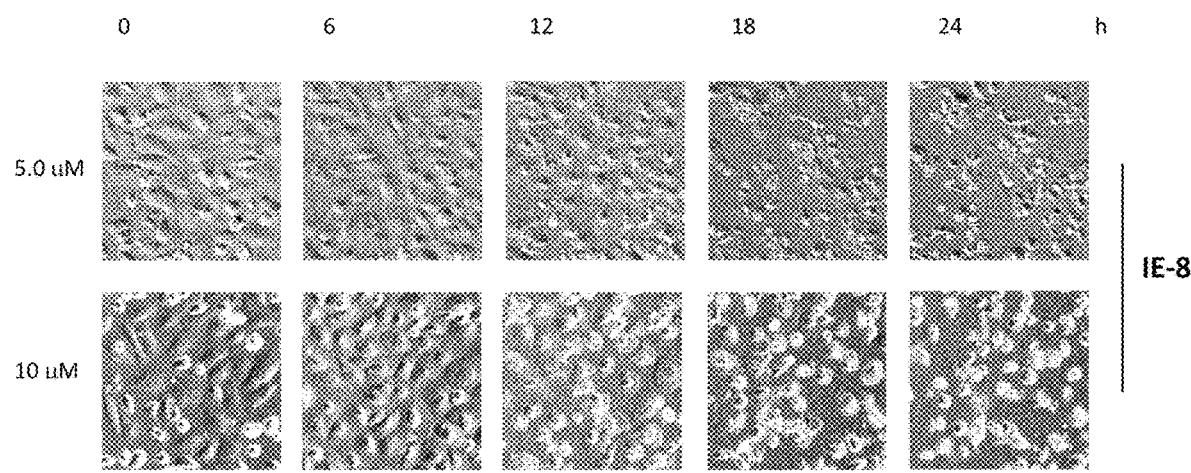

FIG. 31B shows DU145 cells that were treated with increasing concentration of IE-8 (top: 5.0 mM; bottom: 10.0 mM), and images were taken even 6 hours over a period of 24 h on a live cell microscope (Visitron Systems, Puchheim. Germany) using a 40× oil immersion DIC objective and the imaging software VisiView. At increasing doses, the induction of vacuoles emerges at earlier times. This vacuolisation—which ultimately leads to cell lysis—is reminiscent of the morphological signature of methuosis and paraptosis, non-apoptotic cell death mechanisms, which entail the extreme displacement of the cytoplasm with fluid-filled vacuoles.

Figure 31C:
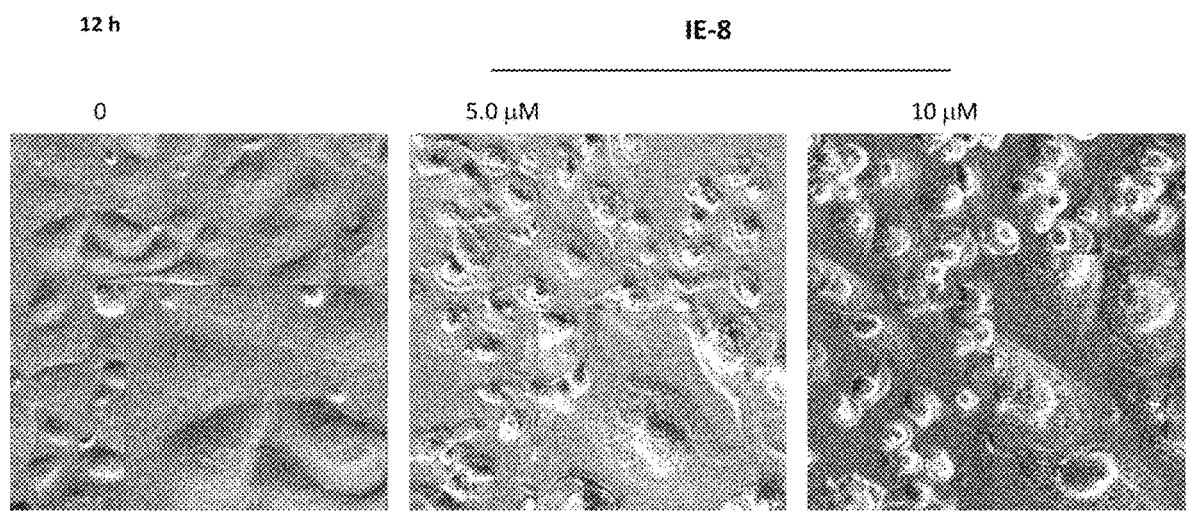

FIG. 31C shows a magnified view of selected images.

Figure 32:
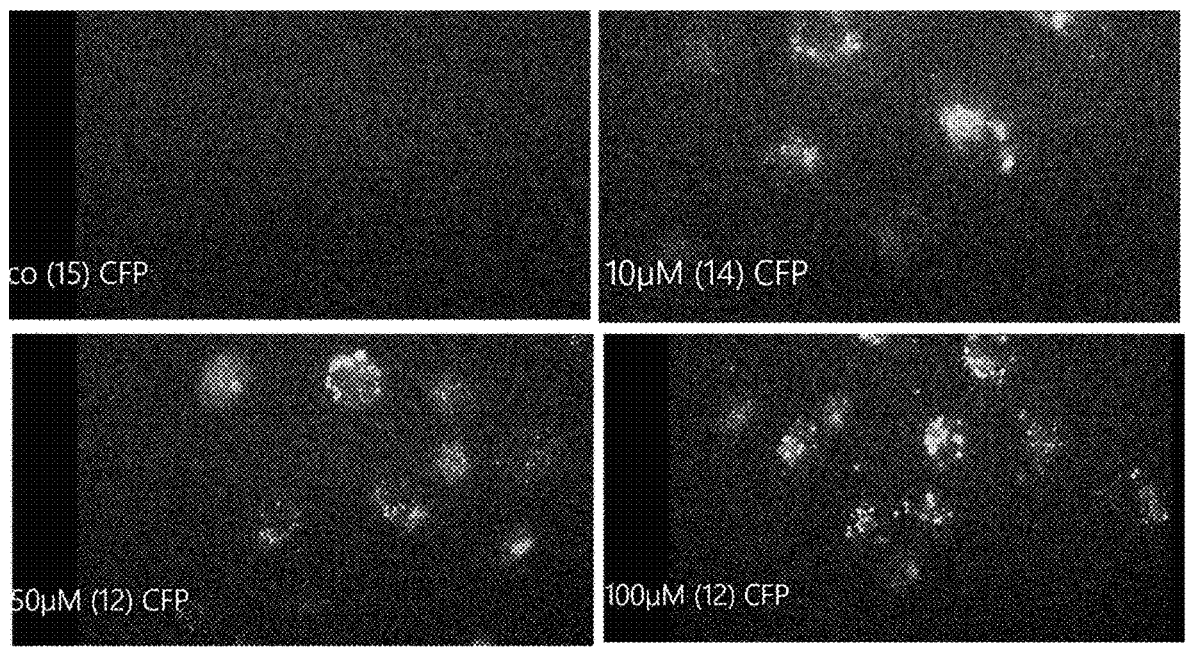

FIG. 32 shows DU145 cells that were treated with the denoted concentrations of IE-8 (10 µM, 50 µM, or 100 µM) and intracellular drug accumulation was imaged at 3 h intervals on a live cell microscope (Visitron Systems, Puchheim. Germany) using a 40× oil immersion DIC objective and VisiView® software. LEDs were used for widefield DIC and fluorescence (436/20 nm excitation and 480/40 nm bandpass filter for (CFP) fluorescence illumination (Visitron Systems). Images were taken with a sCMOS 4.2MPxl digital camera. There is a dose-dependent induction of aggresome-like perinuclear structures (presumed to be IE-8 bound on Stat3, detected by the compound's inherent fluorescence). The images shown were taken at 3 h.

Figure 33A:
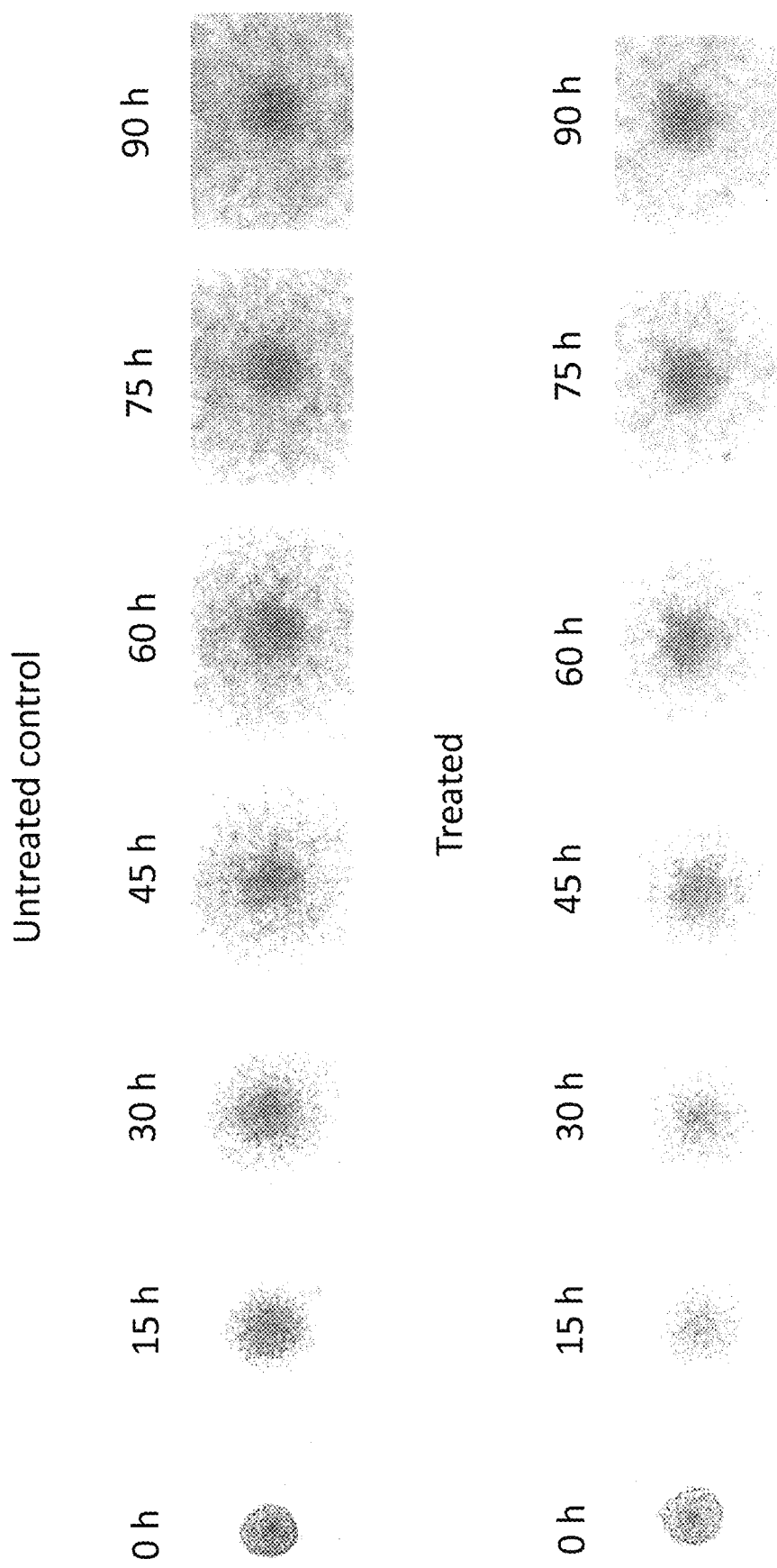

FIG. 33A shows monitoring of over 90 hours of the anti-invasive activity of IE-8 in the HT1080 spheroid model by the JuliBr system. Representative images of control (untreated; top panel) and IE-8 treated (bottom panel) spheroids, showing inhibition of protrusion formation conferred by IE-8, over 90 h.

Figure 33B:
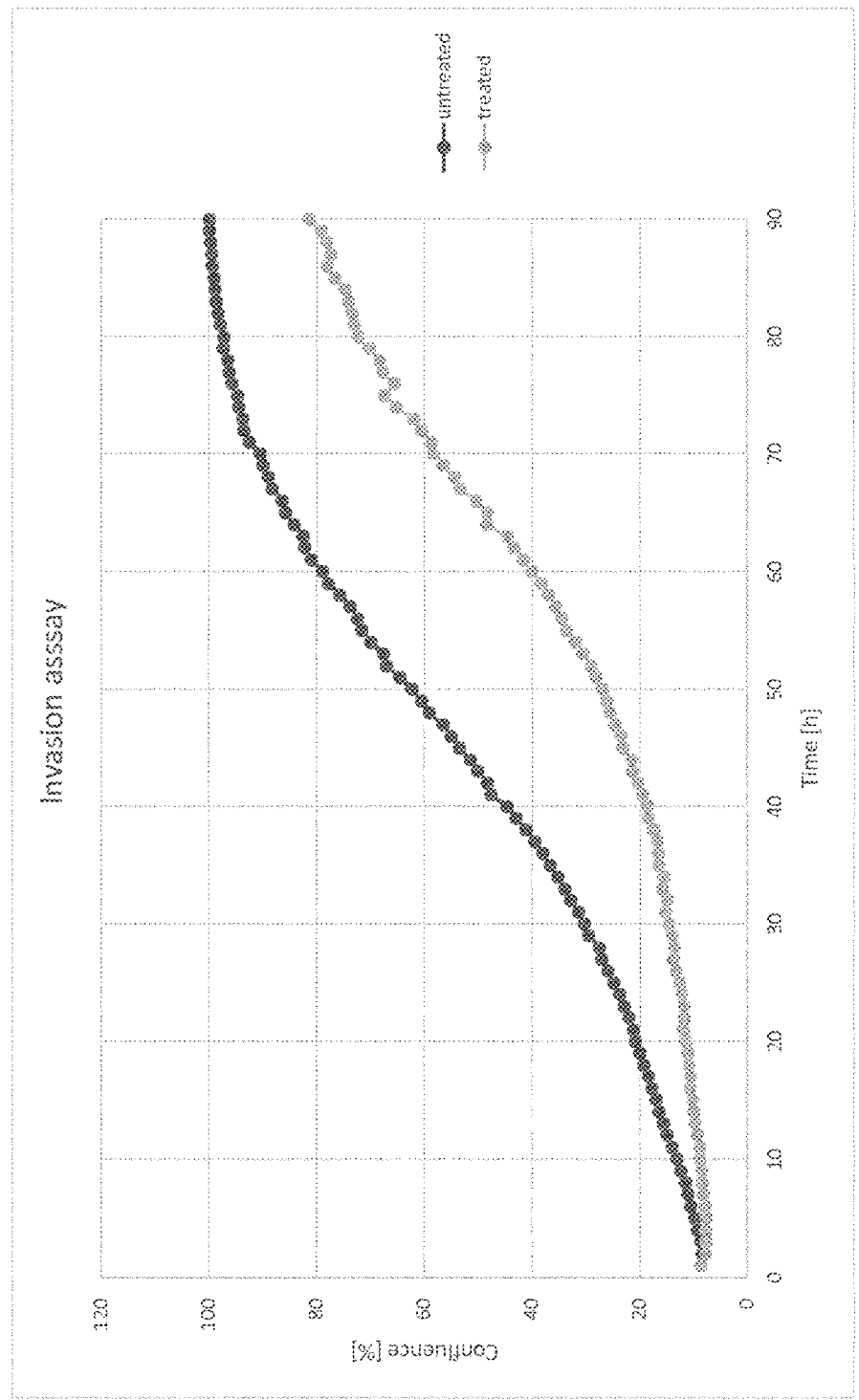

FIG. 33B shows a time-dependent anti-invasive activity of IE-8 compared to untreated controls. Measurements of the cross-sectional area of spheroids embedded in matrigel.

DETAILED DESCRIPTION OF THE INVENTION

In one aspect, the invention provides compounds of Formula I:

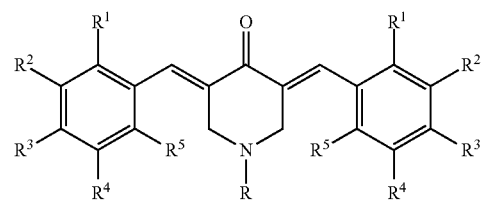

or a pharmaceutically acceptable derivative thereof, wherein

R is selected from:
(a) —H, —($C_1$-$C_6$)alkyl, —($C_2$-$C_6$)alkenyl, —($C_2$-$C_6$)alkynyl, —($C_3$-$C_8$)cycloalkyl, —($C_6$-$C_{14}$)bicycloalkyl, —($C_5$-$C_{20}$)tricycloalkyl, —($C_5$-$C_8$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, 4 or 5 independently selected $R^6$ groups; and (b) —$(C_6$-$C_{14})$aryl, —$(C_1$-$C_6)$alkyl-$(C_6$-$C_{14})$aryl, "-(5- to 10-membered)heteroaryl, and —$(C_1$-$C_6)$alkyl-(5- to 10-membered)heteroaryl, each of which is unsubstituted or substituted with 1, 2, 3, 4 or 5 independently selected $R^6$ groups:

$R^6$ is selected from:

(a) —H, —$(C_1$-$C_6)$alkyl, —$(C_2$-$C_6)$alkenyl, —$(C_2$-$C_6)$alkynyl, —$(C_1$-$C_6)$alkoxy, and —$(C_3$-$C_8)$cycloalkyl; and (b) -halo, —C(halo)$_3$, —CH(halo)$_2$, —CH$_2$(halo), —CN, —NO, —NO$_2$, —N$_3$, —OH, —SH, —N(R$^7$)$_2$, —NH(OH), —C(=O)R$^7$, —C(=O)OR$^7$, —OC(=O)R$^7$, —C(=O)N(R$^7$)$_2$, —N(R$^7$)C(=O)R$^7$, —N(R$^7$)C(=O)N(R$^7$)$_2$, —OC(=O)N(R$^7$)$_2$ and —N(R$^7$)C(=O)OR$^7$;

$R^1$, $R^2$, $R^3$, $R^4$ and $R^5$ are independently selected from:

(a) —H, —$(C_1$-$C_6)$alkyl, —$(C_2$-$C_6)$alkenyl, —$(C_2$-$C_6)$alkynyl, and —$(C_1$-$C_6)$alkoxy; and (b) -halo, —C(halo)$_3$, —CH(halo)$_2$, —CH$_2$(halo), —CN, —NO, —NO$_2$, —N$_3$, —OH, —SH, —N(R$^7$)$_2$, —NH(OH), —C(=O)R$^7$, —C(=O)OR$^7$, —OC(=O)R$^7$, —C(=O)N(R$^7$)$_2$, —N(R$^7$)C(=O)R$^7$, —N(R$^7$)C(=O)N(R$^7$)$_2$, —OC(=O)N(R$^7$)$_2$, and —N(R$^7$)C(=O)OR$^7$;

each $R^7$ is independently selected from —H, —$(C_1$-$C_6)$alkyl, —$(C_2$-$C_6)$alkenyl, and —$(C_2$-$C_6)$alkynyl.

In one embodiment R is hydrogen.

In certain embodiments, Compounds of the Invention are Compounds of Formula IA, or a pharmaceutically acceptable derivative thereof:

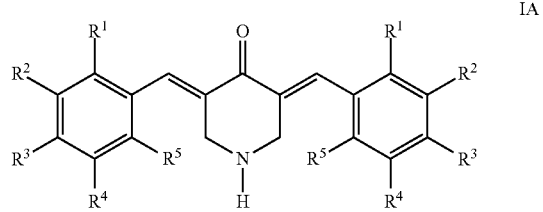

IA wherein i) $R^1$, $R^2$, $R^3$, $R^4$, and $R^5$ are the same, which are hydrogen; or ii) $R^2$, $R^3$, $R^4$, and $R^5$ are the same, which are hydrogen; and $R^1$ is —$(C_1$-$C_6)$alkyl, —$(C_1$-$C_6)$alkoxy, —OH, —NO, —NO$_2$, —N$_3$, —N(R$^7$)$_2$, —NH(OH), or halo, wherein $R^7$ is —H or —$(C_1$-$C_6)$alkyl. One embodiment provides that $R^1$ is —NH(OH). In one embodiment, $R^1$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that $R^1$ is —NO$_2$. In another preferred embodiment, $R^1$ is hydroxyl. In another preferred embodiment, $R^1$ is —$(C_1$-$C_6)$alkyl, more preferably methyl, ethyl, iso-propyl, or tert-butyl, and most preferably methyl. Another preferred embodiment provides that $R^1$ is —$(C_1$-$C_6)$alkoxy, still more preferably methoxy, ethoxy, iso-propyloxy, or tert-butyloxy, and most preferably methoxy; or iii) $R^1$, $R^3$, $R^4$, and $R^5$ are the same, which are hydrogen; and $R^2$ is —$(C_1$-$C_6)$alkyl, —$(C_1$-$C_6)$alkoxy, —OH, —NO, —NO$_2$, —N$_3$, —N(R$^7$)$_2$, —NH(OH), or halo, wherein $R^7$ is —H or —$(C_1$-$C_6)$alkyl. One embodiment provides that $R^2$ is —NH(OH). In one embodiment, $R^2$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that $R^2$ is —NO$_2$. In another preferred embodiment, $R^2$ is hydroxyl. In another preferred embodiment, $R^2$ is —$(C_1$-$C_6)$alkyl, more preferably methyl, ethyl, iso-propyl, or tert-butyl, and most preferably methyl. Another preferred embodiment provides that $R^2$ is —$(C_1$-$C_6)$alkoxy, still more preferably methoxy, ethoxy, iso-propyloxy, or tert-butyloxy, and most preferably methoxy; or iv) $R^1$, $R^2$, $R^4$, and $R^5$ are the same, which are hydrogen; and $R^3$ is —$(C_1$-$C_6)$alkyl, —$(C_1$-$C_6)$alkoxy, —OH, —NO, —NO$_2$, —N$_3$, —N(R$^7$)$_2$, —NH(OH), or halo, wherein R is —H or —$(C_1$-$C_6)$alkyl. One embodiment provides that $R^3$ is —NH(OH). In one embodiment, $R^3$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that $R^3$ is —NO$_2$. In another preferred embodiment, $R^3$ is hydroxyl. In another preferred embodiment, $R^3$ is —$(C_1$-$C_6)$alkyl, more preferably methyl, ethyl, iso-propyl, or tert-butyl, and most preferably methyl. Another preferred embodiment provides that $R^3$ is —$(C_1$-$C_6)$alkoxy, still more preferably methoxy, ethoxy, iso-propyloxy, or tert-butyloxy, and most preferably methoxy; or v) $R^1$, $R^2$, $R^3$, and $R^5$ are the same, which are hydrogen; and $R^4$ is —$(C_1$-$C_6)$alkyl, —$(C_1$-$C_6)$alkoxy, —OH, —NO, —NO$_2$, —N$_3$, —N(R$^7$)$_2$, —NH(OH), or halo, wherein $R^7$ is —H or —$(C_1$-$C_6)$alkyl. One embodiment provides that $R^4$ is —NH(OH). In one embodiment, $R^4$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that $R^4$ is —NO$_2$. In another preferred embodiment, $R^4$ is hydroxyl. In another preferred embodiment, $R^4$ is —$(C_1$-$C_6)$alkyl, more preferably methyl, ethyl, iso-propyl, or tert-butyl, and most preferably methyl. Another preferred embodiment provides that $R^4$ is —$(C_1$-$C_6)$alkoxy, still more preferably methoxy, ethoxy, iso-propyloxy, or tert-butyloxy, and most preferably methoxy; or vi) $R^1$, $R^2$, $R^3$, and $R^4$ are the same, which are hydrogen; and $R^7$ is —$(C_1$-$C_6)$alkyl, —$(C_1$-$C_6)$alkoxy, —OH. —NO, —NO$_2$, —N$_3$, —N(R$^7$)$_2$, —NH(OH), or halo, wherein $R^7$ is —H or —$(C_1$-$C_6)$alkyl. One embodiment provides that $R^5$ is —NH(OH). In one embodiment, $R^5$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that $R^5$ is —NO$_2$. In another preferred embodiment. $R^5$ is hydroxyl. In another preferred embodiment, $R^5$ is —$(C_1$-$C_6)$alkyl, more preferably methyl, ethyl, iso-propyl, or tert-butyl, and most preferably methyl Another preferred embodiment provides that $R^5$ is —$(C_1$-$C_6)$alkoxy, still more preferably methoxy, ethoxy, iso-propyloxy, or tert-butyloxy, and most preferably methoxy.

In another embodiment, $R^1$, $R^2$, $R^3$, $R^4$, and $R^5$ are the same, which are hydrogen. In another preferred embodiment, $R^1$, $R^2$, $R^4$, and $R^5$ are the same, which are hydrogen; and $R^3$ is methyl, methoxy, —NO$_2$, or hydroxyl.

Further embodiments in accordance with Formula IA, or a pharmaceutically acceptable derivative thereof, provide that i) $R^3$, $R^4$, and $R^5$ are the same, which are hydrogen; and $R^1$ and $R^5$ are —$(C_1$-$C_6)$alkyl, —$(C_1$-$C_6)$alkoxy, —OH, —NO, —NO$_2$, —N$_3$, —N(R$^7$)$_2$, —NH(OH), or halo, wherein $R^7$ is —H or —$(C_1$-$C_6)$alkyl, and wherein $R^1$ and $R^5$ can be either the same or different. One embodiment provides that at least one of $R^1$ and $R^5$ is —NH(OH). In one embodiment, at least one of $R^1$ and $R^5$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^1$ and $R^5$ is —$NO_2$. In another preferred embodiment, at least one of $R^1$ and R is hydroxyl. In another preferred embodiment, at least one of $R^1$ and $R^5$ is —($C_1$-$C_6$)alkyl, more preferably methyl, ethyl, iso-propyl, or tert-butyl, and most preferably methyl. Another preferred embodiment provides that at least one of $R^1$ and $R^5$ is —($C_1$-$C_6$)alkoxy, still more preferably methoxy, ethoxy, iso-propyloxy, or tert-butyloxy, and most preferably methoxy; or ii) $R^2$, $R^4$, and $R^5$ are the same, which are hydrogen; and $R^1$ and $R^3$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^1$ and $R^3$ can be either the same or different. One embodiment provides that at least one of $R^1$ and $R^3$ is —NH(OH). In one embodiment, at least one of $R^1$ and $R^3$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^1$ and $R^3$ is —$NO_2$. In another preferred embodiment, at least one of $R^1$ and $R^3$ is hydroxyl. In another preferred embodiment, at least one of $R^1$ and $R^3$ is —($C_1$-$C_6$)alkyl, more preferably methyl, ethyl, iso-propyl, or tert-butyl, and most preferably methyl. Another preferred embodiment provides that at least one of $R^1$ and $R^3$ is —($C_1$-$C_6$)alkoxy, still more preferably methoxy, ethoxy, iso-propyloxy, or tert-butyloxy, and most preferably methoxy; or iii) $R^2$, $R^3$, and R are the same, which are hydrogen; and $R^1$ and $R^4$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^1$ and $R^4$ can be either the same or different. One embodiment provides that at least one of $R^1$ and $R^4$ is —NH(OH). In one embodiment, at least one of $R^1$ and $R^4$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^1$ and $R^4$ is —$NO_2$. In another preferred embodiment, at least one of $R^1$ and $R^4$ is hydroxyl. In another preferred embodiment, at least one of $R^1$ and $R^4$ is —($C_1$-$C_6$)alkyl, more preferably methyl, ethyl, iso-propyl, or tert-butyl, and most preferably methyl. Another preferred embodiment provides that at least one of $R^1$ and $R^4$ is —($C_1$-$C_6$)alkoxy, still more preferably methoxy, ethoxy, iso-propyloxy, or tert-butyloxy, and most preferably methoxy; or iv) $R^2$, $R^3$, and $R^4$ are the same, which are hydrogen; and $R^1$ and $R^5$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^1$ and $R^5$ can be either the same or different. One embodiment provides that at least one of $R^1$ and $R^5$ is —NH(OH). In one embodiment, at least one of $R^1$ and $R^5$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^1$ and $R^5$ is —$NO_2$. In another preferred embodiment, at least one of $R^1$ and $R^5$ is hydroxyl. In another preferred embodiment, at least one of $R^1$ and $R^5$ is —($C_1$-$C_6$)alkyl, more preferably methyl, ethyl, iso-propyl, or tert-butyl, and most preferably methyl. Another preferred embodiment provides that at least one of $R^1$ and $R^5$ is —($C_1$-$C_6$)alkoxy, still more preferably methoxy, ethoxy, iso-propyloxy, or tert-butyloxy, and most preferably methoxy; or v) $R^1$, $R^4$, and $R^5$ are the same, which are hydrogen; and $R^2$ and $R^3$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^2$ and $R^3$ can be either the same or different. A preferred embodiment provides that at least one of $R^2$ and $R^3$ is —NH(OH). In one embodiment, at least one of $R^2$ and $R^3$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^2$ and $R^3$ is —$NO_2$. In another preferred embodiment, at least one of $R^2$ and $R^3$ is hydroxyl. In another preferred embodiment, at least one of $R^2$ and $R^3$ is —($C_1$-$C_6$)alkyl, more preferably methyl, ethyl, iso-propyl, or tert-butyl, and most preferably methyl. Another preferred embodiment provides that at least one of $R^2$ and $R^3$ is —($C_1$-$C_6$)alkoxy, still more preferably methoxy, ethoxy, iso-propyloxy, or tert-butyloxy, and most preferably methoxy; or vi) $R^1$, $R^3$, and R are the same, which are hydrogen; and $R^2$ and $R^4$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^2$ and $R^4$ can be either the same or different. One embodiment provides that at least one of $R^2$ and $R^4$ is —NH(OH). In one embodiment, at least one of $R^2$ and $R^4$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^2$ and $R^4$ is —$NO_2$. In another preferred embodiment, at least one of $R^2$ and $R^4$ is hydroxyl. In another preferred embodiment, at least one of $R^2$ and $R^4$ is —($C_1$-$C_6$)alkyl, more preferably methyl, ethyl, iso-propyl, or tert-butyl, and most preferably methyl. Another preferred embodiment provides that at least one of $R^2$ and $R^4$ is —($C_1$-$C_6$)alkoxy, still more preferably methoxy, ethoxy, iso-propyloxy, or tert-butyloxy, and most preferably methoxy; or vii) $R^1$, $R^3$, and $R^4$ are the same, which are hydrogen; and $R^2$ and $R^5$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^2$ and $R^5$ can be either the same or different. One embodiment provides that at least one of $R^2$ and $R^5$ is —NH(OH). In one embodiment, at least one of $R^2$ and $R^5$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^2$ and R is —$NO_2$. In another preferred embodiment, at least one of $R^2$ and $R^5$ is hydroxyl. In another preferred embodiment, at least one of $R^2$ and $R^5$ is —($C_1$-$C_6$)alkyl, more preferably methyl, ethyl, iso-propyl, or tert-butyl, and most preferably methyl. Another preferred embodiment provides that at least one of $R^2$ and $R^5$ is —($C_1$-$C_6$)alkoxy, still more preferably methoxy, ethoxy, iso-propyloxy, or tert-butyloxy, and most preferably methoxy; or viii) $R^1$, $R^2$, and $R^5$ are the same, which are hydrogen; and $R^3$ and $R^4$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^3$ and $R^4$ can be either the same or different. One embodiment provides that at least one of $R^3$ and $R^4$ is —NH(OH). In one embodiment, at least one of $R^3$ and $R^4$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^3$ and $R^4$ is —$NO_2$. In another preferred embodiment, at least one of $R^3$ and $R^4$ is hydroxyl. In another preferred embodiment, at least one of $R^3$ and $R^4$ is —($C_1$-$C_6$)alkyl, more preferably methyl, ethyl, iso-propyl, or tert-butyl, and most preferably methyl. Another preferred embodiment provides that at least one of $R^3$ and $R^4$ is —($C_1$-$C_6$)alkoxy, still more preferably methoxy, ethoxy, iso-propyloxy, or tert-butyloxy, and most preferably methoxy; or ix) $R^1$, $R^2$, and $R^4$ are the same, which are hydrogen; and $R^3$ and R are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^3$ and $R^5$ can be either the same or different. One embodiment provides that at least one of $R^3$ and $R^5$ is —NH(OH). In one embodiment, at least one of $R^3$ and $R^5$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^3$ and $R^5$ is —$NO_2$. In another preferred embodiment, at least one of $R^3$ and $R^5$ is hydroxyl. In another preferred embodiment, at least one of $R^3$ and $R^5$ is —($C_1$-$C_6$)alkyl, more preferably methyl, ethyl, iso-propyl, or tert-butyl, and most preferably methyl. Another preferred embodiment provides that at least one of $R^3$ and $R^5$ is —($C_1$-$C_6$)alkoxy, still more preferably methoxy, ethoxy, iso-propyloxy, or tert-butyloxy, and most preferably methoxy; or x) $R^1$, $R^2$, and $R^3$ are the same, which are hydrogen; and $R^4$ and R are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^4$ and $R^5$ can be either the same or different. One embodiment provides that at least one of $R^4$ and $R^5$ is —NH(OH). In one embodiment, at least one of $R^4$ and $R^5$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^4$ and $R^5$ is —$NO_2$. In another preferred embodiment, at least one of $R^4$ and $R^5$ is hydroxyl. In another preferred embodiment, at least one of $R^4$ and $R^5$ is —($C_1$-$C_6$)alkyl, more preferably methyl, ethyl, iso-propyl, or tert-butyl, and most preferably methyl. Another preferred embodiment provides that at least one of $R^4$ and $R^5$ is —($C_1$-$C_6$)alkoxy, still more preferably methoxy, ethoxy, iso-propyloxy, or tert-butyloxy, and most preferably methoxy.

A preferred embodiment provides that $R^1$, $R^2$, and $R^5$ are the same, which are hydrogen; and $R^3$ and $R^4$ are methyl, methoxy, —$NO_2$, or hydroxyl, which can be either the same or different.

Still further embodiments in accordance with Formula IA, or a pharmaceutically acceptable derivative thereof, provide that i) $R^4$ and $R^5$ are the same, which are hydrogen; and $R^1$, $R^2$, and $R^3$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^1$, $R^2$, and $R^3$ can be either the same or different. One embodiment provides that at least one of $R^1$, $R^2$, and $R^3$ is —NH(OH). In one embodiment, at least one of $R^1$, $R^2$, and $R^3$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^1$, $R^2$, and $R^3$ is —$NO_2$. In another preferred embodiment, at least one of $R^1$, $R^2$, and $R^3$ is hydroxyl. In another preferred embodiment, at least one of $R^1$, $R^2$, and $R^3$ is —($C_1$-$C_6$) alkyl, more preferably methyl, ethyl, iso-propyl, or tert-butyl, and most preferably methyl. Another preferred embodiment provides that at least one of $R^1$, $R^2$, and $R^3$ is —($C_1$-$C_6$)alkoxy, still more preferably methoxy, ethoxy, iso-propyloxy, or tert-butyloxy, and most preferably methoxy; or ii) $R^1$ and $R^5$ are the same, which are hydrogen; and $R^2$, $R^3$ and $R^4$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^2$, $R^3$ and $R^4$ can be either the same or different. One embodiment provides that at least one of $R^2$, $R^3$ and $R^4$ is —NH(OH). In one embodiment, at least one of $R^2$, $R^3$ and $R^4$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^2$, $R^3$ and $R^4$ is —$NO_2$. In another preferred embodiment, at least one of $R^2$, $R^3$ and $R^4$ is hydroxyl. In another preferred embodiment, at least one of $R^2$, $R^3$ and $R^4$ is —($C_1$-$C_6$)alkyl, more preferably methyl, ethyl, iso-propyl, or tert-butyl, and most preferably methyl. Another preferred embodiment provides that at least one of $R^2$, $R^3$ and $R^4$ is —($C_1$-$C_6$)alkoxy, still more preferably methoxy, ethoxy, iso-propyloxy, or tert-butyloxy, and most preferably methoxy; or iii) $R^1$ and $R^5$ are the same, which are hydrogen; and $R^3$, $R^4$ and $R^5$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^7$ is —H or —($C_1$-$C_6$)alkyl, and wherein $R^3$, $R^4$ and $R^5$ can be either the same or different. One embodiment provides that at least one of $R^3$, $R^4$ and $R^5$ is —NH(OH). In one embodiment, at least one of $R^3$, $R^4$ and $R^5$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^3$, $R^4$ and $R^5$ is —$NO_2$. In another preferred embodiment, at least one of $R^3$, $R^4$ and $R^5$ is hydroxyl. In another preferred embodiment, at least one of $R^3$, $R^4$ and $R^5$ is —($C_1$-$C_6$)alkyl, more preferably methyl, ethyl, iso-propyl, or tert-butyl, and most preferably methyl. Another preferred embodiment provides that at least one of $R^3$, $R^4$ and $R^5$ is —($C_1$-$C_6$)alkoxy, still more preferably methoxy, ethoxy, iso-propyloxy, or tert-butyloxy, and most preferably methoxy; or iv) $R^3$ and $R^5$ are the same, which are hydrogen; and $R^1$, $R^2$ and $R^4$ are —($C_1$-$C_6$)alkyl, —($C_1$-$C_6$)alkoxy, —OH, —NO, —$NO_2$, —$N_3$, —$N(R^7)_2$, —NH(OH), or halo, wherein $R^1$ is —H or —($C_1$-$C_6$)alkyl, and wherein $R^1$, $R^2$ and $R^4$ can be either the same or different. One embodiment provides that at least one of $R^1$, $R^2$ and $R^4$ is —NH(OH). In one embodiment, at least one of $R^1$, $R^2$ and $R^4$ is a primary amine, secondary amine or tertiary amine, wherein the secondary amine or tertiary amine is substituted by —($C_1$-$C_6$)alkyl, preferably to methyl or ethyl, respectively. A preferred embodiment provides that at least one of $R^1$, $R^2$ and $R^4$ is —$NO_2$. In another preferred embodiment, at least one of $R^1$, $R^2$ and $R^4$ is hydroxyl. In another preferred embodiment, at least one of $R^1$, $R^2$ and $R^4$ is —($C_1$-$C_6$)alkyl, more preferably methyl, ethyl, iso-propyl, or tert-butyl, and most preferably methyl. Another preferred embodiment provides that at least one of $R^1$, $R^2$ and $R^4$ is —($C_1$-$C_6$)alkoxy, still more preferably methoxy, ethoxy, iso-propyloxy, or tert-butyloxy, and most preferably methoxy; or v) $R^3$ and $R^4$ are the same, which are hydrogen; and $R^1$, $R^2$ and $R^5$ are —$(C_1$-$C_6)$alkyl, —$(C_1$-$C_6)$alkoxy, —OH, —NO, —NO$_2$, —N$_3$, —N$(R^7)_2$, —NH(OH), or halo, wherein $R^7$ is —H or —$(C_1$-$C_6)$alkyl, and wherein $R^1$, $R^2$ and $R^5$ can be either the same or different. One embodiment provides that at least one of $R^1$, $R^2$ and $R^5$ is —NH(OH). In one embodiment, at least one of $R^1$, $R^2$ and $R^5$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^1$, $R^2$ and $R^5$ is —NO$_2$. In another preferred embodiment, at least one of $R^1$, $R^2$ and $R^5$ is hydroxyl. In another preferred embodiment, at least one of $R^1$, $R^2$ and $R^5$ is —$(C_1$-$C_6)$alkyl, more preferably methyl, ethyl, iso-propyl, or tert-butyl, and most preferably methyl. Another preferred embodiment provides that at least one of $R^1$, $R^2$ and $R^5$ is —$(C_1$-$C_6)$alkoxy, still more preferably methoxy, ethoxy, iso-propyloxy, or tert-butyloxy, and most preferably methoxy; or vi) $R^2$ and R are the same, which are hydrogen; and $R^1$, $R^3$ and $R^4$ are —$(C_1$-$C_6)$alkyl, —$(C_1$-$C_6)$alkoxy, —OH, —NO, —NO$_2$, —N$_3$, —N$(R^7)_2$, —NH(OH), or halo, wherein $R^7$ is —H or —$(C_1$-$C_6)$alkyl, and wherein $R^1$, $R^3$ and $R^4$ can be either the same or different. One embodiment provides that at least one of $R^1$, $R^3$ and $R^4$ is —NH(OH). In one embodiment, at least one of $R^1$, $R^3$ and $R^4$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^1$, $R^3$ and $R^4$ is —NO$_2$. In another preferred embodiment, at least one of $R^1$, $R^3$ and $R^4$ is hydroxyl. In another preferred embodiment, at least one of $R^1$, $R^3$ and $R^4$ is —$(C_1$-$C_6)$alkyl, more preferably methyl, ethyl, iso-propyl, or tert-butyl, and most preferably methyl. Another preferred embodiment provides that at least one of $R^1$, $R^3$ and $R^4$ is —$(C_1$-$C_6)$alkoxy, still more preferably methoxy, ethoxy, iso-propyloxy, or tert-butyloxy, and most preferably methoxy; or vii) $R^2$ and $R^4$ are the same, which are hydrogen; and $R^1$, $R^3$ and $R^5$ are —$(C_1$-$C_6)$alkyl, —$(C_1$-$C_6)$alkoxy, —OH, —NO, —NO$_2$, —N$_3$, —N$(R^7)_2$, —NH(OH), or halo, wherein $R^7$ is —H or —$(C_1$-$C_6)$alkyl, and wherein $R^1$, $R^3$ and $R^5$ can be either the same or different. One embodiment provides that at least one of $R^1$, $R^3$ and $R^5$ is —NH(OH). In one embodiment, at least one of $R^1$, $R^3$ and $R^5$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^1$, $R^3$ and $R^5$ is —NO$_2$. In another preferred embodiment, at least one of $R^1$, $R^3$ and $R^5$ is hydroxyl. In another preferred embodiment, at least one of $R^1$, $R^3$ and $R^5$ is —$(C_1$-$C_6)$alkyl, more preferably methyl, ethyl, iso-propyl, or tert-butyl, and most preferably methyl. Another preferred embodiment provides that at least one of $R^1$, $R^3$ and $R^5$ is —$(C_1$-$C_6)$alkoxy, still more preferably methoxy, ethoxy, iso-propyloxy, or tert-butyloxy, and most preferably methoxy; or viii) $R^2$ and $R^3$ are the same, which are hydrogen; and $R^1$, $R^4$ and $R^5$ are —$(C_1$-$C_6)$alkyl, —$(C_1$-$C_6)$alkoxy, —OH, —NO, —NO$_2$, —N$_3$, —N$(R^7)_2$, —NH(OH), or halo, wherein $R^7$ is —H or —$(C_1$-$C_6)$alkyl, and wherein $R^1$, $R^4$ and $R^5$ can be either the same or different. One embodiment provides that at least one of $R^1$, $R^4$ and $R^5$ is —NH(OH). In one embodiment, at least one of $R^1$, $R^4$ and $R^5$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^1$, $R^4$ and $R^5$ is —NO$_2$. In another preferred embodiment, at least one of $R^1$, $R^4$ and $R^5$ is hydroxyl. In another preferred embodiment, at least one of $R^1$, $R^4$ and $R^5$ is —$(C_1$-$C_6)$alkyl, more preferably methyl, ethyl, iso-propyl, or tert-butyl, and most preferably methyl. Another preferred embodiment provides that at least one of $R^1$, $R^4$ and $R^5$ is —$(C_1$-$C_6)$alkoxy, still more preferably methoxy, ethoxy, iso-propyloxy, or tert-butyloxy, and most preferably methoxy; or ix) $R^1$ and $R^4$ are the same, which are hydrogen; and $R^2$, $R^3$ and $R^5$ are —$(C_1$-$C_6)$alkyl, —$(C_1$-$C_6)$alkoxy, —OH, —NO, —NO$_2$, —N$_3$, —N$(R^7)_2$, —NH(OH), or halo, wherein $R^7$ is —H or —$(C_1$-$C_6)$alkyl, and wherein $R^2$, $R^3$ and $R^5$ can be either the same or different. One embodiment provides that at least one of $R^2$, $R^3$ and $R^5$ is —NH(OH). In one embodiment, at least one of $R^2$, $R^3$ and $R^5$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^2$. $R^3$ and $R^5$ is —NO$_2$. In another preferred embodiment, at least one of $R^2$. $R^3$ and $R^5$ is hydroxyl. In another preferred embodiment, at least one of $R^2$, $R^3$ and $R^5$ is —$(C_1$-$C_6)$alkyl, more preferably methyl, ethyl, iso-propyl, or tert-butyl, and most preferably methyl Another preferred embodiment provides that at least one of $R^2$, $R^3$ and $R^5$ is —$(C_1$-$C_6)$alkoxy, still more preferably methoxy, ethoxy, iso-propyloxy, or tert-butyloxy, and most preferably methoxy; or x) $R^1$ and $R^3$ are the same, which are hydrogen; and $R^2$, $R^4$ and $R^5$ are —$(C_1$-$C_6)$alkyl, —$(C_1$-$C_6)$alkoxy, —OH, —NO, —NO$_2$, —N$_3$, —N$(R^7)_2$, —NH(OH), or halo, wherein $R^1$ is —H or —$(C_1$-$C_6)$alkyl, and wherein $R^2$, $R^4$ and $R^5$ can be either the same or different. One embodiment provides that at least one of $R^2$, $R^4$ and $R^5$ is —NH(OH). In one embodiment, at least one of $R^2$, $R^4$ and $R^5$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^2$, $R^4$ and $R^5$ is —NO$_2$. In another preferred embodiment, at least one of $R^2$, $R^4$ and $R^5$ is hydroxyl. In another preferred embodiment, at least one of $R^2$, $R^4$ and $R^5$ is —$(C_1$-$C_6)$alkyl, more preferably methyl, ethyl, iso-propyl, or tert-butyl, and most preferably methyl. Another preferred embodiment provides that at least one of $R^2$, $R^4$ and $R^5$ is —$(C_1$-$C_6)$alkoxy, still more preferably methoxy, ethoxy, iso-propyloxy, or tert-butyloxy, and most preferably methoxy.

In a preferred embodiment, $R^1$ and $R^5$ are the same, which are hydrogen; and $R^2$, $R^3$ and $R^4$ are methyl, methoxy, —NO$_2$, or hydroxyl, which can be either the same or different.

Yet further embodiments in accordance with Formula IA, or a pharmaceutically acceptable derivative thereof, provide that i) $R^1$ is hydrogen; and $R^2$, $R^3$, $R^4$, and $R^5$ are —$(C_1$-$C_6)$alkyl, —$(C_1$-$C_6)$alkoxy, —H, —NO, —NO$_2$, —N$_3$, —N$(R^7)_2$, —NH(OH), or halo, wherein $R^1$ is —H or —$(C_1$-$C_6)$alkyl, and wherein $R^2$, $R^3$, $R^4$, and $R^5$ can be either the same or different. One embodiment provides that at least one of $R^2$, $R^3$, $R^4$, and $R^5$ is —NH(OH). In one embodiment, at least one of $R^2$, $R^3$, $R^4$, and $R^5$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^2$, $R^3$, $R^4$, and $R^5$ is —NO$_2$. In another preferred embodiment, at least one of $R^2$, $R^3$, $R^4$, and $R^5$ is hydroxyl. In another preferred embodiment, at least one of $R^2$, $R^3$, $R^4$, and $R^5$ is —$(C_1$-$C_6)$alkyl, more preferably methyl, ethyl, iso-propyl, or tert-butyl, and most preferably methyl. Another preferred embodiment provides that at least one of $R^2$, $R^3$, $R^4$, and $R^5$ is —$(C_1$-$C_6)$alkoxy, still more preferably methoxy, ethoxy, iso-propyloxy, or tert-butyloxy, and most preferably methoxy; or ii) $R^2$ is hydrogen; and $R^1$, $R^3$, $R^4$, and $R^5$ are —$(C_1$-$C_6)$ alkyl, —$(C_1$-$C_6)$alkoxy, —OH, —NO, —$NO_2$, —$N_3$, —$N(R^7)_2$, —NH(OH), or halo, wherein $R^7$ is —H or —$(C_1$-$C_6)$alkyl, and wherein $R^1$, $R^3$, $R^4$, and $R^5$ can be either the same or different. One embodiment provides that at least one of $R^1$, $R^3$, $R^4$, and $R^5$ is —NH(OH). In one embodiment, at least one of $R^1$, $R^3$, $R^4$, and $R^5$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^1$, $R^3$, $R^4$, and $R^5$ is —$NO_2$. In another preferred embodiment, at least one of $R^1$, $R^3$, $R^4$, and $R^5$ is hydroxyl. In another preferred embodiment, at least one of $R^1$, $R^3$, $R^4$, and $R^5$ is —$(C_1$-$C_6)$alkyl, more preferably methyl, ethyl, iso-propyl, or tert-butyl, and most preferably methyl. Another preferred embodiment provides that at least one of $R^1$, $R^3$, $R^4$, and $R^5$ is —$(C_1$-$C_6)$alkoxy, still more preferably methoxy, ethoxy, iso-propyloxy, or tert-butyloxy, and most preferably methoxy; or iii) $R^1$ is hydrogen; and $R^1$, $R^2$, $R^4$, and $R^5$ are —$(C_1$-$C_6)$ alkyl, —$(C_1$-$C_6)$alkoxy, —OH, —NO, —$NO_2$, —$N_3$, —$N(R^7)_2$, —NH(OH), or halo, wherein $R^7$ is —H or —$(C_1$-$C_6)$alkyl, and wherein $R^1$, $R^2$, $R^4$, and $R^5$ can be either the same or different. One embodiment provides that at least one of $R^1$, $R^2$, $R^4$, and $R^5$ is —NH(OH). In one embodiment, at least one of $R^1$, $R^2$, $R^4$, and $R^5$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^1$, $R^2$, $R^4$, and $R^5$ is —$NO_2$. In another preferred embodiment, at least one of $R^1$, $R^2$, $R^4$, and $R^5$ is hydroxyl. In another preferred embodiment, at least one of $R^1$, $R^2$, $R^4$, and $R^5$ is —$(C_1$-$C_6)$alkyl, more preferably methyl, ethyl, iso-propyl, or tert-butyl, and most preferably methyl. Another preferred embodiment provides that at least one of $R^1$, $R^2$, $R^4$, and $R^5$ is —$(C_1$-$C_6)$alkoxy, still more preferably methoxy, ethoxy, iso-propyloxy, or tert-butyloxy, and most preferably methoxy; or iv) $R^4$ is hydrogen; and $R^1$, $R^2$, $R^3$, and R are —$(C_1$-$C_6)$ alkyl, —$(C_1$-$C_6)$alkoxy. —OH, —NO, —$NO_2$, —$N_3$, —$N(R^7)_2$, —NH(OH), or halo, wherein $R^7$ is —H or —$(C_1$-$C_6)$alkyl, and wherein $R^1$, $R^2$, $R^3$, and R can be either the same or different. One embodiment provides that at least one of $R^1$, $R^2$, $R^3$, and R is —NH(OH). In one embodiment, at least one of $R^1$, $R^2$, $R^3$, and R is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^1$, $R^2$, $R^3$, and R is —$NO_2$. In another preferred embodiment, at least one of $R^1$, $R^2$, $R^3$, and R is hydroxyl. In another preferred embodiment, at least one of $R^1$, $R^2$, $R^3$, and R is —$(C_1$-$C_6)$alkyl, more preferably methyl, ethyl, iso-propyl, or tert-butyl, and most preferably methyl. Another preferred embodiment provides that at least one of $R^1$, $R^2$, $R^3$, and R is —$(C_1$-$C_6)$alkoxy, still more preferably methoxy, ethoxy, iso-propyloxy, or tert-butyloxy, and most preferably methoxy; or v) R is hydrogen; and $R^1$, $R^2$, $R^3$, and $R^4$ are —$(C_1$-$C_6)$ alkyl, —$(C_1$-$C_6)$alkoxy, —OH, —NO, —$NO_2$, —$N_3$, —$N(R^7)_2$, —NH(OH), or halo, wherein $R^7$ is —H or —$(C_1$-$C_6)$alkyl, and wherein $R^1$, $R^2$, $R^3$, and $R^4$ can be either the same or different. One embodiment provides that at least one of $R^1$, $R^2$, $R^3$, and $R^4$ is —NH(OH). In one embodiment, at least one of $R^1$, $R^2$, $R^3$, and $R^4$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^1$, $R^2$, $R^3$, and $R^4$ is —$NO_2$. In another preferred embodiment, at least one of $R^1$, $R^2$, $R^3$, and $R^4$ is hydroxyl. In another preferred embodiment, at least one of $R^1$, $R^2$, $R^3$, and $R^4$ is —$(C_1$-$C_6)$alkyl, more preferably methyl, ethyl, iso-propyl, or tert-butyl, and most preferably methyl Another preferred embodiment provides that at least one of $R^1$, $R^2$, $R^3$, and $R^4$ is —$(C_1$-$C_6)$alkoxy, still more preferably methoxy, ethoxy, iso-propyloxy, or tert-butyloxy, and most preferably methoxy.

Yet a further embodiment in accordance with Formula IA, or a pharmaceutically acceptable derivative thereof, provides that $R^1$, $R^2$, $R^3$, $R^4$, and $R^5$ are —$(C_1$-$C_6)$alkyl, —$(C_1$-$C_6)$alkoxy, —OH, —NO, —$NO_2$, —$N_3$, —$N(R^7)_2$, —NH(OH), or halo, wherein $R^1$ is —H or —$(C_1$-$C_6)$alkyl, and wherein $R^1$, $R^2$, $R^3$, $R^4$, and $R^5$ can be either the same or different. One embodiment provides that at least one of $R^1$, $R^2$, $R^3$, $R^4$, and $R^5$ is —NH(OH). In one embodiment, at least one of $R^1$, $R^2$, $R^3$, $R^4$, and $R^5$ is a primary amine, secondary amine or tertiary amine, wherein the secondary amine or tertiary amine is substituted by —$(C_1$-$C_6)$alkyl, preferably to methyl or ethyl, respectively. A preferred embodiment provides that at least one of $R^1$, $R^2$, $R^3$, $R^4$, and $R^5$ is —$NO_2$. In another preferred embodiment, at least one of $R^1$, $R^2$, $R^3$, $R^4$, and $R^5$ is hydroxyl. In another preferred embodiment, at least one of $R^1$, $R^2$, $R^3$, $R^4$, and $R^5$ is —$(C_1$-$C_6)$alkyl, more preferably methyl, ethyl, iso-propyl, or tert-butyl, and most preferably methyl. Another preferred embodiment provides that at least one of $R^1$, $R^2$, $R^3$, $R^4$, and $R^5$ is —$(C_1$-$C_6)$alkoxy, still more preferably methoxy, ethoxy, iso-propyloxy, or tert-butyloxy, and most preferably methoxy.

Unless specified otherwise, $R^1$, $R^2$, $R^3$, $R^4$, and $R^5$ groups of the following Compounds of the Invention are as defined above in Formula IA.

One embodiment of the invention provides a Compound of Formula I, or a pharmaceutically acceptable derivative thereof, wherein R is substituted —$(C_1$-$C_6)$alkyl, such as —$(C_1$-$C_6)$alkyl substituted with 1, 2, 3, 4, or 5 independently selected R groups, wherein $R^6$ preferably is hydrogen, —$(C_1$-$C_6)$alkyl, —$(C_1$-$C_6)$alkoxy, nitro, nitroso, hydroxylamino, amine, alkylamine (—$NHR^7$), or dialkylamine (—$N(R^7)_2$), wherein $R^1$ is independently selected from hydrogen or —$(C_1$-$C_6)$alkyl group.

In a preferred embodiment, R is —$(C_1$-$C_6)$alkyl which is unsubstituted (e.g., methyl, ethyl, iso-propyl, tert-butyl).

In a more preferred embodiment, the invention provides a compound of Formula IC-5, or a pharmaceutically acceptable derivative thereof:

IC-5

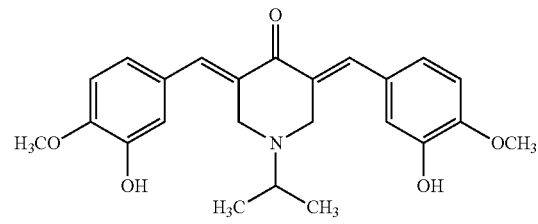

Another embodiment of the invention provides a compound, or a pharmaceutically acceptable derivative thereof, wherein R is substituted -(5-membered)heteroaryl, such as -(5-membered)heteroaryl substituted with 1, 2, 3, or 4 independently selected $R^6$, wherein $R^6$ preferably is hydrogen, —($C_1$-$C_6$)alkyl, —($C_1$-$C_6$)alkoxy, nitro, nitroso, hydroxylamino, amine, alkylamine (—$NHR^7$), or dialkylamine (—N($R^7$)$_2$), wherein $R^1$ is independently selected from hydrogen or —($C_1$-$C_6$)alkyl group.

In a preferred embodiment, R is -(5-membered)heteroaryl which is unsubstituted.

In certain embodiments, R is substituted -(5-membered)heteroaryl which can be thiazolyl, thiophenyl, pyrrolyl, oxazolyl, oxadiazolyl, isoxazolyl, isothiazolyl, imidazolyl, furazanyl, furanyl, 1-$R^6$-tetrazolyl, 1-$R^6$-pyrazolyl, 1-$R^6$-triazolyl, 1-$R^6$-pyrrolyl, 1,2,5-thiadiazolyl, 1,2,3,5-oxatriazolyl, 1,2,3,4-oxatriazolyl, wherein $R^6$ is as defined above.

Still another embodiment of the invention provides a compound of Formula I. or a pharmaceutically acceptable derivative thereof, wherein R is substituted —($C_1$-$C_6$)alkyl-(5-membered)heteroaryl, such as —($C_1$-$C_6$)alkyl-(5-membered)heteroaryl substituted with 1, 2, 3, 4, or 5 independently selected $R^6$, wherein $R^6$ preferably is hydrogen, —($C_1$-$C_6$)alkyl, —($C_1$-$C_6$)alkoxy, nitro, nitroso, hydroxylamino, amine, alkylamine (—$NHR^7$), or dialkylamine (—N($R^7$)$_2$), wherein $R^7$ is independently selected from hydrogen or —($C_1$-$C_6$)alkyl group.

In a preferred embodiment, R is —($C_1$-$C_6$)alkyl-(5-membered)heteroaryl which is unsubstituted. In another preferred embodiment R is —$CH_2$-(5-membered)heteroaryl which is unsubstituted. In a further preferred embodiment R is —$CH_2$—$CH_2$-(5-membered)heteroaryl which is unsubstituted.

In certain embodiments, R is substituted —($C_1$-$C_6$)alkyl-(5-membered)heteroaryl, which can be —($C_1$-$C_6$)alkyl-(thiazolyl), —($C_1$-$C_6$)alkyl-(thiophenyl), —($C_1$-$C_6$)alkyl-(pyrrolyl), —($C_1$-$C_6$)alkyl-(oxazolyl), —($C_1$-$C_6$)alkyl-(oxadiazolyl), —($C_1$-$C_6$)alkyl-(isoxazolyl), —($C_1$-$C_6$)alkyl-(isothiazolyl). —($C_1$-$C_6$)alkyl-(imidazolyl), —($C_1$-$C_6$)alkyl-(furazanyl), —($C_1$-$C_6$)alkyl-(furanyl), —($C_1$-$C_6$)alkyl-(1-$R^6$-tetrazolyl), —($C_1$-$C_6$)alkyl-(1-$R^6$-pyrazolyl), —($C_1$-$C_6$)alkyl-(1-$R^6$-triazolyl), —($C_1$-$C_6$)alkyl-(1-$R^6$-pyrrolyl), —($C_1$-$C_6$)alkyl-(1,2,5-thiadiazolyl), —($C_1$-$C_6$)alkyl-(1,2,3,5-oxatriazolyl), —($C_1$-$C_6$)alkyl-(1,2,3,4-oxatriazolyl), wherein $R^6$ is as defined above.

Yet another embodiment of the invention provides a compound, or a pharmaceutically acceptable derivative thereof, wherein R is substituted -(6-membered)heteroaryl, such as -(6-membered)heteroaryl substituted with 1, 2, 3, 4, or 5 independently selected $R^6$, wherein $R^1$ preferably is hydrogen, —($C_1$-$C_6$)alkyl, —($C_1$-$C_6$)alkoxy, nitro, nitroso, hydroxylamino, amine, alkylamine (—$NHR^7$), or dialkylamine (—N($R^7$)$_2$), wherein $R^7$ is independently selected from hydrogen or —($C_1$-$C_6$)alkyl group.

In a preferred embodiment, R is -(6-membered)heteroaryl, which is unsubstituted.

In certain embodiments, R is substituted -(6-membered)heteroaryl, which can be pyridyl, pyrimidinyl, triazinyl, pyridazinyl, pyrazinyl, 4H-pyranyl, or 2H-pyranyl.

A further embodiment of the invention provides a compound, or a pharmaceutically acceptable derivative thereof, wherein R is substituted —($C_1$-$C_6$)alkyl-(6-membered)heteroaryl, such as —($C_1$-$C_6$)alkyl-(6-membered)heteroaryl substituted with 1, 2, 3, 4, or 5 independently selected $R^6$, wherein $R^6$ preferably is hydrogen, —($C_1$-$C_6$)alkyl, —($C_1$-$C_6$)alkoxy, nitro, nitroso, hydroxylamino, amine, alkylamine (—$NHR^7$), or dialkylamine (—N($R^7$)$_2$), wherein $R^7$ is independently selected from hydrogen or —($C_1$-$C_6$)alkyl group.

In a preferred embodiment, R is —($C_1$-$C_6$)alkyl-(6-membered)heteroaryl which is unsubstituted. In another preferred embodiment, R is —$CH_2$-(6-membered)heteroaryl which is unsubstituted. In yet another preferred embodiment, R is —$CH_2$—$CH_2$-(6-membered)heteroaryl which is unsubstituted.

In certain embodiments, R is substituted —($C_1$-$C_6$)alkyl-(6-membered)heteroaryl which can be —($C_1$-$C_6$)alkyl-(pyridyl), —($C_1$-$C_6$)alkyl-(pyrimidinyl), —($C_1$-$C_6$)alkyl-(triazinyl), —($C_1$-$C_6$)alkyl-(pyridazinyl), —($C_1$-$C_6$)alkyl-(pyrazinyl), —($C_1$-$C_6$)alkyl-(4H-pyranyl), or —($C_1$-$C_6$)alkyl-(2H-pyranyl).

In a yet further embodiment of the invention. R is substituted —($C_1$-$C_6$)alkyl-($C_6$-$C_{14}$)aryl, such as —($C_1$-$C_6$)alkyl-($C_6$-$C_4$)aryl substituted with 1, 2, 3, 4, or 5 independently selected $R^6$, wherein $R^6$ preferably is hydrogen, —($C_1$-$C_6$)alkyl, —($C_1$-$C_6$)alkoxy, nitro, nitroso, hydroxylamino, amine, alkylamine (—$NHR^7$), or dialkylamine (—N($R^7$)$_2$), wherein $R^7$ is independently selected from hydrogen or —($C_1$-$C_6$)alkyl group.

In a preferred embodiment, R is —($C_1$-$C_6$)alkyl-($C_6$-$C_{14}$)aryl which is unsubstituted.

In a more preferred embodiment, R is benzyl which is unsubstituted.

In another embodiment of the invention, R is substituted —($C_6$-$C_1$)aryl, such as —($C_6$-$C_{14}$)aryl substituted with 1, 2, 3, 4, or 5 independently selected $R^6$, wherein $R^6$ preferably is hydrogen, —($C_1$-$C_6$)alkyl, —($C_1$-$C_6$)alkoxy, nitro, nitroso, hydroxylamino, amine, alkylamine (—$NHR^7$), or dialkylamine (—N($R^7$)$_2$), wherein $R^7$ is independently selected from hydrogen or —($C_1$-$C_6$)alkyl group.

In a preferred embodiment, R is —($C_6$-$C_{14}$)aryl which is unsubstituted.

In a most preferred embodiment, the invention provides a compound of Formula IE, or a pharmaceutically acceptable derivative thereof, wherein R is phenyl which is unsubstituted:

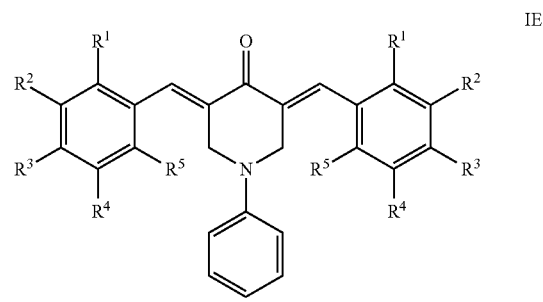

IE

Wherein $R^1$, $R^2$, $R^3$, $R^4$ and $R^5$ are as defined above in Formula IA.

In a preferred embodiment, the invention provides a compound of Formula IE-1, or a pharmaceutically acceptable derivative thereof:

IE-1

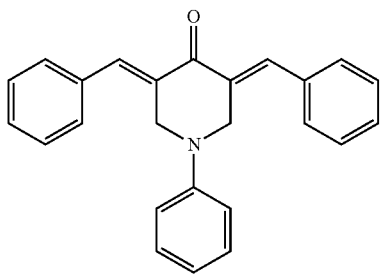

In another preferred embodiment, the invention provides a compound of Formula IE-2, or a pharmaceutically acceptable derivative thereof:

IE-2

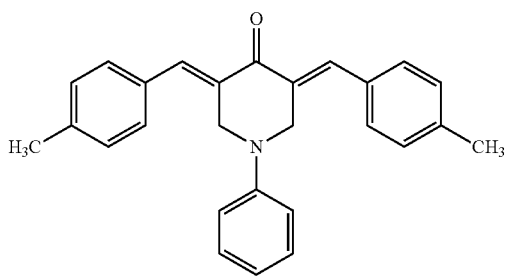

In another preferred embodiment, the invention provides a compound of Formula IE-3, or a pharmaceutically acceptable derivative thereof:

IE-4

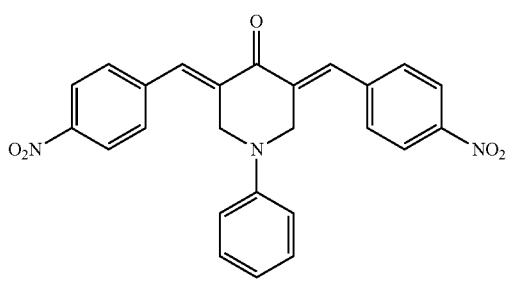

In another preferred embodiment, the invention provides a compound of Formula IE-4, or a pharmaceutically acceptable derivative thereof:

IE-4

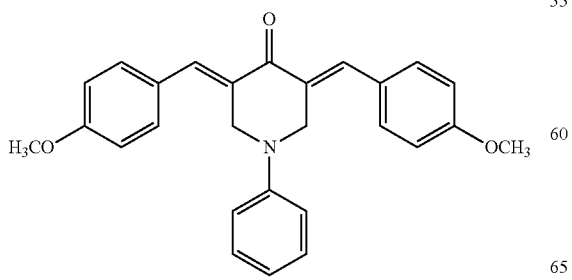

In another preferred embodiment, the invention provides a compound of Formula IE-5, or a pharmaceutically acceptable derivative thereof:

IE-5

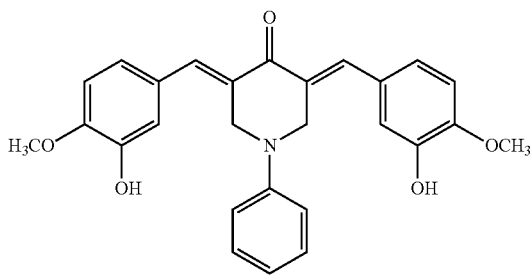

In another preferred embodiment, the invention provides a compound of Formula IE-6, or a pharmaceutically acceptable derivative thereof:

IE-6

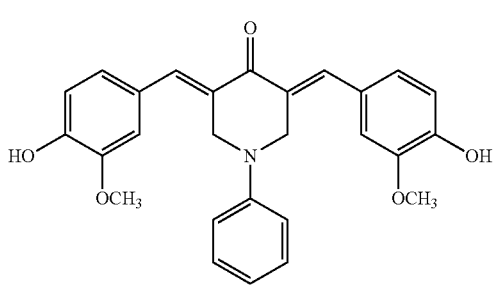

In another preferred embodiment, the invention provides a compound of Formula IE-7, or a pharmaceutically acceptable derivative thereof:

IE-7

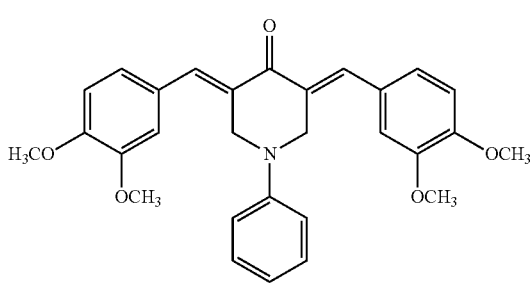

In another preferred embodiment, the invention provides a compound of Formula IE-8, or a pharmaceutically acceptable derivative thereof:

IE-8

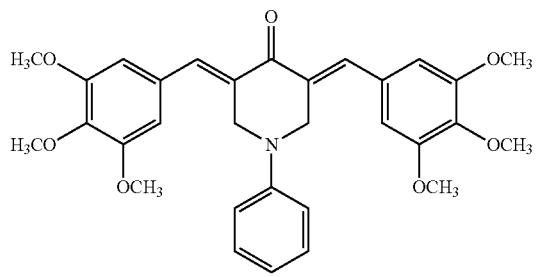

In one embodiment, Compound IE-8, or a pharmaceutically acceptable derivative thereof, is combined with an anticancer drug. In another embodiment, Compound IE-8, or a pharmaceutically acceptable derivative thereof, is combined with a taxane. In another embodiment, Compound IE-8, or a pharmaceutically acceptable derivative thereof, is combined with Paclitaxel. In another embodiment, Compound IE-8, or a pharmaceutically acceptable derivative thereof, is combined with a ruthenium-based compound. In another embodiment, Compound IE-8, or a pharmaceutically acceptable derivative thereof, is combined with a platinum-based compound. In another embodiment, Compound IE-8, or a pharmaceutically acceptable derivative thereof, is combined with oxaliplatin. In another embodiment, Compound IE-8, or a pharmaceutically acceptable derivative thereof, is combined with cisplatin.

In one embodiment, Compounds of Formula I, or a pharmaceutically acceptable derivative thereof, may exhibit chiral substituents, resulting in a chiral Compound of Formula I.

In another embodiment, Compounds of Formula I, or a pharmaceutically acceptable derivative thereof, may exhibit achiral substituents, resulting in an achiral Compound of Formula I.

In another embodiment, a pharmaceutically acceptable derivative of a Compound of Formula I is a pharmaceutically acceptable salt.

Synthesis of Compounds of Formula I

The Compounds of the Invention can be prepared using methods known to those skilled in the art in view of this disclosure, or by illustrative methods shown in the schemes below. For example, the Compounds of Formula I can be prepared using conventional organic synthesis in view of this disclosure, or by the illustrative methods defined in Method A and B below. Detailed synthetic procedures of selected Compounds of the Invention are described in the working examples set forth below.

Compounds of the Invention can be generally obtained via aldol condensation reaction catalyzed by a suitable reagent depending on the chemical reactivity of the starting materials. The catalyst can be any suitable agent to trigger an aldol condensation, such as a catalyst selected from the group consisting of Lewis acid (e.g., $TiCl_4$), Lewis base (e.g., $CaCl_2$), Brønsted acid (e.g., acetic acid), and Brønsted base (e.g., sodium hydroxide). In certain embodiments. N-substituted-4-piperidone can be reacted with two equivalents of an appropriately substituted benzaldehyde in the presence of an applicable Brønsted base (Method A) or Brønsted acid (Method B) in a suitable solvent (such as ethanol) to give Compounds of Formula I.

Uses and Methods of Compounds of Formula I

In accordance with the disclosure, the Compounds of Formula I are used for the treatment or prevention of a disorder.

In one embodiment, Compounds of Formula I can be used to treat or prevent disorders such as cancer, autoimmune disorders, inflammatory disorders, or fibrotic disorders.

The present disclosure further provides Compounds of Formula I, which can be used to treat or prevent disorders such as cancer, autoimmune disorders, inflammatory disorders, or fibrotic disorders, wherein said disorders are associated with an aberrant Stat3 pathway activity, and wherein Compounds of Formula I act as inhibitors of phosphorylated Stat3, that is, of the overall Stat3 pathway activity.

In another embodiment, a Compound of Formula I can be used to treat or prevent autoimmune disorders and/or inflammatory disorders. Certain autoimmune disorders may be associated with inflammatory disorders. Then again, certain inflammatory diseases may be caused by an autoimmune disorder. Therefore, particular disorders may be characterized as both autoimmune and inflammatory disorders.

In another embodiment, a Compound of Formula I can be used to treat or prevent an inflammatory bowel disease, arthritis, autoimmune demyelination disorder, Alzheimer's disease, stroke, ischemia reperfusion injury, cachexia, asthma, and multiple sclerosis, and the like.

Also provided herein are Compounds of Formula I directed at treating or preventing autoimmune disorders and/or inflammatory disorders, wherein the disorder is associated with an aberrant Stat3 pathway activity.

In another embodiment, a Compound of Formula I can be used to treat or prevent fibrotic disorders.

In another embodiment, a Compound of Formula I can be used to treat or prevent a vascular fibrosis, pulmonary fibrosis, pancreatic fibrosis, liver fibrosis, renal fibrosis,

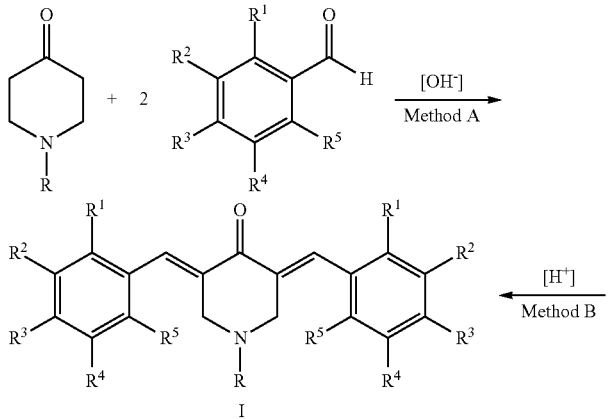

musculoskeletal fibrosis, cardiac fibrosis, skin fibrosis, eye fibrosis, glaucoma, progressive systemic sclerosis (PSS), chronic graft versus-host disease, scleroderma, Peyronie's disease, post-cystoscopic urethral stenosis, idiopathic and pharmacologically induced retroperitoneal fibrosis, mediastinal fibrosis, progressive massive fibrosis, proliferative fibrosis, neoplastic fibrosis, and the like.

In another embodiment, a Compound of Formula I can be used to treat or prevent a fibrotic disorder, wherein the disorder is associated with an aberrant Stat3 pathway activity.

In one embodiment, a Compound of Formula I can be used to treat or prevent cancer.

In another embodiment, a Compound of Formula I can be used to treat or prevent breast cancer, head and neck cancer, lung cancer, ovarian cancer, pancreatic cancer, colorectal carcinoma, prostate cancer, cervical cancer, renal cancer, skin cancer, hepatocellular carcinoma, liver cancer, esophageal cancer, cervical cancer, glioma, bladder cancer, endometrial cancer, bile duct cancer, bone cancer, retinoblastoma, gallbladder cancer, pituitary cancer, rectal cancer, salivary gland cancer, nasal pharyngeal, sarcoma, brain cancer, gastric cancer, multiple myeloma, leukemia, thyroid cancer, lymphoma, and the like.

In another embodiment, a Compound of Formula I can be used to treat or prevent skin cancer, leukemia, prostate cancer, colon cancer, lung cancer, and ovarian cancer.

In another embodiment, a Compound of Formula I can be used to treat or prevent cancer stem cells. Cancer stem cells, which represent a small percentage of cancer cells, are known to be tumorigenic, i.e. they exhibit the exclusive potential to regenerate tumor cells. Cancer cells comprising such cancer stem cells are therefore particularly resistant to common chemotherapeutic or radiotherapeutic treatment. Even though initial therapeutic approaches may be successful, any residual cancer stem cell has the potential to produce novel, aggressive and/or resistant cancer cells. Therefore, these cells are generally linked with continued malignant growth, cancer metastasis, recurrence, and cancer drug resistance. Cancer stem cells were found in a series of cancer types, including, but are not limited to, breast cancer, head and neck cancer, lung cancer, ovarian cancer, pancreatic cancer, colorectal carcinoma, prostate cancer, melanoma, multiple myeloma, Kaposi sarcoma, Ewing's sarcoma, liver cancer, medulloblastoma, brain tumors, and leukemia. In view of this aspect, the present disclosure further relates to Compounds of the Invention which can be used to treat or prevent cancer stem cells, wherein at least one cancer stem cell is resistant towards chemotherapy or radiotherapy.

The present disclosure further relates to Compounds of Formula I which can be used to treat or prevent metastatic cancer cells. In another embodiment, a Compound of Formula I can be used to treat or prevent metastatic cancer cells, wherein at least one metastatic cancer cell is resistant towards chemotherapy or radiotherapy. In yet another embodiment, a Compound of Formula I can be used to treat or prevent metastatic cancer cells, wherein the metastasis is formed by cancer cells comprising at least one cancer stem cell, and wherein at least one cancer cell is resistant towards chemotherapy or radiotherapy.

Due to their activity, Compounds of Formula I, or a pharmaceutically acceptable derivative thereof, are advantageously useful in veterinary and human medicine. As described above, Compounds of Formula I, or a pharmaceutically acceptable derivative thereof, are useful for treating or preventing a disorder in a subject, e.g. mammal.

When administered to a subject, Compounds of Formula I, or a pharmaceutically acceptable derivative thereof, are, in one embodiment, administered as a component of a composition that comprises in addition to the Compound of the Invention a pharmaceutically acceptable carrier or excipient. The compositions, which comprise a Compound of Formula I, or a pharmaceutically acceptable derivative thereof, can be administered orally. Compounds of Formula I, or a pharmaceutically acceptable derivative thereof, can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the Compound of Formula I, or a pharmaceutically acceptable derivative thereof.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of Compounds of Formula I, or a pharmaceutically acceptable derivative thereof, into the bloodstream.

In specific embodiments, it can be desirable to administer the Compounds of Formula I, or a pharmaceutically acceptable derivative thereof, locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Compounds of Formula I, or a pharmaceutically acceptable derivative thereof, into the central nervous system or gastrointestinal tract by any suitable route, including intraventricular, intrathecal, and epidural injection, and enema Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Compounds of Formula I can be formulated as a suppository, with traditional binders and excipients such as triglycerides.

In another embodiment, the Compounds of Formula I, or a pharmaceutically acceptable derivative thereof, can be delivered in a vesicle, in particular a liposome (see Langer, "New Methods of Drug Delivery," Science 249:1527-1533 (1990); Lopez-Berestein, "Treatment of Systemic Fungal Infections with Liposomal-Amphotericin B," Liposomes in the Therapy of Infectious Disease and Cancer, pp. 317-327 (1989); and Treat et al., "Liposome encapsulated doxorubicin—preliminary results of phase I and phase II trials" Liposomes in the Therapy of Infectious Disease and Cancer, pp. 353-365 (1989)).

In another embodiment, the Compounds of Formula I, or a pharmaceutically acceptable derivative thereof, can be delivered in a controlled-release system or sustained-release system (see, e.g., Goodson, "Dental Applications," pp. 115-138 in Medical Applications of Controlled Release, Vol. 2, Applications and Evaluation, Langer and Wise, eds., CRC Press (1984), hereafter "Goodson"). Other controlled- or sustained-release systems discussed in the review by Langer, Science 249:1527-1533 (1990) can be used. In one embodiment, a pump can be used (Langer, Science 249:1527-1533 (1990); Sefton, "Implantable Pumps," in CRC Crit. Rev. Biomed. Eng. 14(3); 201-240 (1987); Buchwald et al., "Long-term, Continuous Intravenous Heparin Administration by an Implantable Infusion Pump in Ambulatory Patients with Recurrent Venous Thrombosis," Surgery 88:507-516 (1980); and Saudek et al., "A Preliminary Trial of the Programmable Implantable Medication System for Insulin Delivery," New Engl. J. Med. 321:574-579 (1989)). In another embodiment, polymeric materials can be used (see Goodson; Smolen et al., "Drug Product Design and Performance," Controlled Drug Bioavailability Vol. 1, John Wiley & Sons, New York (1984); Langer et al., "Chemical and Physical Structure of Polymers as Carriers for Controlled Release of Bioactive Agents: A Review," J. Macromol. Sci. Rev. Macromol. Chem. C23(1):61-126 (1983); Levy et al., "Inhibition of Calcification of Bioprosthetic Heart Valves by Local Controlled-Release Diphosphonate," Science 228:190-192 (1985); During et al., "Controlled Release of Dopamine from a Polymeric Brain Implant: In Vivo Characterization," Ann. Neurol. 25:351-356 (1989); and Howard et al., "Intracerebral drug delivery in rats with lesion-induced memory deficits," J. Neurosurg. 71:105 (1989)). In yet another embodiment, a controlled- or sustained-release system can be placed in proximity of a target of the Compounds of Formula I, thus requiring only a fraction of the systemic dose.

The compositions can optionally comprise a suitable amount of a pharmaceutically acceptable excipient so as to provide the form for proper administration to the subject. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a subject. Water is a particularly useful excipient when a Compound of Formula I is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The compositions, if desired, can also contain minor amounts of wetting or emulsifying agents, or pH buffering agents. Specific examples of pharmaceutically acceptable carriers and excipients that can be used to formulate oral dosage forms are described in the Handbook of Pharmaceutical Excipients, (Amer. Pharmaceutical Ass'n, Washington, DC, 1986), incorporated herein by reference.

The compositions can take the form of solutions, suspensions, emulsion, tablets, pills, pellets, multiparticulates, capsules, capsules containing liquids, powders, multiparticulates, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described by Radebough et al., "Preformulation." pp. 1447-1676 in Remington's Pharmaceutical Sciences Vol. 2 (Gennaro, ed., 19th ed., Mack Publishing, Easton, PA, 1995).

In one embodiment, the Compounds of Formula I are formulated in accordance with routine procedures as a composition adapted for oral administration to human beings. A Compound of Formula I to be orally delivered can be in the form of tablets, capsules, gel caps, caplets, lozenges, aqueous or oily solutions, suspensions, granules, powders, emulsions, syrups, or elixirs, for example. When a Compound of Formula I is incorporated into oral tablets, such tablets can be compressed, tablet triturates, enteric-coated, sugar-coated, film-coated, multiply compressed or multiply layered. Techniques and compositions for making solid oral dosage forms are described in Pharmaceutical Dosage Forms: Tablets (Lieberman et al., eds., 2nd ed., Marcel Dekker, Inc., 1989 & 1990). Techniques and compositions for making tablets (compressed and molded), capsules (hard and soft gelatin) and pills are also described by King, "Tablets, Capsules, and Pills," pp. 1553-1593 in Remington's Pharmaceutical Sciences (Osol, ed., 16th ed., Mack Publishing, Easton, PA, 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in Pharmaceutical Dosage Forms: Disperse Systems (Lieberman et al., eds., 2nd ed., Marcel Dekker, Inc., 1996 & 1998).

When a Compound of Formula I is to be injected parenterally, it can be, e.g., in the form of an isotonic sterile solution. Alternatively, when a Compound of Formula I is to be inhaled, it can be formulated into a dry aerosol or can be formulated into an aqueous or partially aqueous solution.

An orally administered Compound of Formula I can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Compounds of Formula I can be formulated for intravenous administration. In one embodiment, compositions for intravenous administration comprise sterile isotonic aqueous buffer. Where necessary, the compositions can also include a solubilizing agent. A Compound of Formula I for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of Formula I is to be administered by infusion, it can be dispensed, for example, with an infusion bottle containing sterile pharmaceutical grade water or saline. Where a Compound of Formula I is administered by injection, an ampule of sterile water for injection or saline can be provided so that the ingredients can be mixed prior to administration.

The Compounds of Formula I, or a pharmaceutically acceptable derivative thereof, can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the disclosure. The disclosure thus encompasses single unit dosage forms suitable for oral administration such as, but not limited to, tablets, capsules, gel caps, and caplets that are adapted for controlled- or sustained-release.

Controlled- or sustained-release pharmaceutical compositions can have a common goal of improving drug therapy over that achieved by their non-controlled or non-sustained release counterparts. In one embodiment, a controlled- or sustained-release composition comprises a minimal amount of a Compound of Formula I to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Compound of Formula I, and can thus reduce the occurrence of adverse side effects.

Controlled- or sustained-release compositions can be designed to immediately release an amount of a Compound of Formula I, or a pharmaceutically acceptable derivative thereof, that promptly produces the desired therapeutic or prophylactic effect, and gradually and continually release other amounts of the Compound of Formula I to maintain this level of therapeutic or prophylactic effect over an extended period of time. To maintain a constant level of the Compound of Formula I in the body, the Compound of Formula I can be released from the dosage form at a rate that will replace the amount of Compound of Formula I being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Compound of Formula I, or a pharmaceutically acceptable derivative thereof, that is effective in the treatment or prevention of a disorder can be determined by standard clinical techniques. In addition, in vitro or in vivo assays can optionally be employed to help identify optimal dosage ranges. The precise dose to be employed will also depend on the route of administration, and the seriousness of the disorder and can be decided according to the judgment of a practitioner and/or each subject's circumstances. Suitable effective dosage amounts, however, will, in one embodiment, range from about 0.05 mg/kg to 0.1 mg/kg, from about 0.1 mg/kg to 100 mg/kg, from about 0.1 mg/kg to 0.5 mg/kg, from about 0.5 mg/kg to 1 mg/kg, from about 1 mg/kg to 5 mg/kg, from about 5 mg/kg to 10 mg/kg, from about 10 mg/kg to 15 mg/kg, from about 15 mg/kg to 20 mg/kg, from about 20 mg/kg to 30 mg/kg, from about 30 mg/kg to 40 mg/kg, from about 40 mg/kg to 50 mg/kg, from about 50 mg/kg to 60 mg/kg, from about 60 mg/kg to 70 mg/kg, from about 70 mg/kg to 80 mg/kg, from about 80 mg/kg to 90 mg/kg, from about 90 mg/kg to 100 mg/kg, based on the body weight of the subject.

In one embodiment, an effective dosage amount is administered about every 96 h until the disorder is abated. In another embodiment, an effective dosage amount is administered about every 72 h until the disorder is abated. In another embodiment, an effective dosage amount is administered about every 24 h until the disorder is abated. In another embodiment, an effective dosage amount is administered about every 12 h until the disorder is abated. In another embodiment, an effective dosage amount is administered about every 8 h until the disorder is abated. In another embodiment, an effective dosage amount is administered about every 6 h until the disorder is abated. In another embodiment, an effective dosage amount is administered about every 4 h until the disorder is abated.

The effective dosage amounts described herein refer to total amounts administered; that is, if more than one Compound of Formula I, or a pharmaceutically acceptable derivative thereof, is administered, the effective dosage amounts correspond to the total amount administered.

The methods for treating or preventing a disorder in a subject identified as in need thereof can further comprise administering to the subject a Compound of Formula I, or a pharmaceutically acceptable derivative thereof (i.e., a first therapeutic agent), another therapeutic agent (i.e., a second therapeutic agent, another therapeutic drug, or a second therapeutic drug).

The second therapeutic agent can be, but is not limited to, an anticancer drug, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an agent for treating or preventing an autoimmune disorder and/or an inflammatory disorder, an agent for treating or preventing fibrotic disorders, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, an agent for treating depression, a pharmaceutically acceptable derivative thereof, or any mixture thereof.

In the present disclosure, anticancer drugs (i.e. anticancer agents) are preferred as another therapeutic agents (i.e. a second therapeutic agent).

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Insel, "Analgesic-Antipyretic and Anti-inflammatory Agents and Drugs Employed in the Treatment of Gout," pp. 617-657 in Goodman & Gilman's The Pharmacological Basis of Therapeutics (Goodman et al., Eds., 9th Ed., McGraw-Hill, New York 1996), and Hanson, "Analgesic, Antipyretic and Anti-Inflammatory Drugs," pp. 1196-1221 in Remington: The Science and Practice of Pharmacy Vol 2 (Gennaro, ed., 19th ed., Mack Publishing, Easton, PA, 1995), which are hereby incorporated by reference in their entireties.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful Cox-II inhibitors and 5-lipoxygenase inhibitors, as well as combinations thereof, are described in U.S. Pat. No. 6,136,839. Examples of useful Cox-11 inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

The second therapeutic agent can also be an agent useful for reducing any potential side effects of a Compound of Formula I For example, the second therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, a pharmaceutically acceptable derivative thereof, or any mixture thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, xibenolol, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, zimeldine, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable derivative thereof, or any mixture thereof.

In the present disclosure, the second therapeutic agent (i.e. another therapeutic agent) is preferably an anticancer drug (i.e. an anticancer agent). In a preferred embodiment, Compounds of the Invention are useful in combination with members of the taxane compound class. One embodiment of the disclosure provides the combination of Compounds of the Invention with Paclitaxel. In another preferred embodiment, Compounds of the Invention are useful in combination with ruthenium-based compounds. In another preferred embodiment, Compounds of the Invention are useful in combination with platinum-based compounds. One embodiment of the disclosure provides the combination of Compounds of the Invention with oxaliplatin. Another embodiment of the disclosure provides the combination of Compounds of the Invention with cisplatin.

Compound of the Invention may be combined with further anticancer drugs. Examples of further useful anticancer drugs include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflomithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, compounds of the class of taxane, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride, a pharmaceutically acceptable derivative thereof, or any mixture thereof.

Examples of other anticancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3, CARN 700; cartilage derived inhibitor; carzelesin; casein kinase inhibitors (ICOS); castanospermine; cecropin B; cetrorelix; chlorlns; chloroquinoxaline sulfonamide; cetuximab; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil, diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; EGFR inhibitors, elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostnecin; fotemustine; gadolinium texaphyrin; gallium nitrate; galocitabine; ganirelix; gefitinib; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; MEK inhibitor; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer drug; mycaperoxide B; mycobacterial cell wall extract myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; ruthenium compounds; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, a pharmaceutically acceptable derivative thereof, or any mixture thereof.

Examples of useful therapeutic agents for treating or preventing autoimmune disorders or inflammatory disorders include, but are not limited to, inhibitors of TNF-alpha; inhibitors of IL-15; inhibitors of MICA; inhibitors of MICB; inhibitors of ULBP-1; inhibitors of ULBP-2; inhibitor of ULBP-3; inhibitors of IL-10, a pharmaceutically acceptable derivative thereof, or any mixture thereof.

Examples of useful therapeutic agents for treating or preventing a fibrotic disorder include, but are not limited to, antagonists of CCR2; inhibitors of TGF-0 type 1 receptor; inhibitors of Smad3; inhibitors of tyrosine kinases, such as Imatinib or Nintedanib; inhibitors of HMG-CoA reductase, a pharmaceutically acceptable derivative thereof, or any mixture thereof. [Rosenbloo, J., et al., *Biochimica et Biophysica Acta,* 2012, 1832, 1088]

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing epilepsy include, but are not limited to, carbamazepine; ethosuximide; gabapentin; lamotrigine; phenobarbital; phenytoin; primidone; valproic acid; trimethadione; benzodiazepines; γ vinyl GABA; acetazolamide; felbamate, a pharmaceutically acceptable derivative thereof, or any mixture thereof.

Examples of useful therapeutic agents for treating or preventing stroke include, but are not limited to, anticoagulants such as heparin; agents that break up clots such as streptokinase or tissue plasminogen activator; agents that reduce swelling such as mannitol or corticosteroids; acetylsalicylic acid, a pharmaceutically acceptable derivative thereof, or any mixture thereof.

Examples of useful therapeutic agents for treating or preventing a seizure include, but are not limited to, carbamazepine; ethosuximide; gabapentin; lamotrignine; phenobarbital; phenytoin; primidone; valproic acid; trimethadione; bemzodiaepines; gabapentin; lamotrigine; γ-vinyl GABA; acetazolamide; felbamate, a pharmaceutically acceptable derivative thereof, or any mixture thereof.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; antihistamines; a pharmaceutically acceptable derivative thereof; or any mixture thereof.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; ziprasidone; a pharmaceutically acceptable derivative thereof; or any mixture thereof.

Examples of useful therapeutic agents for treating or preventing Huntington's chorea include, but are not limited to, haloperidol; pimozide, a pharmaceutically acceptable derivative thereof, or any mixture thereof.

Examples of useful therapeutic agents for treating or preventing ALS include, but are not limited to, baclofen; neurotrophic factors; riluzole; tizanidine; benzodiazepines, such as clonazepan; dantrolene, a pharmaceutically acceptable derivative thereof, or any mixture thereof.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; antidepressant drugs such as those given above; a pharmaceutically acceptable derivative thereof; or any mixture thereof.

Examples of useful therapeutic agents for treating or preventing a migraine include, but are not limited to, alpiropride; bromocriptine; dihydroergotamine; dolasetron; ergocornine; ergocominine; ergocryptine; ergonovine; ergot; ergotamine; flumedroxone acetate; fonazine; ketanserin; lisuride; lomerizine; methylergonovine; methysergide; metoprolol; naratriptan; oxetorone; pizotyline; propranolol; risperidone; rizatriptan; sumatriptan; timolol; trazodone; zolmitriptan, a pharmaceutically acceptable derivative thereof, or any mixture thereof.

Examples of useful therapeutic agents for treating or preventing vomiting include, but are not limited to, 5-HT3 receptor antagonists, such as ondansetron, dolasetron, granisetron, and tropisetron; dopamine receptor antagonists, such as prochlorperazine, thiethylperazine, chlorpromazin, metoclopramide, and domperidone; glucocorticoids, such as dexamethasone; benzodiazepines, such as lorazepam and alprazolam; a pharmaceutically acceptable derivative thereof; or any mixture thereof.

Examples of useful therapeutic agents for treating or preventing dyskinesia include, but are not limited to, reserpine; tetrabenazine, a pharmaceutically acceptable derivative thereof, or any mixture thereof.

Examples of useful therapeutic agents for treating or preventing depression include, but are not limited to, tricyclic antidepressants, such as amitryptyline, amoxapine, bupropion, clomipramine, desipramine, doxepin, imipramine, maprotilinr, nefazadone, nortriptyline, protriptyline, trazodone, trimipramine, and venlaflaxine; selective serotonin reuptake inhibitors, such as citalopram. (S)-citalopram, fluoxetine, fluvoxamine, paroxetine; and setraline; monoamine oxidase inhibitors, such as isocarboxazid, pargyline, phenelzine, and tranylcypromine; psychostimulants, such as dextroamphetamine and methylphenidate, a pharmaceutically acceptable derivative thereof, or any mixture thereof.

In one embodiment, the second therapeutic agent is administered in an effective amount.

An effective amount of the second therapeutic agent(s) will be known to those skilled the art depending on the agent. However, it is well within the skilled artisan's purview to determine the second therapeutic agent's optimal effective-amount range. A Compound of Formula I, or a pharmaceutically acceptable derivative thereof, and the second therapeutic agent combined can act either additively or synergistically to treat the same disorder, or they can act independently of each other such that the Compound of Formula I, or a pharmaceutically acceptable derivative thereof, treats or prevents a first disorder and the second therapeutic agent treats or prevents a second disorder, which can be the same as the first disorder or another disease. In one embodiment of the disclosure, where a second therapeutic agent is administered to a subject for treatment of a disorder (e.g., cancer), the minimal effective amount of the Compound of Formula I, or a pharmaceutically acceptable derivative thereof, will be less than its minimal effective amount would be where the second therapeutic agent is not administered. In this embodiment, the Compound of Formula I, or a pharmaceutically acceptable derivative thereof, and the second therapeutic agent can act synergistically to treat or prevent a disorder. In one embodiment, a Compound of Formula I is administered concurrently with a second therapeutic agent as a single composition comprising an effective amount of a Compound of Formula I, or a pharmaceutically acceptable derivative thereof, and an effective amount of the second therapeutic agent. Alternatively, a composition comprising an effective amount of a Compound of Formula I, or a pharmaceutically acceptable derivative thereof, and a second composition comprising an effective amount of the second therapeutic agent are concurrently administered. In another embodiment, an effective amount of a Compound of Formula I, or a pharmaceutically acceptable derivative thereof, is administered prior or subsequent to administration of an effective amount of the second therapeutic agent. In this embodiment, the Compound of Formula I, or a pharmaceutically acceptable derivative thereof, is administered while the second therapeutic agent exerts its therapeutic effect, or the second therapeutic agent is administered while the Compound of Formula I, or a pharmaceutically acceptable derivative thereof, exerts its therapeutic effect for treating or preventing a disorder.

A Compound of Formula I, or a pharmaceutically acceptable derivative thereof, and a second therapeutic agent can act additively or synergistically. In one embodiment, an effective amount of a Compound of Formula I, or a pharmaceutically acceptable derivative thereof, and an effective amount of a second therapeutic agent act synergistically. In this embodiment, the effective amount of a Compound of Formula I may be an amount of from 0.1 µM to 15 µM, preferably 0.2 µM, 0.3 µM, 0.4 µM, 0.5 µM, 0.6 µM, 0.7 µM, 0.8 µM, 1.0 µM, 1.2 µM, 1.4 µM, 1.6 µM, 2.0 µM, 2.5 µM, 3.0 µM, 4.0 µM, 5.0 µM, 6.0 µM, 7.0 µM, 8.0 µM, 9.0 µM, or 10.0 µM. The effective amount of a second therapeutic agent may be an amount of from 0.001 µM to 200 µM, preferably 0.0001 µM, 0.0003 µM, 0.001 µM, 0.003 µM, 0.005 µM, 1.0 µM, 2.0 µM, 4.0 µM, 6.0 µM, 8.0 µM, 10 µM, 20 µM, 30 µM, 40 µM, 50 µM, 60 µM, 70 µM, 80 µM, 100 µM, 120 µM, 140 µM, 160 µM, 180 µM, or 200 µM. In a preferred embodiment, an effective amount of a Compound of Formula I, or a pharmaceutically acceptable derivative thereof, and an effective amount of an anticancer drug act synergistically. In another embodiment, an effective amount of a Compound of Invention selected from Table 1, or a pharmaceutically acceptable derivative thereof, and an effective amount of an anticancer drug act synergistically. In another embodiment, an effective amount of Compound IE-8, or a pharmaceutically acceptable derivative thereof, and an effective amount of an anticancer drug act synergistically. In another embodiment, the anticancer drug is selected from the group consisting of taxanes, platinum-based compounds, and ruthenium-based compounds. In another embodiment, the anticancer drug is selected from the group consisting of paclitaxel, cisplatin, and oxaliplatin.

In a preferred embodiment, 0.8 µM or more of IE-8 and 40 µM or more of cisplatin act synergistically.

In another preferred embodiment, 1.0 µM or more of IE-8 and 20 µM or more of cisplatin act synergistically.

In another preferred embodiment, 0.4 µM or more of IE-8 and 0.003 µM or more of paclitaxel act synergistically.

The synergistic effect of a Compound of Formula I or a pharmaceutically acceptable derivative thereof, and a second therapeutic agent may be determined by any related art method suitable therefore. In one embodiment, the method is a biochemical method. In another embodiment, the biochemical method includes, but is not limited to, Combination Index Assay, Colony Formation assay, Cell Viability Assay (e.g., MTT assay or SRB assay).

In one embodiment, the synergistic effect may depend on the order of administering a Compound of Formula I, or a pharmaceutically acceptable derivative thereof, and a second therapeutic agent. In one embodiment, synergism is achieved when a Compound of Formula I, or a pharmaceutically acceptable derivative thereof, is administered concurrently with a second therapeutic agent; for example, a composition comprising an effective amount of a Compound of Formula I, or a pharmaceutically acceptable derivative thereof, and an effective amount of a second therapeutic agent can be administered. Alternatively, synergism is achieved when a composition comprising an effective amount of a Compound of Formula I, or a pharmaceutically acceptable derivative thereof, and a different composition comprising an effective amount of a second therapeutic agent can be concurrently administered. In another embodiment, synergism is achieved when an effective amount of a Compound of Formula I is administered prior or subsequent to administration of an effective amount of a second therapeutic agent. In this embodiment, the Compound of Formula I, or a pharmaceutically acceptable derivative thereof, is administered while the second therapeutic agent exerts its therapeutic effect, or the second therapeutic agent is administered while the Compound of Formula I, or a pharmaceutically acceptable derivative thereof, exerts its therapeutic effect for treating or preventing a disorder. In a preferred embodiment, a Compound of Formula I and an anticancer drug are administered. In another embodiment, a Compound of Formula I selected from Table 1 and an anticancer drug are administered. In another embodiment, Compound IE-8 and an anticancer drug are administered. In another embodiment, Compound IE-8 and a taxane, ruthenium-based compound, or platinum-based compound are administered. In another embodiment. Compound IE-8 and paclitaxel, oxaliplatin, or cisplatin are administered.

In one embodiment, the anticancer activity of a Compound of Formula I, or a pharmaceutically acceptable derivative thereof, is enhanced by the combination with a second anticancer drug. In another embodiment, the anticancer activity of a second anticancer drug is enhanced by the combination with a Compound of Formula I, or a pharmaceutically acceptable derivative thereof. In one embodiment, the second anticancer drug is selected from the group consisting of taxanes, ruthenium-based compounds, and platinum-based compounds. In another embodiment, the second anticancer drug is selected from the group consisting of paclitaxel, oxaliplatin, and cisplatin. In one embodiment, the Compound of Formula I is selected from Table 1. In another embodiment, IA-8 is combined with paclitaxel. In another embodiment, IA-8 is combined with oxaliplatin. In another embodiment, IA-8 is combined with cisplatin. In another embodiment, IB-8 is combined with paclitaxel. In another embodiment, IB-8 is combined with oxaliplatin. In another embodiment, IB-8 is combined with cisplatin. In another embodiment, ID-8 is combined with paclitaxel. In another embodiment, ID-8 is combined with oxaliplatin. In another embodiment, ID-8 is combined with cisplatin. In another embodiment, IE-8 is combined with paclitaxel. In another embodiment, IE-8 is combined with oxaliplatin. In another embodiment, IE-8 is combined with cisplatin.

In one embodiment, the combination of a Compound of Formula I, or a pharmaceutically acceptable derivative thereof, and another anticancer agent (i.e. a second anticancer agent, another anticancer drug, or a second anticancer drug) acts synergistically with regard to the anticancer activity (e.g., see Examples 15, 18, or 19 for synergism). In one embodiment, the second anticancer drug is selected from the group consisting of taxanes, ruthenium-based compounds, and platinum-based compounds. In another embodiment, the second anticancer drug is selected from the group consisting of paclitaxel, oxaliplatin, and cisplatin. In one embodiment, the Compound of Formula I is selected from Table 1. In another embodiment, IA-8 is combined with paclitaxel. In another embodiment, IA-8 is combined with oxaliplatin. In another embodiment, IA-8 is combined with cisplatin. In another embodiment, IB-8 is combined with paclitaxel. In another embodiment, IB-8 is combined with oxaliplatin. In another embodiment, IB-8 is combined with cisplatin. In another embodiment, ID-8 is combined with paclitaxel. In another embodiment, ID-8 is combined with oxaliplatin. In another embodiment, ID-8 is combined with cisplatin. In another embodiment, IE-8 is combined with paclitaxel. In another embodiment, IE-8 is combined with oxaliplatin. In another embodiment, IE-8 is combined with cisplatin.

In one embodiment, the sensitivity of a cancer cell towards a second anticancer drug is enhanced by the combination of said second anticancer drug with a Compound of Formula I, or a pharmaceutically acceptable derivative thereof (e.g., see Examples 15, 16, or 17 for Chemosensitization). In one embodiment, the second anticancer drug is selected from the group consisting of taxanes, ruthenium-based compounds, and platinum-based compounds. In another embodiment, the second anticancer drug is selected from the group consisting of paclitaxel, oxaliplatin, and cisplatin. In one embodiment, the Compound of Formula I is selected from Table 1. In another embodiment, IA-8 is combined with paclitaxel. In another embodiment, IA-8 is combined with oxaliplatin. In another embodiment, IA-8 is combined with cisplatin. In another embodiment, IB-8 is combined with paclitaxel. In another embodiment, IB-8 is combined with oxaliplatin. In another embodiment, IB-8 is combined with cisplatin. In another embodiment, ID-8 is combined with paclitaxel. In another embodiment, ID-8 is combined with oxaliplatin. In another embodiment, ID-8 is combined with cisplatin. In another embodiment, IE-8 is combined with paclitaxel. In another embodiment, IE-8 is combined with oxaliplatin. In another embodiment, IE-8 is combined with cisplatin. In another embodiment, the cancer cell is a cancer stem cell. In another embodiment, the cancer cell is a metastatic cancer cell.

A composition of the disclosure is prepared by a method comprising admixing a Compound of Formula I, or a pharmaceutically acceptable derivative thereof, with a pharmaceutically acceptable carrier or excipient. Admixing can be accomplished using methods known for admixing a compound (or derivative) and a pharmaceutically acceptable carrier or excipient. In one embodiment, the Compound of Formula I, or a pharmaceutically acceptable derivative thereof, is present in the composition in an effective amount.

A Compound of Formula I, or a pharmaceutically acceptable derivative thereof, or a pharmaceutical composition as described above may be useful in the treatment or prevention of a disorder, wherein the treatment or prevention further comprises other methods for treating or preventing a disorder. Such other methods for the treatment of cancer include, but are not limited to, radiotherapy, immunotherapy, or surgery. In one embodiment, the Compound of the Invention and the other method may be applied simultaneously. In another embodiment, the administration of the Compound of the Invention takes place before or after the time period in which the other method, such as radiotherapy, immunotherapy, or surgery is applied to the subject. In a preferred embodiment, the effect of the other methods (such as radiotherapy or immunotherapy) is enhanced by the administration of the Compound of the Invention (e.g., see Example 14 for Radiosensitization).

The inventors showed that Compounds of Formula I, or a pharmaceutically acceptable derivative thereof, are inhibitors of Stat3 pathway activity (e.g., see Example 10). The disclosure also relates to methods for inhibiting Stat3 pathway activity in a cell, preferably a cancer cell, comprising administering to the cell a Compound of Formula I, or a pharmaceutically acceptable derivative thereof.

The inhibition of Stat3 pathway activity comprises any aspect of inhibition, wherein the Stat3 pathway activity is reduced. The inhibition of Stat3 pathway activity by Compounds of Formula I may occur via, but is not limited to, inhibiting phosphorylated (activated) Stat3 (pStat3), inhibiting Stat3-mediated transcription (e.g., by targeting DNA binding site of Stat3), blocking Stat3 dimerization (e.g., by targeting the $SH_2$ domain of Stat3), inhibiting nuclear import and/or export of Stat3 (e.g., by targeting importins alpha ($\alpha$) 3, alpha ($\alpha$) 5, alpha ($\alpha$) 7, importin beta ($\beta$), exportin 1, and the like), inhibiting the phosphorylation of Stat3 (e.g., by targeting EGFR agonism, TKR activity, JAK activity, SFK activity, and the like), and inducing dephosphorylation of pSta3.

In one embodiment, the inhibition of Stat3 pathway activity occurs via inhibition of phosphorylated (activated) Stat3 (pStat3).

In one embodiment, Compounds of Formula I, or a pharmaceutically acceptable derivative thereof, inhibit the Stat3 pathway activity in a cell resulting in a reduction of pStat3. In another embodiment, Compounds of Formula I, or a pharmaceutically acceptable derivative thereof, inhibit the Stat3 pathway activity in a cell resulting in a reduction of Bcl-2, Bcl-xL, and/or survivin. In another embodiment, Compounds of Formula I, or a pharmaceutically derivative thereof, inhibit the Stat3 pathway activity in a cell resulting in a reduction of DNA repair factors (such as BRCA1, FANCD2, EME1, MUS81, and the like). In another embodiment, Compounds of Formula I, or a pharmaceutically derivative thereof, inhibit the Stat3 pathway activity in a cell resulting in a reduction of metastasis-involved protein MMP-9. In a further embodiment, Compounds of Formula I, or a pharmaceutically acceptable derivative thereof, inhibit the Stat3 pathway activity in a cell resulting in a reduction of pStat3, Bcl-2, Bcl-xL, and/or survivin. In a further embodiment, Compounds of Formula I, or a pharmaceutically acceptable derivative thereof, inhibit the Stat3 pathway activity in a cell resulting in a reduction of pStat3, Bcl-2 Bcl-xL, survivin, and/or DNA repair factors (such as BRCA1, FANCD2, EME1, MUS81, and the like). In a further embodiment, Compounds of Formula I, or a pharmaceutically acceptable derivative thereof, inhibit the Stat3 pathway activity in a cell resulting in a reduction of pStat3, Bcl-2. Bcl-xL, survivin, DNA repair factors (such as BRCA1. FANCD2, EME1, MUS81, and the like), and/or metastasis-involved protein MMP-9.

In one embodiment, the resulting reduction of pSta3, Bcl-2, Bcl-xL, survivin, DNA repair factors (such as BRCA1, FANCD2, EME1, MUS81, and the like), and/or metastasis-involved protein MMP-9 induces cell death of the cell, wherein the cell death is apoptosis. In another embodiment, the resulting reduction of pStat3, Bcl-2, Bcl-xL, survivin, DNA repair factors (such as BRCA1, FANCD2, EME1, MUS81, and the like), and/or metastasis-involved protein MMP-9 induces cell death of the cell, wherein the cell death is paraptosis. In another embodiment, the resulting reduction of pStat3, Bcl-2, Bcl-xL, survivin, DNA repair factors (such as BRCA1, FANCD2, EME1, MUS81, and the like), and/or metastasis-involved protein MMP-9 induces cell death of the cell, wherein the cell death is methuosis. In yet another embodiment, the resulting reduction of pSta3, Bcl-2, Bcl-xL, survivin, DNA repair factors (such as BRCA1, FANCD2, EME1, MUS81, and the like), and/or metastasis-involved protein MMP-9 induces cell death of the cell, wherein the cell death is apoptosis and methuosis. In another embodiment, the resulting reduction of pStat3, Bcl-2, Bcl-xL, survivin, DNA repair factors (such as BRCA1, FANCD2, EME1, MUS81, and the like), and/or metastasis-involved protein MMP-9 induces cell death of the cell, wherein the cell death is apoptosis and paraptosis.

In a further another embodiment, the resulting reduction of p pStat3, Bc-2, Bc-xL, survivin, DNA repair factors (such as BRCA1, FANCD2, EME, MUS81, and the like), and/or metastasis-involved protein MMP-9 induces cell death of the cell, wherein the cell death is methuosis and paraptosis. In yet another embodiment, the resulting reduction of pStat3. Bcl-2, Bcl-xL, survivin, DNA repair factors (such as BRCA1, FANCD2, EME1, MUS81, and the like), and/or metastasis-involved protein MMP-9 induces cell death of the cell, wherein the cell death is apoptosis, methuosis and paraptosis.

In one embodiment, the cell is a cancer cell.

In another embodiment, the cancer cell is resistant towards chemotherapy.

In another embodiment, the cancer cell is resistant towards radiotherapy.

In another embodiment, the cancer cell is resistant towards chemotherapy and radiotherapy.

In another embodiment, the cell is a metastatic cancer cell.

In another embodiment, the metastatic cancer cell is resistant towards chemotherapy.

In another embodiment, the metastatic cancer cell is resistant towards radiotherapy.

In another embodiment, the metastatic cancer cell is resistant towards chemotherapy and radiotherapy.

In another embodiment, the cell is a cancer stem cell.

In another embodiment, the cancer stem cell is resistant towards chemotherapy.

In another embodiment, the cancer stem cell is resistant towards radiotherapy.

In another embodiment, the cancer stem cell is resistant towards chemotherapy and radiotherapy.

The method of inhibiting Stat3 pathway activity by a Compound of Formula I, or a pharmaceutically acceptable derivative thereof, can be carried out in vitro, for example, as an assay to select cells that express aberrant Stat3 activity and, accordingly, are useful as part of an assay to select Compounds of the Invention useful for treating or preventing a disorder, preferably cancer, autoimmune disorder, inflammatory disorder, or fibrotic disorder. The method is also useful for inhibiting Stat3 pathway activity in a cell in vivo, in a subject, by contacting a cell, in a subject, with an effective amount of a Compound of Formula I, or a pharmaceutically acceptable derivative thereof. In one embodiment, the method is useful for treating or preventing cancer in a subject. In another embodiment, the method is useful for treating or preventing an autoimmune disorder in a subject. In another embodiment, the method is useful for treating or preventing an inflammatory disorder in a subject. In another embodiment, the method is useful for treating or preventing a fibrotic disorder in a subject.

The Compounds of Formula I, or a pharmaceutically acceptable derivative thereof, can be assayed in vitro or in vivo for the desired therapeutic or prophylactic activity prior to use in a subject. Animal model systems can be used to demonstrate safety and efficacy.

The present disclosure further provides Compounds of Formula I for use as a fluorescent probe. In one embodiment, a Compound of Formula I is used as a fluorescent probe in a cell. In another embodiment, a Compound of Formula I is used as a fluorescent probe in a cancer cell. In another embodiment, the cancer cell is a metastatic cancer cell. In another embodiment, the cancer cell is a cancer stem cell. Based on the intrinsic fluorescence of Compounds of the Invention, said fluorescence may be exploited to visualize, track, and/or quantify the Compounds of the Invention in a cell or tissue. The localization of Compounds of the Invention within certain cells (e.g., cancer stem cells) or tissue may be achieved by any method suitable for detecting fluorescence, such as fluorescence microscopy, or FACS (Fluorescence-Activated Cell Sorter).

In another aspect, the present disclosure provides a use of a Compound of Formula I as a radiolabeled probe.

Definitions

Terms as set forth hereinafter are generally to be understood in their common sense unless indicated otherwise.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless specifically stated otherwise.

The term "about." as used herein in connection with a measured quantity, refers to the normal variations in that measured quantity, as expected by the skilled artisan making the measurement and exercising a level of care commensurate with the objective of measurement and the precision of the measuring equipment. Typically, the term "about" includes the recited number+10%. Thus, "about 10" means 9 to 11.

Terms like "obtainable" and "obtained" are used interchangeably. This, e.g., means that, unless the context clearly dictates otherwise, the term "obtained" does not mean to indicate that e.g. an embodiment must be obtained by e.g. the sequence of steps following the term "obtained" even though such a limited understanding is always included by the terms "obtained" as a preferred embodiment.

The terms "isolated" or "purified" as used herein refer to a material that is substantially or essentially free from components that normally accompany it in its native state. Purity and homogeneity are typically determined using analytical chemistry techniques such as polyacrylamide gel electrophoresis or high performance liquid chromatography.

The term "aromatic" refers to a cyclic or polycyclic moiety having a conjugated unsaturated (4n+2)π electron system (where n is a positive integer), sometimes referred to as a delocalized n electron system.

"—$(C_1$-$C_6)$alkyl" means a straight chain or branched non-cyclic hydrocarbon having from 1 to 6 carbon atoms. Representative straight chain —$(C_1$-$C_6)$alkyls include methyl, ethyl, n-propyl, n-butyl, n-pentyl, and n-hexyl. Representative branched —$(C_1$-$C_6)$alkyls include, but are not limited thereto, iso-propyl, sec-butyl, iso-butyl, tert-butyl, iso-pentyl, neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—$(C_2$-$C_6)$alkenyl" means a straight chain or branched non-cyclic hydrocarbon having from 2 to 6 carbon atoms and including at least one carbon-carbon double bond. Representative straight chain and branched $(C_2$-$C_6)$alkenyls include, but are not limited thereto, vinyl, allyl, 1-butenyl, 2-butenyl, iso-butylenyl, 1-pentenyl, 2-pentenyl, 3-methyl- 1-butenyl, 2-methyl-2-butenyl, 2,3-dimethyl-2-butenyl, 1-hexenyl, 2-hexenyl, 3-hexenyl and the like.

"—$(C_2-C_6)$alkynyl" means a straight chain or branched non-cyclic hydrocarbon having from 2 to 6 carbon atoms and including at least one carbon-carbon triple bond. Representative straight chain and branched $(C_2-C_6)$alkynyls include, but are not limited thereto, acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl and the like.

"—$(C_1-C_6)$alkoxy" means a straight chain or branched non-cyclic hydrocarbon having one or more ether groups and from 1 to 6 carbon atoms. Representative straight chain and branched —$(C_1-C_6)$alkoxys include, but are not limited thereto, methoxy, ethoxy, propoxy, butoxy, pentoxy, hexoxy, methoxymethyl, 2-methoxyethyl, 5-methoxypentyl, 3-ethoxybutyl, and the like.

"—$(C_3-C_8)$cycloalkyl" means a saturated cyclic hydrocarbon having from 3 to 8 carbon atoms. Representative $(C_3-C_8)$cycloalkyls include, but are not limited thereto, -cyclopropyl, -cyclobutyl, -cyclopentyl, -cyclohexyl, -cycloheptyl, and -cyclooctyl.

"—$(C_5-C_8)$cycloalkenyl" means a cyclic non-aromatic hydrocarbon having at least one carbon-carbon double bond in the cyclic system and from 5 to 8 carbon atoms. Representative —$(C_5-C_8)$cycloalkenyls include, but are not limited thereto, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl and the like.

"—$(C_6-C_{14})$bicycloalkyl" means a bicyclic hydrocarbon ring system having from 6 to 14 carbon atoms and at least one saturated cyclic alkyl ring. Representative —$(C_6-C_{14})$bicycloalkyls include, but are not limited thereto, -indanyl, -norbornyl, -1,2,3,4-tetrahydronaphthalenyl, -5,6,7,8-tetrahydronaphthalenyl, -perhydronaphthalenyl, bicyclo[2.2.1]hexyl, bicyclo[2.2.1]heptyl, bicyclo[2.2.2]octyl, bicyclo[3.3.1]heptyl, bicyclo[3.2.1]octyl, bicyclo[3.3.1]nonyl, bicyclo[3.3.2]decyl, bicyclo[3.3.3]undecyl, bicyclo[4.2.2]decyl, bicyclo[4.3.2]undecyl, bicyclo[4.3.1]decyl, and the like.

"—$(C_8-C_{20})$tricycloalkyl" means a tricyclic hydrocarbon ring system having from 8 to 20 carbon atoms and at least one saturated cyclic alkyl ring. Representative —$(C_8-C_{20})$tricycloalkyls include, but are not limited thereto, -pyrenyl, -adamantyl, noradamantyl, -1,2,3,4-tetrahydroanthracenyl, -perhydroanthracenyl-aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]azulenyl, hexadecahydrocycloocta[b]naphthalenyl, hexadecahydrocyclohepta[a]heptalenyl, tricyclo-pentadecanyl, tricyclo-octadecanyl, tricyclo-nonadecanyl, tricyclo-icosanyl, and the like.

"—$(C_7-C_{14})$bicycloalkenyl" means a bi-cyclic hydrocarbon ring system having at least one carbon-carbon double bond in each ring and from 7 to 14 carbon atoms. Representative —$(C_7-C_{14})$bicycloalkenyls include, but are not limited thereto, -bicyclo[3.2.0]hept-2-enyl, -indenyl, -pentalenyl, -naphthalenyl, -azulenyl, -heptalenyl, -1,2,7,8-tetrahydronaphthalenyl, norbornenyl, and the like.

"—$(C_8-C_{20})$tricycloalkenyl" means a tri-cyclic hydrocarbon ring system having at least one carbon-carbon double bond in each ring and from 8 to 20 carbon atoms. Representative —$(C_5-C_{20})$tricycloalkenyls include, but are not limited thereto, -anthracenyl, -phenanthrenyl, -phenalenyl, -acenaphthalenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta [a,c] cyclooctenyl, 2,3,4,5,6,7,8,9,10,11,12,13-dodecahydro-1H-dibenzo[a,d]cyclononenyl, and the like.

"-(3- to 7-membered)heterocycle" or "-(3- to 7-membered)heterocyclo" means a 3- to 7-membered monocyclic heterocyclic ring which is either saturated, or unsaturated non-aromatic. A 3-membered heterocycle can contain up to 1 heteroatom, a 4-membered heterocycle can contain up to 2 heteroatoms, a 5-membered heterocycle can contain up to 4 heteroatoms, a 6-membered heterocycle can contain up to 4 heteroatoms, and a 7-membered heterocycle can contain up to 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include, but are not limited thereto, pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"—$(C_6-C_{14})$aryl" means a cyclic, aromatic hydrocarbon group having from 6 to 14 carbon atoms and from 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). Representative —$(C_6-C_{14})$aryls include, but are not limited thereto, phenyl, naphthyl, azulenyl, biphenylenyl, s-indacenyl, acenaphthylenyl, fluorenyl, phenalenyl, phenanthrenyl, anthracenyl, and the like.

"—$(C_1-C_6)$alkyl-$(C_6-C_{14})$aryl" as used herein means a hydrocarbon chain containing 1 to 6 carbon atoms linking a —$(C_6-C_{14})$aryl group with the compound of Formula I via the nitrogen atom of the piperid-4-one moiety.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroary's rings contain at least one carbon atom. Representative -(5- to 10-membered)heteroaryls include, but are not limited thereto, pyridyl, furl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl. A preferred -(5- to 10-membered)heteroaryl is a "-(5- or 6-membered)heteroaryl".

"—($C_1$-$C_6$)alkyl-(5- to 10-membered)heteroaryl" as used herein means a hydrocarbon chain containing 1 to 6 carbon atoms linking a -(5- to 10-membered)heteroaryl group with the compound of Formula I via the nitrogen atom of the piperid-4-one moiety.

"-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include, but are not limited thereto, pyridyl, 2H-pyranyl, 4H-pyranyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, 1,2,4-triazinyl, and thiophenyl.

"—($C_1$-$C_6$)alkyl-(5- or 6-membered)heteroaryl" as used herein means a hydrocarbon chain containing 1 to 6 carbon atoms linking the compound of Formula I with a -(5- or 6-membered)heteroaryl group via the nitrogen atom of the piperid-4-one moiety.

"—$CH_2$(halo)" means a methyl group where one of the hydrogens of the methyl group has been replaced with a halogen. Representative —$CH_2$(halo) groups include, but are not limited thereto, —$CH_2F$, —$CH_2Cl$, —$CH_2Br$, and —$CH_2I$.

"—CH(halo)$_2$" means a methyl group where two of the hydrogens of the methyl group have been replaced with a halogen. Representative —CH(halo)$_2$ groups include, but are not limited thereto, —$CHF_2$, —$CHCl_2$, —$CHBr_2$, CHBrCl, CHClI, and —$CHI_2$.

"—C(halo)$_3$" means a methyl group where each of the hydrogens of the methyl group has been replaced with a halogen. Representative —C(halo)$_3$ groups include, but are not limited thereto, —$CF_3$, —$CCl_3$, —$CBr_3$, and —$Cl_3$.

"—Halo", "—Halogen" or "halide" means —F, —Cl, —Br, or —I.

The term "hydroxyl" as used herein is represented by the formula —OH.

The term "nitrile" as used herein is represented by the formula —CN.

The term "nitroso" as used herein is represented by the formula —NO.

The term "nitro" as used herein is represented by the formula —$NO_2$.

The term "azide" as used herein is represented by the formula —$N_3$.

As used herein, the term "amino" or "amino group" refers to —$NH_2$.

As used herein, the term "thiol" refers to —SH.

As used herein, the term "hydroxylamino" refers to —NH(OH).

Useful mercaptoalkyl groups include any of the above-mentioned $C_{1-6}$ alkyl groups, and preferably any of the above-mentioned $C_{1-6}$ alkyl groups, substituted by a —SH group.

As used herein, the term "carboxy" refers to —C(=O)OH.

Useful carboxylate groups include any of the above-mentioned $C_{1-6}$ alkyl groups, and preferably any of the above-mentioned $C_{1-6}$ alkyl groups, substituted by —COOH.

As used herein, the term "caroxy ester" refers to —C(=O)O$R^7$, wherein $R^7$ preferably is selected from a —($C_1$-$C_6$)alkyl group.

Useful alkylamino and dialkylamino groups are —NH$R^7$ and N($R^7$)$_2$, wherein each $R^7$ is independently selected from a —($C_1$-$C_6$)alkyl group, respectively.

Useful alkylcarbonyl groups include a carbonyl group, i.e., —C(=O)—, substituted by any of the above-mentioned $C_{1-6}$ alkyl groups.

Useful alkylcarbonyloxy or acyloxy groups, i.e. —OC(=O)$R^7$, include oxygen substituted by one of the above-mentioned alkylcarbonyl groups.

As used herein, the term "carboxamido" refers to a radical of formula —C(=O)N($R^7$)$_2$, wherein $R^7$ are each independently hydrogen. —($C_1$-$C_6$)alkyl, —($C_2$-$C_6$)alkenyl, or —($C_2$-$C_6$)alkynyl. Exemplary carboxamido groups include —$CONH_2$, —CON(H)$CH_3$, and —CON($CH_3$)$_2$.

The phrase "pyridyl group" means

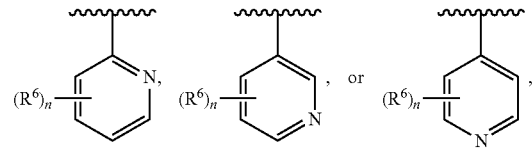

where $R^6$ and n are defined as above for Compounds of Formula I.

The phrase "pyrimidinyl group" means

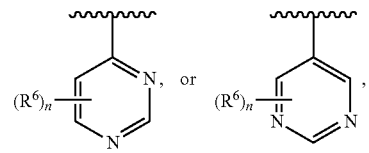

where $R^6$ and n are defined as above for Compounds of Formula I.

The phrase "triazinyl group" means

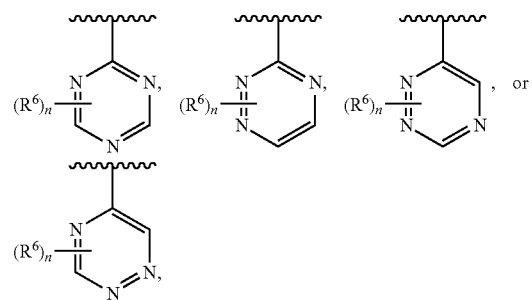

where $R^6$ and n are defined as above for Compounds of Formula I.

The phrase "pyridazinyl group" means

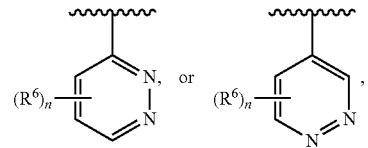

where $R^6$ and n are defined as above for Compounds of Formula I.

The phrase "pyrazinyl group" means

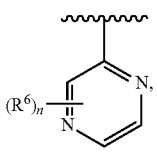

where $R^6$ and n are defined as above for Compounds of Formula I.

The phrase "4H-pyranyl group" means

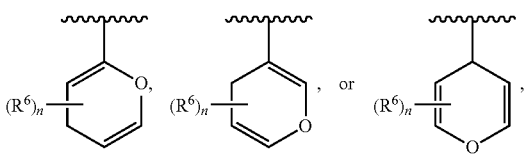

where $R^6$ and n are defined as above for Compounds of Formula I.

The phrase "2H-pyranyl group" means

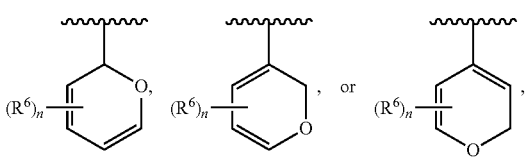

where $R^6$ and n are defined as above for Compounds of Formula I.

The phrase "thiazolyl group" means

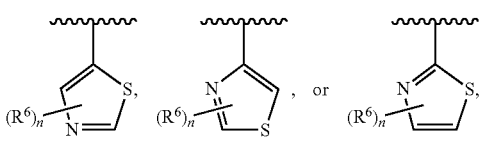

where $R^6$ and n are defined as above for Compounds of Formula I.

The phrase "thiophenyl group" means

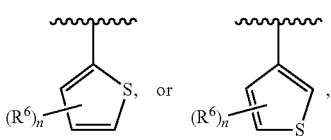

where $R^6$ and n are defined as above for Compounds of Formula I.

The phrase "pyrrolyl group" means

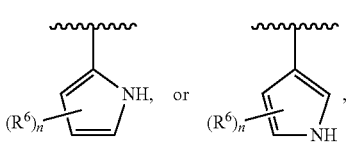

where $R^6$ and n are defined as above for Compounds of Formula I.

The phrase "oxazolyl group" means

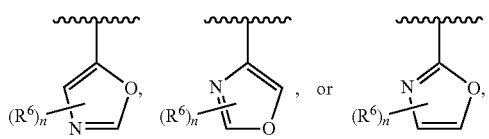

where $R^6$ and n are defined as above for Compounds of Formula I.

The phrase "oxadiazolyl group" means

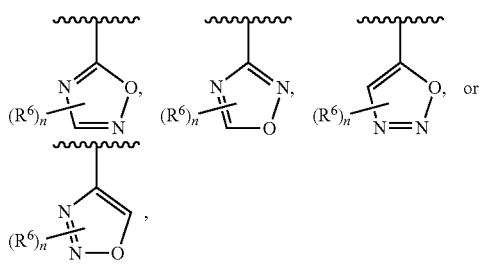

where $R^6$ and n are defined as above for Compounds of Formula I.

The phrase "isoxazolyl group" means

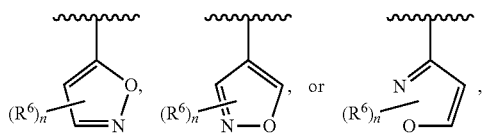

where $R^6$ and n are defined as above for Compounds of Formula I.

The phrase "isothiazolyl group" means

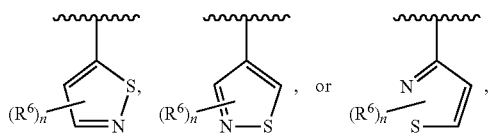

where $R^6$ and n are defined as above for Compounds of Formula I.

The phrase "imidazolyl group" means

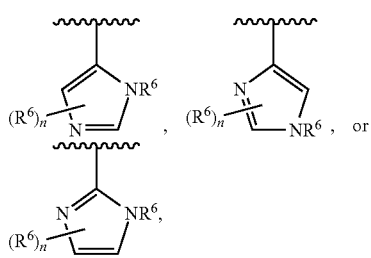

where $R^6$ and n are defined as above for Compounds of Formula I.

The phrase "furazanyl group" means

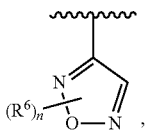

where $R^6$ and n are defined as above for Compounds of Formula I.

The phrase "furanyl group" means

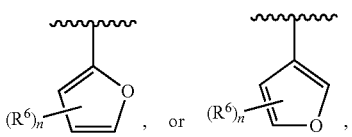

where $R^6$ and n are defined as above for Compounds of Formula I.

The phrase "1-$R^6$-tetrazolyl group" means

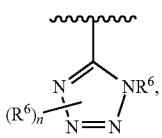

where $R^6$ and n are defined as above for Compounds of Formula I.

The phrase "1-$R^6$-pyrazolyl group" means

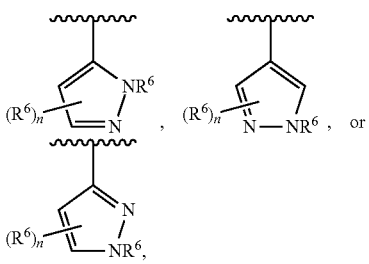

where $R^6$ and n are defined as above for Compounds of Formula I.

The phrase "1-$R^6$-triazolyl group" means

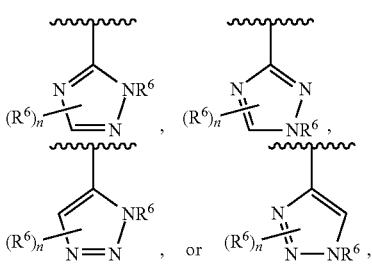

where $R^6$ and n are defined as above for Compounds of Formula I.

The phrase "1-$R^6$-pyrrolyl group" means

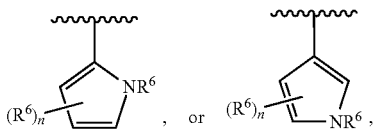

where $R^6$ and n are defined as above for Compounds of Formula I.

The phrase "1,2,5-thiadiazolyl group" means

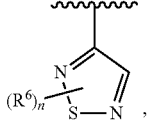

where $R^6$ and n are defined as above for Compounds of Formula I.

The phrase "1,2,3,5-oxatriazolyl group" means

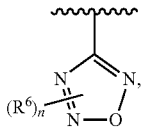

where $R^6$ and n are defined as above for Compounds of Formula I.

The phrase "1,2,3,4-oxatriazolyl group" means

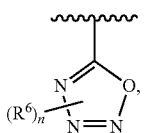

where $R^6$ and n are defined as above for Compounds of Formula I.

A Compound of Formula I can contain one or more asymmetric centers and can thus give rise to enantiomers, diastereomers, and other stereoisomeric forms. Unless specifically otherwise indicated, the disclosure encompasses Compounds with all such possible forms as well as their racemic and resolved forms or any mixture thereof. When a Compound of Formula I contains an olefinic double bond or other center of geometric asymmetry, and unless specifically otherwise indicated, it is intended to include all "geometric isomers", e.g., both E and Z geometric isomers. Unless specifically otherwise indicated, all "tautomers". e.g., ketone-enol, amide-imidic acid, lactam-lactim, enamine-imine, amine-imine, and enamine-enimine tautomers, are intended to be encompassed by the disclosure as well.

As used herein, the terms "stereoisomer", "stereoisomeric form", and the like are general terms for all isomers of individual molecules that differ only in the orientation of their atoms in space. It includes enantiomers and isomers of Compounds with more than one chiral center that are not mirror images of one another ("diastereomers").

The term "chiral center" refers to a carbon atom to which four different groups are attached.

A "chiral" compound as used herein, refers to a compound including at least one chiral center.

An "achiral" compound as used herein, refers to a compound not including a chiral center.

The term "enantiomer" or "enantiomeric" refers to a molecule that is non-superimposable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The phrase "pharmaceutically acceptable derivative", as used herein, includes any pharmaceutically acceptable salt, solvate, radiolabeled, stereoisomer, enantiomer, diastereomer, other stereoisomeric form, racemic mixture, geometric isomer, and/or tautomer, e.g., of a compound of Formula I of the invention. In one embodiment, the pharmaceutically acceptable derivative is a pharmaceutically acceptable salt, solvate, radiolabeled, stereoisomer, enantiomer, diastereomer, other stereoisomeric form, racemic mixture, geometric isomer, and/or tautomer, e.g., of a compound of Formula I of the invention. In another embodiment, the pharmaceutically acceptable derivative is a pharmaceutically acceptable salt, e.g., of a compound of Formula I of the invention.

The phrase "pharmaceutically acceptable salt", as used herein, is any pharmaceutically acceptable salt that can be prepared from a compound of Formula I including a salt formed from an acid and a basic functional group, such as a nitrogen group, of a compound of Formula I. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound of Formula I having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl,N-ethylamine; diethylamine; triethylamine; mono-, bis-, or tris-(2-hydroxy-($C_1$-$C_6$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. One skilled in the art will recognize that, e.g., acid addition salts of a Compound of Formula I can be prepared by reaction of the Compounds with the appropriate acid via a variety of known methods.

Compounds of Formula I encompass all solvates of Compounds of Formula I. "Solvates" are known in the art and are considered to be a combination, physical association and/or solvation of a compound of Formula I with a solvent molecule e.g., a disolvate, monosolvate or hemisolvate when the ratio of the solvent molecule to the molecule of the compound of Formula I is 2:1, 1:1 or 1:2, respectively. This physical association involves varying degrees of ionic and covalent bonding, including hydrogen bonding. In certain instances, the solvate can be isolated, for example, when one or more solvent molecules are incorporated into the crystal lattice of a crystalline solid. Thus, "solvate", as used herein, encompasses both solution-phase and isolatable solvates. A compound of Formula I of the invention may be present as a solvated form with a pharmaceutically acceptable solvent, such as water, methanol, ethanol, and the like, and it is intended that the invention include both solvated and unsolvated compound of Formula I forms. As "hydrate" relates to a particular subgroup of solvates, i.e., where the solvent molecule is water, hydrates are included within the solvates of the invention. Preparation of solvates is known in the art. For example, M. Caira et al., *J. Pharmaceut. Sci.*, 93(3); 601-611 (2004), describes the preparation of solvates of fluconazole with ethyl acetate and with water. Similar preparations of solvates, hemisolvate, hydrates, and the like are described by E. C. van Tonder et al., *AAPS Pharm. Sci. Tech.*, 5(1), article 12 (2004), and A. L. Bingham et al., *Chem. Commun.*, 603-604 (2001). A typical, non-limiting, process involves dissolving the compound of Formula I in a desired amount of the desired solvent (organic, water or mixtures thereof) at temperatures above about 20° C. to about 25° C., cooling the solution at a rate sufficient to form crystals, and isolating the crystals by known methods. e.g., filtration. Analytical techniques, for example, infrared spectroscopy, can be used to show the presence of the solvent in a crystal of the solvate.

In addition, one or more hydrogen, carbon or other atoms of a Compound of Formula I can be replaced by a radioactive isotope of the hydrogen, carbon or other atoms. Such a "radiolabeled", "radiolabeled form", and the like of a Compound of Formula I, each of which is encompassed by the disclosure, is useful as a research and/or diagnostic tool in metabolism pharmacokinetic studies and in binding assays. "Radioactive", as used herein with respect to an atom, means an atom that comprises a radioactive atom and therefore the specific radioactivity thereof is above the background level of radioactivity. Examples of radioactive isotopes that can be incorporated into a Compound of Formula I of the disclosure include isotopes of hydrogen, carbon, nitrogen, oxygen, phosphorous, sulfur, fluorine, chlorine, bromine, and iodine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I, respectively. In one embodiment, a radiolabeled Compound of Formula I contains 1, 2, 3, 4, or more radioactive isotopes, each of which is independently selected from hydrogen, carbon, nitrogen, oxygen, phosphorous, sulfur, fluorine, chlorine, bromine, and iodine. In another embodiment, a radiolabeled Compound of Formula I contains 1 or 2 radioactive isotopes, each of which is independently selected from hydrogen, carbon, nitrogen, oxygen, phosphorous, sulfur, fluorine, chlorine, bromine, and iodine. In another embodiment, a radiolabeled Compound of Formula I contains 1 radioactive isotope which is selected from hydrogen, carbon, nitrogen, oxygen, phosphorous, sulfur, fluorine, chlorine, bromine, and iodine. In another embodiment, a radiolabeled Compound of Formula I contains 1, 2, 3, 4, or more radioactive isotopes, each of which is independently selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Compound of Formula I contains 1 or 2 radioactive isotopes, each of which is independently selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Compound of Formula I contains 1 radioactive isotope which is selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Compound of Formula I contains 1, 2, 3, 4, or more radioactive isotopes, each of which is independently selected from $^2$H, $^3$H, $^{13}$C, $^{14}$C, $^{15}$N, $^{18}$O, $^{32}$P, and $^{125}$I. In another embodiment, a radiolabeled Compound of Formula I contains 1 or 2 radioactive isotopes, each of which is independently selected from $^3$H, $^{14}$C, $^{15}$N, $^{18}$O, $^{32}$P, and $^{125}$I. In another embodiment, a radiolabeled Compound of Formula I contains 1 (one) radioactive isotope which is selected from $^3$H, $^{14}$C, $^{15}$N, $^{18}$O, $^{32}$P, and $^{125}$I.

Radiolabeled Compounds of the disclosure can be prepared by methods known in the art. For example, tritiated Compounds of Formula I can be prepared by introducing tritium into the particular Compound of Formula I, for example, by catalytic dehalogenation with tritium. This method can include reacting a suitably halogen-substituted precursor of a Compound of Formula I with tritium gas in the presence of a suitable catalyst, for example, Pd/C, in the presence or absence of a base. Other suitable methods for preparing tritiated Compounds can be found in Filer, "The Preparation and Characterization of Tritiated Neurochemicals," Chapter 6, pp. 155-192 in *Isotopes in the Physical and Biomedical Sciences, Vol. 1, Labeled Compounds (Part A)* (1987). $^{14}$C-labeled Compounds can be prepared by employing starting materials having a $^{14}$C carbon. Compounds containing piperazine isotopically enriched with $^{13}$C and/or $^{15}$N can be prepared as described in, e.g., FIG. 5A and the associated description, of U.S. Pat. No. 7,355,045 B2.

The term "taxane", "taxanes" or "taxane compound" means a member of the taxane family that is effective against cancer. The anticancer activity of a taxane may be based on the same or similar mechanism of paclitaxel. The exemplary taxane compounds include but are not limited to paclitaxel, docetaxel, nab-paclitaxel, and abraxane and the like. Paclitaxel is preferred.

The term "ruthenium-based compound" or "ruthenium-based compounds" refer to a coordination complex or an organometallic complex of ruthenium which is effective against cancer. Representative examples include, but not limited thereto, NAMI-A (Imidazolium trans-imidazoledimethyl sulfoxide-tetrachlororuthenate), KP1019, (Indazolium trans-[tetrachloridobis(1H-indazole)ruthenate(III)]), RAPTA ([Ru($\eta_6$-arene)Cl$_2$(PTA)], PTA=1,3,5-triaza-7-phosphatricyclo-[3.3.1.1]decane) complexes, and the like.

The term "platinum-based compound" or "platinum-based compounds" refer to a coordination complex or an organometallic complex of platinum which is effective against cancer. Representative examples include, but not limited thereto, cisplatin, oxaliplatin, carboplatin, satraplatin, nedaplatin, and the like.

The phrase "effective amount", when used in connection with another therapeutic agent or a second therapeutic agent means an amount for providing the therapeutic effect of the second therapeutic agent. The phrase "effective amount", when used in connection with a Compound of Formula I means an amount for providing the therapeutic effect of the Compound of Formula I.

As used herein, the terms "cancer" and "cancerous" refer to or describe the physiological condition in a subject, e.g., mammal, in which a population of cells are characterized by unregulated cell growth. "Cancer cells" and "tumor cells" as used herein refer to the total population of cells derived from a tumor including both non-tumorigenic cells, which comprise the bulk of the tumor cell population, and tumorigenic stem cells (cancer stem cells). Examples of cancer include, but are not limited to, carcinoma, lymphoma, blastoma, sarcoma, and leukemia. More particular examples of cancer is selected from the group consisting of breast cancer, head and neck cancer, lung cancer, ovarian cancer, pancreatic cancer, prostate cancer, renal cancer, skin cancer, hepatocellular carcinoma, esophageal cancer, cervical cancer, glioma, bladder cancer, endometrial cancer, bile duct cancer, bone cancer, retinoblastoma, gallbladder cancer, pituitary cancer, rectal cancer, salivary gland cancer, nasal pharyngeal, sarcoma, brain cancer, gastric cancer, multiple myeloma, leukemia, thyroid cancer, and lymphoma, squamous cell cancer, small-cell lung cancer, non-small cell lung cancer, adenocarcinoma of the lung, squamous carcinoma of the lung, cancer of the peritoneum, gastrointestinal cancer, glioblastoma, liver cancer, hepatoma, colon cancer, colorectal cancer, endometrial carcinoma, uterine carcinoma, salivary gland carcinoma, kidney cancer, vulvar cancer, hepatic carcinoma, and various types of head and neck cancer.

"Surgery" means any therapeutic or diagnostic procedure that involves methodical action of the hand or of the hand with an instrument, on the body of a human or other mammal, to produce a curative, remedial, or diagnostic effect.

"Radiation therapy" means exposing a patient to high-energy radiation, including without limitation x-rays, gamma rays, and neutrons. This type of therapy includes without limitation external-beam therapy, internal radiation therapy, implant radiation, brachytherapy, systemic radiation therapy, and radiotherapy.

"Chemotherapy" means the administration of at least one anticancer drug such as, antineoplastic agents, chemotherapeutic agents, chemopreventive agents, and/or other agents to a cancer patient by various methods, including intravenous, oral, intramuscular, intraperitoneal, intravesical, subcutaneous, transdermal, buccal, or inhalation or in the form of a suppository. Chemotherapy may be given prior to surgery to reduce the size of a tumor prior to a surgical procedure to remove it, after surgery or radiation therapy to prevent the growth of any remaining cancer cells in the body.

"Immunotherapy" as used herein refers to a treatment, wherein a part of the own immune system targets cancer cells. Representative examples of immunotherapy include, but not limited to, monoclonal antibody (e.g., inhibitors of PD-1 or PD-L1), Car T-Cell therapy, cancer vaccine, and the like. Treatment that induce cancer cell death in a way that said cancer cells elicit a specific immune response are also referred to as "immunogenic cancer cell death (ICD) inducers". ICD inducers (such as radiation, or oxaliplatin) can activate the immune system through immunogenic signals and further determine the outcome of anticancer therapy. In addition, some chemotherapeutic agents provoke immunogenic cancer cell death (ICD), meaning that they induce tumor cell death in a way that those cells elicit a specific immune response.

The expression "anticancer drug" or "anticancer agent" refers to any chemotherapeutic, immunotherapeutic or immunomodulatory, antiangiogenic, hormonal or naturally occurring, semi-synthetic or synthetic therapeutic drug or agent effective to treat or prevent cancer. Representative examples of anticancer agents are listed above.

"Apoptosis" as used herein, refers to a common form of programmed cell death that can be induced by any signaling pathway associated with cell death via apoptosis (e.g., intrinsic pathway or extrinsic pathway). Characteristics of this form of cell death includes, but not limited to, shrinking of cell body, intact and/or blebbing (zeiosis) of cell membrane, collapse of cytoskeleton before death, dilated endoplasmic reticulum, loss of ribosomes from external membranes, intact mitochondria with release of cytochrome c and ATP synthesis, compact and condensed cytoplasm with intact organelles, and shrinking of nucleus fragmenting.

"Paraptosis" as used herein, refers to a form of non-apoptotic programmed cell death that can be induced by any signaling pathway associated with cell death via paraptosis (e.g., mitogen-activated protein kinase pathway, MAPK). Characteristics of this form of cell death includes, but not limited to, intact cell membrane, collapse of cytoskeleton before cell death, intact lysosome, cytoplasmic vacuolation, mitochondrial swelling without ATP synthesis, and lack of fragmentation of nucleus.

"Methuosis" as used herein, refers to a form of non-apoptotic programmed cell death that can be induced by signaling pathways associated with cell death via methuosis. In certain cancer cells (e.g., glioblastoma and gastric carcinoma cells) methuosis is triggered by constitutive stimulation of Ras signaling pathways. Characteristics of this form of cell death includes, but not limited to, stimulation of macropinocytosis, defects in clathrin-independent endocytic vesicle trafficking, and accumulation of large vacuoles disrupting cellular membrane integrity.

"Tumor" as used herein refers to any mass of tissue that result from excessive cell growth or proliferation, either benign (noncancerous) or malignant (cancerous) including precancerous lesions.

"Metastasis" or "metastatic cancer" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The term "autoimmune disease" or "autoimmune disorder" means a disease or disorder arising from an abnormal immune response directed against an individual's own tissues (i.e. autoimmunity). In a series of diseases, such as rheumatoid arthritis, inflammatory bowel disease, or diabetes, autoimmune disorder is closely associated with an inflammation disorder. Autoimmune disorders may or may not be associated with inflammation. Therefore, certain disorders may be characterized as both autoimmune and inflammatory disorders. Examples of autoimmune disorders include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus. Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, Takayasu arteritis, temporal arteritis/giant cell arteritis, ulcerative colitis, uveitis, vasculitides such as dermatitis herpetiformis vasculitis, vitiligo. Wegener's granulomatosis, and the like.

The term "inflammatory disease" or "inflammatory disorder" generally refers to any disease, condition or disorder associated with inflammation, preferably chronic inflammation. In a series of diseases, such as rheumatoid arthritis, inflammatory bowel disease, or diabetes, inflammation disorder is closely associated with an autoimmune disorder. Inflammation may or may not be caused by an autoimmune disorder. Thus, certain disorders may be characterized as both autoimmune and inflammatory disorders. An inflammatory disorder may arise from pathogens, external injuries (e.g., scrapes), chemical exposition, radiation, or may result from an autoimmune disease including, but not limited to, cystitis, or dermatitis. Examples of inflammatory disorders include, but are not limited to, asthma, encephalitis, inflammatory bowel disease, chronic obstructive pulmonary disease (COPD), allergic disorders, septic shock, pulmonary fibrosis, undifferentiated spondyloarthropathy, undifferentiated arthropathy, arthritis, cachexia, inflammatory osteolysis, and chronic inflammation resulting from chronic viral, bacteria infections, and the like.

The term "fibrotic disorder" or "fibrotic disease" generally refers to any disease, condition or disorder associated with fibrosis (i.e. scarring). Fibrosis means the accumulation of excess fibrous connective tissue in an organ or tissue undergoing a reparative or reactive process. Examples of a fibrotic disorder or fibrotic disease include, but not limited thereto, acute and chronic forms of fibrosis of organs, comprising etiological variations of pulmonary fibrosis (comprising interstitial lung disease and fibrotic lung disease), liver fibrosis, cardiac fibrosis (comprising myocardial fibrosis), kidney fibrosis including chronic renal failure, skin fibrosis (comprising Scleroderma), keloids and hypertrophic Scars, bone marrow fibrosis (comprising myelofibrosis). Further Examples of fibrotic disorders encompass various types of ocular scarring (comprising proliferative vitreoretinopathy and scarring resulting from Surgery to treat cataract or glaucoma), inflammatory bowel disease of variable etiology, macular degeneration, Grave's ophthalmopathy, drug induced ergotism, psoriasis, glioblastoma in Li-Fraumeni Syndrome, Sporadic glioblastoma, myeloid leukemia, acute myelogenous leukemia, myelodysplastic Syndrome, myeloproferative Syndrome, gynecological cancer, Kaposi's Sarcoma, Hansen's disease, collagenous colitis, and the like.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Terms such as "treating" or "treatment" or "to treat" as used herein refer to both 1) therapeutic measures that cure, slow down, lessen symptoms of, and/or halt progression of a diagnosed pathologic condition or disorder, and 2) prophylactic or preventative measures that prevent or slow the development of a targeted pathologic condition or disorder. Thus those in need of treatment include those already with the disorder; those prone to have the disorder; and those in whom the disorder is to be prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer into soft tissue and bone; inhibition of or an absence of tumor metastasis; inhibition or an absence of tumor growth; relief of one or more symptoms associated with the specific cancer; reduced morbidity and mortality; and improvement in quality of life.

As used herein, the term "inhibiting" or "to inhibit" and their grammatical equivalents, when used in the context of a bioactivity, refer to a down-regulation of the bioactivity, which may reduce or eliminate the targeted function, such as the production of a protein or the phosphorylation of a molecule. When used in the context of a disorder or disease, the terms refer to success at preventing the onset of symptoms, alleviating symptoms, or eliminating the disease, condition or disorder.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient.

Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, marmitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

EXAMPLES

In the following, the invention is described with reference to non-limiting Examples. These Examples are provided for the purpose of illustration only, and the invention is not limited to these Examples, but rather encompasses all variations that are evident as a result of the teaching provided herein.

The Compounds of the Invention can be prepared according to the synthetic scheme outlined above and the Examples referring to Methods A and B, respectively, as described in the following. However, the preparation of the Compounds of the Inventions is not limited to these two methods but may vary depending on the chemical and physical properties of the applied N-substituted-4-piperidone and substituted aldehyde, respectively. Therefore, the preparation of the Compounds may require modifications, which are however, within the routine work of a skilled person.

The Examples below demonstrated the efficacy of Compounds of Formula I. or a pharmaceutically acceptable salt thereof, alone or in combination with other anticancer drugs in treating cancer. The potency of Compounds of the Invention to induce radio- and/or chemosensitization in cancer cells, wherein the cancer cells were optionally resistant to radiotherapy or to anticancer drugs was further shown. Synergistic effects of combinations of a Compound of Formula I, or a pharmaceutically acceptable salt thereof, with established anticancer drugs (e.g., cisplatin, or paclitaxel) were demonstrated in different cancer cell lines. The following Examples further illustrated the potent and selective pStat3 inhibition of Compounds of Formula I in various cancer cells in vitro and in vivo. Moreover, in vivo experiments demonstrated an overall prolonged survival of cancer-bearing mice and effective downregulation of the pStat3 levels in tumor sections of treated mice.

Chemical Synthesis and Characterization

Synthesis

Method A. Sodium hydroxide solution (10% in water, 2.0 mL) was added drop wise to the solution of appropriate N-substituted-4-piperidinone (1.0 mmol) and the appropriate aryl aldehyde (2.0 mmol) in ethanol (5.0 mL) at room temperature. The reaction mixture was stirred at room temperature for 16 h. Upon completion of the reaction, the reaction mixture was filtered. The solid was washed with cold ethanol (1.0 mL) followed by water (5.0 mL) and dried in vacuum at 40-45° C.

Method B. The solution of the appropriate N-substituted-4-piperidinone (1.0 mmol) and appropriate aryl aldehyde (2.0 mmol) in glacial acetic acid (3.0 mL) was bubbled with dry hydrogen chloride gas for 20-25 min. The reaction mixture was stirred at room temperature for 16 h and filtered. The solid was washed with cold ethanol (2.0 mL) and then stirred in aqueous sodium carbonate (10%, 10 mL) for 15 minutes and filtered again. The separated solid was washed with water and dried in vacuum at 40-45° C.

Characterization

Melting points (mp) were performed using a Mel-temp instrument and were uncorrected. Infrared (IR) spectra were recorded using a Perkin Elmer Paragon 500 FT-IR instrument. $^1$H NMR spectra were obtained using a Varian Unity Inova 400 MHz instrument. Chemical shifts (δ) were reported at 20° C. in parts per million (ppm) downfield from internal tetramethylsilane (Me$_4$Si). High-resolution mass spectra (HRMS) and low-resolution mass spectra (LRMS) were provided by the Mass Spectrometry Laboratory, University of South Carolina, Columbia. TLC plates (silica gel (60 F$_{254}$) on aluminum) procured from Merck were used to monitor reactions. Visualization was achieved with UV light at 254 nm and/or 366 nm, 12 vapor staining, or ninhydrin spray.

Aqueous solubility of Compounds of the Invention was measured with a modified version of the MultiScreen Solubility Filter Plate protocol (Millipore). This assay was based on the shake-flask equilibrium method and utilizes UV-Vis spectroscopy to quantify the unknown samples. The assay was conducted at room temperature at pH 7.4. Standard curves covering a range from 3.13-500 μM were generated for each compound using a 4:1 mixture of aqueous buffer (45 mM ethanolamine, 45 mM potassium dihydrogen phosphate 45 mM potassium acetate, pH 7.4) to acetonitrile.

Compound of the Invention was dissolved in DMSO, and the final DMSO concentration was 5% (v/v). Each sample was analyzed by UV-Vis spectroscopy at 10 nm increments from 260-600 nm to determine the optimal wavelength for detection and construct standard curves. To measure the aqueous solubility of the Compounds of the Invention, a 500 µM solution of each Compound of the Invention was prepared in aqueous buffer, mixed for 6 h, and briefly centrifuged to pellet any undissolved compound. A 4:1 mixture of supernatant to acetonitrile was added to a 96-well acrylic plate and analyzed by UV-Vis spectroscopy. Drug concentration in the supernatant was determined from the standard curve using the formula; aqueous solubility=$A_{max}$÷slope of standard curve×1.25 (multiplied by 1.25 to correct for acetonitrile dilution).

Example 1

Preparation of 3,5-Di(3-hydroxy-4-methoxylbenzyliden)-1-isopropylpiperidin-4-one (IC-5) according to Method A. Yellow solid (110 mg, 34%), mp=165-168° C., $R_f$=0.42 [ethyl acetate; hexane; methanol (3:1:0.1)]; FT-IR (KBr): ν 3264, 3022, 2968, 2917, 2833, 2804, 1656, 1582, 1548, 1527, 1503, 1462, 1454, 1435, 1364, 1255, 1211, 1177, 1134, 1005, 935, 867, 800; $^1$H NMR (CDCl$_3$): δ 7.69 (s, 2H), 7.01 (d, J=4.0 Hz, 2H), 6.97 (dd, J=4.0, 8.0 Hz, 2H), 6.90 (d, J=8.0 Hz, 2H), 3.94 (s, 6H), 3.87 (s, 4H), 2.95 (m, 1H), 1.08 (d, J=4.0 Hz, 6H); LRMS (E) m/z 409 (M$^+$, 100%).

Example 2

Preparation of 3,5-Di(4-methylbenzylidene)-1-phenylpiperidin-4-one (IE-2) according to Method A. Yellow solid (73 mg, 34%), mp=173-176° C., $R_f$=0.22 [ethyl acetate: hexane (1:9)]; FT-IR (KBr): ν 3020, 2913, 2872, 1668, 1597, 1573, 1498, 1458, 1354, 1239, 1177, 1042, 982, 817; $^1$H NMR (CDCl$_3$): δ 7.85 (s, 2H), 7.33 (d, J=7.7 Hz, 4H), 7.29 (d, J=7.7 Hz, 4H), 7.12 (t, J=7.7 Hz, 2H), 6.78 (t, J=7.7 Hz, 1H), 6.71 (d, J=7.7 Hz, 2H), 4.61 (s, 4H), 2.40 (s, 6H); $^{13}$C NMR (CDCl$_3$): δ 187.3, 149.0, 139.6, 137.5, 132.3, 132.2, 130.5, 129.6, 129.2, 120.1, 116.7, 51.5, 21.5; LRMS (EI) m/z 379 (M$^+$, 100%). HRMS (EI) calcd for C$_{27}$H$_{25}$NO 379,1931. found 379.1936.

Example 3

Preparation of 3,5-Di(4-nitrobenzylidene)-1-phenylpiperidin-4-one (IE-3) according to Method B. Light brown solid (25 mg, 20%), mp=184-188° C., $R_f$=0.19 [ethyl acetate:hexane (2:3)]; FT-IR (KBr): ν 3044, 2929, 1680, 1667, 1613, 1595, 1514, 1493, 1460, 1342, 1260, 1195, 1107, 997, 852; H NMR (DMSO-d6): δ 8.30 (d, J=8.4 Hz, 4H), 7.81 (d, J=8.4 Hz, 4H), 7.79 (s, 2H), 7.06 (t, J=7.7 Hz, 2H), 6.68 (t, J=7.7 Hz, 1H), 6.56 (d. J=7.7 Hz, 2H), 4.72 (s, 4H); $^{13}$C NMR (DMSO-d6): δ 186.8, 148.4, 147.8, 141.3, 136.8, 135.2, 132.1, 129.7, 124.2, 120.0, 116.3, 50.5; LRMS (EI) m/z 441 (M$^+$, 100%). HRMS (EI) calcd for C$_{25}$H$_{19}$N$_3$O$_5$ 441.1322, found 441.1325.

Example 4

Preparation of 3,5-Di(4-methoxybenzylidene)-1-phenylpiperidin-4-one (IE-4) according to Method A. Yellow solid (20 mg, 8.5%), mp=152-155° C., $R_f$=0.21 [ethyl acetate:hexane (1:4)]; FT-IR (KBr): ν 3000, 2960, 2931, 2836, 1662, 1594, 1561, 1493, 1450, 1418, 1299, 1252, 1166, 1024, 975, 828; $^1$H NMR (CDCl$_3$): δ 7.83 (s, 2H), 7.39 (d, J=8.4 Hz, 4H), 7.13 (t, J=8.4 Hz, 2H), 6.97 (d, J=8.4 Hz, 4H), 6.79 (t, J=8.4 Hz, 1H), 6.73 (dd, J=8.4 Hz, 2H), 4.60 (s, 4H), 3.86 (s, 6H); $^{13}$C NMR (CDCl$_3$): δ 187.1, 160.4, 149.1, 137.1, 132.3, 131.2, 129.2, 127.8, 120.1, 116.8, 114.2, 55.4, 51.5; LRMS (EI) m/z 411 (M$^+$, 100%). HRMS (EI) calcd for C$_{27}$H$_{25}$NO$_3$ 411.1833, found 411.1834.

Example 5

Preparation of 3,5-Di(3-hydroxy-4-methoxybenzylidene)-1-phenylpiperidin-4-one (IE-5) according to Method B. Yellow solid (20 mg, 16%), mp=142-146° C., $R_f$=0.21 [ethyl acetate:hexane (2:3)]: FT-R (KBr): ν 3410, 3288, 3020, 2962, 2839, 1649, 1573, 1509, 1440, 1211, 1126, 1016, 995, 866; $^1$H NMR (CDCl$_3$): δ 7.78 (s, 2H), 7.15 (t, J=7.7 Hz, 2H), 7.04 (s, 2H), 6.99 (d, J=8.4 Hz, 2H), 6.93 (d, J=8.4 Hz, 2H), 6.79 (t, J=8.4 Hz 1H), 6.75 (d, J=8.4 Hz, 2H), 4.62 (s, 4H), 3.96 (s, 6H); $^{13}$C NMR (CDCl$_3$): δ 187.2, 149.0, 147.5, 145.5, 137.2, 131.6, 129.2, 128.7, 123.9, 120.0, 116.8, 116.2, 110.6, 56.0, 51.5; LRMS (EI) m/z 443 (M$^+$, 100%). HRMS (EI) calcd for C$_{27}$H$_{25}$NO$_5$ 443.1733, found 443.1733.

Example 6

Preparation of 3,5-Di(4-hydroxy-3-methoxybenzylidene)-1-phenylpiperidin-4-one (IE-6) according to Method B. Orange solid (80 mg, 64%), mp=139-143° C., $R_f$=0.29 [ethyl acetate:hexane (2:3)]; FT-IR (KBr): ν 3508, 3061, 2939, 2835, 1642, 1578, 1552, 1490, 1445, 1377, 1309, 1205, 1131, 1004, 933; $^1$H NMR (DMSO-d6): δ 7.64 (s, 2H), 7.09 (s, 2H), 7.05 (t, J=7.7 Hz, 2H), 7.01 (d, J=8.4 Hz, 2H), 6.89 (d, J=8.4 Hz, 2H), 6.66 (t, J=7.7 Hz, 1H), 6.62 (d, J=7.7 Hz, 2H), 4.68 (s, 4H), 3.81 (s, 6H); $^{13}$C NMR (DMSO-d6): δ 186.4, 149.0, 148.8, 148.0, 137.6, 130.9, 129.6, 126.5, 124.8, 119.5, 116.3, 116.2, 115.4, 56.1, 50.7; LRMS (EI) m/z 443 (M$^+$, 100%). HRMS (EI) calcd for C$_{27}$H$_{25}$NO$_5$ 443.1726, found 443.1733.

Example 7

Preparation of 3,5-Di(3,4-dimethoxybenzylidene)-1-phenylpiperidin-4-one (IE-7) according to Method B. Yellow solid (28 mg, 21%), mp=144-148° C., $R_f$=0.25 [ethyl acetate:hexane (3:7)]; FT-IR (KBr): ν 3020, 2935, 2865, 2837, 1662, 1591, 1573, 1509, 1499, 1467, 1446, 1374, 1352, 1316, 1273, 1243, 1209, 1136, 1017, 846, 811; $^1$H NMR (CDCl$_3$): δ 7.83 (s, 2H), 7.13 (t, J=7.7 Hz, 2H), 7.05 (d, J=8.4 Hz, 2H), 6.96 (s, 2H), 6.95 (d, J=8.4 Hz, 2H), 6.79 (t, J=7.7 Hz, 1H), 6.73 (d, J=7.7 Hz, 2H), 4.64 (s, 4H), 3.94 (s, 6H), 3.92 (s, 6H); $^{13}$C NMR (CDCl$_3$): 187.0, 150.1, 149.0, 148.9, 137.5, 131.4, 129.2, 128.1, 123.8, 120.1, 116.6, 113.7, 111.1, 56.0 (for both OCH$_3$ groups), 51.4; LRMS (EI) m/z 471 (M$^+$, 100%). HRMS (EI) calcd for C$_{29}$H$_{29}$NO$_5$ 471.2033, found 471.2046.

Example 8

Preparation of 3,5-Di(3,4,5-trimethoxybenzylidene)-1-phenylpiperidin-4-one (IE-8) according to Method B. Yellow solid (100 mg, 33%), mp=134-136° C., $R_f$=0.55 [ethyl acetate:hexane (2:3)]; FT-IR (KBr): ν 3473, 3020, 2935, 2834, 1659, 1594, 1577, 1497, 1450, 1415, 1385, 1360, 1241, 1213, 1186, 1120, 1046, 1038, 996, 963, 835; $^1$H NMR (CDCl$_3$): δ 7.82 (s, 2H), 7.16 (t, J=8.0 Hz, 2H), 6.81

(t, J=8.0 Hz, 1H), 6.74 (d, J=8.0 Hz, 2H), 6.66 (s, 4H), 4.67 (s br, 4H), 3.93 (s, 6H), 3.91 (s, 12H); $^{13}$C NMR (CDCl$_3$): δ 186.9, 153.2, 148.7, 139.3, 137.9, 132.3, 130.6, 129.3, 120.2, 116.5, 107.9, 61.0, 56.3, 51.3; LRMS (EI) m/z 531 (M$^+$, 100%). HRMS (EI) calcd for $C_{31}H_{33}NO_7$ 531.2257, found 531.2254. Solubility in aqueous buffer: 200±30 µM.

Biological Assays

Compounds of the Invention were tested according to the following protocols.

Cell Culture

DU145, MDA-MB-468, A549, and the A2780-cisplatin resistant cells (European Collection of Authenticated Cell Cultures, ECACC)) were cultured in a suitable culture medium (Dulbecco's Modified Eagle's Medium—high glucose, RPMI-1640 Medium; Sigma Life Sciences), supplemented with 2 mM Glutamine (L-Glutamine solution 200 mM, sterile filtered; Sigma Life Sciences) and 10% FBS (Fetal Bovine Serum, heat inactivated, sterile filtered; biowest). MDA-MB-435B16, L1210, HT1080, A431, and HCT116 cells were purchased from the American Type Culture Collection (ATCC) and the HCT116-oxaliplatin resistant cells were established at the Institute of Cancer Research, Medical University of Vienna, Austria. In the case of the resistant cells, 1 µM cisplatin and 10 µM oxaliplatin, respectively, was added every 3 passages, to maintain resistance in the respective cell lines. All cells were grown and maintained as adherent monolayer cultures.

For cell spheroid formation, HCT116-oxaliplatin resistant cells, A2780-cisplatin resistant cells, and HT1080 cells were seeded in Corning® Spheroid opaque-walled 96 well Microplates (ultra-low attachment; Nuclon™ Sphera™, Thermofisher) at densities of 2000 cells/well in 100 µl of cell solution and allowed to grow for 4 days, before any manipulation.

Cell Viability Determination for Single Drug Studies (2D)

The following procedures were performed as previously described [Adams, B. K., et al *Bioorg. Med. Chem.* 2004, 12, 3871 Pati, H. N., et al. *Eur. J. Med. Chem.* 2008, 43, 1; Dimmock J. R., et al. *Med, Chem.* 2001, 44, 586; Gregory, M., et al. *Med. Chem. Res.* 2013, 22, 5588; Adams, B. K., et al. *Anticancer Drugs* 2005, 16, 263; Lee, L., et al. *J. Med. Chem.* 2010, 53, 325; Rae, J. M., et al. *Breast Cancer Res. Treat.* 2007, 104, 13].

For studies using B16 and L1210 cell lines, the cells were subjected to a continuous 72 h exposure to a Compound of the Invention and the cytotoxicity was determined using an MTT (3-(4,5-dimethylthiazol-2-yl)-2,5-diphenyltetrazolium; Sigma Life Sciences) assay as described previously.

For cytotoxicity studies with the MDA-MB-435 cell line, cells were determined as previously described using the sulforhodamine B (SRB, acid form; Aldrich Chemistry) assay. Briefly, the cells were plated in 96-well plates at predetermined densities, allowed to adhere for 24 h, and then treated with vehicle (DMSO) or a Compound of the Invention for 48 h. The cells were then fixed, stained with SRB dye, and cell densities determined by absorbance of SRB at 560 nm to construct concentration-response curves. The IC$_{50}$ values were interpolated from these concentration-response curves and represent the mean of 4 independent experiments, with each concentration tested in triplicate.

Celltitre-Glo® 3D Cell Viability Assay

Spheroid cells were treated by adding 100 µl of 2-fold the desired compound concentration and incubated at 37° C. for 96 h. At the end of drug incubation, both the plates and the CellTitre-Glo® reagent (previously thawn overnight in the fridge) were equilibrated at room temperature for at least 30 min. Subsequently, 100 µl of cell solution were carefully removed from each well, without disrupting the spheroid and equal volume of CellTitre-Glo® reagent was added. Cell lysis was performed by vigorously shaking the plate for 5 min. To stabilize the luminescent signal, the plate was incubated in the dark at RT for another 30 min before luminescence was recorded on a plate reader. The cell viability of treated samples was normalised to the untreated controls.

The diameters of spheroid cells were determined using Cell^F Imaging Software. A diameter corresponds to the mean value of one horizontal and one vertical measurement.

Spheroid Invasion Assay

Multicellular spheroids from HT-1080 cells were grown for 4 days in RPMI 1640 medium in 96-well plates (Nunclon Sphera, Thermo Fisher) and their size was measured with an inverted microscope (Olympus CKX41, 4× objective) and Cell^F software. Spheroids of well comparable size (diameter: ca. 500-600 µm; matched pairs with differences in max, diameter<25 µm within each pair) were selected for the spheroid invasion assay. Growth factor reduced Matrigel (Becton Dickinson) was thawed on ice and diluted in 4° C. cold medium to a final concentration of 300 µg/mL with or without IE-8. One hundred fifty microliter of these solutions were added to the wells containing spheroids in 50 µL medium. The plate was incubated in a humidified atmosphere with 5% CO2 in air at 37° C. Both untreated and treated spheroids were monitored simultaneously with a JuliBr live cell analyzer (NanoEntek) for 90 h to visualize spheroid invasion, and every hour the relative cross-sectional area of the spheroids was measured.

Annexin V/PI (Apoptosis Assay)

Cells were seeded in 24-well plates at densities of 10×10$^4$ cells/well (A2780-cisplatin resistant) and 1.6×10$^4$ cells/well (DU145) and allowed to grow at 37° C. overnight prior to treatment. DU145 cells were treated with IE-8 alone or in combination with other anticancer drugs. In one experiment, the cells were treated with IE-8 for 48 h continuously. In the combination treatments, IE-8 and paclitaxel were added at the same time and processed 48 h later. A2780 cis-res cells were either treated with IE-8 for 24 h or were first treated with cisplatin for 1 h and IE-8 was added 4 h later, and left overnight (in the combination experiments). At the end of the drug incubations, the supernatant along with the trypsinised cells were collected in falcon tubes and spun for 3 min at 300 g. Cell pellets were resuspended in PBS and transferred to fresh Eppendorf tubes. After a final round of centrifugation, cell pellets were gently resuspended in 150 µl of a Annexin V-FITC labelled solution in binding buffer (2 µl per 150 µl buffer; Binding buffer: 10 mM Hepes/NaOH, pH 7.4, 140 mM NaCl and 2.5 mM CaCl$_2$) and incubated in the dark at 37° C. for 15 min. Cells were subsequently stained with 150 µl of a 200 mg/mL PI-solution and samples were immediately processed with the flow cytometer. In the utilised Guava programme InCyte, settings were adjusted to achieve optimum separation between live and apoptotic cells. The data were analysed and presented using the FlowJo software.

Electrophoretic Mobility Shift Assay (EMSA)

Nuclear extracts from cells were prepared using the Active Motif Nuclear Extract kit following the manufacturer's protocol, in the presence of protease inhibitor mix (1× Complete; Roche) and phosphatase inhibitor (1× phosSTOP; Roche). Protein concentrations were determined by the Bradford method. 20 µg of nuclear extracted protein were incubated with the indicated concentrations of IE-8 and stattic for 1 h prior to incubation for another hour with $^{32}$P-labeled double-stranded oligonucleotide containing the high-affinity sis-inducible element (hSIE) probe SIE (5'-AGCTTCATTTCCCGTAAATCCCTA-3'; Eurofins MWG Operon) derived from the c-fos gene. Binding reactions contained 0.9 µg poly(dI-dC). Competition assays were performed by adding 100× excess cold SIE oligonucleotide (lane C) and non-specific competitor (lane M: FIRE; 5'-AGCGCCTCCCCGGCCGGGG-3'). The DNA-protein complexes were subjected to electrophoresis and resolved on a 5% non-denaturing polyacrylamide gel (30% acrylamide/Bis solution, Bio-Rad) in 0.5% TBE buffer containing 2.5% glycerol (pH 7.8) at 4° C. for 2 h. Once dried, the radioactive signal of the gel was visualized by exposure to Fuji medical X-ray film.

Immunoblotting

Whole cell lysates were prepared by incubation of harvested, trypsinised cells with CelLytic™ lysis buffer (Sigma-Aldrich) supplemented with 1× protease and 1× phosphatase inhibitors (Roche). Protein quantification was carried out using a protein assay kit (Bio-Rad). 40 µg of the lysates were denatured by heating for 5 min at 95° C. in sample buffer containing 100 mM Tris-Cl (pH 6.8), 4% SDS, 10% 2-mercaptoethanol, 20% glycerol, and 0.02% bromophenol blue. Precision Plus Protein Dual colour standards (Bio-Rad) were used as a molecular weight reference. For the detection of STAT3, pSTAT3, α/β tubulin, cleaved PARP, Bcl-2, Bcl-xL, FANCD2, BRCA1, EME1 and MUS81, proteins were separated on a NuPAGE 7% Tris-acetate gel (Life Technologies) and subsequently transferred to polyvinylidene difluoride membranes (Immobilon®-P transfer membrane; Millipore). Survivin and anti-phospho-histone H2AX proteins were resolved on a 12% Bis-Tris gel. Membranes were blocked for 1 h at ambient temperature in a blocking buffer containing 5% w/v Bovine Serum Albumin (BSA; Sigma-Aldrich) in 1×TBS, 0.1% Tween-20. All proteins were identified by incubation in a 1:1000 dilution of the respective polyclonal antibodies (Cell signaling) in blocking buffer overnight at 4° C. and subsequent incubation for 1 h with an anti-rabbit or anti-mouse secondary antibody (Cell signalling) at a dilution of 1:1000. The α/β tubulin (1:2000; Cell Signaling) and the anti-phospho-histone H2AX Antibody (1:500; Millipore) were used in the denoted dilutions. Antibody binding was visualized by enhanced chemiluminescence (Amersham) on autoradiography film (Kodak-X-Omat). Alternatively Images were captured by the GelDoc-It Imaging System Fusion Fx7 (Vilber Lourmat, Germany).

Trans AM® Stat Family ELISA Assay

The Active Motif TransAMX Stat Family ELISA kit was utilized to study the specificity of IE-8 for Stat3, 20 µg of whole cell extract was used and Stat activity was assessed according to the manufacturer's protocol. Briefly, 30 µl of Complete Binding Buffer (provided and supplemented with 2 µl of 1M DTT and 10 µl of Herring sperm DNA per ml of Binding Buffer AM6) was added to each well used. 20 µl of sample (nuclear extract diluted in Complete Lysis Buffer) per well, were used, while Complete Lysis Buffer (provided and supplemented with 1 µl of 1 M DTT and 10 µl of Protease Inhibitor Cocktail per ml of Lysis Buffer AM1) only, was used for blanks. The plate was sealed with the provided adhesive cover and incubated for 1 hour at room temperature, with mild agitation, on a rocking platform. At the end of incubation, the wells were washed 3 times with 200 µl 1× Wash Buffer (provided). 100 µl of one of the diluted Stat antibodies (1:1000 dilution in 1× Antibody binding buffer for the Stat3, Stat1, Stat5A and Stat5B antibodies) were added to all the used wells. The plate was covered and incubated for 1 hour at room temperature without agitation. The wells were washed 3 times with 200 µl 1× wash buffer. 100 ul of diluted HRP-conjugated antibody (1:1000 dilution in 1× antibody binding buffer) were subsequently added. The plate was once again covered and incubated without agitation for 1 hour at room temperature. During this incubation time, the Developing solution was equilibrated at room temperature. At the end of incubation, the wells were washed 4 times with 200 µl 1× Wash Buffer. 100 µl of room-temperature Developing solution were added to all the used well. The plate was incubated for 10 minutes at room temperature, protected from direct light. 100 µl of Stop solution (provided) were added. Absorbance was read on a spectrophotometer immediately thereafter, at 450 nm, with a reference wavelength of 655 nm.

Immunofluorescence Staining

For Stat3, pStat3 staining, 2.5×10$^4$ cells/ml were plated on 13-mm glass cover slip (VWR) in 24 well plates, allowed to adhere and processed the next day. Cells were treated with IE-8 for 18 h, and subsequently washed in ice cold PBS and fixed with 2% paraformaldehyde PFA (Alfa Aesar) for 10 min at room temperature, followed by permeabilization with PBS containing 0.5% Triton X-100 for 10 min. Cells were blocked in PBS 5% BSA for 1 h at ambient temperature. Respective proteins were identified by incubation for 4 h with anti-Stat3 and anti-pStat3 rabbit polyclonal antibodies (1:1000, Cell signalling) or anti-phospho-Histone H2A.X mouse monoclonal (1:500; Millipore) diluted in a PBS 1% BSA buffer. Cells were incubated with a secondary fluorescent conjugated antibody Alexa Fluor 488 (1:500; Life Technologies) for 2 h at RT. Nuclei were stained using propidium iodide (2 µg/ml; Sigma-Aldrich) and mounted on glass slides with mounting medium (Dako).

Confocal Microscopy

Cell nuclei and protein levels were visualized by confocal microscopy (objective ×40, Leica TCS SP2). Nuclear images were acquired by sequential scanning using the LAS AF Lite programme. In the case of IE-8 detection only, the blue fluorescent agent was excited with a UV-laser (364 nm) and detected using the DAPI filter. PI was excited with the 488 line of an argon-ion laser and detected at 642 nm. The fluorescence of IE-8 was detected and imaged by z-stack acquisition using the Leica SP2 microscope software. In all cases the operating conditions were such that detectable signals of IE-8 could not be obtained for cell samples not treated with drugs.

To quantify γ-H2AX foci from images obtained using the protocol above, the program CellProfiler was utilized. Each cell nucleus was identified and the number of foci within computationally counted. The number of foci was taken as an average from the first 30 cells measured with a detection threshold of 0.3.

Combination Index (CI) Analysis

The software Calcusyn was utilized for analysis of drug interactions using the Chou-Talalay combination index method (Chou, T.-C. Drug Combination Studies and Their Synergy Quantification Using the Chou-Talalay Method. [*Cancer Res.* 70, 440-446 (2010)]

The affected fractions were calculated from the SRB or MTT assay absorbance values and were registered to derive the respective CI values and isobolograms. A CI value of less than 1 (one) indicates synergy.

Sulforhodamine B (SRB) Cell Growth Inhibition Assay for Drug Combination Studies The SRB assay was used to assess cell growth inhibition by IE-8 alone and in combination with cisplatin. Cells were drug treated with IE-8 at 70% confluency for 18 h or 1 h, media was replaced and cells were allowed to grow for 96 h. For combination studies drug treatments were sequential with IE-8 applied first followed by cisplatin for 1 h. After 96 h, cells were fixed with ice cold 10% trichloroacetic acid and stained with 0.4% sulphorhodamine B in 1% acetic acid. After drying plates overnight at room temperature, SRB was resuspended with 10 mM Tris base at pH 10.5. Absorbance was read at 540 nm and results were normalized to untreated controls. For analysis of $GC_{50}$ values and statistical significance, non-linear regression analysis with a comparison of fits was performed with the GraphPad Prism 6.0 software.

Colony Formation Assay for Combination Drug Studies

Clonogenic assay or colony formation assay is an in vitro cell survival assay based on the ability of a single cell to grow into a colony. The colony is defined to consist of at least 50 cells. The assay essentially tests every cell in the population for its ability to undergo "unlimited" division. Clonogenic assay is the method of choice to determine cell reproductive death after treatment with ionizing radiation, but can also be used to determine the effectiveness of other cytotoxic agents. Only a fraction of seeded cells retains the capacity to produce colonies.

DU145 cells were seeded at 1000 cells/well in 6-well plates and allowed to adhere overnight. Cells were treated after seeding with IE-8, paclitaxel, and a combination thereof, and incubated without any further manipulation for 10 days until the control (untreated) wells had <200 colonies formed. Colonies were fixed with ice-cold 100% Methanol, washed with PBS, stained with crystal violet (0.5% w/v) for 5 minutes and counted using a colony-counting function of the Fusion 15.12 software.

HCT116-oxaliplatin res cells were seeded at 2000 cells/well in 6-well plates and allowed to adhere overnight. The next day, oxaliplatin and IE-8 were added simultaneously. First, the specific amount of cells solution was removed from each well and afterwards the same volume of the appropriate drug dilution was added to achieve the right concentration. IE-8 was diluted in DMA. Cells were also treated with Oxaliplatin and IE-8 alone. The plates were left the incubator and the cells were allowed to grow colonies for 10 days. After 10 days the entire cell solution was removed from each well, which was subsequently washed with 500 µl of PBS. 1 ml of cold 100% methanol was added and the plates were incubated for 30 minutes at 4 C. After a second wash, the cells were stained with 1 ml of crystal blue staining dye for 2-3 minutes, rinsed with water, allowed to dry overnight and the colonies were quantified using a gel imaging system (Fusion Fx7) and its in-built colony counter software.

X-Ray Radiation

The X-Ray radiation facility provided an AGO HS MP-1 X-ray machine with a Varian ND1-321 tube used to produce X rays at a dose rate of 1 Gy/min.

Sulphorhodamine B (SRB) Growth Inhibition Assay for Radiosensitization

Stock cultures were trypsinised and 2500 cells were seeded into each well of 96-well, flat-bottomed microtiter plates, in a volume of 200 µl and left to adhere overnight at 37° C. The desired concentrations of IE-8 or curcumin were prepared in culture medium immediately before use. Medium in wells was removed and 200 µl of drug medium mixture was added. Three replicates were used for each drug concentration. One solvent control lane was included in each experiment. Plates were incubated for 18 h at 37° C. At the end of the drug treatment, the media was replaced with 200 µl of fresh media. Subsequently the plates were irradiated at 0, 2, 4 and 6 Gy. The plates were incubated for three days in a humidified incubator at 37° C. with 5% $CO_2$. The media in the wells was removed and 100 µl of ice-cold 10% (wt/vol) trichloroethanoic acid (TCA) was added per well, to fix the cells. The plates were then incubated at 4° C. for 20 minutes and were subsequently washed four times with tap water. Cells were stained with 100 µl of 0.4% (wt/vol) SRB in 1% acetic acid, per well, to allow visualization of cellular proteins, for 20 minutes at room temperature. Unbound dye was removed by washing five times with 1% acetic, and plates were left to dry overnight at room temperature. The next day, the dye was solubilized by the addition of 100 µl of 10 mM Tris base into each well. Plates were left at room temperature for 20 minutes, and the optical density (OD) at 540 nm was determined using a microplate reader (Thermo). Growth inhibition was expressed as the fraction of control A540 (surviving fraction) and calculated from the following equation; fraction of control A540=OD of untreated control at each radiation dose. The mean surviving fraction for each drug concentration for each radiation dose was calculated. Dose response curves were platted and the IC50 values, i.e. the drug concentration required to produce 50% of the OD of the untreated control, were determined from the respective curves.

Colony Formation Assay for Radiosensitization

Stock cultures were trypsinised and $2.5 \times 10^4$ cells were seeded into 6-well plates and incubated at 37° C. for 24-48 hours. When cells reached 700% confluency, they were treated with IE-8 (0, 0.8, 1, and 1.2 µM) for 18 hours. After drug treatment, cells were harvested by trypsinisation and re-seeded. After 3 hours, cells were irradiated with 0, 2, 4, 5 or 8 Gy. Plates were then incubated for 14 days at 37° C. with 5% $CO_2$. After this incubation, plates were washed with tap water and fixed. Colonies were stained for 30 minutes at room temperature with 1% (w/v) crystal violet (Sigma-Aldrich) in 10% ethanol, and subsequently dried overnight at room temperature. Colonies consisting of at least 50 cells were counted for each treatment. The number of colonies in unirradiated wells was used to determine the plating efficiency (number of colonies/number of cells seeded). The following formula was used to calculate survival fraction:

$$\text{Survival Fraction} = \frac{\text{Number of colonies}}{\text{Number of cells seeded} \times \text{Plating efficiency}}$$

Modified Single Cell Gel Electrophoresis (Comet)

The following procedure for the modified single-cell gel electrophoresis (comet) assay [Hartley. J. M., et al. *Drug-DNA Interact. Protoc. Methods Mol. Biol.* 2010, 613, 267] was applied to measure DNA interstrand crosslinking (ICL) induced by platinum drug in DU145 and A549 cells. Exponentially growing cells were treated for 1 h with different concentrations of cisplatin and collected after 0, 9, 24 and 48 h. All procedures were carried out on ice. Cells were diluted to a final concentration of $2.5 \times 10^4$ cells/ml and irradiated with X-ray (15 Gy) in order to deliver a fixed number of random DNA strand breaks (except for the untreated unirradiated control). Cells were embedded in 1% agarose on a precoated microscope slide, and each sample was prepared in duplicate. In subdued light, cells were lysed for 1 h in lysis buffer (100 mM disodium EDTA, 2.5 M NaCl, 10 mM Tris-HCl pH 10.5 and 1% Triton X-100 added at use) and then washed four times in distilled water every 15 min. Slides were incubated in alkali buffer (50 mM NaOH, 1 mM disodium EDTA, pH 12.5) for 45 min followed by electrophoresis in the same buffer for 25 min at 18 V (0.6 V/cm), 250 mA. Finally, the slides were rinsed in neutralising buffer (0.5 M Tris-HCl, pH 7.5) then in saline and allowed to dry overnight at room temperature. Re-hydrated slides were stained with propidium iodide (2.5 mg/ml) for 30 min, rinsed in distilled water and oven-dried. Images were visualised using a NIKON inverted microscope (Chiyoda, Tokyo, Japan) with high-pressure mercury light source, 510-560 nm excitation filter and 590 nm barrier filter at 20× magnification. Images were captured using an on-line CCD camera and analysed using the Komet Analysis software 4.02 (Andor Technology, Belfast, UK). For each duplicate slide. 25 cells were analysed. The tail moment for each image was calculated as the product of the percentage of DNA in the comet tail and the distance between the means of the head and tail distributions (Olive P. L., et al, *Radiat Res* 122, 86). DNA ICL after drug treatment was expressed as the percentage decrease in tail moment compared with irradiated controls calculated by the formula:

% Decrease in tail moment=[1−(TMdi−TMcu/Tci−TMcu)]×100 where TMdi=tail moment of drug-treated irradiated sample; TMcu=tail moment of untreated, unirradiated control; and TMci=tail moment of untreated, irradiated control.

The following procedure for the modified single-cell gel electrophoresis (comet) assay[Hartley, J. M., et al. *Drug-DNA Interact. Protoc. Methods Mol. Biol.* 2010, 613, 267] was applied to measure DNA interstrand crosslinking (ICL) induced by platinum drug in A2780cisplatin resistant and A2780 parental cells. Cells were seeded in 6-well plates at densities of $8\times10^1$ cells/well (A2780 cis-res) and $5\times10^5$ cells/well (A2780 parental) and left to adhere overnight at 37° C. The next day, cells were treated with cisplatin for 1 h and incubated in drug-free medium for up to 48 h. When required, IE-8 was added 3 h past the cisplatin incubation. At every experimental point, the corresponding sample was treated with 1.5 μM MMS (Methyl methanesulfonate) in serum-free media for 30 min. After removal of the MMS solution, cells were trypsinised and collected by centrifugation at 300 g. Cell pellets were resuspended in 2 ml of freezing mix and stored at −80° C. until further processing. The day before conducting the Comet assay, all buffers were prepared fresh and stored at 4° C. overnight. The next day, cells were thawed, washed, resuspended in 3 ml serum-free media and counted. Cells were diluted to a final volume of 200 μl.

50 ml of 0.8% (w/v) low-melting agarose in MilliQ water were prepared by heating up until a homogenous solution was obtained. The solution was then allowed to cool down and kept in a 50° C. water bath. To each cell suspension, 400 μl of agarose were added and the suspension was briefly mixed by pipetting. 200 μl of that mixture were spotted twice on a pre-coated microscope slide and quickly covered with square cover slips. The microscope slides were placed on ice until the agarose solution fully set. Cover slips were gently removed and slides were placed in a container (kept on ice) and lysed for 1 h with 495 ml cold lysis buffer plus 5 ml Triton X-100, in the dark. Afterwards, slides were washed 4 times, for 15 min each time, with 250 ml of cold water and then transferred to the electrophoresis gel tank. There, the slides were incubated with 31 of cold alkali buffer for 45 min in the dark, followed by electrophoresis at 22 V (172 mA) for 30 min. Upon completion of the electrophoresis, slides were placed on a rack and washed twice with 1 ml neutralisation buffer. After a final wash with PBS, slides were left to dry overnight. The next day, slides were rehydrated with 2 ml of water, left for at least 30 min and stained with a 2.5 μg/ml PI solution for 15 min in the dark. Afterwards, they were washed twice with water and left once again to dry. To visualise the stained DNA, a fluorescence microscope was used. 50 comets per slide were randomly selected (scanning the whole slide area) and scored with the Comet Assay IV programme. Results were expressed as Tail moment values, as derived by the programme.

RT-PCR

After drug-treatment cells were harvested by trypsinisation followed by centrifugation. Cell pellets were washed in PBS before RNA extraction using the RNeasy Plus Mini-kit (Qiagen). 1 μg RNA was used for cDNA generation using the High Capacity cDNA Reverse Transcription Kit (Life Technologies). TaqMan Gene Expression Assays (Life Technologies) for FANCD2, BRCA1, EME1 and MUS81 were used to quantify changes in gene expression. Primer/probe mixes were diluted 1:10 with TaqMan 2× Universal PCR Mastermix (Life Technologies) and 50 ng cDNA per reaction used. PCR was performed using an Applied Biosystems 7500 RT-PCR machine with 10 minutes at 95° C. followed by 45 cycles of 95° C./60° C. for 15 seconds and 1 minute respectively. Fold change was calculated using the comparative CT method normalizing to GAPDH expression.

Wound Healing Assay

DU145 cells were seeded in 6-well cell culture plates with Dulbecco's modified Eagle's medium/high glucose containing 10% FBS. After the cells reached 100% confluence, the monolayer was scratched using a 10-ml pipette tip and washed once with PBS, to remove non-adherent cells. Cells had been pre-treated with DMSO, 1 μM IE-8, and 5 μM Stattic in culture medium for 16 hours. After drug incubation and wound induction, the medium was replaced with fresh drug-free medium and cells were observed under the microscope at the denoted time points.

In Vivo Survival Experiment

Six- to eight-week old female Balb/c mice (weighing about 20 g) were purchased from the Harlan Laboratories, San Pietro al Natisone, Italy. The animals were kept in a pathogen-free environment, and every procedure was done in a laminar airflow cabinet. HCT16-oxaliplatin resistant cells ($5\times10^5$) were injected subcutaneously into the right flank of female Balb/c mice. The animals were treated with IE-8 intraperitoneally (30 mg kg-1; solutions freshly prepared in the standard mixture of 1% DMSO, Cremophor, Ethanol and $H_2O$) on days 10, 13 and 17. The animals were controlled for distress development every day. No body weight loss was observed during the course of the experiment. Control and treatment group n=4.

Immunohistochemistry for In Vivo Survival Experiment

Mice were treated as described in the survival experiments but were sacrificed 24 h post administration of the compound or vehicle, intraperitoneally.

Live Cell Microscopy $5\times10^4$ DU145 cells were seeded in 8-well chamber slides (Ibidi, Martinsried, Germany). After 24 h, cells were treated with the denoted concentration (μM) IE-8 and intracellular drug accumulation was imaged at 3 h intervals on a live cell microscope (Visitron Systems, Puchheim, Germany) using a 40× oil immersion DIC objective and VisiView® software.

LEDs were used for widefield DIC and fluorescence (436/20 nm excitation and 480/40 nm bandpass filter for (CFP) fluorescence illumination (Visitron Systems). Images were taken with a sCMOS 4.2MPxl digital camera.

Example 9

Identification of Compounds of the Invention as potent anticancer drugs. The cytotoxicity of numerous Compounds of the Invention was evaluated in vitro with the MTT assay in murine B16 (melanoma) and L1210 (lymphoma) cells after 72 h exposure (Table 1). Several Compounds, IA-8, IB-8, ID-8, and IE-8, were further evaluated for their antiproliferative activity against the human breast melanoma cell line, MDA-MB-435 (Table 2). Compound IA-8 was the most potent with the lowest $IC_{50}$ value of 0.088 μM, followed IE-8 (0.15 μM), IB-8 (0.19 μM), and ID-8 (0.76 μM). Because of its favorable aqueous solubility, Compound IE-8 was selected over analog IA-8 for further biological evaluation. The concentration that inhibited cell growth by 50% ($IC_{50}$, μM) was determined for the respective Compound from three independent experiments, and the mean values are presented in Tables 1 and 2.

TABLE 1

Antiproliferative Effects of numerous Compounds of Invention against B16 and L1210 cancer cell lines.

| Compound | Structure | $IC_{50}$ (μM) B16 | L1210 |
|---|---|---|---|
| IA-1 | 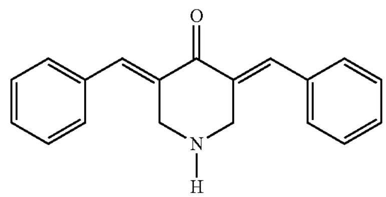 [SMILES: O=C1/C(=C/c2ccccc2)CNC/C1=C\c1ccccc1] | 5.0 ± 1.0 | 0.5 ± 0.2 |
| IA-2 | 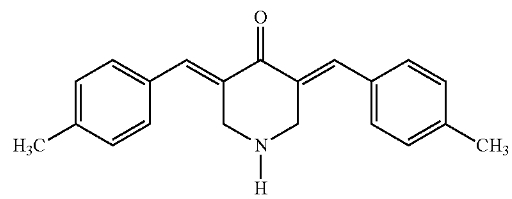 [SMILES: O=C1/C(=C/c2ccc([N+](=O)[O-])cc2)CNC/C1=C\c1ccc([N+](=O)[O-])cc1] | 8.0 ± 4.0 | 3.1 ± 0.1 |
| IA-3 | 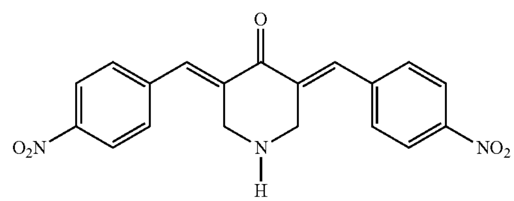 | 15.0 ± 7.0 | 0.3 ± 0.1 |
| IA-4 | 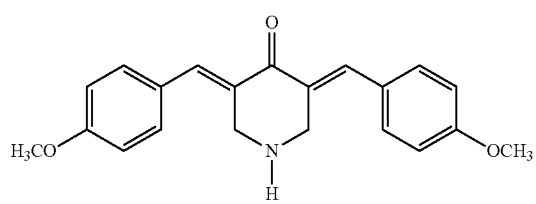 [SMILES: COc1ccc(/C=C2\CNC/C(=C\c3ccc(OC)cc3)C2=O)cc1] | 43.0 ± 1.0 | 35.0 ± 8.0 |
| IA-5 | 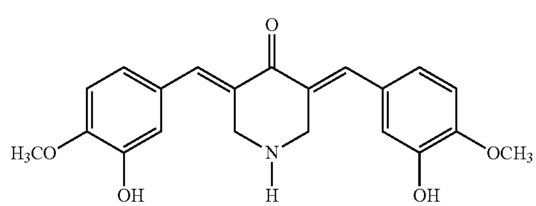 [SMILES: COc1ccc(/C=C2\CNC/C(=C\c3ccc(OC)c(O)c3)C2=O)cc1O] | 3.0 ± 1.0 | 0.9 ± 0.3 |
| IA-6 | 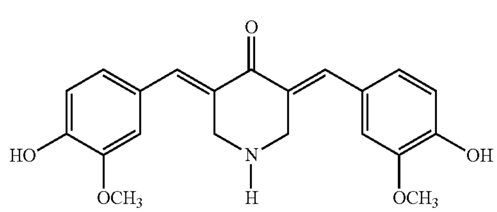 [SMILES: COc1cc(/C=C2\CNC/C(=C\c3ccc(O)c(OC)c3)C2=O)ccc1O] | 1.3 ± 0.6 | 0.9 ± 0.4 |

TABLE 1-continued

Antiproliferative Effects of numerous Compounds of Invention against B16 and L1210 cancer cell lines.

| Compound | Structure | IC$_{50}$ (μM) B16 | L1210 |
|---|---|---|---|
| IA-7 | 3,4-dimethoxybenzylidene on each side of N-H piperidin-4-one | 2.3 ± 0.5 | 0.6 ± 0.2 |
| IA-8 | 3,4,5-trimethoxybenzylidene on each side of N-H piperidin-4-one | 0.30 ± 0.15 | 0.32 ± 0.01 |
| IB-1 | benzylidene on each side of N-CH$_3$ piperidin-4-one | 5.0 ± 2.0 | 2.4 ± 0.3 |
| IB-2 | 4-methylbenzylidene on each side of N-H piperidin-4-one | 41.0 ± 6.0 | 35.0 ± 5.0 |
| IB-3 | 4-nitrobenzylidene on each side of N-CH$_3$ piperidin-4-one | 41.0 ± 2.0 | 1.3 ± 0.15 |
| IB-4 | 4-methoxybenzylidene on each side of N-CH$_3$ piperidin-4-one | 23 ± 14 | 62.0 ± 1.0 |
| IB-5 | 3-hydroxy-4-methoxybenzylidene on each side of N-CH$_3$ piperidin-4-one | 2.1 ± 0.1 | 0.8 ± 0.4 |

TABLE 1-continued

Antiproliferative Effects of numerous Compounds of Invention against B16 and L1210 cancer cell lines.

| Compound | Structure | IC$_{50}$ (μM) B16 | L1210 |
|---|---|---|---|
| IB-6 | 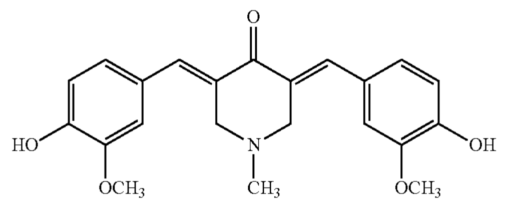 [SMILES: COc1cc(/C=C2\CN(C)C/C(=C\c3ccc(O)c(OC)c3)C2=O)ccc1O] | 1.8 ± 0.3 | 1.9 ± 0.4 |
| IB-7 | 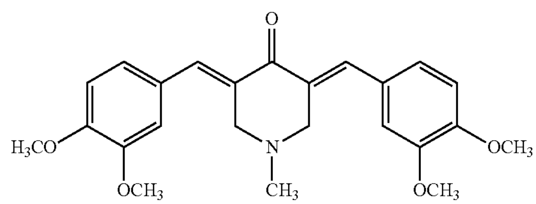 [SMILES: COc1ccc(/C=C2\CN(C)C/C(=C\c3ccc(OC)c(OC)c3)C2=O)cc1OC] | 1.3 ± 0.1 | 1.0 ± 0.6 |
| IB-8 | 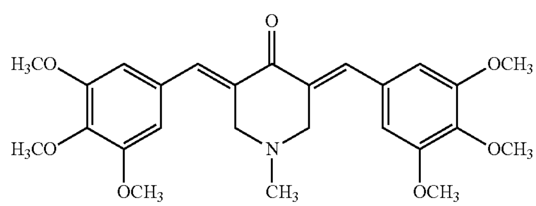 [SMILES: COc1cc(/C=C2\CN(C)C/C(=C\c3cc(OC)c(OC)c(OC)c3)C2=O)cc(OC)c1OC] | 0.31 ± 0.02 | 0.37 ± 0.10 |
| IC-1 | 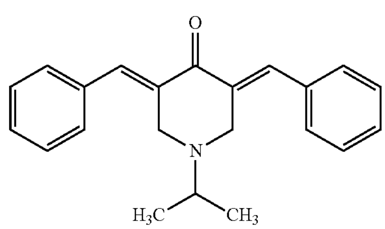 [SMILES: CC(C)N1C/C(=C\c2ccccc2)C(=O)/C(=C/c2ccccc2)C1] | 2.3 ± 0.3 | 3.1 ± 0.1 |
| IC-2 | 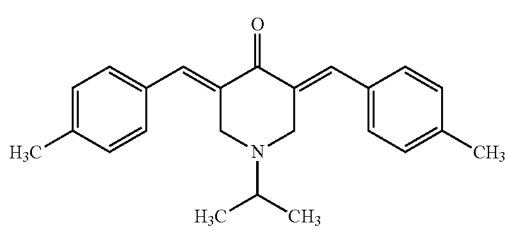 | 4.0 ± 2.0 | 2.5 ± 0.7 |
| IC-3 | 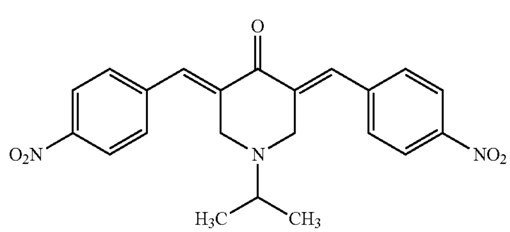 [SMILES: CC(C)N1C/C(=C\c2ccc([N+](=O)[O-])cc2)C(=O)/C(=C/c2ccc([N+](=O)[O-])cc2)C1] | 3.7 ± 0.6 | 0.9 ± 0.6 |

TABLE 1-continued

Antiproliferative Effects of numerous Compounds of Invention against B16 and L1210 cancer cell lines.

| Compound | Structure | IC$_{50}$ (μM) B16 | IC$_{50}$ (μM) L1210 |
|---|---|---|---|
| IC-4 | | 6.0 ± 2.0 | 3.8 ± 0.3 |
| IC-5 | | 1.1 ± 0.4 | 0.4 ± 0.1 |
| IC-6 | | 2.2 ± 0.2 | 2.2 ± 0.2 |
| IC-7 | | 2.4 ± 0.4 | 2.2 ± 0.2 |
| IC-8 | | 25.6 ± 12.5 | 47.0 ± 11.0 |
| ID-1 | | 3.1 ± 0.1 | 3.4 ± 0.5 |

TABLE 1-continued

Antiproliferative Effects of numerous Compounds of Invention against B16 and L1210 cancer cell lines.

| Compound | Structure | IC$_{50}$ (μM) | |
| --- | --- | --- | --- |
| | | B16 | L1210 |
| ID-2 | [3,5-bis(4-methylbenzylidene)-1-benzyl-4-piperidone] | 14.0 ± 4.0 | 9.0 ± 5.0 |
| ID-3 | [3,5-bis(4-nitrobenzylidene)-1-benzyl-4-piperidone] | 2.5 ± 0.7 | 2.0 ± 1.0 |
| ID-4 | [3,5-bis(4-methoxybenzylidene)-1-benzyl-4-piperidone] | 27 ± 9 | 8.0 ± 4.0 |
| ID-5 | [3,5-bis(3-hydroxy-4-methoxybenzylidene)-1-benzyl-4-piperidone] | 2.4 ± 0.5 | 3.1 ± 0.1 |
| ID-6 | [3,5-bis(4-hydroxy-3-methoxybenzylidene)-1-benzyl-4-piperidone] | 2.0 ± 0.5 | 2.8 ± 0.4 |

TABLE 1-continued

Antiproliferative Effects of numerous Compounds of Invention against B16 and L1210 cancer cell lines.

| Compound | Structure | IC$_{50}$ (μM) B16 | IC$_{50}$ (μM) L1210 |
|---|---|---|---|
| ID-7 | [3,5-bis(3,4-dimethoxybenzylidene)-1-benzylpiperidin-4-one] | 2.0 ± 0.4 | 3.3 ± 0.1 |
| ID-8 | [3,5-bis(3,4,5-trimethoxybenzylidene)-1-benzylpiperidin-4-one] | 2.4 ± 0.6 | 3.6 ± 2.1 |
| IE-1 | [3,5-dibenzylidene-1-phenylpiperidin-4-one] | 7.0 ± 4.0 | 4.0 ± 2.0 |
| IE-2 | [3,5-bis(4-methylbenzylidene)-1-phenylpiperidin-4-one] | >100 | >100 |
| IE-3 | [3,5-bis(4-nitrobenzylidene)-1-phenylpiperidin-4-one] | 65.0 ± 7.0 | 65.0 ± 7.0 |

TABLE 1-continued

Antiproliferative Effects of numerous Compounds of Invention against B16 and L1210 cancer cell lines.

| Compound | Structure | IC$_{50}$ (μM) B16 | IC$_{50}$ (μM) L1210 |
|---|---|---|---|
| IE-4 | (structure: 3,5-bis(4-methoxybenzylidene)-1-phenylpiperidin-4-one) | 37.0 ± 6.0 | 55.0 ± 7.0 |
| IE-5 | (structure: 3,5-bis(3-hydroxy-4-methoxybenzylidene)-1-phenylpiperidin-4-one) | 19.0 ± 2.0 | 6.0 ± 4.0 |
| IE-6 | (structure: 3,5-bis(4-hydroxy-3-methoxybenzylidene)-1-phenylpiperidin-4-one) | 2.9 ± 0.4 | 2.8 ± 0.4 |
| IE-7 | (structure: 3,5-bis(3,4-dimethoxybenzylidene)-1-phenylpiperidin-4-one) | 1.3 ± 0.1 | 2.9 ± 0.9 |
| IE-8 | (structure: 3,5-bis(3,4,5-trimethoxybenzylidene)-1-phenylpiperidin-4-one) | 0.30 ± 0.03 | 0.36 ± 0.03 |

TABLE 2

Antiproliferative Effects of selected Compounds
of Invention against MDA-MB-435 cancer cell line.

| Compound | IC$_{50}$ (µM) |
| --- | --- |
| IA-8 | 0.088 |
| IB-8 | 0.19 |
| ID-8 | 0.76 |
| IE-8 | 0.15 |

Example 10

Figure 1A:
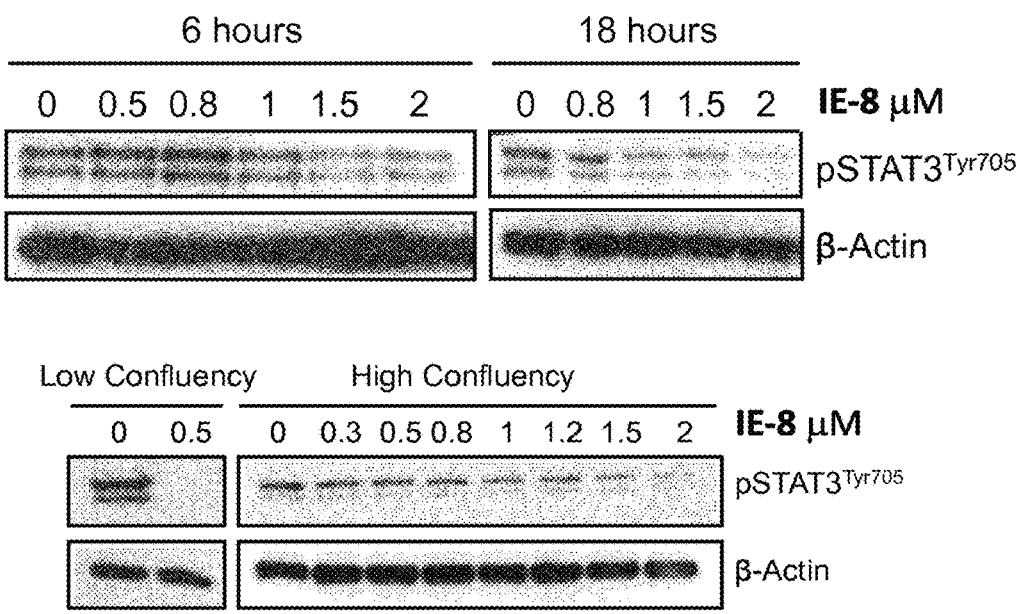
FIG. 1A shows immunoblots showing that the inhibition of pStat3$^{Tyr705}$ in DU145 cells by IE-8 is dependent upon the duration of treatment and the confluency of cells at the time of treatment, with an inverse relationship between confluency and the inhibitory effect of IE-8.
Figure 1B:
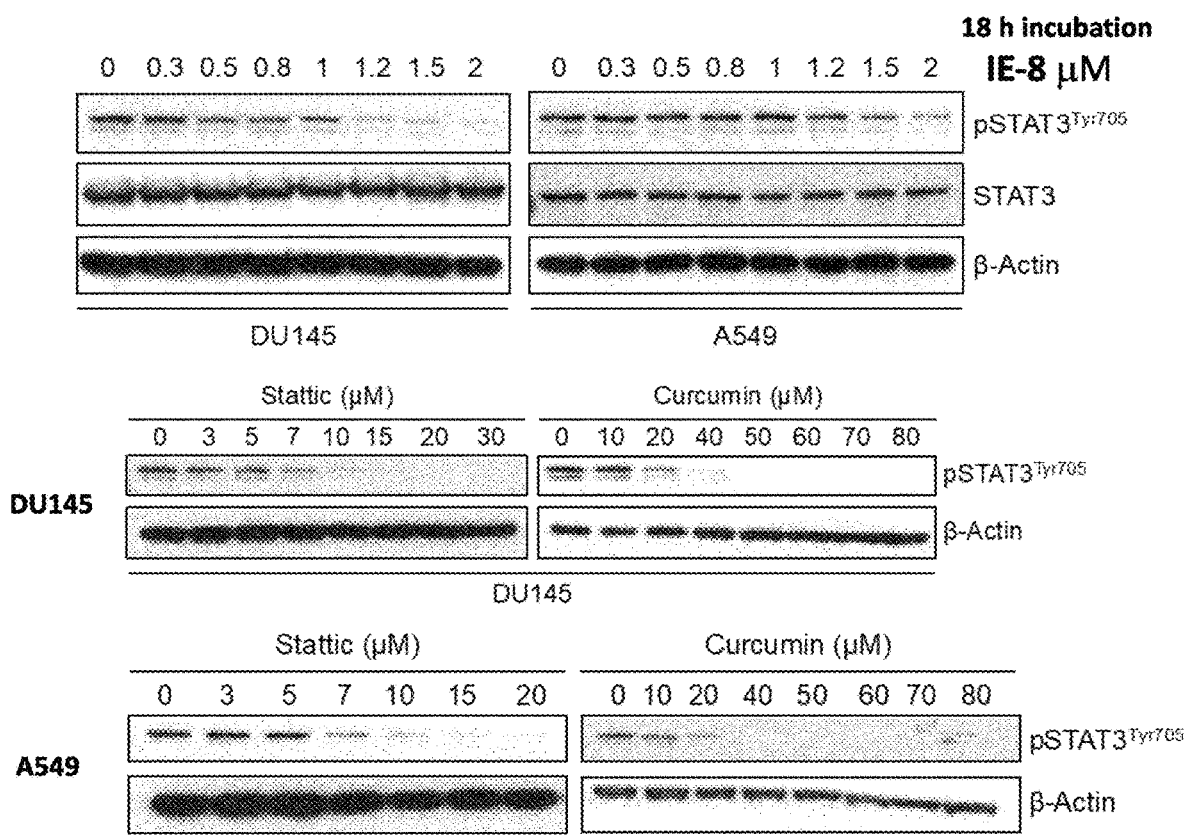
FIG. 1B shows in the top panel: Upon 18 h drug treatment of DU145 and A549 cancer cells, respectively, IE-8 inhibits pStat3$^{Tyr705}$ levels without affecting the total Stat3 levels. Middle and bottom panels: stattic and curcumin also inhibit pStat3$^{Tyr705}$ in the DU145 and A549 cell lines but much higher doses are required, compared to IE-8.
Figure 1C:
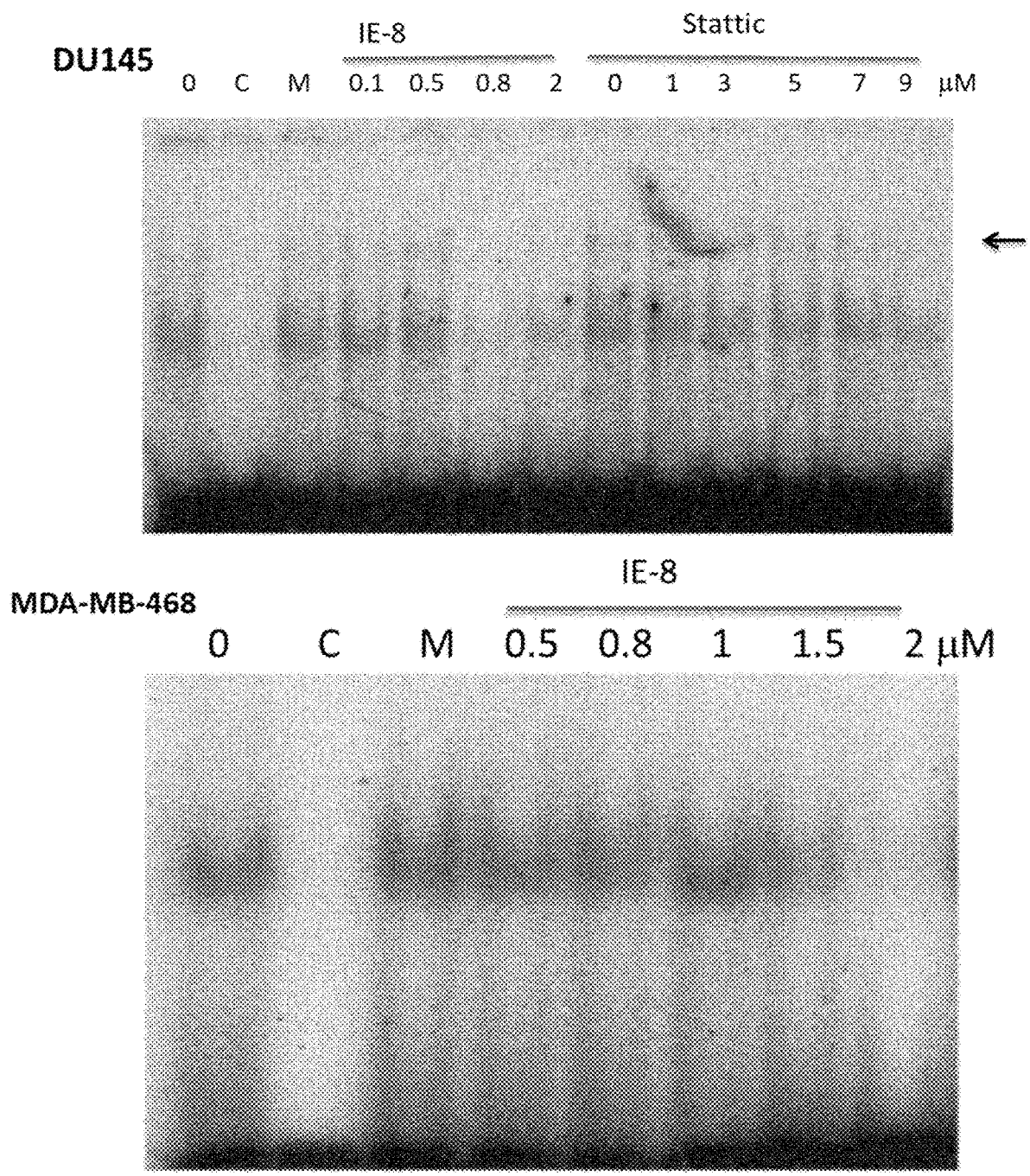
FIG. 1C shows an electrophoretic mobility shift assay (EMSA) showing the inhibition of Stat3 binding to its consensus DNA binding motif: high affinity sis-inducible element (hSIE) derived from the c-fos gene promoter, employing nuclear extracts from DU145 cells (top) and MDA-MB-468 (bottom) cells.
Figure 2A:
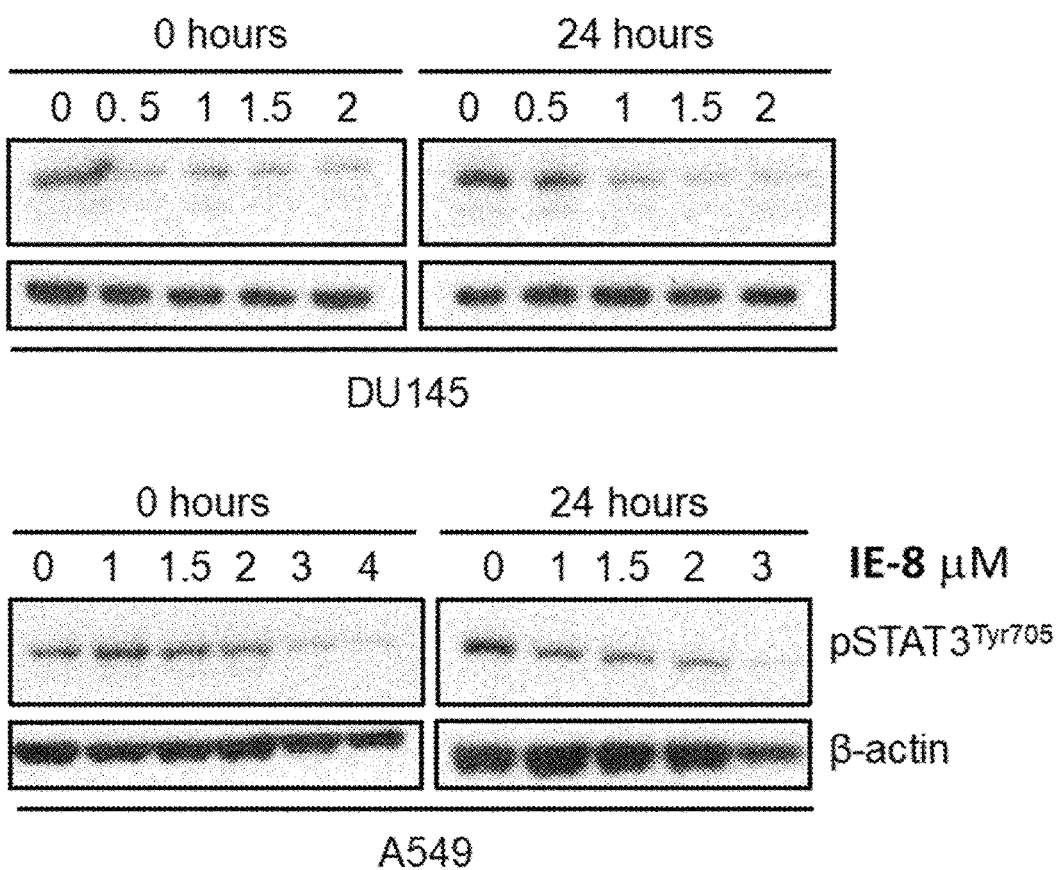
FIG. 2A shows immunoblots showing that in both DU145 (top) and A549 (bottom) cells, an 18 h treatment with IE-8 effectively inhibits pStat3$^{Tyr705}$ levels (0 hours) and this inhibition persists for at least 24 h post drug removal (24 hours).
Figure 2B:
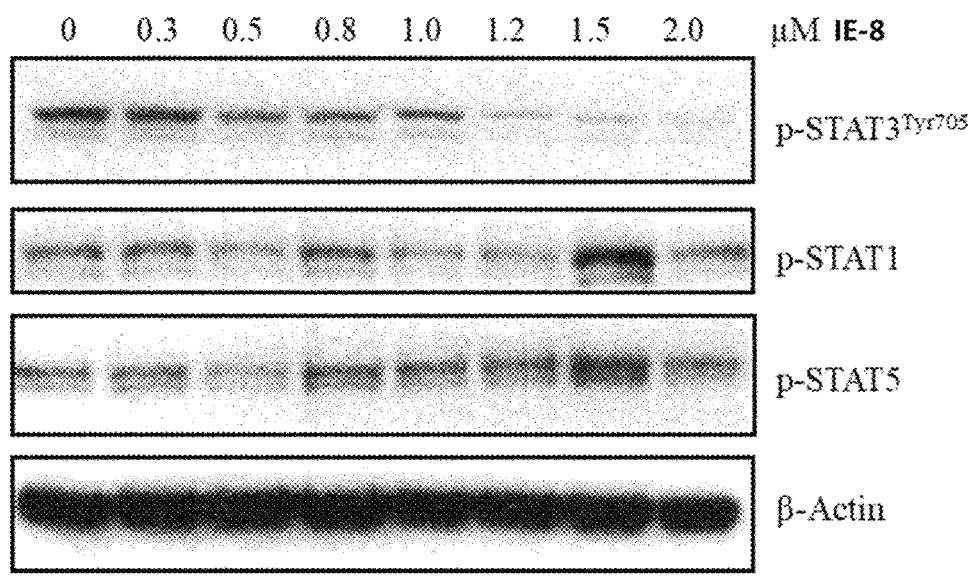
FIG. 2B shows that IE-8 selectively inhibits pStat3$^{Tyr705}$ without inhibiting pStat1$^{Tyr701}$ or pStat5$^{Tyr694}$ in DU145 cells, as determined by immunoblotting following an 18 h treatment with IE-8.
Figure 2C:
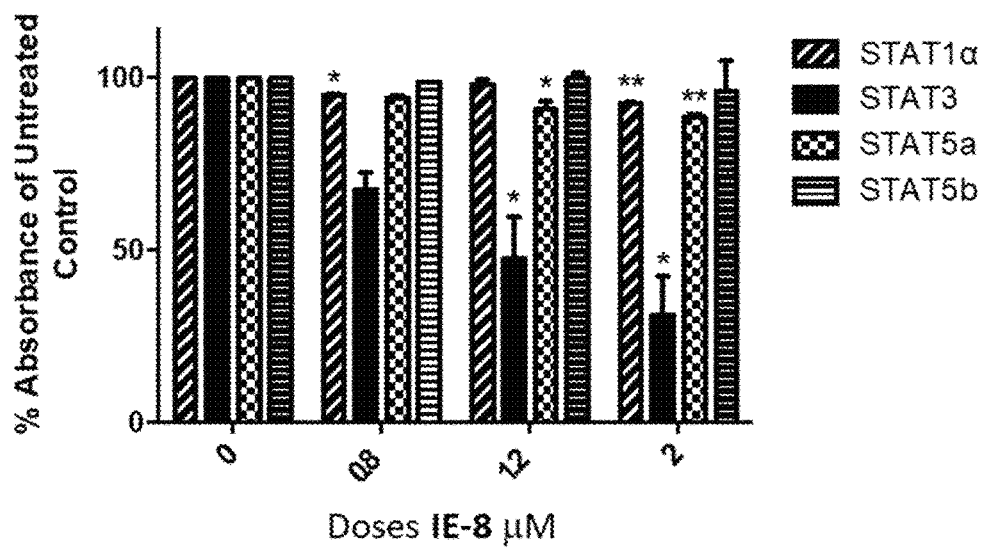
FIG. 2C shows that an 18 h treatment of DU145 cells with IE-8 was shown to selectively inhibit the Stat3-DNA binding activity over that of Stat1α, Stat5a and Stat5b using the TransAM STAT Family ELISA assay.

IE-8 efficiently inhibited pStat3 in DU145 and A549 cancer cells. The effect of Compound IE-8 on Stat3 phosphorylation was examined in the DU145 and A549 cancer cell lines. Compound IE-8 efficiently inhibited the tyrosine (705) phosphorylation for activation of Stat3 in a dose, cell-density and time-dependent manner, in vitro, in cancer cells harboring constitutively active Stat3 (FIG. 1A). Compound IE-8 was more potent at inhibiting pSTAT3 in cells with persistent Stat3 activation (at concentrations >1 µM) than curcumin and stattic (FIG. 1B). It also blocked the Stat3-DNA binding activity at concentrations as low as 0.8 µM in DU145 nuclear extracts, and in MDA-MB-468 nuclear extracts, and did so—in the former extracts—more efficiently than stattic (FIG. 1C). The inhibition of pStat3 by IE-8 persisted for at least 24 h post treatment (FIG. 2A) and was selective for Stat3 over Stat1, Stat5a, and Stat5b which remained largely unaffected, as shown by both immunoblotting and an ELISA assay (FIG. 2B).

Example 11

Figure 3A:
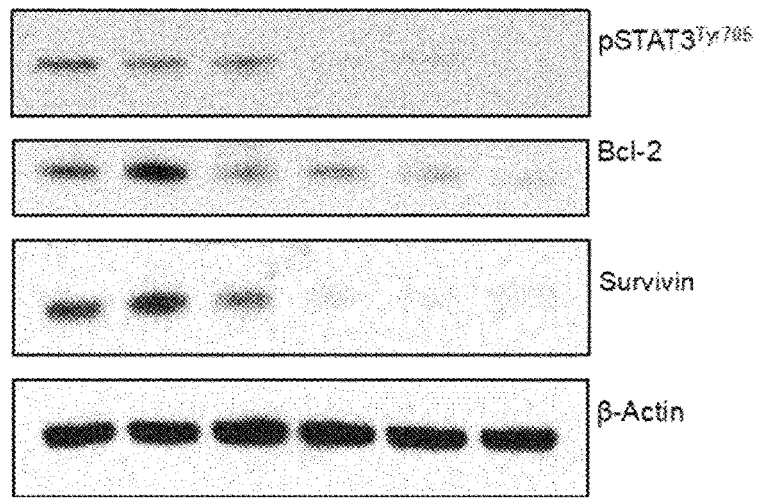
FIG. 3A shows immunoblots showing the downregulation of activated Stat3 (pStat3) and its downstream targets survivin and Bcl-2, in DU145 cells treated with increasing concentration of IE-8 for 18 h.
Figure 3B:
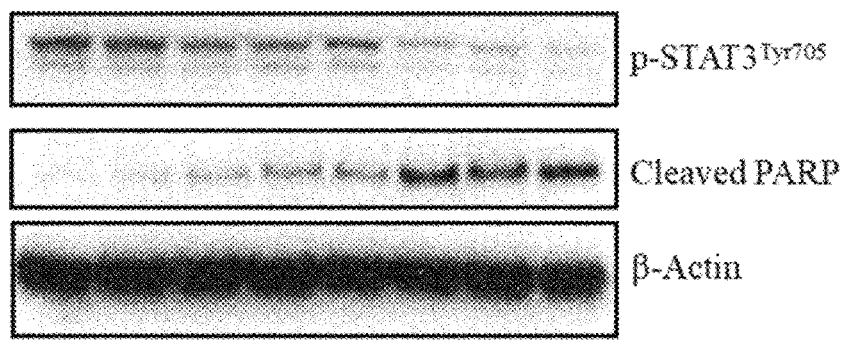
FIG. 3B shows immunoblots of DU145 (top) and A549 (bottom) cells, treated with IE-8 for 18 h, showing the induction of apoptosis with increasing concentrations, as evidenced by the induction of increased levels of cleaved-PARP, concomitant with the pStat3 inhibition.
Figure 3B:
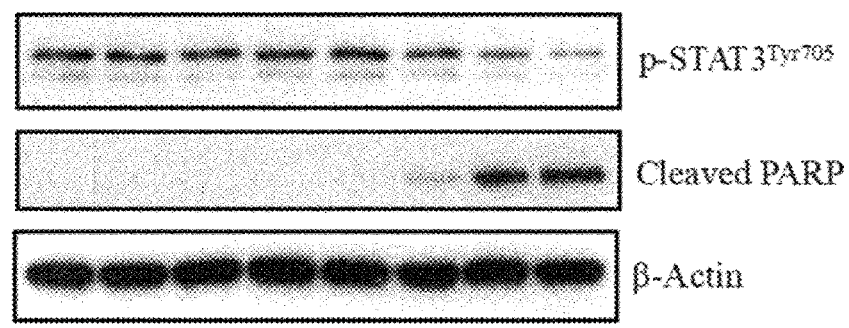
Figure 3C:
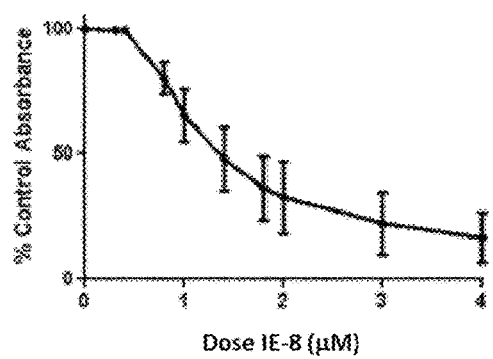
FIG. 3C shows dose-effect curves of IE-8 in DU145 (left) and A549 (right) cells, treated continuously for 96 h. Cell growth inhibition was assessed by the MTT assay.
Figure 3C:
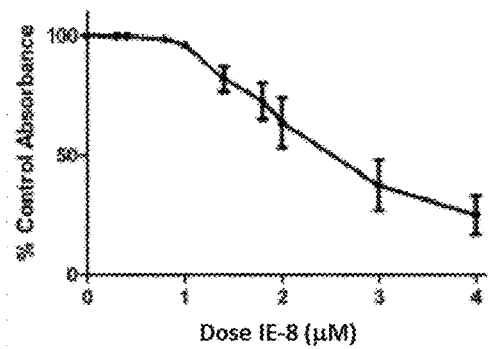
Figure 3D:
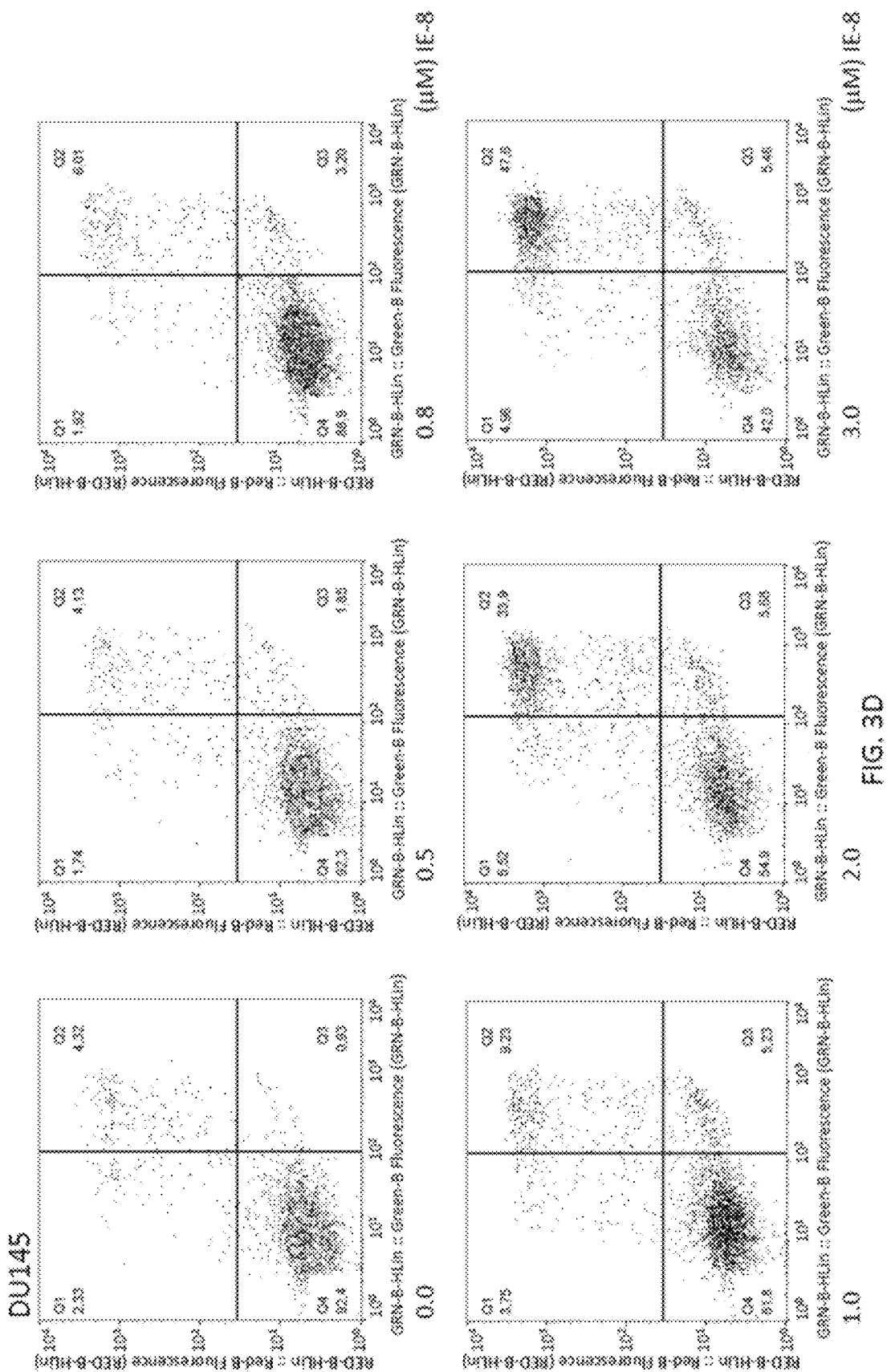
FIG. 3D shows representative scatter plots differentiating viable, apoptotic and necrotic cells based on annexin V-FITC and PI staining, after 24 h incubation of DU145 with increasing concentrations of IE-8.

IE-8 down regulated survivin and Bcl-2, and induces the cleavage of PARP in DU145 and A549 cancer cells. As shown in Example 10, through the selective tyrosine phosphorylation inhibition, IE-8 effectively precluded the Stat3 translocation/accumulation to the nucleus, and therefore reduced the nuclear levels of the activated protein and blocks its DNA binding. As a result, IE-8 downregulated the transcription of key Stat3 target genes involved in cell proliferation and apoptosis such as survivin and Bcl-2 (FIG. 3A). Ultimately it induced cell death via apoptosis as shown by cleaved-PARP induction in DU145 and A549 cells (FIG. 3B) and the Annexin V/PI assay showing a dose-dependent increase in apoptotic cells (FIG. 3D), which would account for its cytotoxic potency in these cell lines (FIG. 3C).

Example 12

Figure 4A:
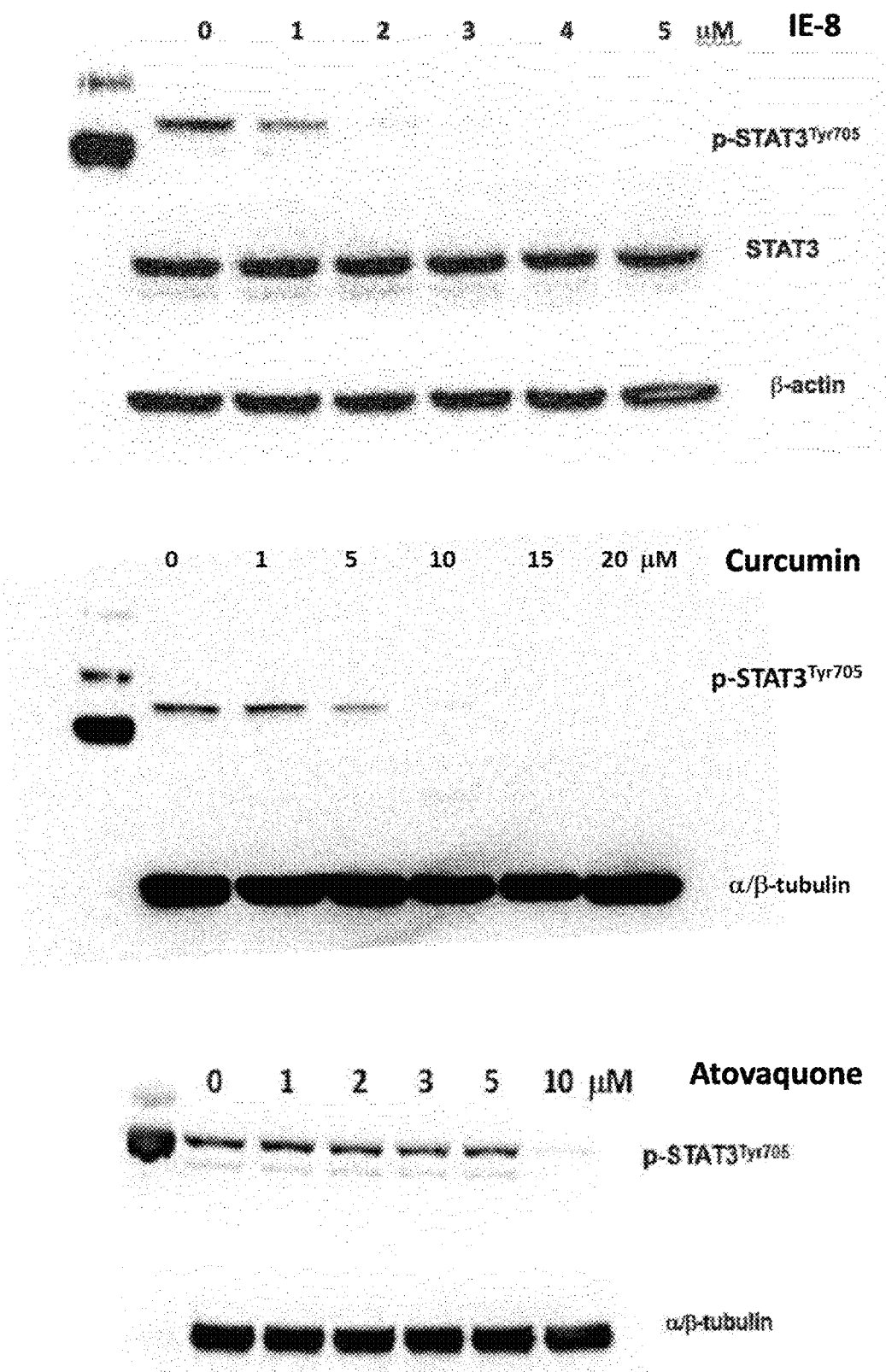
FIG. 4A shows immunoblots showing the inhibition of constitutively active Stat3 in HCT116-oxaliplatin resistant cells, treated for 18 h with IE-8 (top), curcumin (middle) and atovaquone (bottom). IE-8 is the most potent among these inhibitors.
Figure 4B:
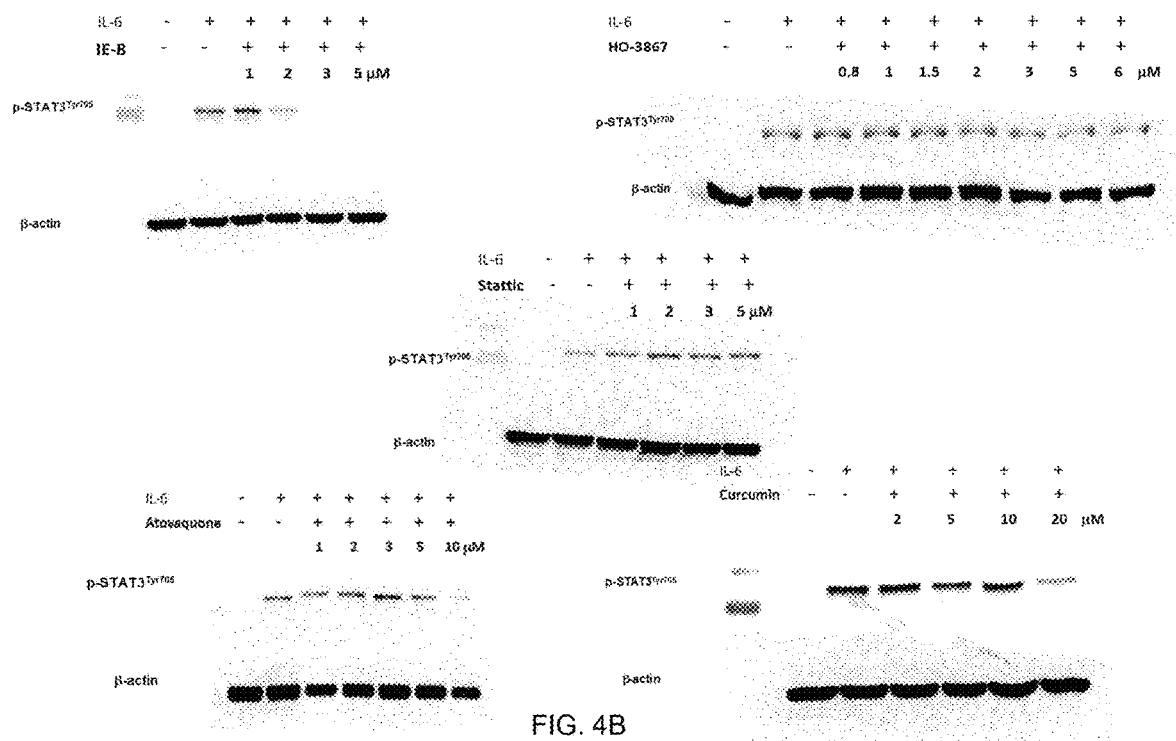
FIG. 4B shows immunoblots showing inhibition of IL-6 induced Stat3 activation in A2780-cisplatin resistant cells, treated for 18 h with IE-8, atovaquone, stattic, curcumin and HO-3867. These cells do not basally express detectable levels of pStat3 and require IL-6 activation. IE-8 is again the most potent inhibitor in this series.
Figure 4C:
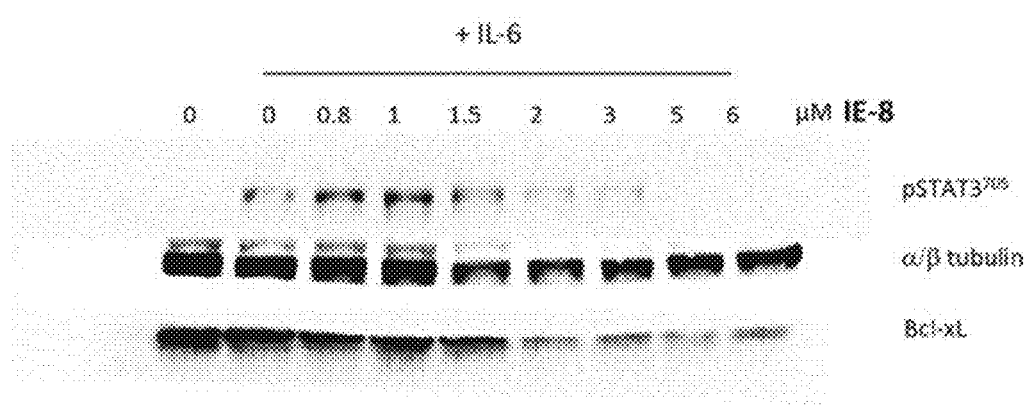
FIG. 4C shows an annexin V/Propidium iodide apoptosis assay in A2780-cisplatin resistant cells treated with increasing concentrations of IE-8 for 24 h.
Figure 4D:
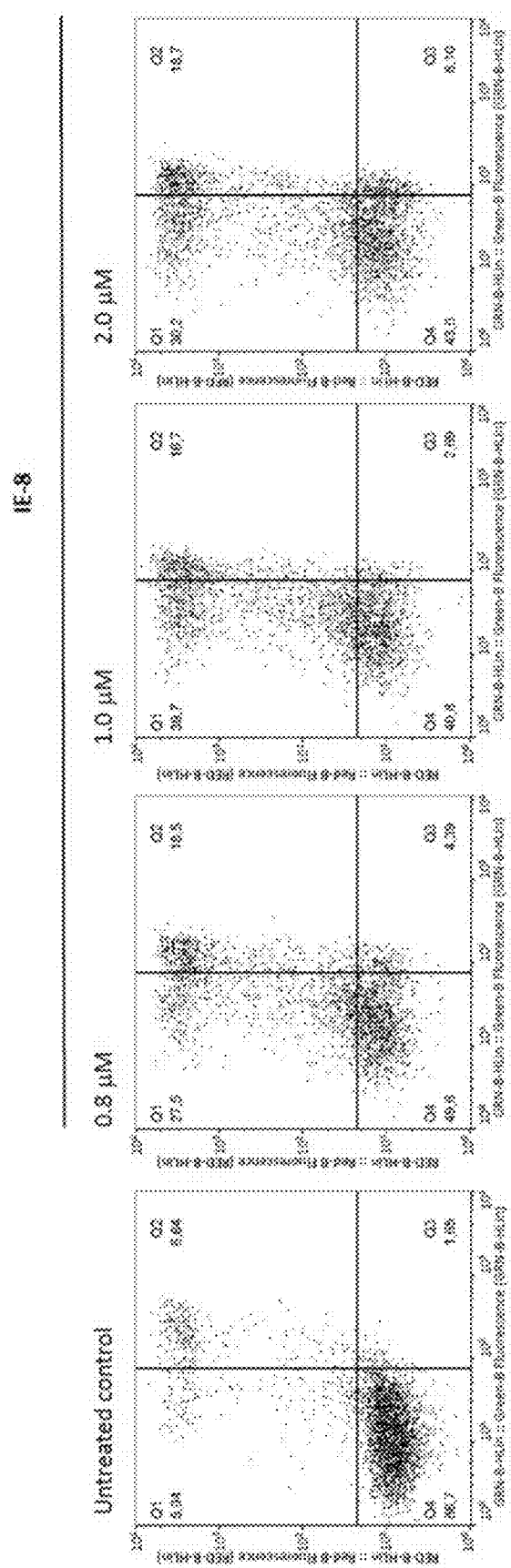
FIG. 4D shows representative histograms.
Figure 4E:
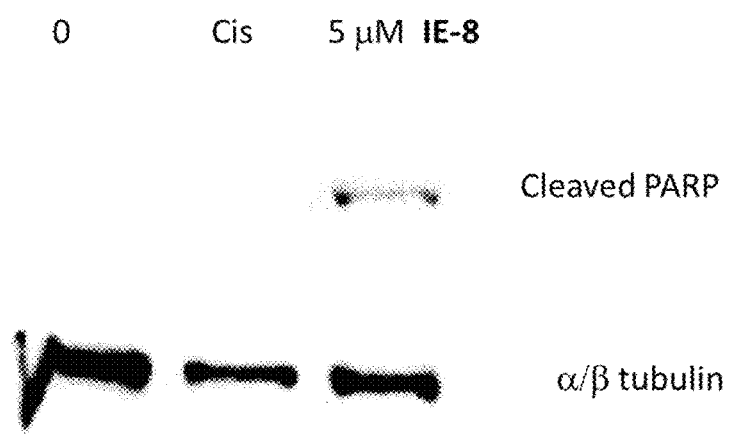
FIG. 4E shows an immunoblot of lysates of the same cells, treated with 5 µM IE-8 for 1 h and left to recover for 24 h in drug-free medium.
Figure 5:
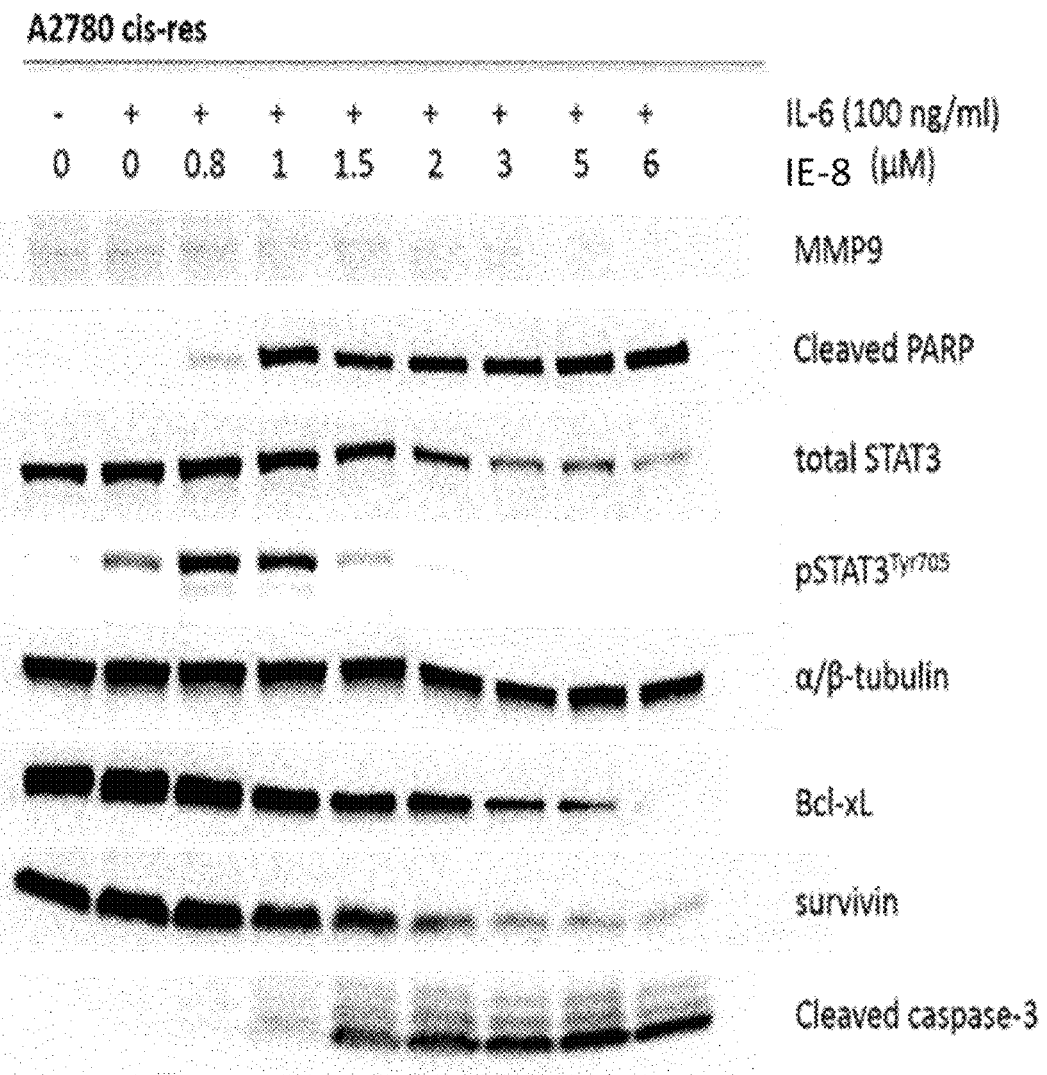
FIG. 5 shows an immunoblot analysis of pStat3 inhibition and induction of apoptosis by IE-8, in A2780-cisplatin resistant cells. Upon cytokine-stimulation (IL-6; 100 ng/ml), Stat3 becomes phosphorylated. Activation of Stat3 is suppressed by applying low IE-8 concentrations, which also achieves the downregulation of the anti-apoptotic proteins Bcl-xL and survivin. Concomitantly, increasing concentrations of IE-8 induce the cleavage of PARP and caspase-3, involved in the apoptosis cascade. IE-8 also downregulates the matrix metalloproteinase MMP-9, involved in tumor invasion, wound healing, carcinogenesis and angiogenesis.

IE-8 efficiently inhibited pStat3, downregulated Bcl-xL and survivin, and induced cleavage of PARP in HCT116-oxaliplatin resistant cells and A2780-cisplatin resistant cells. Compound IE-8 was also shown to be a potent inhibitor of pStat3 in cell lines highly resistant to the DNA-damaging chemotherapeutic agents cisplatin and oxaliplatin. The two cell lines were engineered to become multi-fold resistant to the two clinically-used platinum drugs (derived from the A2780 and HCT16 parental cell lines, respectively). IE-8 efficiently inhibited the constitutively active Stat3 in the HCT116-oxaliplatin resistant cell line (FIG. 4A), but also the cytokine-inducible (IL-6) levels of pStat3 in the A2780-cisplatin resistant subline (FIG. 4B). It should be noted that the total levels of Stat3 remained unaffected (FIG. 4A). In both cellular contexts, IE-8 was more potent than the other small-molecule Stat3 inhibitors tested (atovaquone, stattic, curcumin, and HO-3867). IE-8 was again capable of inhibiting in A2780-cisplatin resistant cells, downstream Stat3 targets, such as the anti-apoptotic protein Bcl-xL, and survivin (FIG. 4C and FIG. 5). As a result, IE-8 induced apoptosis as shown by immunoblotting by the induction of cleaved PARP and cleaved caspase 3, with increasing concentration (FIG. 5) and by the Annexin-V/Propidium iodide assay in these cells, when treated with the agent for 18 h (FIG. 4D). The cellular cleavage of PARP could also be detected by immunoblotting lysates of cells treated with IE-8 for 1 h and left to recover for an extra 24 h (FIG. 4E).

Example 13

Figure 6A:
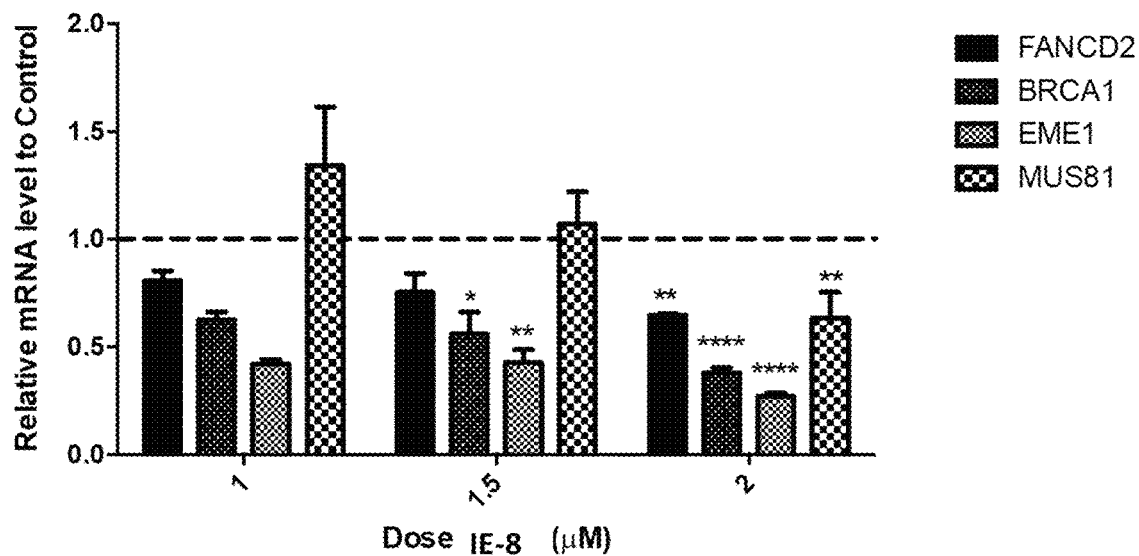
FIG. 6A shows that an inhibition of Stat3 by IE-8 downregulates key DNA ICL repair factors at both the mRNA and protein levels. 18 h treatment of DU145 cells with IE-8 results in a dose-dependent inhibition in mRNA levels of BRCA1, FANCD2, EME1 and MUS81 as detected by RT-PCR.
Figure 6B:
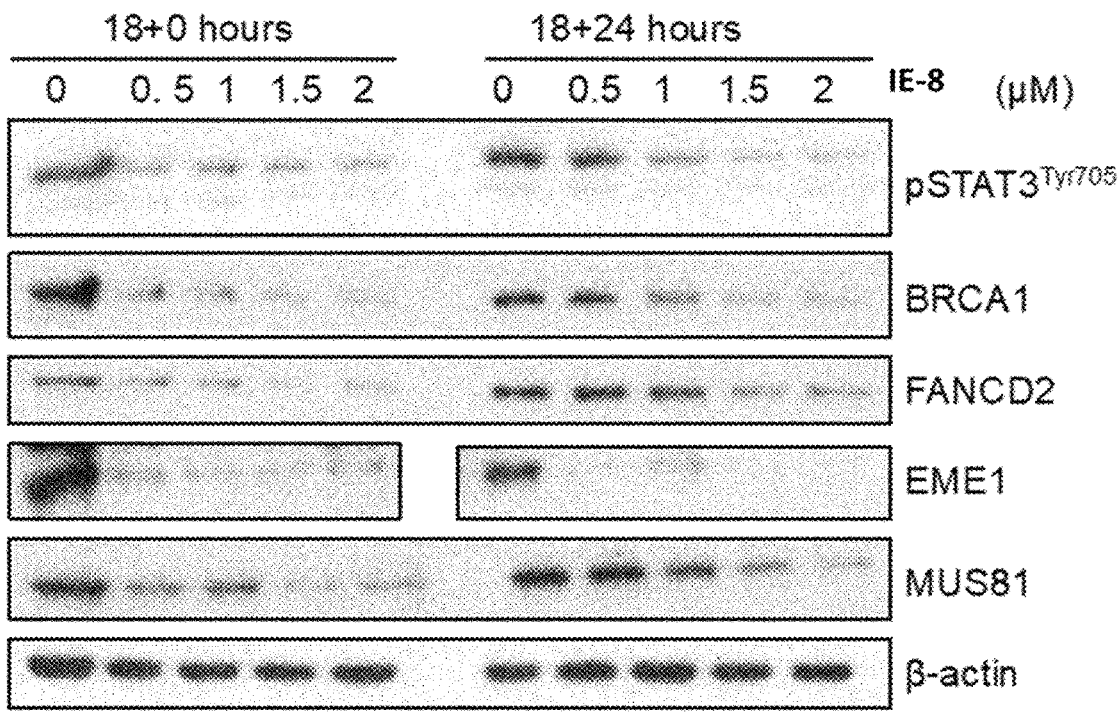
FIG. 6B shows a dose-dependent inhibition in the protein levels of BRCA1, FANCD2, EME1 and MUS81, as detected by immunoblotting is also observed after 18 h of treatment with IE-8, and persists 24 h post-treatment, with cells maintained in drug-free medium.

IE-8 downregulated the expression of BRCA1, FANCD2, EME1 and MUS81 in DU145 cancer cells. Subsequently, the effect of pStat3 inhibition on a number of key repair factors, known to be involved in DNA ICL repair was investigated. As shown in FIGS. 6A-B, IE-8 markedly downregulated the expression of BRCA1, FANCD2, EME1 and MUS81 at both mRNA (FIG. 6A) and protein (FIG. 6B) levels in DU145 cancer cells. This downregulation of the MUS8-EME11 endonuclease complex, which is known to be involved in the unhooking of ICLs by introducing incision at the ICL site, similarly to the XPF-ERCC1 endonuclease, provides a mechanistic rationale for the observed ICL repair defect, mediated by IE-8, and the resulting enhancement of cellular sensitivity to the ICL-producing drugs cisplatin and oxaliplatin.

Example 14

Figure 7A:
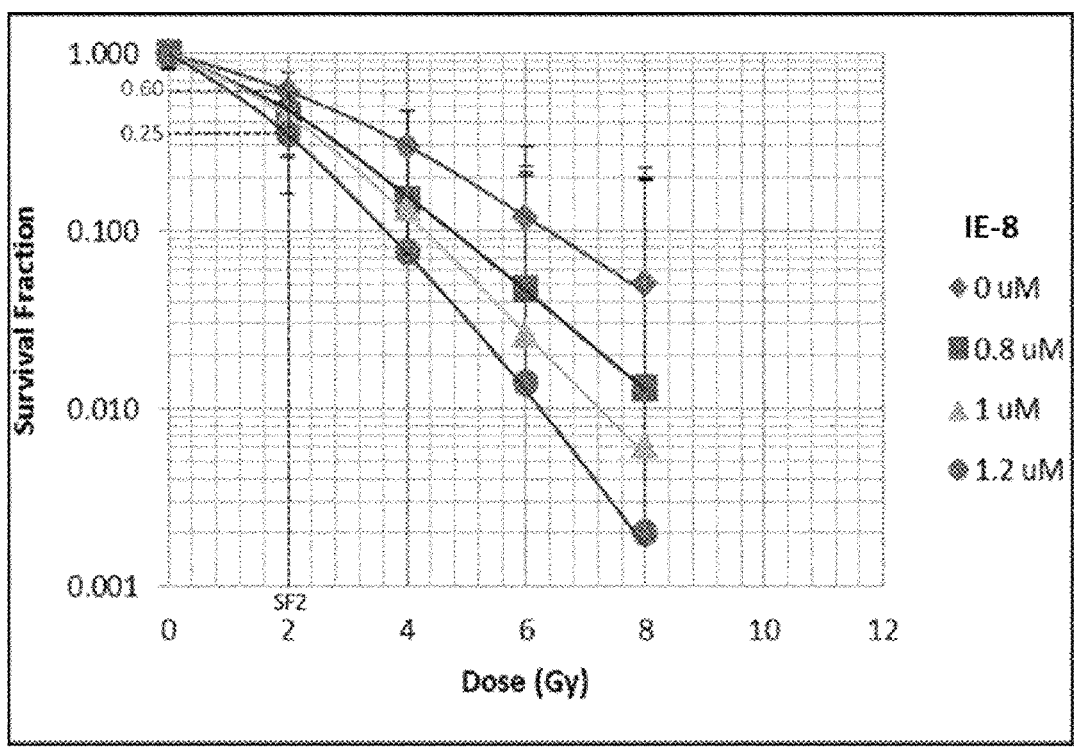
FIG. 7A shows an enhancement of radiation sensitivity of DU145 cells, pretreated for 18 h, with different doses of IE-8 as determined by the clonogenic survival assay. The results are presented as mean of three independent experiments.
Figure 7B:
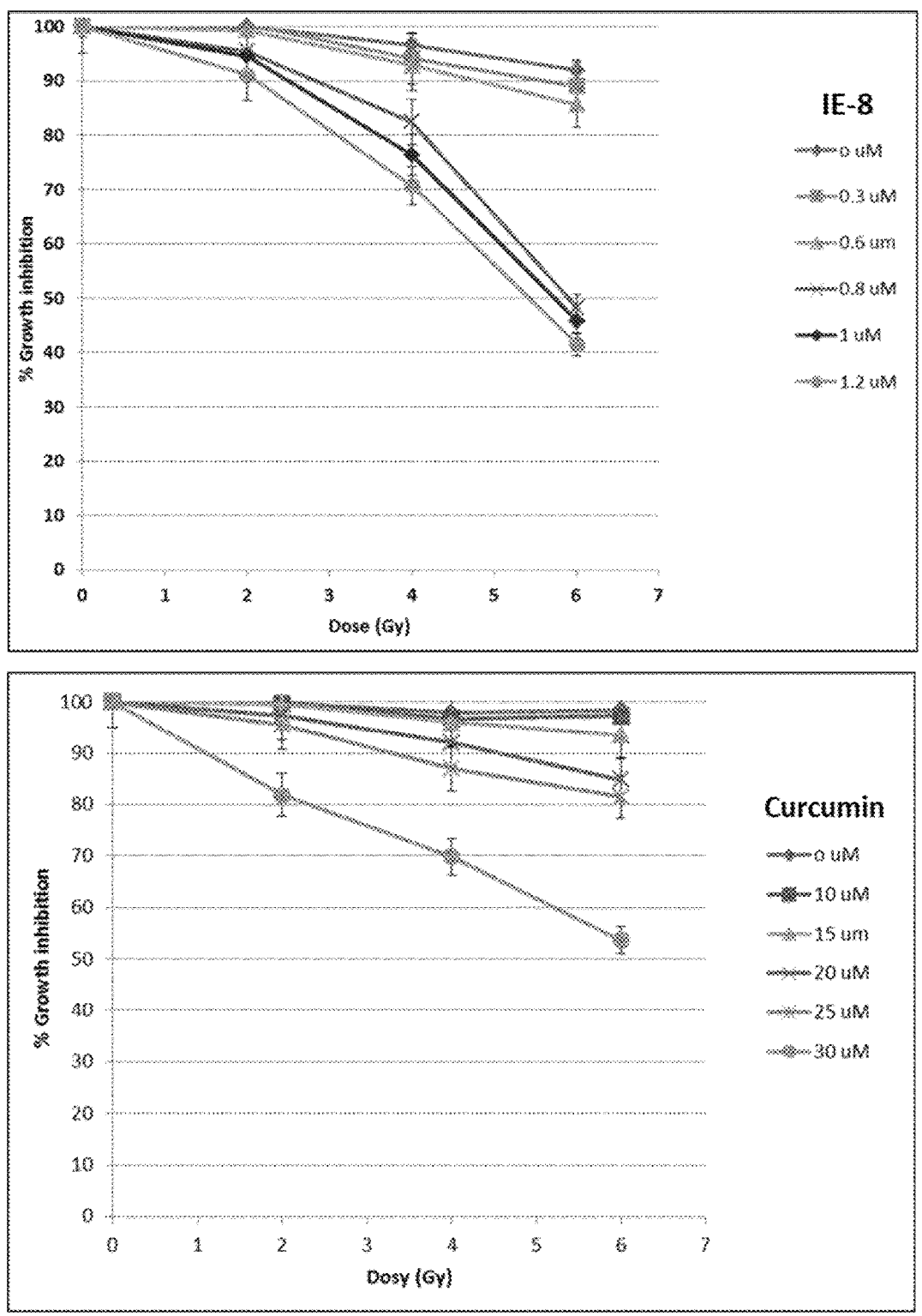
FIG. 7B shows SRB assays probing the sensitivity of DU145 cells to radiation, after pretreatment for 18 h with IE-8 (top) and curcumin (below).

IE-8 induced radiosensitization of DU145 cancer cells. Radiation sensitivity of DU145 cells was enhanced, wherein cancer cells were pretreated for 18 h with different doses of IE-8, and subsequently irradiated. Cell survival was assessed by the colony formation assay (FIG. 7A, Table 3) and SRB (FIG. 7B). Pre-treatment with IE-8 resulted in a dose-dependent decrease in colony formation following irradiation (FIG. 7A, Table 3). Pretreatment with IE-8 (FIG. 7B, top) was more efficient at reducing cell survival, than pretreatment with curcumin (FIG. 7B, bottom), as lower doses of IE-8 yielded a stronger radiosensitization effect (at the same Gy doses utilized).

TABLE 3

Dose-dependent decrease in colony formation after irradiation.

| Dose (Gy)/IE-8 | Survival fraction | | | |
| --- | --- | --- | --- | --- |
| conc. (µM) | 0 | 0.8 | 1 | 1.2 |
| 0 | 1.000 | 1.000 | 1.000 | 1.000 |
| 2 | 0.605 | 0.451 | 0.440 | 0.349 |
| 4 | 0.295 | 0.147 | 0.134 | 0.077 |
| 6 | 0.119 | 0.047 | 0.026 | 0.014 |
| 8 | 0.050 | 0.013 | 0.006 | 0.002 |

Example 15

Figure 8A:
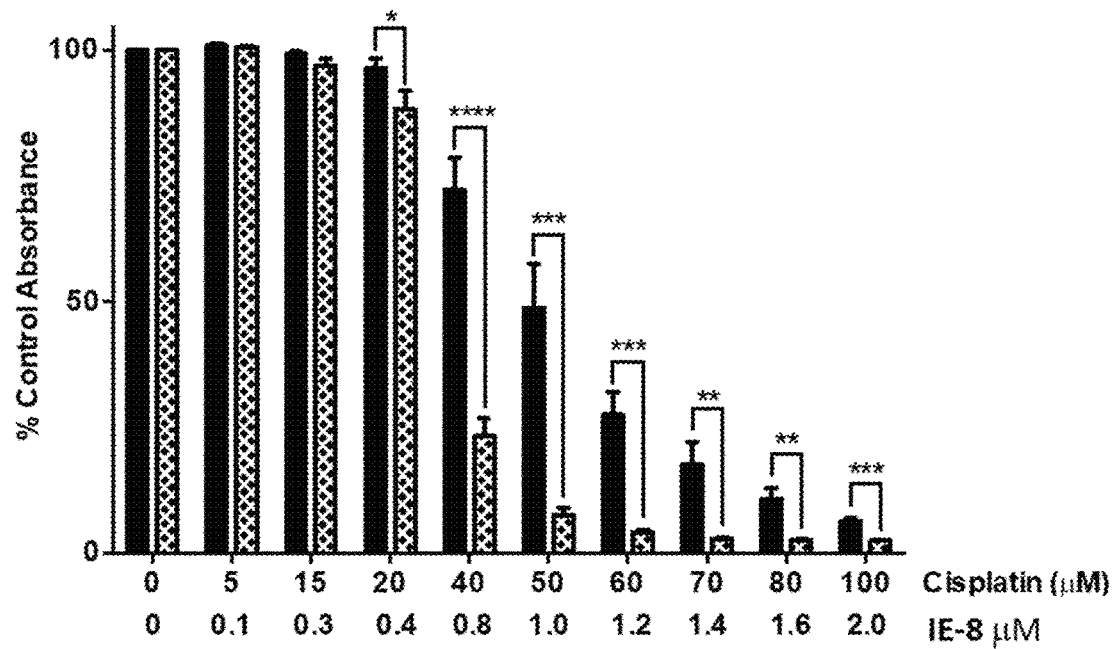
FIG. 8A shows DU145 cells that were treated sequentially with a combination of IE-8 and cisplatin (dashed bars) at a fixed ratio of 1:50. Pretreatment with IE-8 was for 18 h, followed by cisplatin treatment for 1 h (solid bars). Following drug treatments, cells were incubated for a total of 96 h before cell growth inhibition was assessed by the SRB assay. IE-8 pretreatment of cells significantly reduced cisplatin $IC_{50}$ from 49.2 µM to 30.8 µM.
Figure 8B:
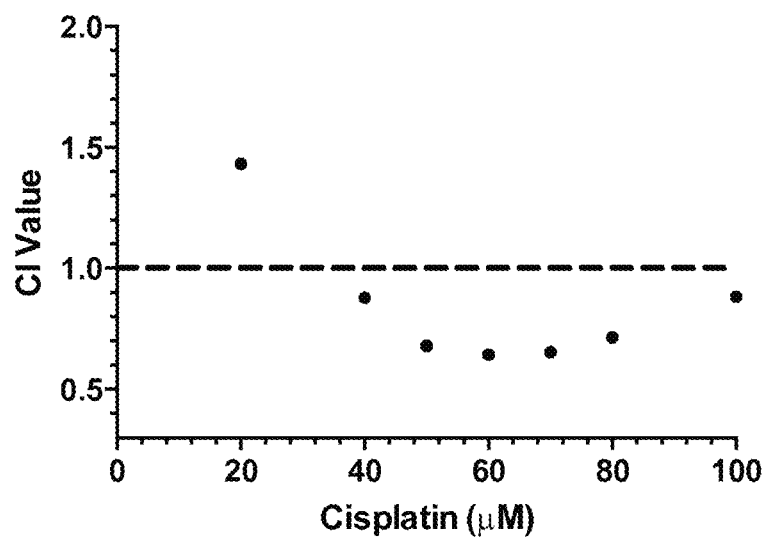
FIG. 8B shows an analysis of the combination of IE-8 with cisplatin that was carried out by the Chou-Talalay combination index analysis. CI values are predominantly below 1 (one), indicating a synergistic interaction between the two agents.
Figure 8C:
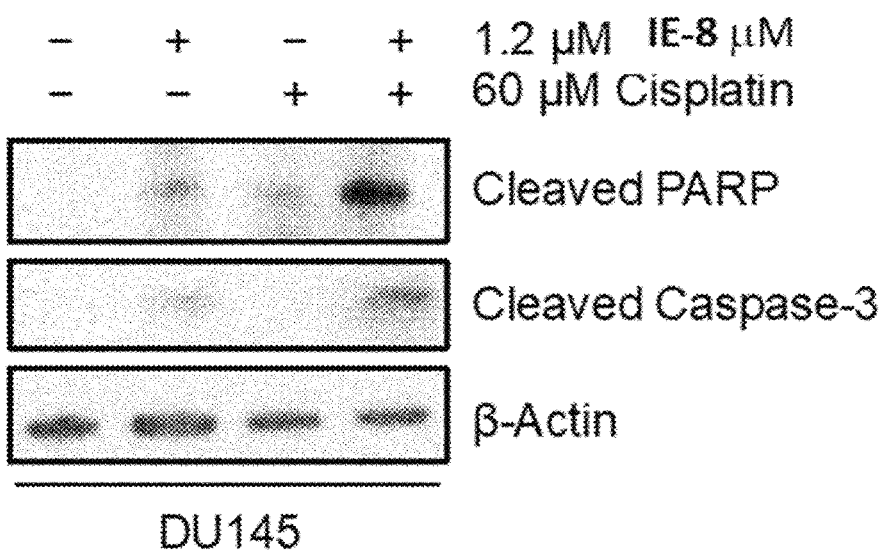
FIG. 8C shows an enhancement of apoptosis as indicated by increased levels of cleaved PARP and cleaved-caspase-3 in the combination treatment, detected by immunoblotting.
Figure 8D:
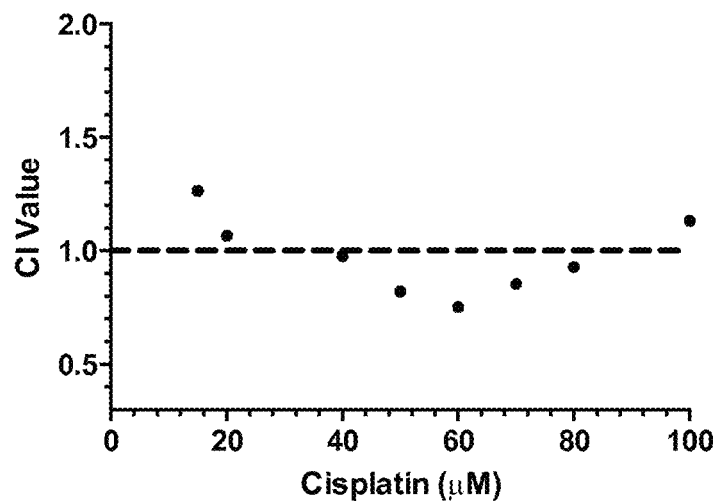
FIG. 8D shows a combination index analysis of stattic in combination treatments with cisplatin at a ratio of 1:5 that yielded lower levels of synergy within a narrower range of doses than the combination treatments of cisplatin with IE-8.
Figure 8E:
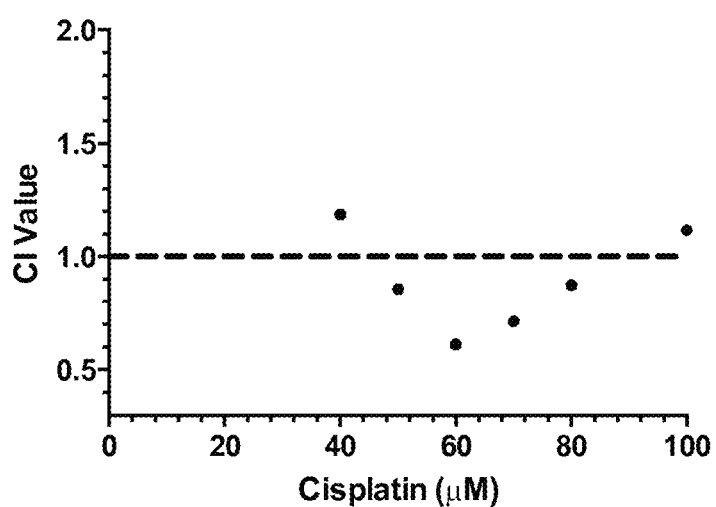
FIG. 8E shows a combination index analysis of curcumin in combination treatments with cisplatin at a ratio of 4:5 that yielded lower levels of synergy within a narrower range of doses than the combination treatments of cisplatin with IE-8.
Figure 9A:
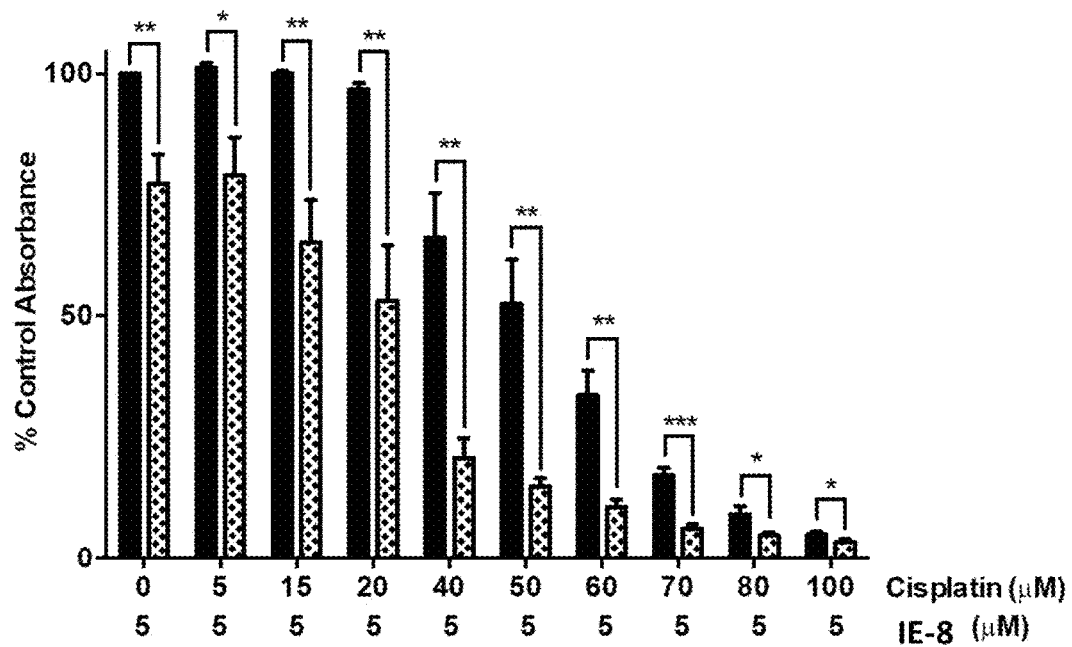
FIG. 9A shows DU145 cells that were acutely treated for 1 h with a constant dose of 5 µM IE-8 (non fixed-ratio) followed by cisplatin treatment (1 h) as before, and a total 96 h incubation in drug-free medium. The combination treatment results in chemosensitization of the DU145 cells to cisplatin and a decrease of cisplatin $IC_{50}$ from 49.3 µM to 19.5 µM, as determined by the SRB assay.
Figure 9B:
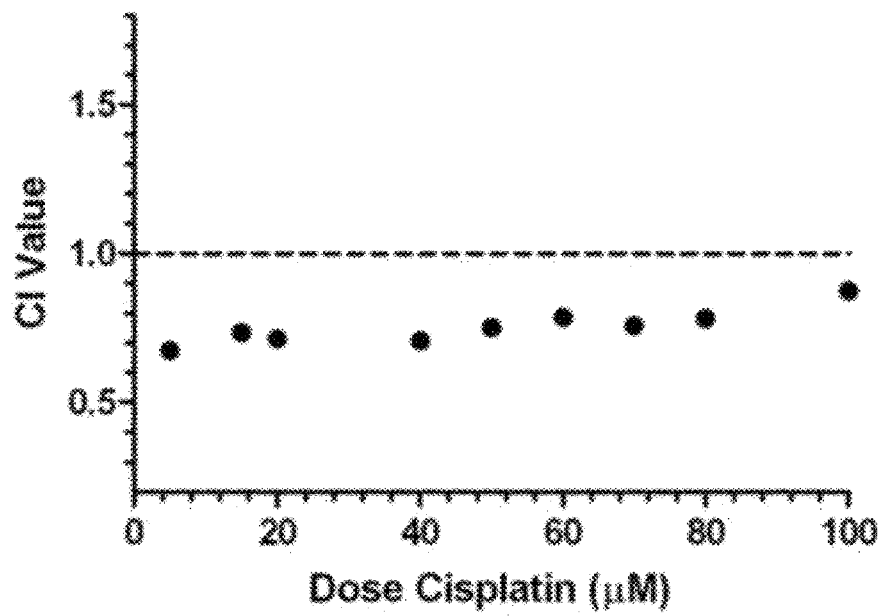
FIG. 9B shows combination indices for combination of 5 µM IE-8 with cisplatin that are all below 1 (one) indicating a synergistic interaction between the two agents.
Figure 9C:
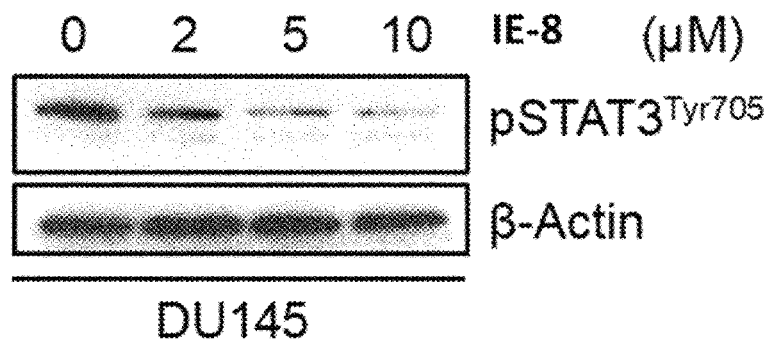
FIG. 9C shows that an 1 h treatment of DU145 cells with IE-8 can effectively inhibit $pStat3^{Tyr705}$ levels.

IE-8 induced chemosensitization of DU145 cancer cells towards cisplatin and synergized with cisplatin. Compound IE-8 further chemosensitizes DU145 cells to cisplatin, when the two agents were administered sequentially (IE-8 for 18 h followed by cisplatin for 1 h) at a fixed concentration ratio of 1:50 (FIG. 8A) achieving synergistic interactions (synergism can be accounted to a combination index (CI) of <1 (one)) for a number of concentrations, in the combination treatments (FIG. 8B). This was mirrored by the enhancement of apoptosis in the combinations as evidenced by an increase in the cellular protein levels of cleaved PARP and cleaved-caspase 3, as detected by immunoblotting (FIG. 8C). IE-8 was able to chemosensitize DU145 cells to cisplatin by achieving higher levels of synergy and at a wider range of concentrations than stattic (FIG. 8D) and curcumin (FIG. 8E), both requiring considerably higher doses. Synergistic interactions were also observed at a different drug schedule (non-fixed ratio), with DU145 cells acutely exposed to a single, non-toxic concentration of IE-8 (5 µM) for 1-h, and subsequently treated with increasing doses of cisplatin for 1 h (FIG. 9A and FIG. 9B). Immunoblotting analysis confirmed that the dose of 5 µM IE-8 was sufficient to inhibit pStat3 during the 1 h of treatment (FIG. 9C).

Example 16

Figure 10A:
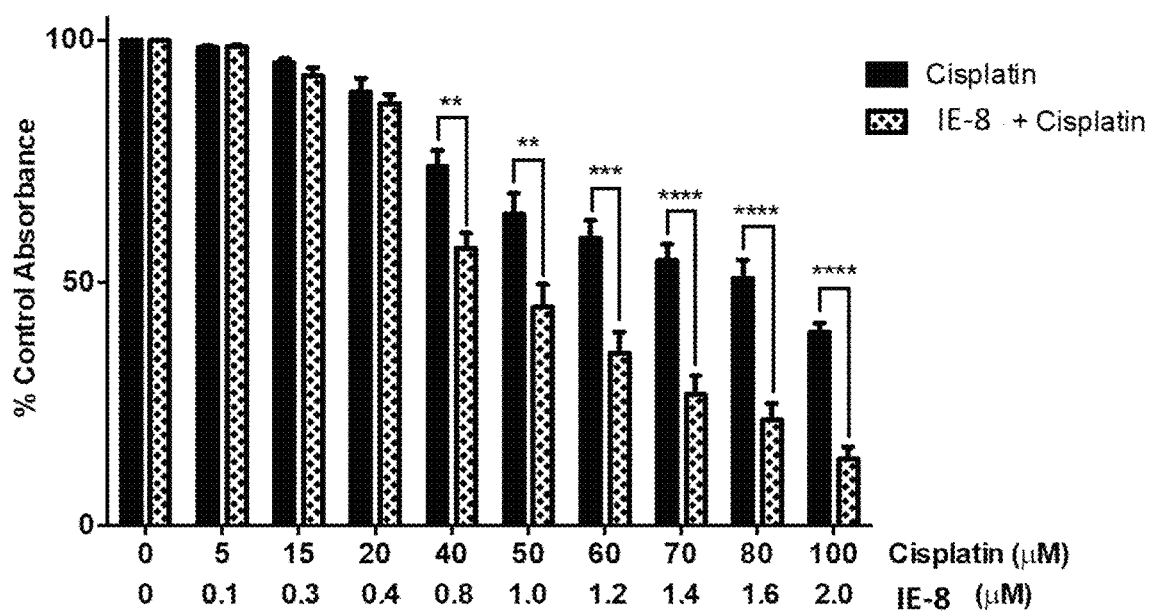
FIG. 10A shows A549 cells that were sequentially treated with a combination of IE-8 and cisplatin at a fixed ratio of 1:50. IE-8 treatment was for 18 h and cisplatin treatment for 1 h. Following drug treatments cells were incubated for a total of 96 h before cell growth inhibition was assessed by the SRB assay. IE-8 pre-treatment of A549 cells significantly reduced cisplatin $IC_{50}$ from 77.8 µM to 45.7 µM.
Figure 10B:
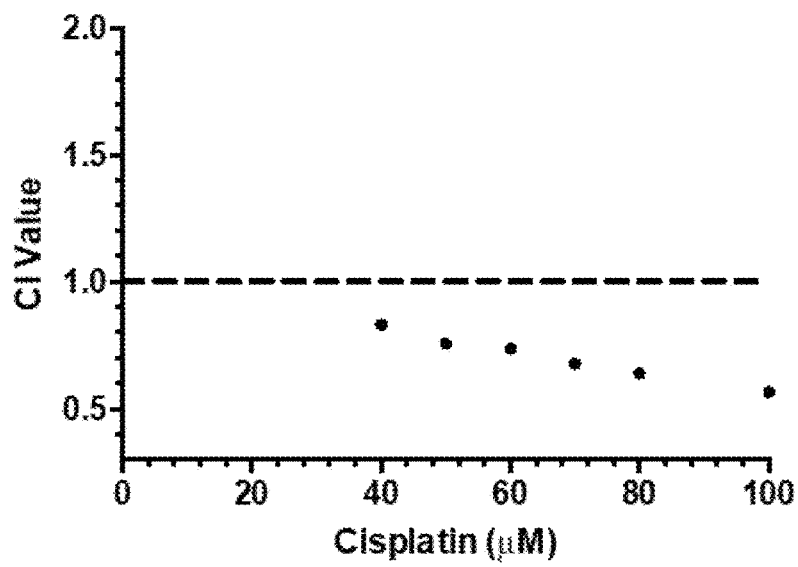
FIG. 10B shows an analysis of the combination of IE-8 with cisplatin that was carried out by the Chou-Talalay combination index analysis. CI values are predominantly below 1 (one), indicating a synergistic interaction between IE-8 and cisplatin.
Figure 10C:
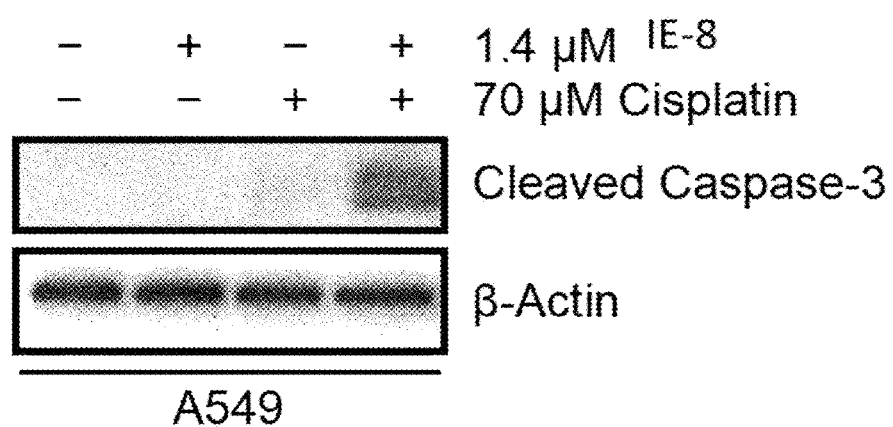
FIG. 10C shows that an apoptosis, as indicated by the levels of cleaved caspase-3 levels, is enhanced in A549 cells treated with a combination of IE-8 and cisplatin compared to cells treated with either drug alone.
Figure 10D:
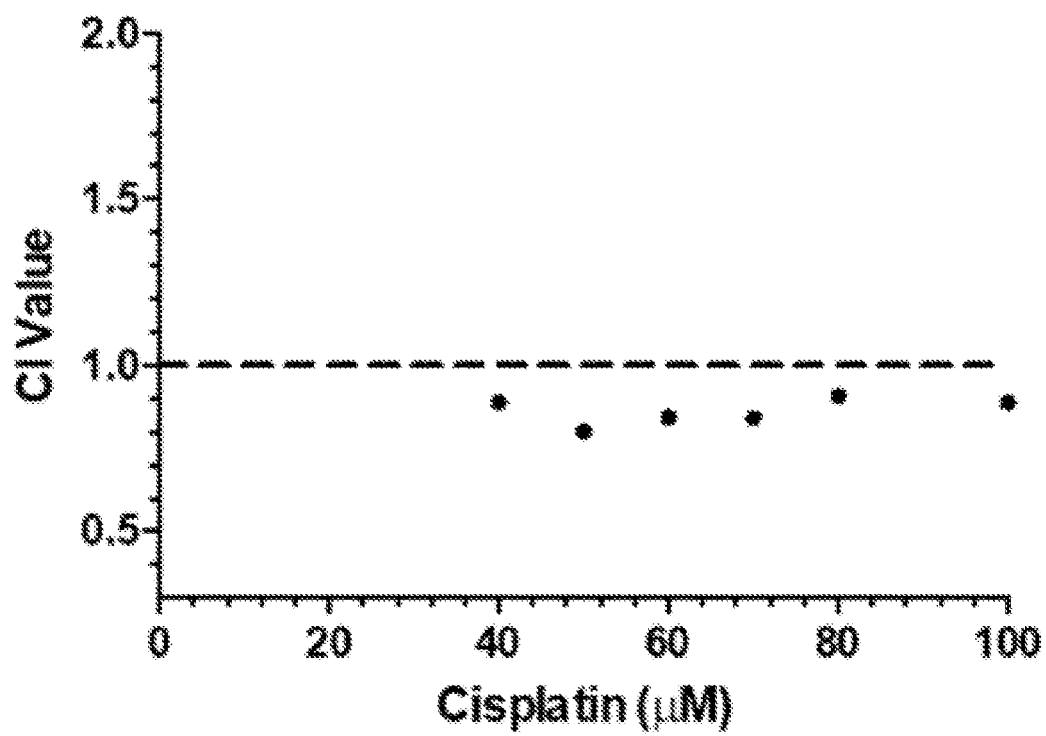
FIG. 10D shows that a combination index analysis of stattic in combination with cisplatin at a ratio of 1:5 yielded lower levels of synergy than the combination treatments of cisplatin with IE-8.
Figure 10E:
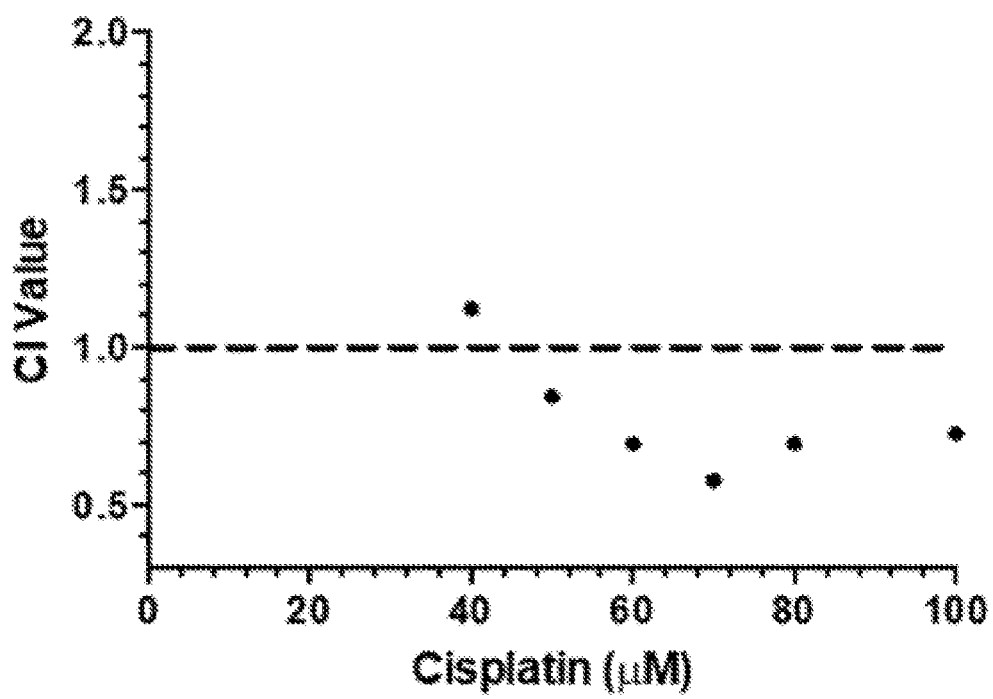
FIG. 10E shows that a combination index analysis of curcumin in combination with cisplatin at a ratio of 4:5 yielded lower levels of synergy than the combination treatments of cisplatin with IE-8.
Figure 11A:
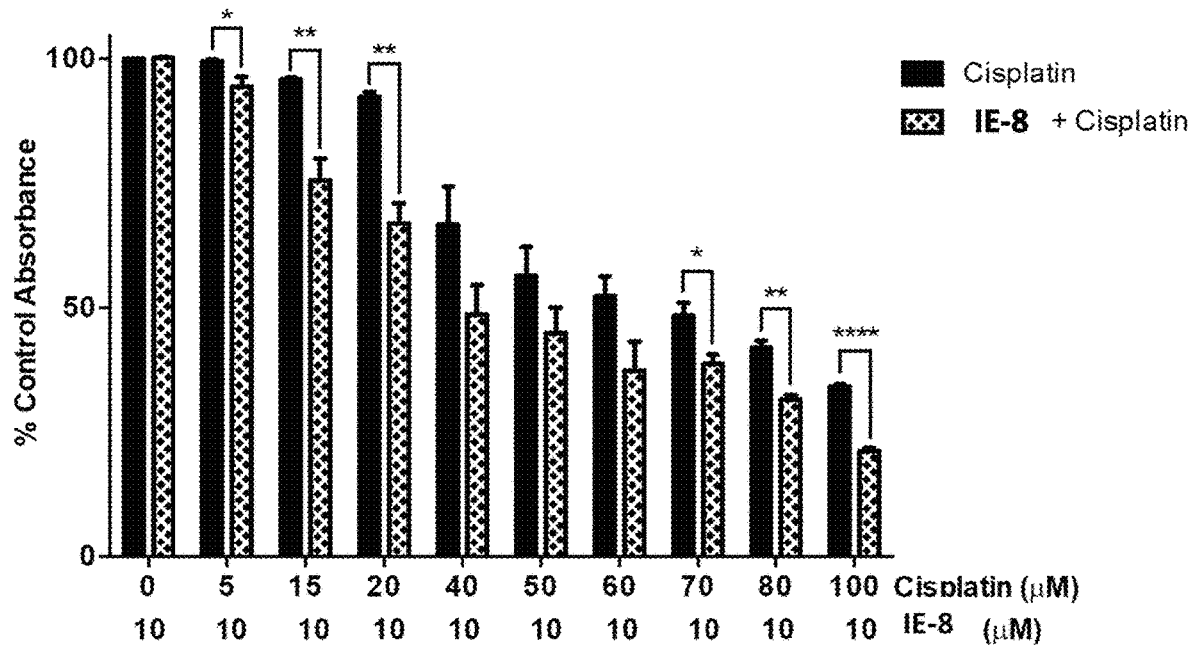
FIG. 11A shows A549 cells that were acutely treated for 1 h with 10 µM IE-8 followed by cisplatin treatment (1 h), and a total of 96 h of incubation in drug-free medium. The combination treatment results in chemosensitization of the A549 cells to cisplatin and a decrease of cisplatin $IC_{50}$ from 64.6 to 39.8 µM, as determined by the SRB assay.
Figure 11B:
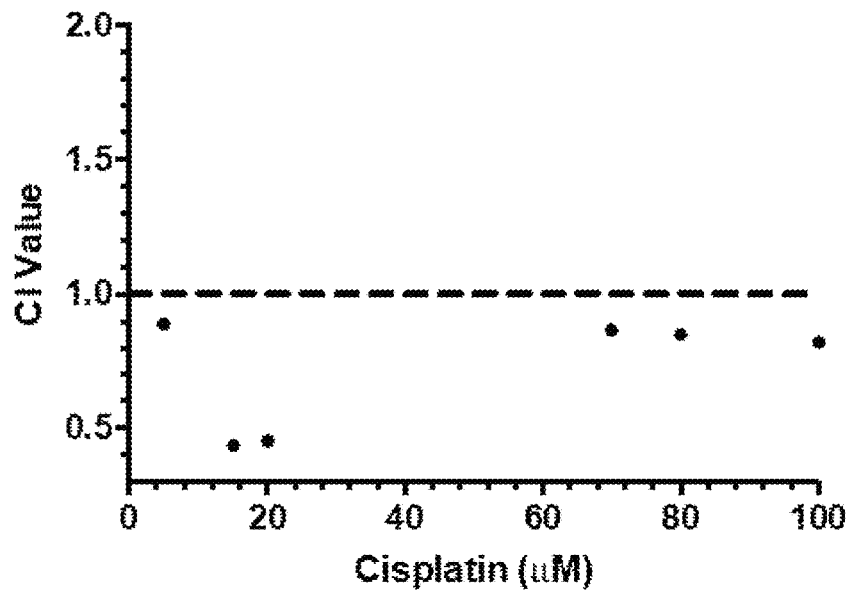
FIG. 11B shows indices for the combination of 10 µM IE-8 with cisplatin that are all below 1 (one) indicating a synergistic interaction between the two agents.
Figure 11C:
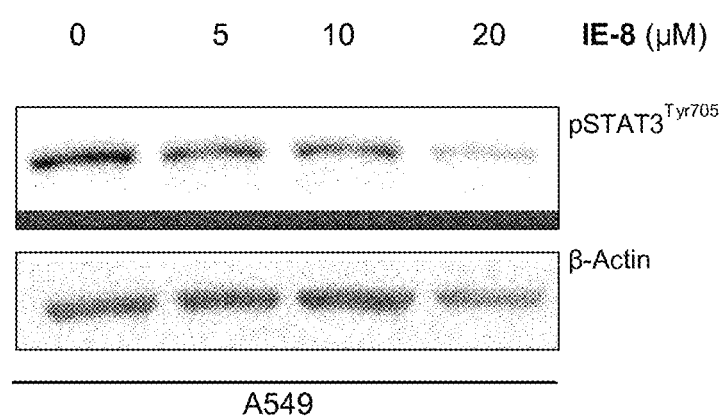
FIG. 11C shows that an 1 h treatment of A549 cells with IE-8 can effectively inhibit $pStat3Tyr^{705}$ levels.

IE-8 induced chemosensitization of A549 cancer cells towards cisplatin. The results observed in Example 15 were successfully reproduced in A549 cells for both drugs schedules; fixed ratio (FIG. 10A, FIG. 10B, FIG. 10C and FIG. 10E) and non-fixed ratio for an acute IE-8 exposure (FIG. 11A, FIG. 11B and FIG. 11C). Again, in the case of the fixed-ratio combination treatments, IE-8 was more effective in enhancing cellular sensitivity to cisplatin, than stattic and curcumin (FIG. 10D and FIG. 10E).

Example 17

Figure 12A:
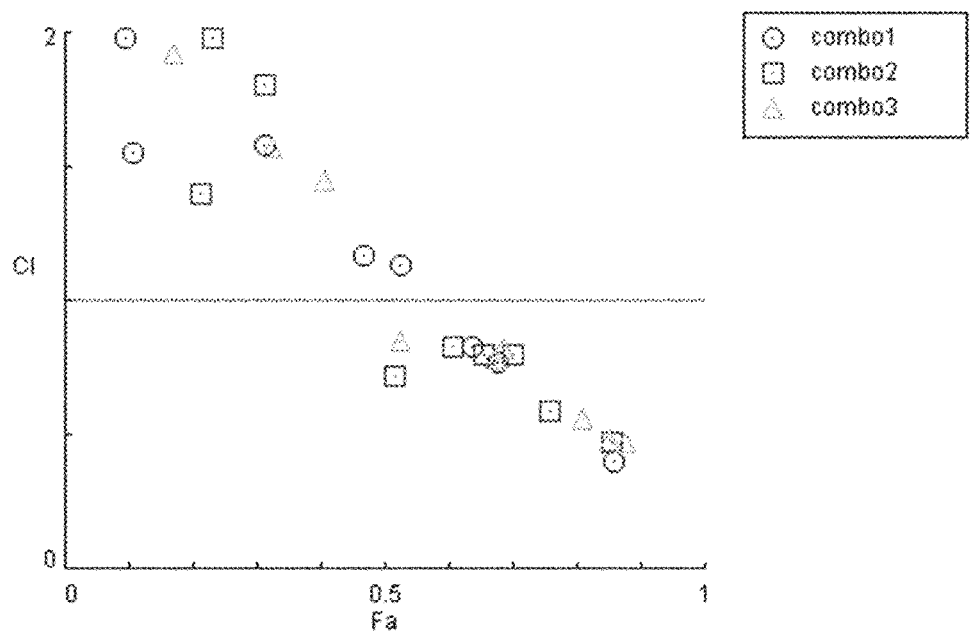
FIG. 12A shows HCT116-oxaliplatin resistant cells that were treated with a constant dose of IE-8 for 1 h (2, 2.5 and 3 µM) and then with increasing doses of oxaliplatin (non-fixed ratio), continuously for 96 h. At the end of incubation, growth inhibition was assessed by the MTT assay. The derived dose-effect curves for the two agents alone and in combination were used to calculate the CI values using the Chou-Talalay methodology.

IE-8 induced chemosensitization of HCT116-oxaliplatin resistant cancer cells towards oxaliplatin. Compound IE-8 was also capable of restoring cellular sensitivity to the highly oxaliplatin resistant HCT116 cells, in various drug schedules (fixed and non-fixed ratio combination treatments), achieving in many instances CI values <1 (FIGS. 12A-E). In Table 4 the Combination Index data illustrated in FIG. 12A is given in detail.

TABLE 4

| Dose of oxaliplatin | Combo1 (2.0 µM of IE-8) | | Combo2 (2.5 µM of IE-8) | | Combo3 (3.0 µM of IE-8) | |
|---|---|---|---|---|---|---|
| (µM) | Effect | CI-value | Effect | CI-value | Effect | CI-value |
| 0.1 | 0.1065 | 1.55750 | 0.5165 | 0.72103 | 0.527 | 0.84895 |
| 1.0 | 0.0954 | 1.97869 | 0.2143 | 1.40479 | 0.171 | 1.92416 |
| 10.0 | 0.1575 | 2.75379 | 0.231 | 1.98514 | 0.3259 | 1.57258 |
| 20.0 | 0.315 | 1.58025 | 0.313 | 1.80484 | 0.4064 | 1.45295 |
| 40.0 | 0.4676 | 1.17153 | 0.6087 | 0.83261 | 0.6743 | 0.78707 |
| 60.0 | 0.5256 | 1.13457 | 0.6559 | 0.80092 | 0.6878 | 0.82136 |
| 80.0 | 0.6386 | 0.82702 | 0.76 | 0.59215 | 0.8108 | 0.55837 |
| 100.0 | 0.678 | 0.77486 | 0.7021 | 0.79926 | 0.8527 | 0.48003 |
| 200.0 | 0.8582 | 0.40162 | 0.855 | 0.47768 | 0.877 | 0.47632 |

Figure 12B:
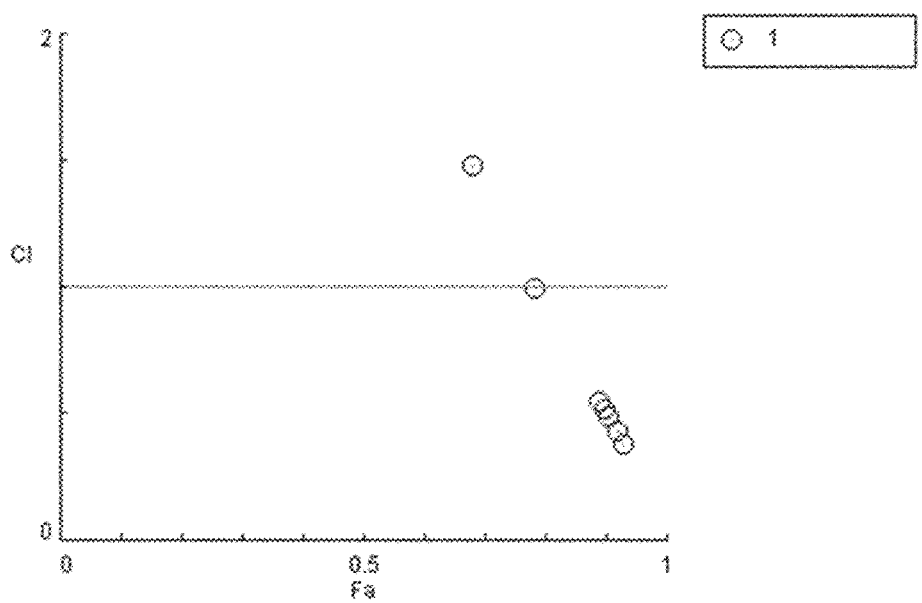
FIG. 12B shows the same cell line that was treated with oxaliplatin for 1 h, and 3 h later, 1 µM IE-8 was added until the end of incubation at 96 h (non-fixed ratio).

In Table 5 the Combination Index data illustrated in FIG. 12B is given in detail.

TABLE 5

| Dose of IE-8 (µM) | Dose of oxaliplatin (µM) | Effect | CI-value |
|---|---|---|---|
| 1.0 | 1.0 | 0.26918 | 5.47555 |
| 1.0 | 10.0 | 0.67993 | 1.48205 |
| 1.0 | 20.0 | 0.78376 | 0.99543 |
| 1.0 | 40.0 | 0.89081 | 0.54394 |

TABLE 5-continued

| Dose of IE-8 (µM) | Dose of oxaliplatin (µM) | Effect | CI-value |
|---|---|---|---|
| 1.0 | 60.0 | 0.89698 | 0.51829 |
| 1.0 | 80.0 | 0.91844 | 0.42794 |
| 1.0 | 200.0 | 0.92998 | 0.37861 |
| 1.0 | 400.0 | 0.90449 | 0.48803 |

Figure 12C:
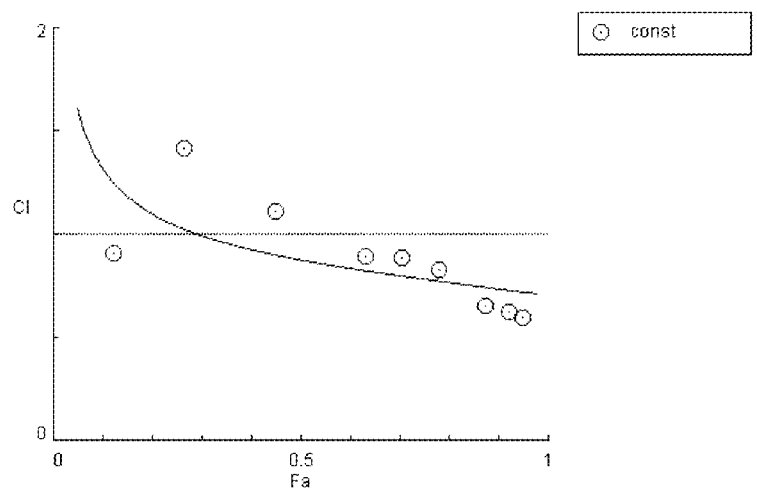
FIG. 12C shows HCT116-oxaliplatin resistant cells that were exposed simultaneously to IE-8 and oxaliplatin at a fixed ratio of 1:80, for 96 h.

In Table 6 the Combination Index data illustrated in FIG. 12C is given in detail.

TABLE 6

Determined CI-values for the combination IE-8:oxaliplatin = 1:80.

| Total Dose (µM) | Effect | CI-Value |
|---|---|---|
| 8.1 | 0.1225 | 0.90843 |
| 24.3 | 0.2653 | 1.41636 |
| 32.4 | 0.4507 | 1.11584 |
| 40.5 | 0.6305 | 0.89794 |
| 48.6 | 0.706 | 0.88492 |
| 56.7 | 0.7812 | 0.82656 |
| 64.8 | 0.8755 | 0.65502 |
| 81.0 | 0.9216 | 0.62665 |
| 97.2 | 0.9492 | 0.59455 |

Figure 12D:
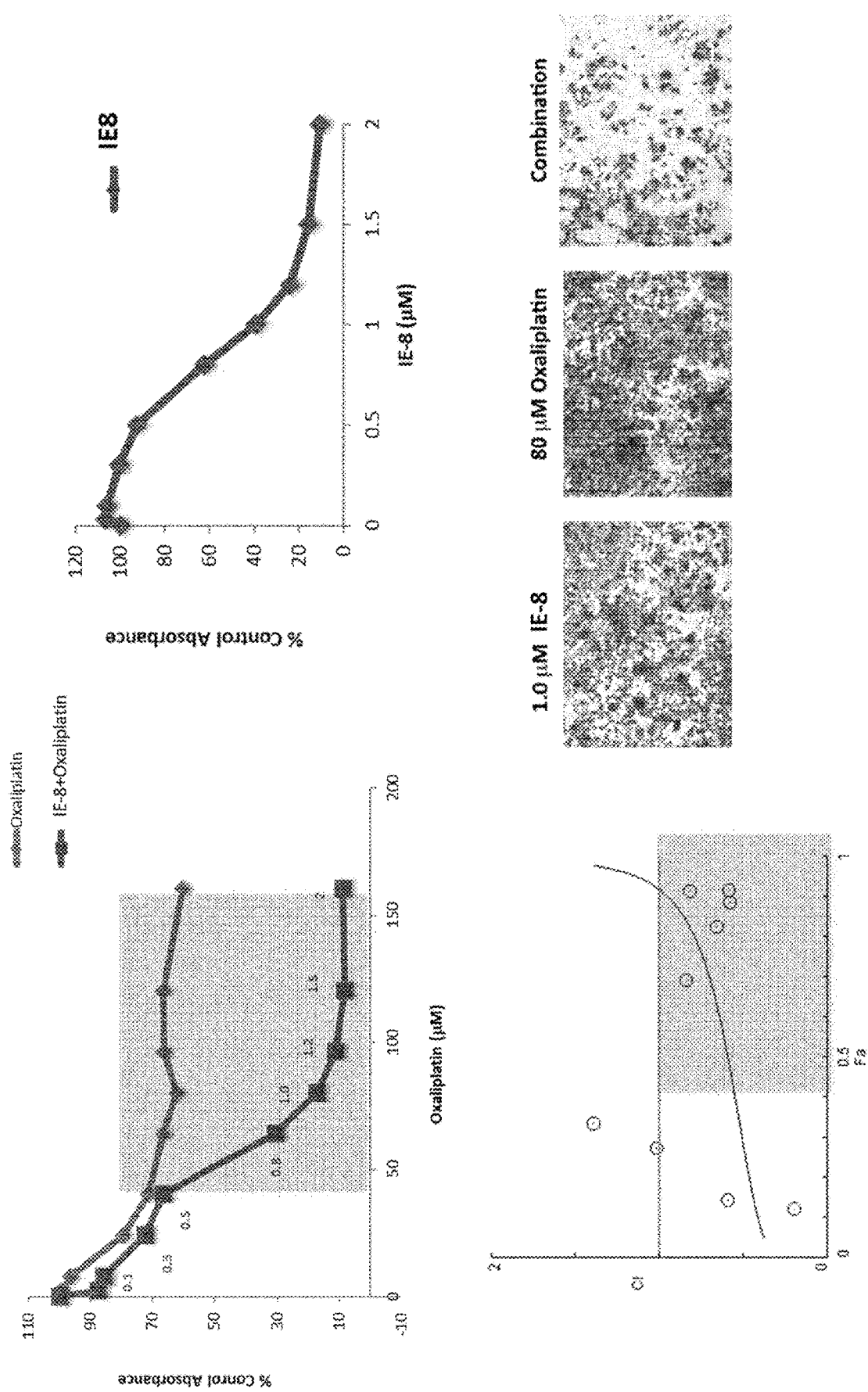
FIG. 12D shows the same cells that were pretreated with IE-8 for 18 h, and then treated with oxaliplatin for 1 h (at a fixed ratio of 1:80). The dose effect curves of each drug alone and the combination (top), the CI analysis (bottom, left) and images of the MTT-stained cells in the respective wells (bottom, right) are presented.

In Table 7 the Combination Index data illustrated in FIG. 12D is given in detail.

TABLE 7

Determined CI-values for the combination IE-8:oxaliplatin = 1:80.

| Total Dose (µM) | Effect | CI-Value |
|---|---|---|
| 2.43 | 0.12378 | 0.20084 |
| 8.1 | 0.14337 | 0.59439 |
| 24.3 | 0.27471 | 1.01690 |
| 40.5 | 0.33526 | 1.39798 |
| 64.8 | 0.69323 | 0.84420 |
| 81.0 | 0.82680 | 0.66156 |
| 97.2 | 0.88780 | 0.58260 |

TABLE 7-continued

Determined CI-values for the combination IE-8:oxaliplatin = 1:80.

| Total Dose (µM) | Effect | CI-Value |
|---|---|---|
| 121.5 | 0.91719 | 0.59418 |
| 162.0 | 0.91229 | 0.82282 |

Figure 12E:
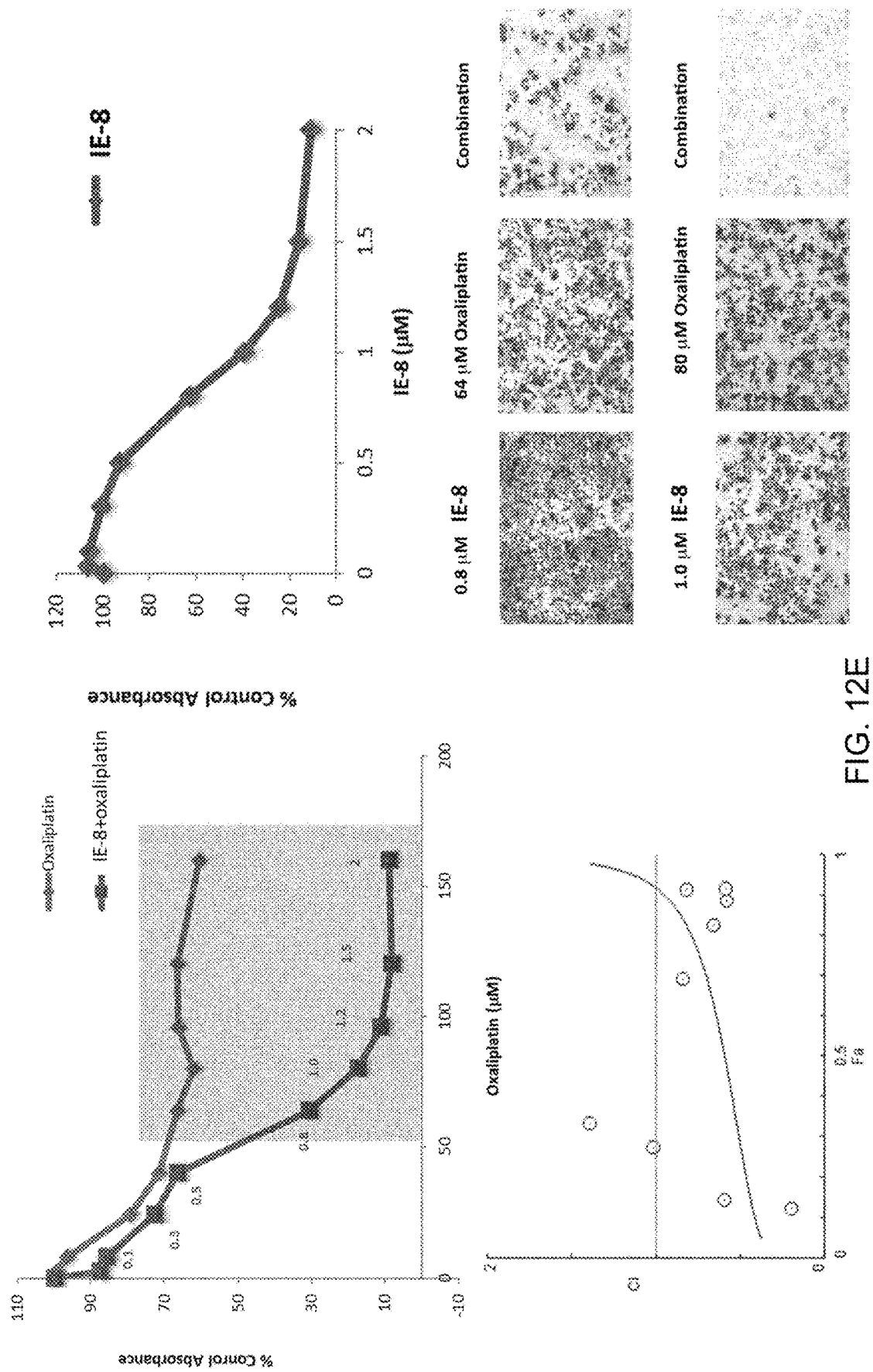
FIG. 12E shows similar types of data as in FIG. 12D, only this time, after the pretreatment with IE-8, cells were treated with oxaliplatin overnight (at a fixed-ratio of 1:80), and then allowed to recover for a total of 96 h in drug-free medium. Interactions with CI<1 are synergistic.

In Table 8 the Combination Index data illustrated in FIG. 12E is given in detail.

TABLE 8

Determined CI-values for the combination IE-8:oxaliplatin = 1:80.

| Total Dose (µM) | Effect | CI-Value |
| --- | --- | --- |
| 2.43 | 0.12378 | 0.20084 |
| 8.1 | 0.14337 | 0.59439 |
| 24.3 | 0.27471 | 1.01690 |
| 40.5 | 0.33526 | 1.39798 |
| 64.8 | 0.69323 | 0.84420 |
| 81.0 | 0.82680 | 0.66156 |
| 97.2 | 0.88780 | 0.58260 |
| 121.5 | 0.91719 | 0.59418 |
| 162.0 | 0.91229 | 0.82282 |

Example 18

IE-8 synergized with oxaliplatin and markedly increased the apoptotic potential of oxaliplatin in HCT116-oxaliplatin resistant cancer cells. A combinational treatment of highly oxaliplatin resistant HCT116 cells with Compound IE-8 and oxaliplatin at fixed ratios of 1:80 or 1:100, respectively, achieved in many instances CI values <1 demonstrating synergism (FIG. 13A and FIG. 13B, Table 9).

TABLE 9

Figure 13A:
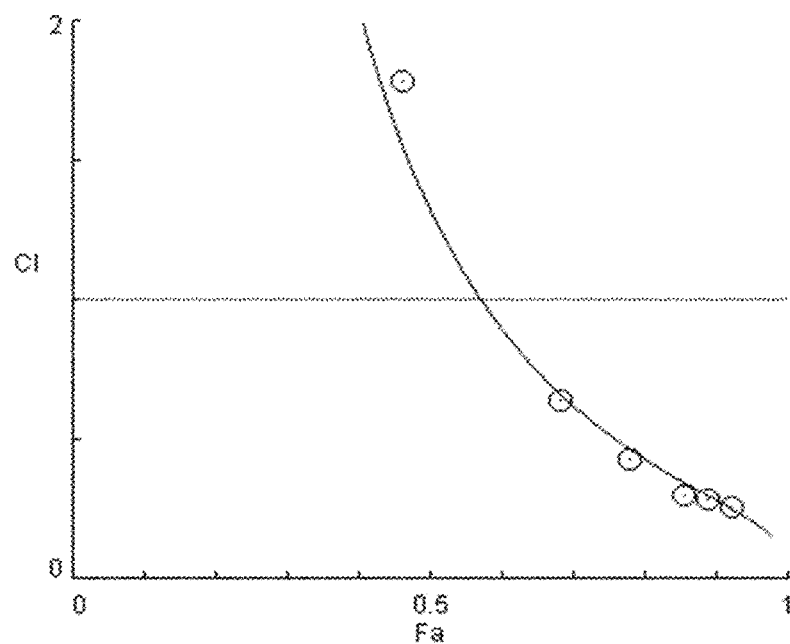
FIG. 13A shows combination index values as derived by the CompuSyn software. The data were extracted by the respective MTT experiments, quantifying the sensitivity of HCT-116-oxaliplatin resistant cells to IE-8, oxaliplatin, and the combination of the two drugs, added simultaneously, at a fixed ratio of 1:80. IE-8 was prepared as a 10 mM stock in DMA (rather than the previous DMSO preparation). Any points (values) below 1 (one), suggest a synergistic interaction between the two drugs.
Figure 13B:
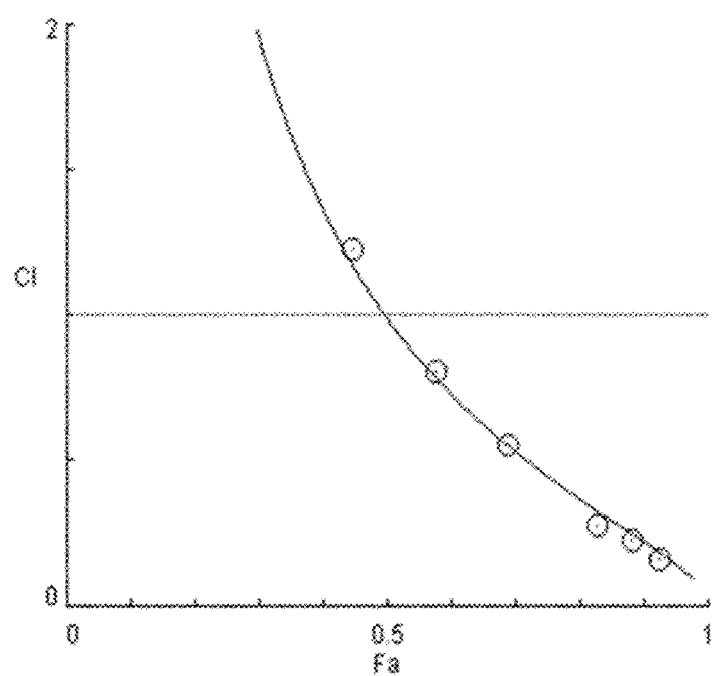
FIG. 13B shows combination index values as derived by the CompuSyn software. The data were extracted by the respective MTT experiments, quantifying the sensitivity of HCT-116-oxaliplatin resistant cells to IE-8, oxaliplatin, and the combination of the two drugs, added simultaneously, at a fixed ratio of 1:100. IE-8 was prepared as a 10 mM stock in DMA (rather than the previous DMSO preparation). Any points (values) below 1 (one), suggest a synergistic interaction between the two drugs.

CI-values illustrated in FIG. 13A (1:80 ratio) and FIG. 13B (1:100 ratio), respectively, in detail.

| IE-8:oxaliplatin = 1:80 | | | IE-8:oxaliplatin = 1:100 | | |
| --- | --- | --- | --- | --- | --- |
| Total Dose (µM) | Effect | CI-Value | Total Dose (µM) | Effect | CI-Value |
| 8.1 | 0.02548 | 150.184 | 10.1 | 0.02716 | 19.1467 |
| 24.3 | 0.21467 | 6.67557 | 30.3 | 0.09489 | 9.58769 |
| 32.4 | 0.33845 | 3.16010 | 40.4 | 0.24428 | 3.00023 |
| 40.5 | 0.46285 | 1.78325 | 50.5 | 0.44782 | 1.23151 |
| 48.6 | 0.68266 | 0.64368 | 60.6 | 0.57789 | 0.81006 |
| 56.7 | 0.78052 | 0.43315 | 70.7 | 0.68845 | 0.55710 |
| 64.8 | 0.85591 | 0.30159 | 80.8 | 0.82861 | 0.27972 |
| 81.0 | 0.88978 | 0.28724 | 101.0 | 0.88224 | 0.22529 |
| 98.2 | 0.92180 | 0.25366 | 121.2 | 0.92594 | 0.16432 |

Figure 14A:
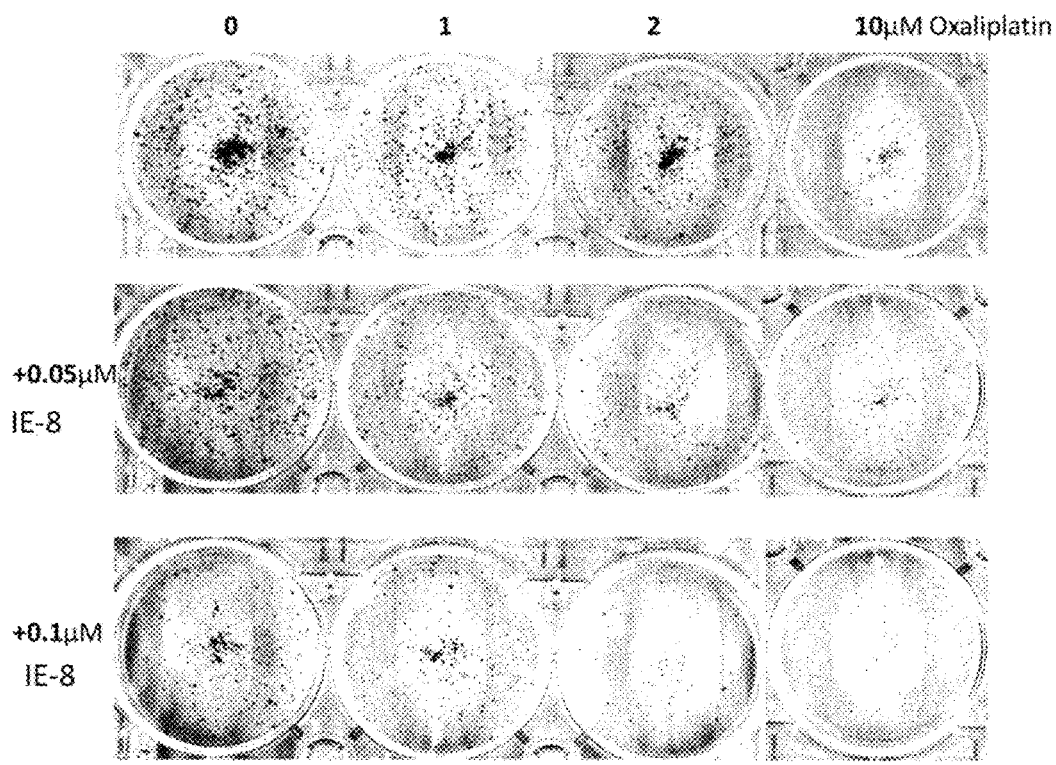
FIG. 14A shows two thousand HCT-116-oxaliplatin resistant cells that were seeded in 6-well plates and allowed to grow overnight. Oxaliplatin. IE-8 and the denoted combination was administered to the adhered cells, which were allowed to form colonies for 10 days. Colonies were stained, representative images were obtained by Fusion FX7 imager.
Figure 14B:
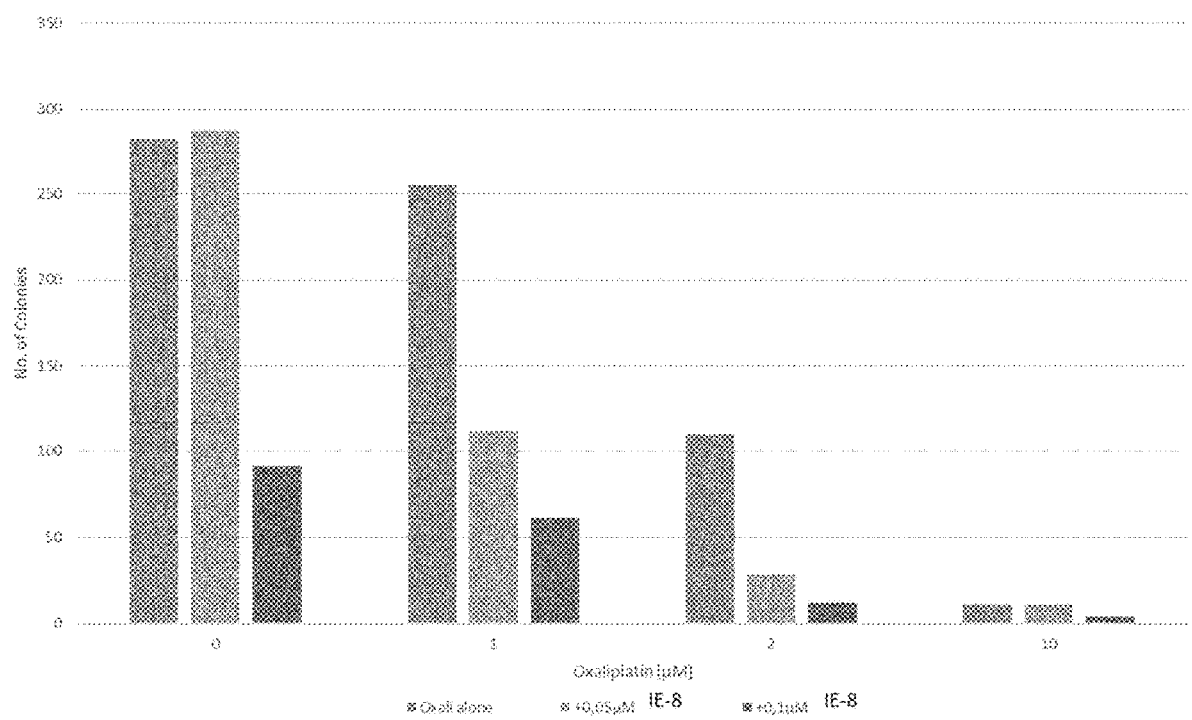
FIG. 14B shows the colonies quantified by the built-in colony counting function.

Fixed-dose combinations of IE-8 and oxaliplatin further reduced the potency of HCT116-oxaliplatin resistant cancer cells to grow into colonies (FIGS. 14A-B). The addition of 0.1 µM IE-8 to 1 µM oxaliplatin reduced the number of colonies from about 260 to about 60. Less than 25 colonies of oxaliplatin resistant HCT116 cell were observed for the combination of 0.1 µM IE-8 to 2 µM oxaliplatin.

Figure 15:
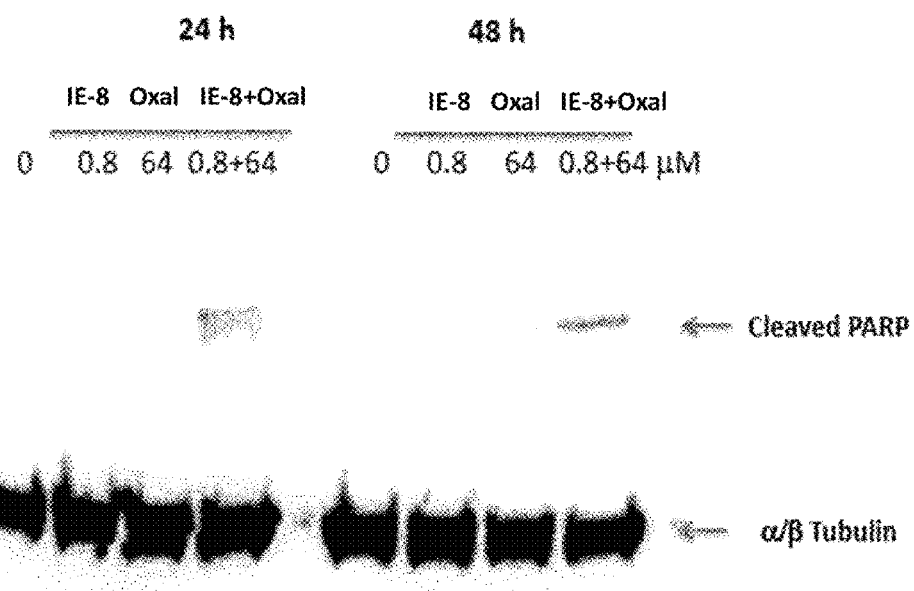
FIG. 15 shows an immunoblotting analysis of HCT-116-oxaliplatin resistant cells treated with IE-8, oxaliplatin and the combination of the two at a 1:80 ratio, for 24 h and 48 h. At the end of each incubation period, proteins were extracted, resolved by electrophoresis, and probed with the corresponding antibodies, for the induction of cleaved PARP, indicative of apoptosis. Detectable levels of cleaved PARP were only obtained in the combination treatment, showing that cotreatment of these highly oxaliplatin-resistant cells with IE-8, results in a marked increase in the apoptotic potential of oxaliplatin.
Figure 16:
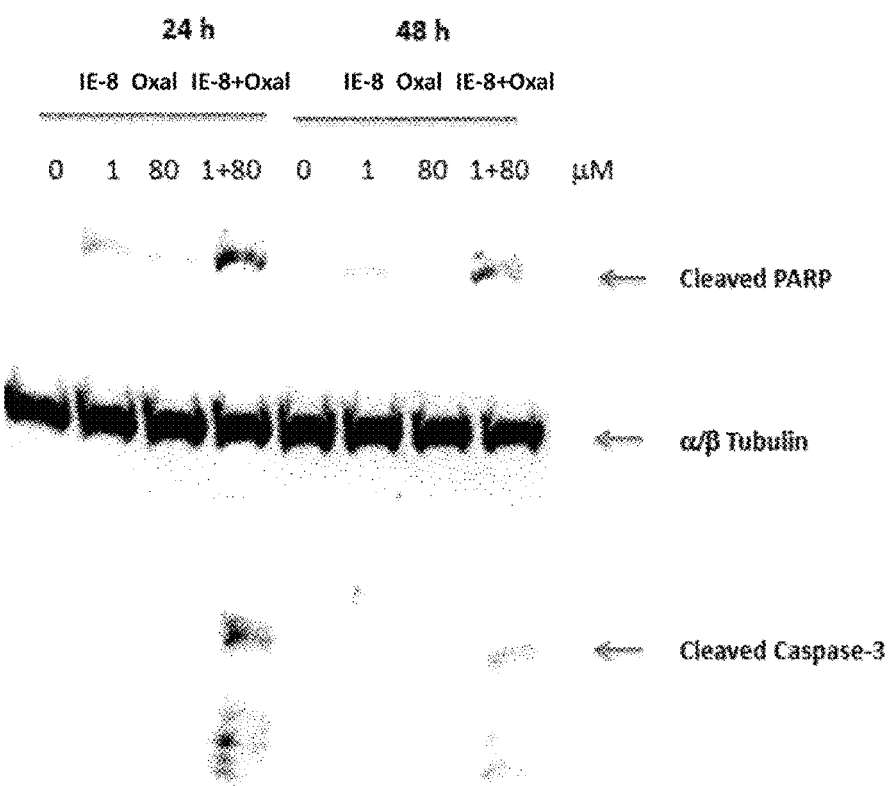
FIG. 16 shows an immunoblotting analysis of HCT-116-oxaliplatin resistant cells treated with IE-8, oxaliplatin and the combination of the two at a 1:80 ratio, for 24 h and 48 h. At the end of each incubation period, proteins were extracted, resolved by electrophoresis, and probed with the corresponding antibodies, for the induction of cleaved caspase-3, indicative of apoptosis. Detectable levels of cleaved caspase-3 were only obtained in the combination treatment, showing that cotreatment of these highly oxaliplatin resistant cells with IE-8, results in a marked increase in the apoptotic potential of oxaliplatin.

Further immunoblotting showed that the fixed combination ratio IE-8/oxaliplatin=1/80 induces apoptosis after 24 h of treatment as shown by cleaved PARP induction and cleaved Caspase-3 in HCT116-oxaliplatin resistant cancer cells, wherein the cleavage of PARP and Caspase-3 would account for the cytotoxic potency (FIG. 15 and FIG. 16). The induction of apoptosis was markedly greater when the two agents (IE-8/oxaliplatin) were used in combination, compared to each agent alone.

Example 19

Figure 17A:
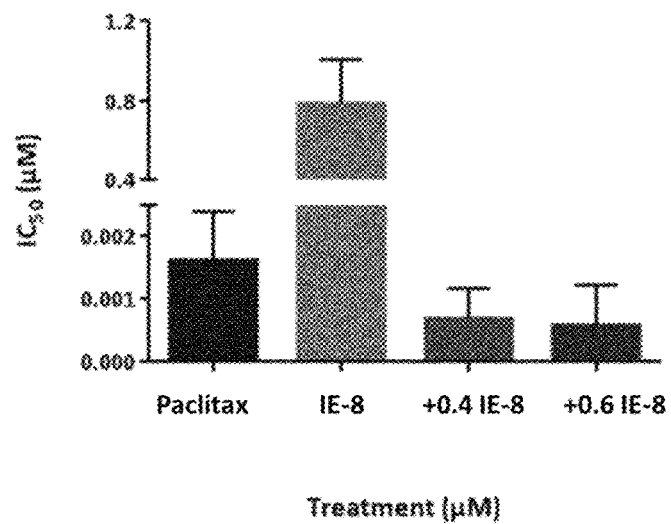
FIG. 17A shows viability of DU145 cells treated with paclitaxel alone and in combination with IE-8, as assessed by the SRB assay. The $IC_{50}$ values (average of three independent experiments) of each agent alone and in combination are shown in the bar diagram.
Figure 17B:
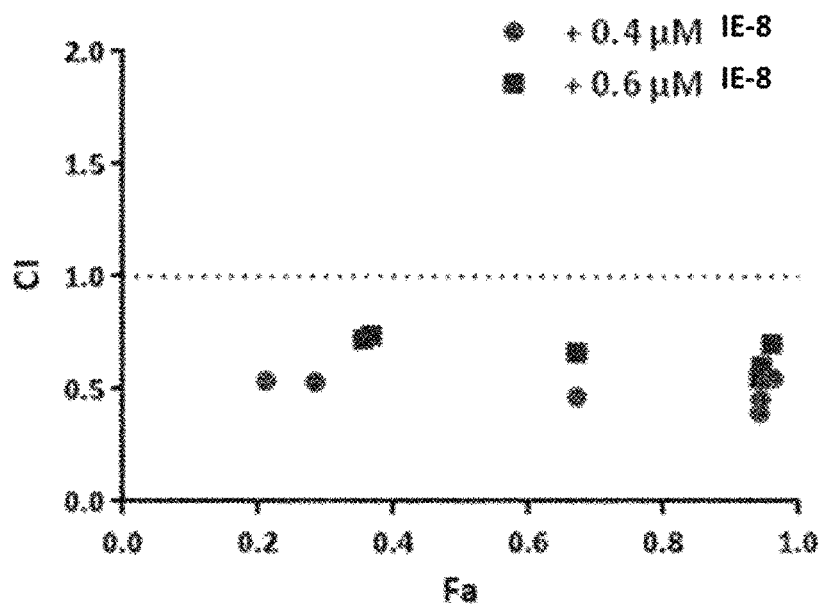
FIG. 17B shows a combination index plot derived by the CompuSyn analysis of the respective "fraction affected" values, and shows the interaction of paclitaxel with two sub-$IC_{50}$ doses of IE-8 (0.4 and 0.6 µM), to be synergistic (average of four independent experiments).
Figure 18A:
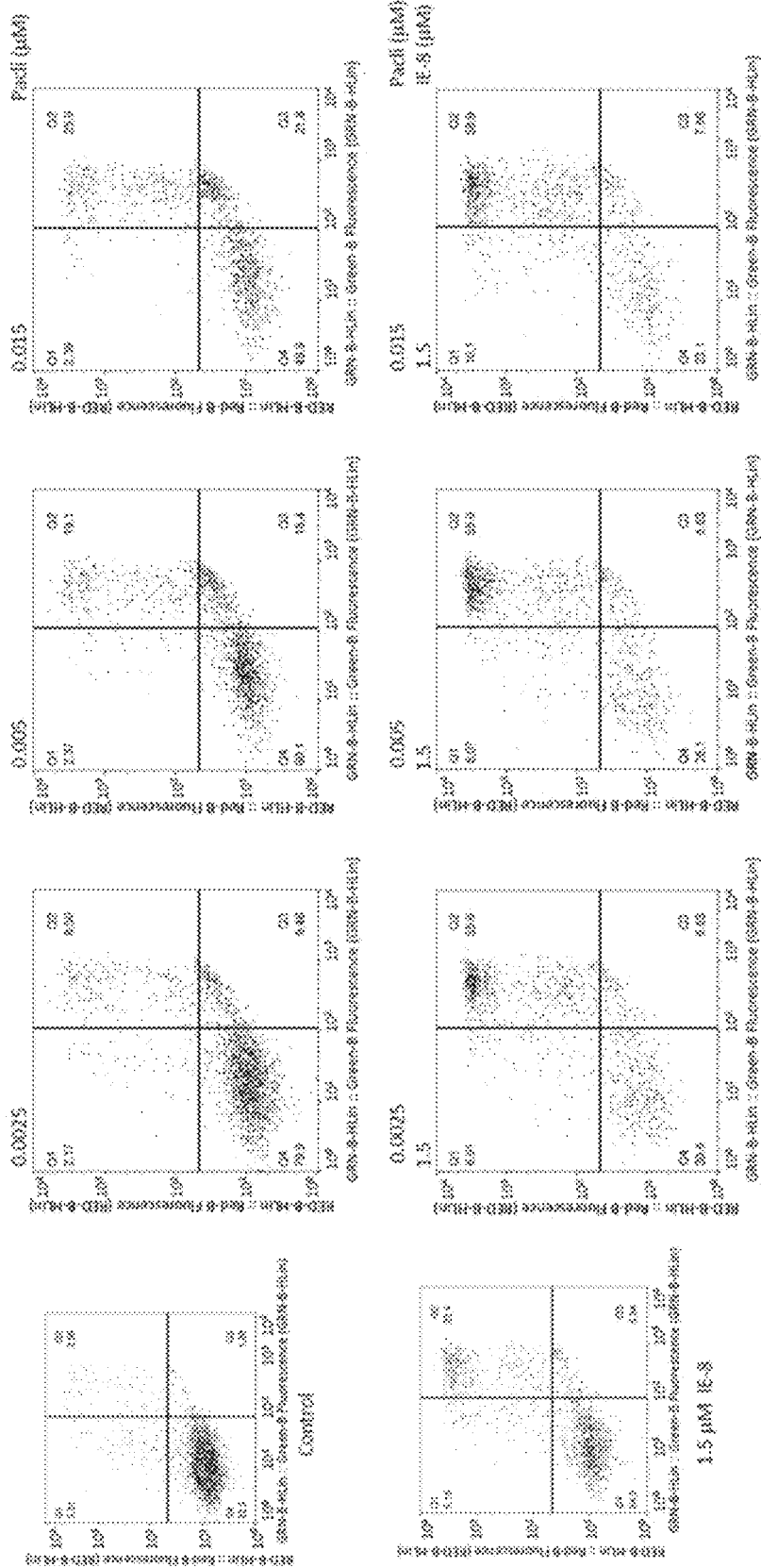
FIG. 18A shows that IE-8 enhances the apoptosis-inducing effect of paclitaxel, in DU145 cells, increasing the number of apoptotic cells, as assessed by the Annexin V/PI assay. Cells were treated with 1.5 µM of IE-8 and/or increasing concentrations of paclitaxel, and assessed after 48 h. Representative histograms of one of three independent experiments of cells treated with 1.5 µM of IE-8, in combination with increasing concentrations of paclitaxel.
Figure 18B:
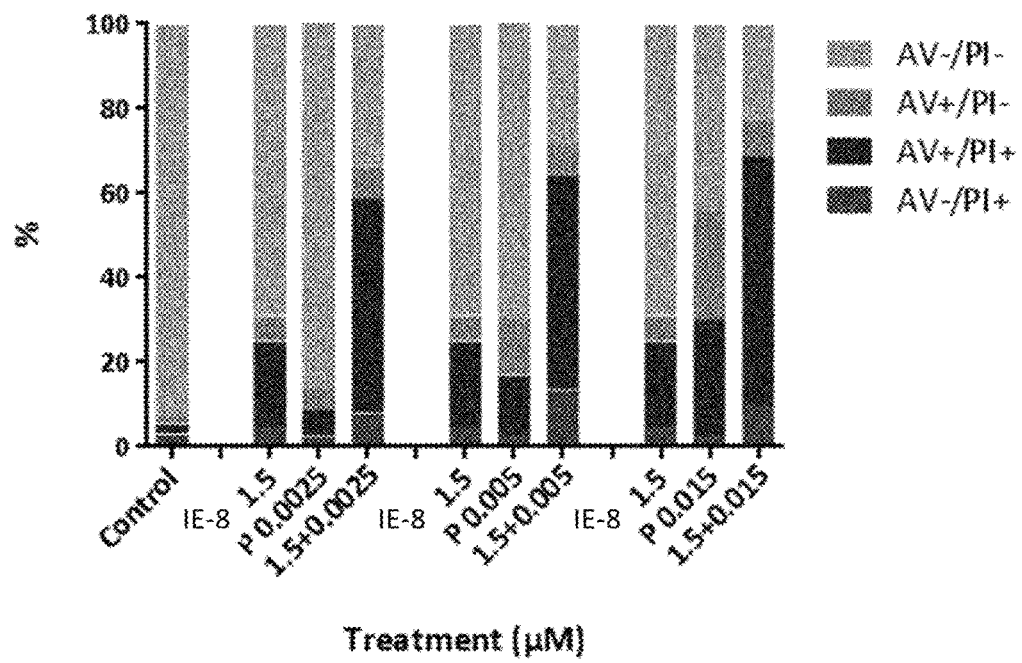
FIG. 18B shows respective bar diagrams (average of three independent experiments) of the combination of IE-8 (1.5 µM) and with increasing doses of paclitaxel.
Figure 19A:
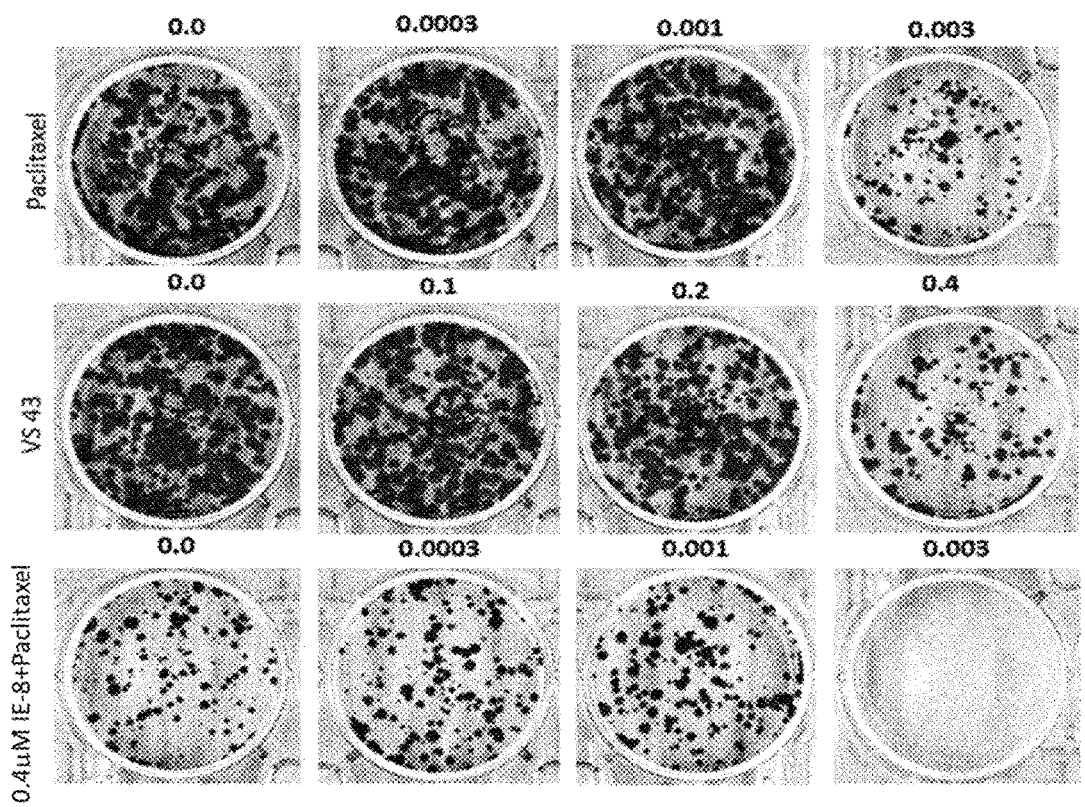
FIG. 19A shows a clonogenic assay evaluating the effect of paclitaxel, IE-8 and their combination in the ability of single cells to form colonies. DU145 were seeded in 6-well plates (1000 cells/well) and were treated with increasing concentration of paclitaxel, IE-8 and their combination, and allowed to grow colonies for 10 days, without any further manipulation. Colonies were fixed and stained with crystal violet (representative images of the plates). When 0.4 µM IE-8 were used in combination with 0.003 µM paclitaxel, no colonies were formed.
Figure 19B:
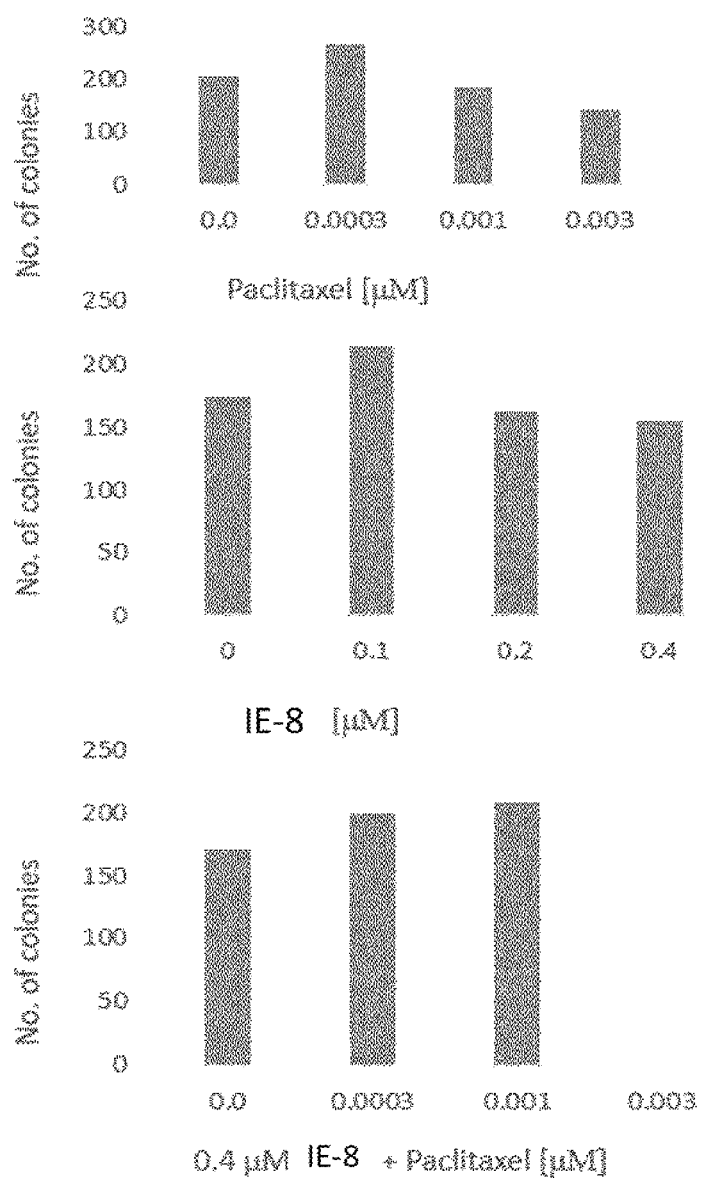
FIG. 19B shows the colonies counted using a colony-counting function of the Fusion 15.12 software. When 0.4 µM IE-8 were used in combination with 0.003 µM paclitaxel, no colonies were formed.

IE-8 synergized with paclitaxel in DU145 cancer cells. A combinational treatment of DU145 cancer cells with Compound IE-8 and paclitaxel resulted in a higher cytotoxicity than single compound treatment, as demonstrated by the considerable decrease of the $IC_{50}$ value below 0.001 µM (FIG. 17A), which was confirmed by CI values <1 (FIG. 17B). As a result, IE-8 enhanced the apoptosis-inducing effect of paclitaxel as shown by the Annexin-V/Propidium iodide assay in these cells, when treated with the agent for 48 h (FIGS. 18A-B). Furthermore, fixed-dose combinations of IE-8 and paclitaxel reduced the potency of DU145 cancer cells to grown into colonies (FIGS. 19A-B).

Example 20

Figure 20A:
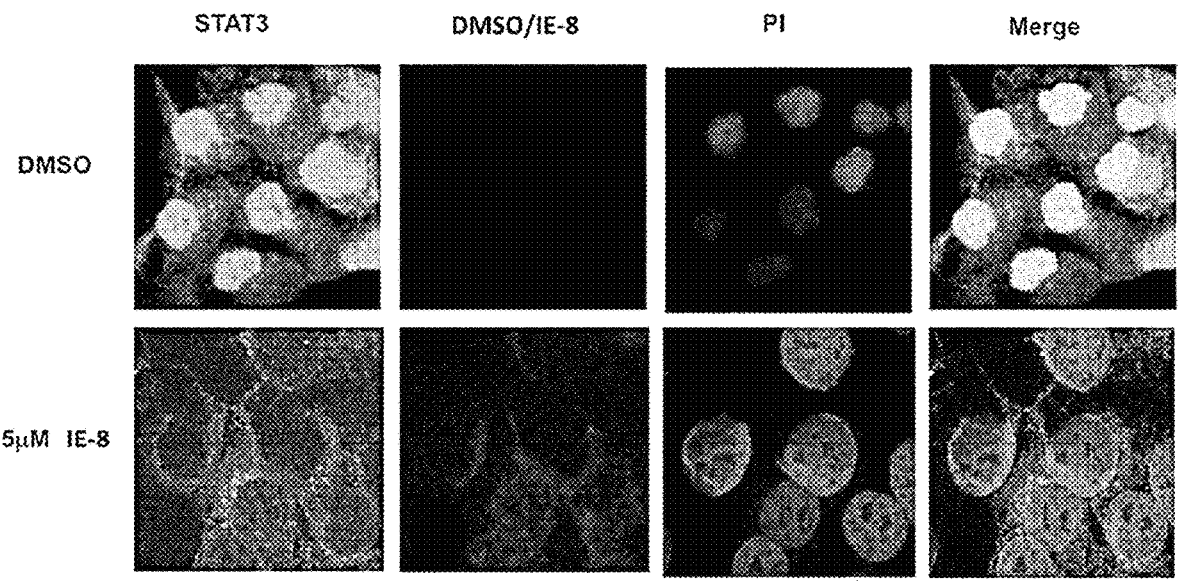
FIG. 20A shows DU145 cells that were treated with 5.0 µM IE-8 for 5 h, washed with PBS, and fixed with 2% paraformaldehyde (PFA). They were subsequently permeabilized and the nuclei stained with propidium iodide (PI) or stained for Stat3 after blocking, and counterstained with a fluorescent secondary antibody, before being subjected to confocal microscopy imaging. The composite image presents the superimposed overlay of IE-8 fluorescence (second column) and the fluorescence PI (third column) and the Stat3 antibody (first column). No fluorescent signal from IE-8 was detected in the control, vehicle-treated cells.
Figure 20B:
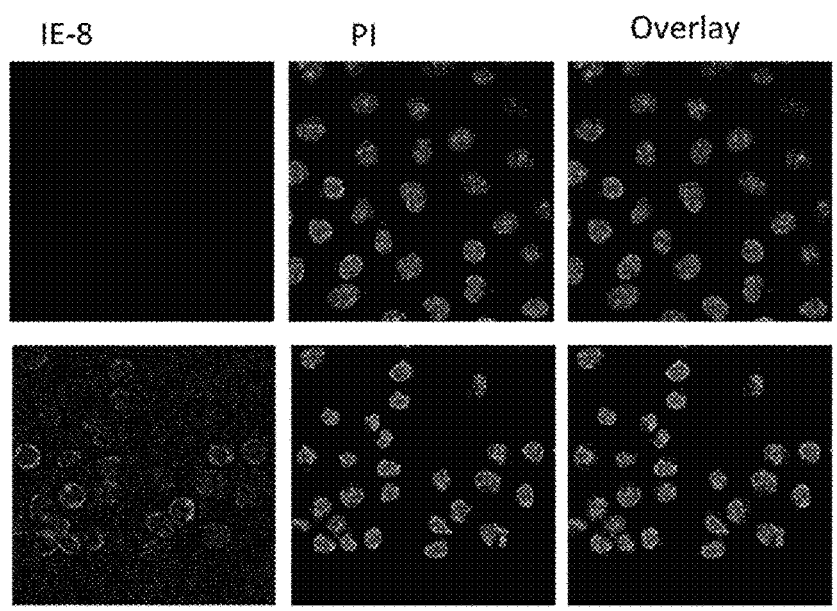
FIG. 20B shows visualization of IE-8, localizing around the nucleus, in MDA-MB-468 cells, after 5 h treatment with 5 µM.
Figure 20C:
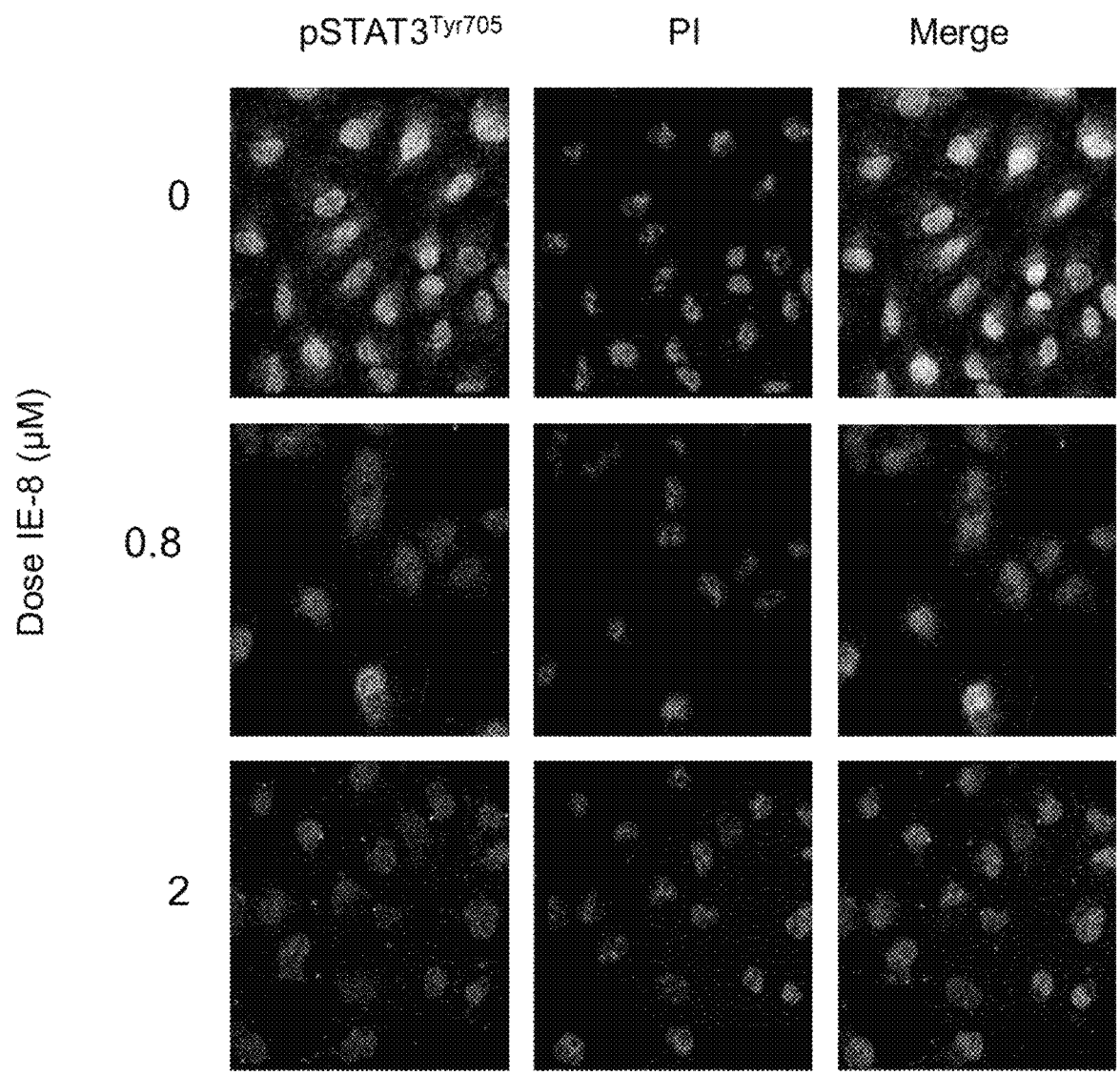
FIG. 20C shows A549 cells treated with 1.2 µM IE-8, for 18 h, and processed as in FIG. 20A, but in this case stained for pSta3, localizing in the nucleus.

Identification of subcellular localization of IE-8 and efficient reduction of cellular pStat3 in DU145 and MDA-MB-468 cancer cells. In confocal microscopy experiments in DU145 and MDA-MB-468 cells exposed to IE-8 (5 µM) for 5 h, the compound's subcellular localization could be detected (FIG. 20A and FIG. 20B) by its blue fluorescence, upon UV excitation. Accordingly, IE-8 penetrated the cellular membrane and remained localized in the cytoplasm. Under these conditions, the levels of nuclear Stat3 were decreased as evidenced from a significant reduction of the immunostaining of the protein in the DU145 nuclei, and instead accumulates in the cytoplasm (FIG. 20A). Similar results were obtained in A549 cells, treated for 18 h with IE-8, and stained for phosphorylated Stat3, with IE-8 markedly decreasing the levels of the activated protein (FIG. 20C).

Example 21

Identification of Stat3 inhibition-mediated modulation of the repair of DNA ICLs by Compound IE-8 in diverse cancer cells. A proposed mechanism of the observed chemosensitization to the DNA-damaging agents cisplatin (and similarly to oxaliplatin) is the Stat3 inhibition-mediated modulation of the repair of the DNA interstrand crosslinks (DNA ICLs) produced by these agents and thought to be the critical cytotoxic lesions. The modified single-cell gel electrophoresis (Comet) assay enables the monitoring of the induction and repair of DNA ICLs in intact cells. As shown in FIGS. 21A-C and FIGS. 22A-C, IE-8 modulated the repair (i.e. 'unhooking') kinetics of the DNA ICLs without affecting their formation. Pretreatment with IE-8, either overnight or acutely for 1 hour, before cisplatin treatment, in DU145 cells (FIG. 22A and FIG. 22B, respectively), and A549 cells (FIG. 22C) impairs the 'unhooking' of the cisplatin-produced ICLs. Since cells can no longer repair this critical lesion, which persists, they become more sensitive to the DNA damaging agents. The same was also observed in A2780-cisplatin resistant cells, treated with IE-8, 3 h post the acute (1 h) cisplatin treatment (FIGS. 23A-C). It is well established that the resistance in this particular subline is due to the enhanced repair of the DNA ICLs. IE-8 effectively inhibited this repair, restoring sensitivity those highly resistant cells to cisplatin. DNA-damage response to cisplatin was enhanced by IE-8 in combination treatments in DU145 cells, pretreated with 1.2 µM IE-8 for 18 h and then with 60 µM cisplatin for 1 h, as assessed by the induction of γ-H2Ax, detected by immunofluorescence (FIG. 21A). The increase in the intensity and extent of nuclear staining for γ-H2Ax and the numerical increase of the detected foci (quantified by Cell Profiler—FIG. 21B) in the combination treatment is in agreement with the persistence of the DNA damage (and particularly the unresolved DNA ICLs) previously documented by the comet assay. The same effect on the induction of γ-H2Ax was observed in immunoblots of A549 cells, treated with IE-8 and cisplatin alone, or with both agents in combination (FIG. 23C).

Example 22

Identification of activity and cytotoxicity of IE-8 in 3D multicellular tumor spheroid cultures from HCT116-oxaliplatin-resistant cells. Compound IE-8 was found to be also cytotoxic in 3D multicellular tumor spheroid cultures, derived from the HCT16-oxaliplatin-resistant cells. Cytotoxicity was assessed by the 3D cell-titre Glo® assay, after a 96 h exposure, and the $IC_{50}$ values were derived. Mirroring the superior activity of IE-8 observed in the 2D monolayer cultures, the tested inhibitors' activity in spheroids, can be ranked as follows: IE-8 (8.5 µM)>Atovaquone (16.5 µM)>HO-3867 (33 µM).

The effects of the treatment with IE-8 on the HCT116-oxaliplatin resistant spheroids' size could be seen in FIG. 24A. Immunoblotting confirmed the inhibition of pStat3 by IE-8 (FIG. 24B) and cleavage of PARP indicated an apoptotic cell death (FIG. 24C).

These data suggest that IE-8 can penetrate the compact cellular environment of the spheroids and exert its biological activity.

Example 25

Figure 25A:
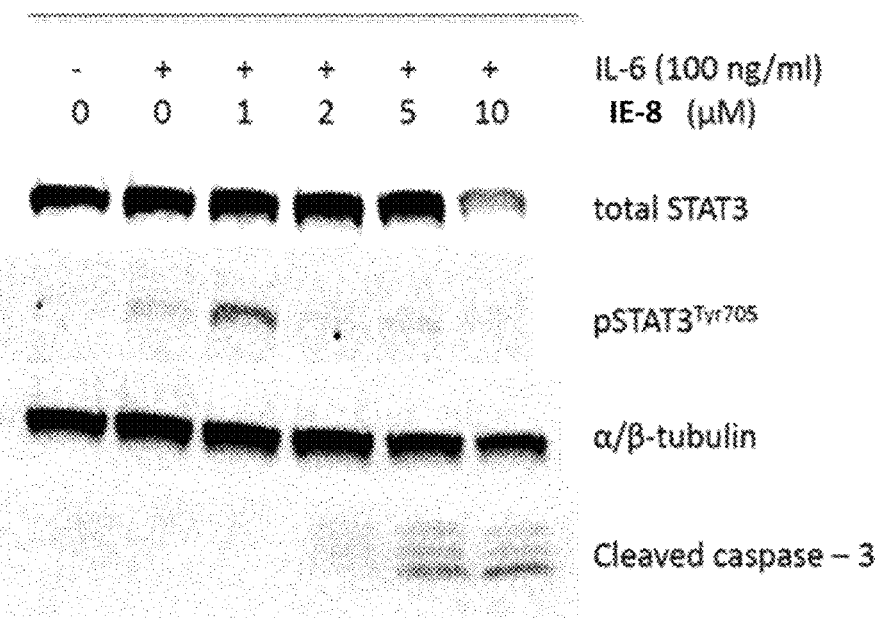
FIG. 25A shows multicellular spheroids derived from A2780-cisplatin resistant cells, allowed to grow for 4 days, and treated with increasing concentrations of IE-8 for 48 h (Immunoblotting). The blot shows inhibition of pStat3 and concomitant induction of apoptosis, at increasing IE-8 concentrations in spheroid cultures, suggesting that IE-8 can efficiently penetrate and exert its biological activity in a 3D cellular model.
Figure 25B:
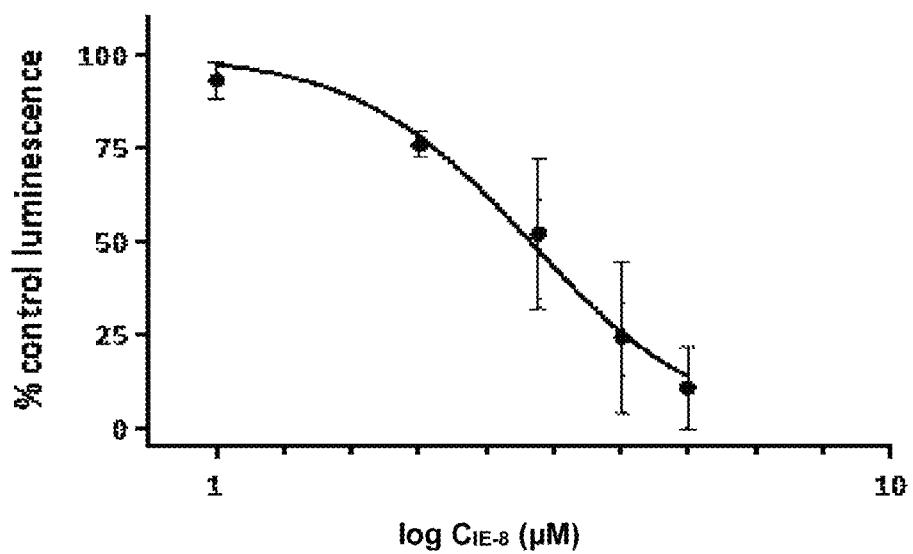
FIG. 25B shows multicellular spheroids derived from A2780-cisplatin resistant cells, allowed to grow for 4 days, and treated with increasing concentrations of IE-8 for 96 h (cell viability assay). An averaged dose-response curve of three independent experiments, using the CellTiter-Glo® 3D Cell Viability Assay, is shown.
Figure 26:
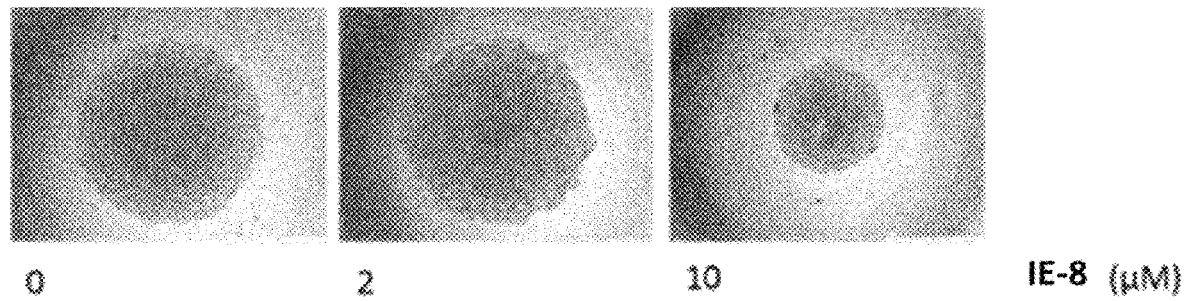
FIG. 26 shows an effect of IE-8 on the size of A2780-cisplatin resistant spheroids. Cells were seeded in ultra-low attachment microplates and left to form spheroids for 4 days. The spheroids were then treated with IE-8 for 96 hours and images were taken using the Cell^F imaging software. Treatment with 10 µM IE-8 markedly decreases the size of the spheroid, compared to the untreated control.

Identification of cytotoxicity and pStat3 inhibition of IE-8 alone or in combination with cisplatin in 3D multicellular tumor spheroid cultures from A2780-cisplatin resistant cells. IE-8 efficiently inhibited the cytokine-inducible (IL-6) levels of pStat3 in the A2780-cisplatin resistant spheroids (FIGS. 25A-B). A visible decrease in spheroid size depending on the concentration of treated IE-8 was demonstrated in FIG. 26. Compound IE-8 again displayed stronger cytotoxic effects than the other small-molecule Stat3 inhibitors atovaquone, stattic, curcumin, and HO-3867 (Table 10). IE-8 was more active in spheroids than all the other inhibitors tested.

TABLE 10

|  | $IC_{50}$ (µM) |
| --- | --- |
| Curcumin | 36.98 ± 9.40 |
| IE-8 | 3.01 ± 0.41 |
| Stattic | 9.14 ± 2.74 |
| HO-3867 | 29.72 ± 7.81 |
| Atovaquone | 24.36 ± 3.36 |

Figure 27:
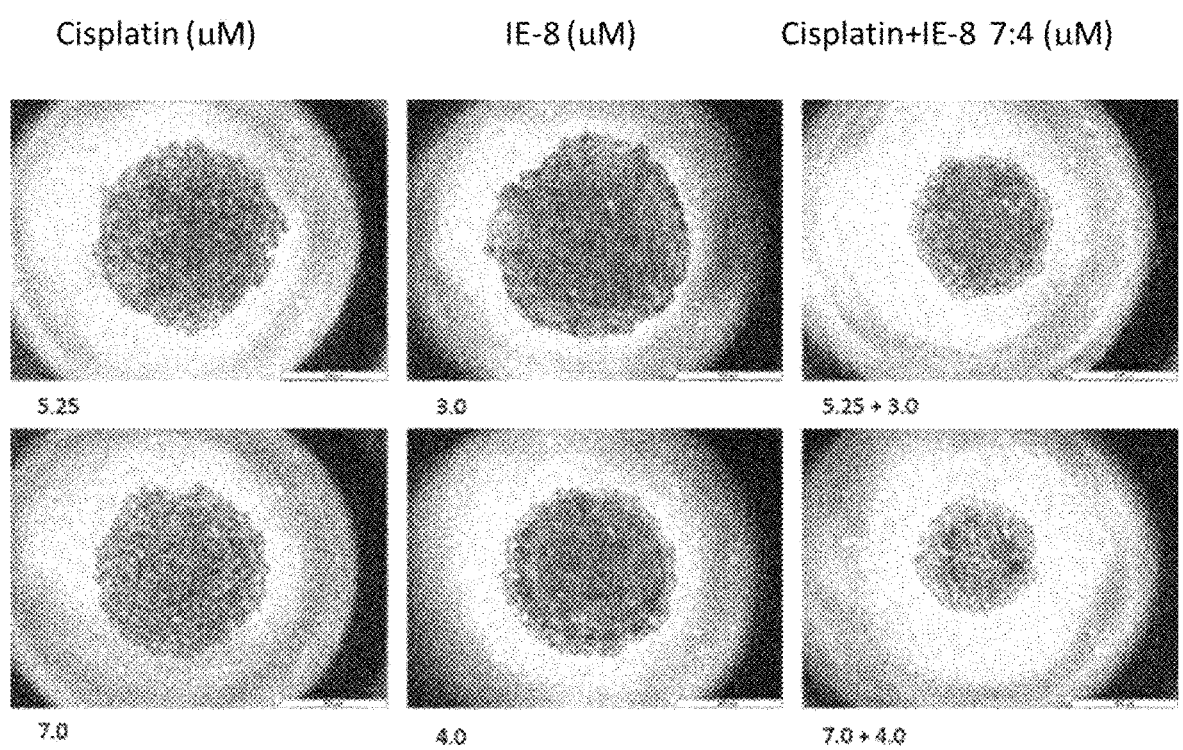
FIG. 27 shows effects of cisplatin, IE-8 and their combination at a fixed ration of 7:4, on the size of A2780-cisplatin resistant spheroids. Representative images of the spheroids using the Cell^F imaging software.

The tumor spheroid diameter from A2780-cisplatin resistant cells decreased from 1202 µm to 834 µm and 820 µm upon 96 hours of single-drug exposition of 7.0 µM of cisplatin and 4.0 µM of IE-8, respectively. In particular, the combination of both cisplatin and IE-8 in the ratio of 7:4 resulted in a significant decrease in tumor spheroid diameter to 576 µm (FIG. 27, Table 11).

TABLE 11

| Cisplatin (µM) | Diameter (µm) | IE-8 (µM) | Diameter (µm) | Cisplatin + IE-8 (µM) | Diameter (µm) |
| --- | --- | --- | --- | --- | --- |
| 0 | 1201.7 | 0 | 1145.0 | 0 + 0 | 1176.0 |
| 1.75 | 1071.4 | 1.0 | 1176.0 | 1.75 + 1.0 | 1049.7 |
| 3.5 | 1047.5 | 2.0 | 1037.0 | 3.5 + 2.0 | 879.4 |
| 5.25 | 916.4 | 3.0 | 990.9 | 5.25 + 3.0 | 687.3 |
| 7.0 | 833.6 | 4.0 | 819.7 | 7.0 + 4.0 | 576.2 |
| 8.75 | 713.0 | 5.0 | 619.8 | 8.75 + 5.0 | 592.8 |

Example 24

Figure 28:
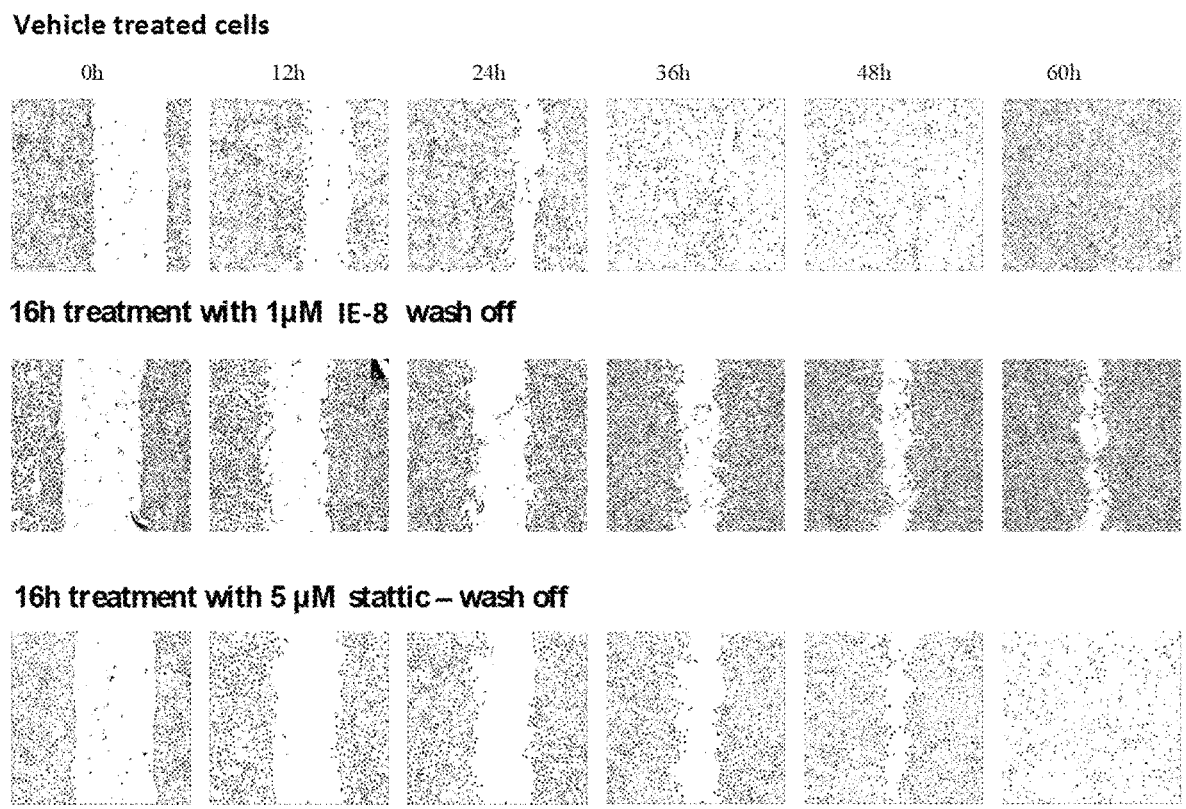
FIG. 28 shows an in vitro scratch assay in DU145 cells. Cells were pretreated with IE-8 and stattic for 18 h, the drugs were washed off and replaced with fresh, drug-free medium, before the cell monolayer was wounded manually. Images were taken at 12 h intervals.

IE-8 blocks cell migration in wound healing assay. Compound IE-8 was able to inhibit cell migration as shown by the wound healing assay in DU145 cells (FIG. 28). Treatment with 1 µM IE-8 for 18 h, prior to the introduction of the wound, prevented its full closure for up to 60 h, as opposed to the untreated control where the wound was closed by 36 h, and the cells treated with a 5-fold higher concentration of stattic.

Example 25

Figure 29A:
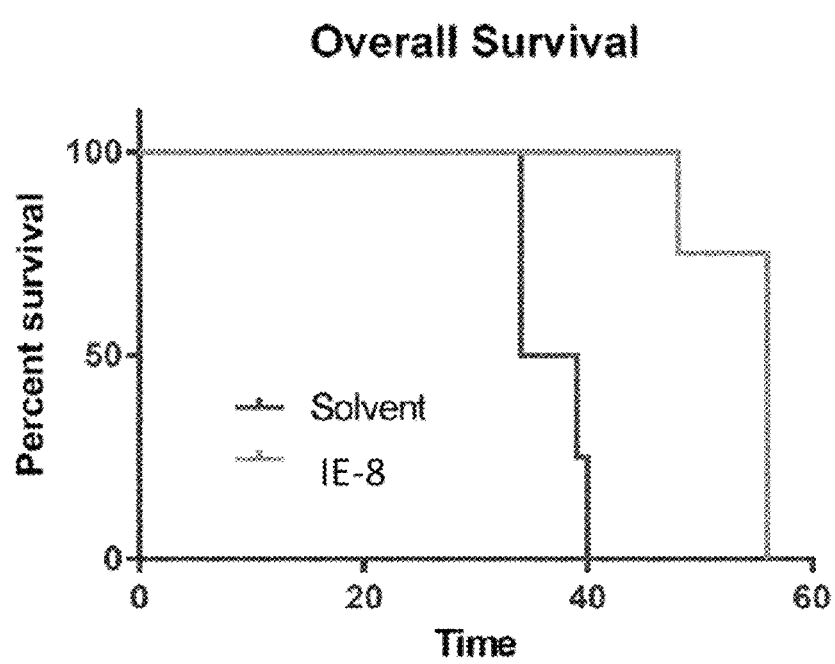
FIG. 29A shows an extension in overall survival of mice, bearing HCT16-oxaliplatin resistant xenografts, treated with vehicle or with 30 mg/kg IE-8 on days 10, 13 and 17. For each group n=4.
Figure 29B:
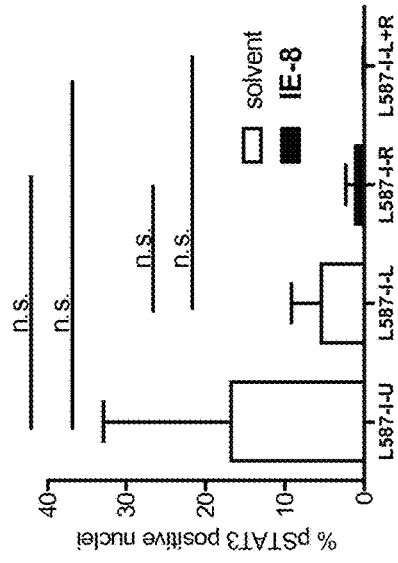
FIG. 29B shows levels of phosphorylated Stat3 expressed as % pStat3 positively stained nuclei, in tissue sections from mice bearing xenografts derived from the denoted cell lines (A549, A431, DU145, and HCT116-oxaliplatin resistant cell line), as assessed by immunohistochemistry. Treatment of the animals with 30 mg/kg IE-8, induced a marked and in many instances significant downregulation of the target macromolecule.
Figure 29B:
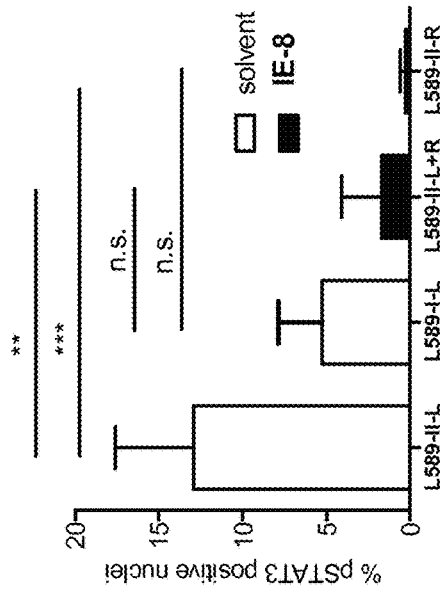
Figure 29B:
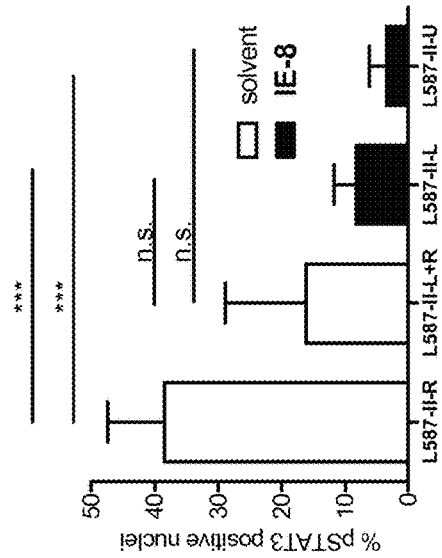
Figure 29B:
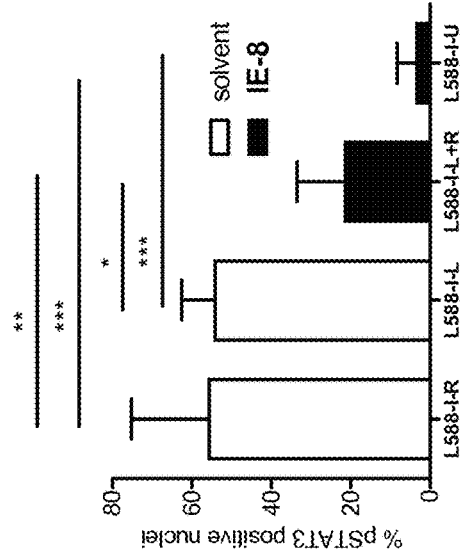

In vivo treatment of cancer. After subcutaneous injection of the HCT16-oxaliplatin resistant cell, mice bearing oxaliplatin resistant colorectal carcinoma tumors, were intraperitoneally treated with IE-8 (30 mg/kg of body weight), on days 10, 13 and 17. IE-8 markedly increased the overall survival of the mice, as treated animals survived about 20 days longer than those without the administration of the Compound (vehicle only) (FIG. 29A). On subsequent experiments on xenografts derived from four different cancer cell lines (A549, A431, DU145 and HCT116-oxaliplatin resistant cells), animals were treated with a single dose of IE-8 (30 mg/kg of body weight) and sacrificed 24 h later. Tissue sections were prepared and immunohistochemistry was performed to quantify the expression of pStat3 in control (solvent only) animals and those treated with IE-8 (FIG. 29B). In all cases, downregulation of the pStat3 levels in vivo, was achieved (in certain instances significant) by a single dose treatment.

Example 26

Detection of intrinsic fluorescence of IE-8. Exposure of A2780, A2780-cisplatin resistant, HCT116, HCT116 oxaliplatin resistant and DU145 cell lines to various concentrations of IE-8 (0, 2, 10, 50 and 100 µM) resulted in a marked dose-dependent increase in the mean fluorescence intensity as detected by FACS, in the Qdot655 channel (and to a lesser extent in the Qdot605 channel), upon a 405 nm excitation (FIGS. 30A-E).

Example 27

IE-8 induced cytoplasmic vacuolisation. DU145 cancer cells were treated with increasing concentration of IE-8 (mM), over 24 h, at 6 h intervals. At increasing doses, the induction of vacuoles emerges at earlier times. This vacuolisation—which ultimately leads to cell lysis—is reminiscent of the morphological signature of methuosis and paraptosis, non-apoptotic cell death mechanisms, which entail the extreme displacement of the cytoplasm with fluid-filled vacuoles. This mechanism of cell death could be particularly important within the context of cancer cells which are inherently resistant to apoptosis-inducing drugs (FIGS. 31A-C)

Example 28

IE-8 treatment induced aggresome-like structures. In live cell microscopy experiments of DU145 cells, there is a dose-dependent induction of aggresome-like perinuclear structures (presumed to be IE-8 bound on Stat3, detected by the compound's inherent fluorescence) (FIG. 32). The images shown were taken at 3 h. Exploiting the intrinsic fluorescence of IE-8, cellular uptake, nuclear accessibility and interaction with the target protein could be monitored directly in situ, without solely relying on a relevant biological read-out (e.g., downregulation of pStat3 levels, as detected by immunoblotting experiments above).

Example 29

IE-8 effectively reduced the invasion of cancer cells. The direct extension and penetration of cancer cells into neighbouring tissue (i.e. invasion) is generally regarded as a key hallmark of malignant tumors. Local invasion is also the first stage in the process that leads to the development of secondary tumors or metastases. In certain types of cancer, such invasion triggers the development of secondary tumors or metastases, causing a higher rate of morbidity. IE-8 was found to be an effective agent to hamper the invasion of fibrosarcoma cells (HT1080). During an observation period of 90 h, the rate of confluence in cancer cells treated with IE-8 (3 µM) was markedly reduced and also delayed with regard to untreated cancer cells (FIGS. 33A-B).

In one embodiment, the invention is directed to the design and synthesis of cytotoxic 3,5-Diarylidenyl-N-Substituted piperid-4-one analogs of curcumin.

STAT3 is constitutively activated in many cancers, leading to survival, proliferation, angiogenesis, immune evasion and metastasis, comprising a promising anti-cancer target. Forty 3,5-diarylidenyl-N-substitutedpiperid-4-ones (DAPs) were designed and synthesized, in which eight different arylidenyl groups substituted with methyl, nitro, hydroxy, and methoxy groups were included. The N-atom of the 4-piperidone core was also modified to contain substituents that varied in size, flexibility, and aromaticity. The goal of this project is to gain insight into the structure-activity relationship of DAPs in order to optimize the cytotoxic activity and water solubility of the compounds. Of the 40 compounds, eight are novel (6e, and 8b-h). The compounds were synthesized by acid or base catalyzed aldol condensation of the respective substituted 4-piperidones with the appropriate benzaldehydes. The products were synthesized in isolated yields of 9-64%. All 40 DAP analogs inhibited the growth of murine L1210 and B16 cancer cells. It was evident that group "h" compounds that contain the 3,4,5-trimethoxybenzylidenyl groups were the most active. The novel N-phenyl substituted compound 8h was selected to be the lead compound on the basis of its cytotoxic potency against L1210, B16, and the human MDA-MB-435 cancer cells ($IC_{50}$ of 0.36, 0.30, and 0.15 µM, respectively), as well as its solubility in water (200 µM). By virtue of its inherent fluorescent properties, compound 8h could be detected by confocal microscopy in the cytoplasm of human A549 lung cancer and MDA-MB-468 breast cancer cells. The microscopy studies further demonstrated that 8 h reduced the nuclear levels of active, phosphorylated STAT3. These results were corroborated by immunoblotting, which showed that at concentrations >1 µM 8 h markedly inhibits both constitutive and IL-6 induced STAT3 activation by 18 h. Additionally, 8 h inhibits the STAT3-DNA binding activity, in DU145 and MDA-MB-468 nuclear extracts. The 8 h-mediated STAT3 inhibition, initiated an increase in the levels of cleaved-PARP along with a reduction in the levels of the STAT-3 regulated gene products, such as survivin, Bcl-2, Bcl-xL suggesting that 8 h selectively inhibits the STAT3 pathway and kills cells through apoptosis. 8 h was more potent, in terms of both its cytotoxicity and its pSTAT3 inhibitory activity, than other small molecule inhibitors (such as, stattic, atovaquone, HO-3867 and curcumin) in all the cell lines tested, including cells highly resistant to the clinically-used drugs cisplatin and oxaliplatin. 8 h proved to be a potent in vitro radio- and chemosensitizing agent, when used in different combination schedules/treatments, achieving synergistic interactions with the platinum drugs and enhancing their apoptosis potential and DNA damage response. A proposed mechanism for this observed sensitization is the impairment that 8 h confers in the unhooking of DNA ICLs produced by cisplatin, in various cellular contexts. 8 h was also active in 3D tumor spheroids, possessing superior cytotoxic activity to the other STAT3 inhibitors tested, downregulating the levels of pSTAT3 and inducing apoptosis. Finally. 8 h was able to inhibit DU145 cell migration in an in vitro wound-healing assay.

Introduction

Signal Transducer and Activator of Transcription 3 (STAT3) has been implicated in the pathogenesis of a variety of human malignancies including head and neck cancer, myeloma, prostate cancer, breast cancer, colon cancer, and ovarian cancer.[1] Persistent activation of STAT3 signaling has been demonstrated to induce cell proliferation and prevent apoptosis in human cancer cells through the dysregulation of key proteins, including cell survival proteins [e.g. (Bcl-xL and Mcl-1], cell cycle regulators (e.g., cyclin D1/D2 and c-Myc), and inducers of angiogenesis including vascular endothelial growth factor (VEGF) and hypoxia-inducible factor 1 (HIF1). Activated STAT3 is also correlated with resistance to both conventional DNA-damaging and molecular targeted therapies.[2] Because of its important role in oncogenesis, STAT3 has attracted much attention as a potential pharmacologic target for cancer treatment.[1d,3] Numerous compounds have been reported to inhibit STAT3 but none have progressed successfully through Phase III clinical trials.[4a-d] Hence, the identification of a clinically active STAT3 inhibitor through rational drug design remains a focal point of research towards development of novel cancer therapeutic agents. However, recently an FDA approved antimicrobial drug, atovaquone.[4d] was identified as a STAT3 inhibitor and anticancer agent, while another agent, napabucasin was granted orphan status as a STAT3-targeted drug.[4c]

Curcumin (1, FIGS. 1A-E) is known to produce a wide variety of effects that could confer anticancer activity;[5] however, it is also known to nonspecifically perturb cell membranes' and multiple cellular pathways; thus, there is a need to identify analogs with more selective effects. Recently, a novel class of curcumin analogs, diarylidenylpiperidones (DAPs), was developed by replacing the β-diketone structure with a 4-piperidone unit.[7] Many DAP analogs have been synthesized, characterized and reported to be generally more potent than the parent curcumin at inhibiting the proliferation of cancer cells in culture.[7e] One of the analogs, a para-fluorinated DAP, HO-3867 (2, Formulae P1) displayed significant cytotoxic activity against human ovarian cancer in animals by targeting the JAK/STAT3 signaling pathway and inhibiting STAT3 phosphorylation.[8] From in silico docking studies, DAP 2 was found to bind a pocket of the DNA-binding domain of STAT3 with high afinity.[8c] HO-3867 displays selective antitumor activity against ovarian xenografts without toxic side effects, demonstrating its potential for further clinical development.[8c,d] In a quest to develop curcumin analogs with improved cytotoxic properties, fifteen readily accessible curcumin analogs were designed and synthesized by replacing the diketone moiety of curcumin with a 4-phenylcyclohexanone moiety.[9] These analogs were cytotoxic against B16 and L1210 murine cancer cell lines in culture. Analog 3 (Formulae P1), which showed $IC_{50}$ values of 0.51 and 1.2 µM, respectively, was the most potent. Since analog 3 is structurally related to DAPs, such as piperidone 2, it was envisaged that it too derives its antiproliferative activity through the inhibition of STAT3 phosphorylation. This contention was confirmed from studies revealing that at a concentration of 2 µM compound 3 almost completely and selectively diminished the level of phosphorylated STAT3 (Y705) in human embryonic kidney 293 (HEK) cells.[10]

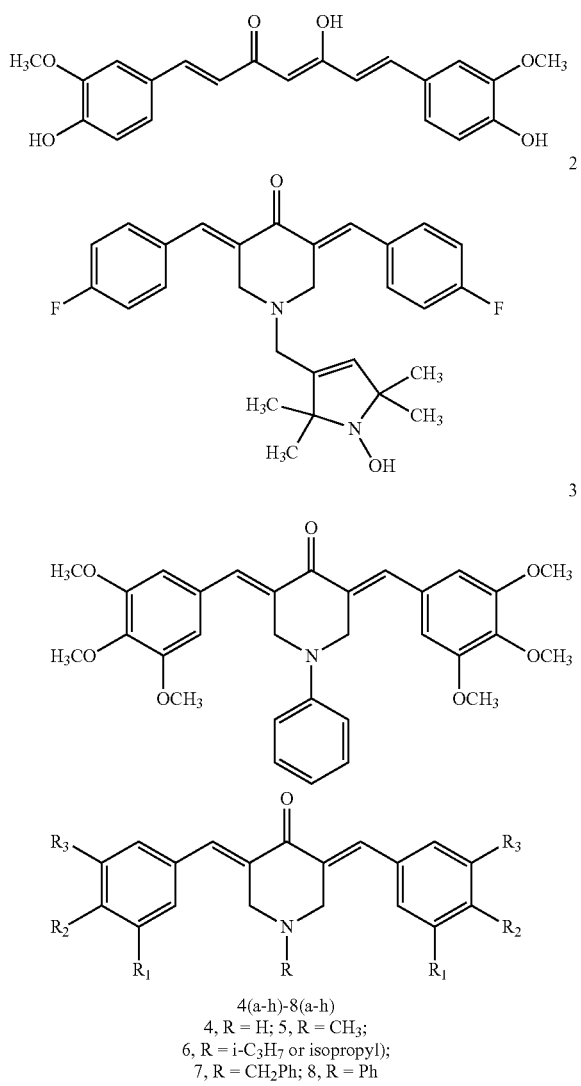

[Formulae P1]

4(a-h)-8(a-h)
4, R = H; 5, R = CH$_3$;
6, R = i-C$_3$H$_7$ or isopropyl);
7, R = CH$_2$Ph; 8, R = Ph The abovementioned findings triggered our interest in developing DAP analogs as small molecule, selective STAT3 inhibitors with cytotoxic activity. Our structural design included the following features: retaining the hydroxy and methoxy groups present in the diarylidenyl moieties of curcumin 1 and compound 3; keeping the 4-phenyl group, but replacing the cyclohexanone moiety with 4-piperidone. The 4-piperidone moiety was selected as it retained the tetrahedral geometry at 4-position and its basic nitrogen atom conferred additional polarity and offered a potential site for hydrochloride salt formation. Accordingly, forty DAP analogs [4(a-h)-8(a-h), Formulae P1] derived from five divergent series of diarylidenylpiperidones were designed and synthesized. These analogs were evaluated for their activity against the growth of B16 and L1210 cancer cells, and a select group of active compounds 4h, 5 h, 7 h, and 8 h were further evaluated for their cytotoxic potency in MDA-MB-435 cells, a cell line derived from the human M14 melanoma cancer. Preliminary studies on the water solubility and cellular uptake of these compounds were also conducted. The most active compound 8h was evaluated for inhibition of STAT3 phosphorylation.

Results and Discussion

Chemistry

Synthesis of the 40 DAPs [4(a-h)-8(a-h)] is depicted in Scheme P1. The compounds were designed in groups of eight different diarylidenyl groups (a-h) attached to five different N-substituted-4-piperidones (4-8). The diarylidenyl groups included phenyl, 4-methylphenyl, 4-nitrophenyl, and various hydroxylated and methoxylated aryl derivatives as depicted in Scheme P1 and Table P1. The N-substitutions included N—H (no substitution), N-methyl, N-isopropyl, N-benzyl, and N-phenyl, which is novel. The 40 DAPs included in this study enabled us to evaluate the effects of size, branching, aromaticity, and flexibility of the N-substituents on cytotoxicity and solubility in aqueous media. The set of analogs also allowed us to optimize the substituents and the pattern of substitution of the diarylidenyl groups as well as the effects on cytotoxicity. Of the 40 compounds, one N-isopropyl analog 6e and seven N-phenyl analogs (8b-h) are novel (references to all previously reported analogs are cited in Table P1). In the N-phenyl series, only dibenzylidenyl analog 8a was previously reported; the report, however, presented only the structure and conformation and no biological studies were included.[11] The DAP analogs were synthesized as disclosed in general methods (A-D) using base or acid catalyzed aldol condensation of a selected N-substituted-4-piperidinone with an appropriate substituted benzaldehyde. The products were obtained in 9-64% yields after purification by precipitation or recrystallization in ethanol or methanol. The structures of all compounds were characterized by IR, NMR spectroscopy and mass spectrometry.

[Scheme P1]

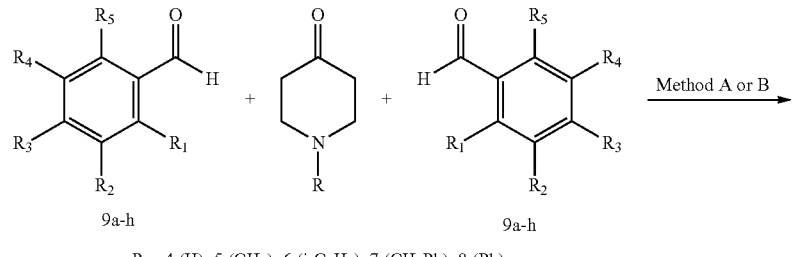

R = 4 (H), 5 (CH$_3$), 6 (i-C$_3$H$_7$), 7 (CH$_2$Ph), 8 (Ph)

-continued

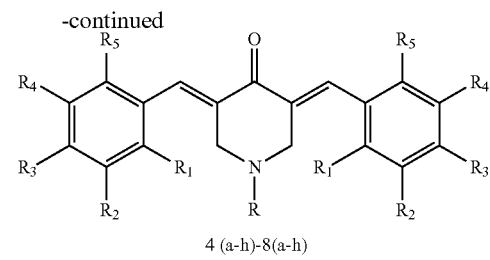

4 (a-h)-8(a-h)

a, $R_1 = H, R_2 = H, R_3 = H, R_4 = H, R_5 = H$
b, $R_1 = H, R_2 = H, R_3 = CH_3, R_4 = H, R_5 = H$
c, $R_1 = H, R_2 = H, R_3 = NO_2, R_4 = H, R_5 = H$
d, $R_1 = H, R_2 = H, R_3 = CH_3, R_4 = H, R_5 = H$
e, $R_1 = H, R_2 = OH, R_3 = OCH_3, R_4 = H, R_5 = H$
f, $R_1 = H, R_2 = OCH_3, R_3 = OH, R_4 = H, R_5 = H$
g, $R_1 = H, R_2 = OCH_3, R_3 = OCH_3, R_4 = H, R_5 = H$
h, $R_1 = H, R_2 = OCH_3, R_3 = OCH_3, R_4 = OCH_3, R_5 = H$

In the case of DAP 5a[12] and 8a.[11] single-crystal X-ray diffraction studies provided additional structural confirmation. The X-ray crystal structure revealed the following structural features: E-configuration of the α,β-exocyclic double bonds; tetrahedral geometry of the piperidone-N atom; equatorial orientation of the N—CH$_3$ group, and a flattened boat conformation of the piperidone core. This conformation was found to be consistent with the published X-ray crystal structure of 5d (p-anisyl analog of 5a).[13] The front and side views of the X-ray crystal structure of N-phenyl DAP 8a show that 8a adopts a unique conformation: the exocyclic double bonds are locked in the E-configuration and the piperidone core adopts a flattened boat conformation. Both features were comparable to the conformation of 5a. However, consistent with the published conformation of N-phenyl-4-piperidone and its derivatives, as determined by single-crystal X-ray diffraction studies and spectroscopic methods,[14] the nitrogen atom in piperidone ring adopted a pyramidal geometry and the N-phenyl ring oriented in the sterically disfavored axial conformation with its plane in perpendicular position to the bis-α,β-conjugated ketone core of the diarylidenylpiperidone unit. Data from experimental[14] and theoretical studies[11] showed that the unique conformation of DAP 8a was a result of through bond interactions between the N-lone pair (donor) orbital into one of the adjacent C═C π* orbitals, and also the delocalization of the N-lone pair orbital into the two σ*C—C orbitals within the piperidone core.

The conformational features of analog 8 h were supported by theoretical studies conducted in our laboratories. Geometry optimizations and calculations of the electrostatic surface potential and dipole moments of compound 8h were performed using Gaussian 09[15] at the B3LYP level of theory with the 6-31 G(d) basis set. WebMO[16] was used as the interface for performing the calculations and viewing the output depicted in FIGS. 3A-D. It is evident that the conformation of 8 h is consistent with the X-ray crystal structure of 8a. Judging from the frontier molecular orbital depictions: the pyramidal configuration of the piperidone-N atom; the axial orientation and perpendicular position of the N-phenyl moiety; the flattened boat configuration of the piperidone core allow for the required antiparallel orientation between the N-lone pair and the central C—C bond, his provides an ideal conformation of 8 h for through bond interactions. Interestingly, a solution of 8 h in 1:1 water:DMSO showed an absorbance at 290 nm, which upon excitation at 290 nm produced a distinct blue emission with humps at 350 and 425 nm.

With the DAP analogs in hand, the water solubility of representative compounds, 4 h, 5 h, 7 h, and 8 h were tested in their free base forms. A published analytical assay derived from the shake-flask solubility method was used.[17] This assay is rapid and highly reproducible, requires only small quantities of material, and provides good correlation with the shake-flask solubility method. It was found that compounds 4h, 5 h, 7 h, and 8 h had solubilities of 70±10, 160±30, 210±20, and 200±30 μM, respectively. These results suggested that these compounds are sufficiently soluble in aqueous media, warranting further investigations into their biological activities.

Biological Activity

The cytotoxicity of the forty DAP analogs was evaluated with the MT assay in murine B16 (melanoma) and L1210 (lymphoma) cells after 72 h exposure.[17] The concentration that inhibited cell growth by 50% (IC$_{50}$, μM) was determined for each compound from three independent experiments, and the mean values are presented in Table P1. The results reveal several interesting points. All 40 DAP analogs were found to be cytotoxic against B16 and L1210 cells. Quite a few analogs showed IC$_{50}$ values in single digit μM or sub-μM ranges. Compounds 4d, 5b, 6 h, 8c, and 8d were moderately active with IC$_{50}$ values between 25-65 μM. With an IC$_{50}$ value of >100 μM, DAP 8b was the least potent among the 40 compounds.

TABLE P1

IC$_{50}$ values (μM) of diarylidenyl N-substitutedpiperid-4-ones against the growth of murine B16 and L1210 cancer cells.

| | 4a[12] | 4b[12b,19] | 4c[7,26,33] | 4d[12b,20] | 4e[21] | 4f[22] | 4g[22] | 4h[23] |
|---|---|---|---|---|---|---|---|---|
| B16 (IC$_{50}$, μM) L1210 (IC$_{50}$, μM) (R = H) | Ta 0.5 ± 0.2 | 8.0 ± 4.0 3.1 ± 0.1 | 15.0 ± 7.0 0.3 ± 0.1 | 43.0 ± 1.0 3.50 ± 8.0 | 3.0 ± 1.0 0.9 ± 0.3 | 1.3 ± 0.6 0.9 ± 0.4 | 2.3 ± 0.5 0.6 ± 0.2 | 0.30 ± 0.15 0.32 ± 0.01 |
| | 5a[12,24] | 5b[12,24b,25] | 5c[26,34] | 5d[12,13,24,25] | 5e[12,26] | 5f[12,27] | 5g[12,26] | 5h[12,28] |
| B16 L1210 (R = CH$_3$) | | 41.0 ± 6.0 35.0 ± 5.0 | 4.0 ± 2.0 1.3 ± 0.15 | 23 ± 14 62.0 ± 1.0 | 2.1 ± 0.1 0.8 ± 0.4 | 1.8 ± 0.3 1.9 ± 0.4 | 1.3 ± 0.1 1.0 ± 0.6 | 0.31 ± 0.02 0.37 ± 0.10 |
| | 6a[12,29] | 6b[12,26] | 6c[26] | 6d[12,26] | 6e | 6f[12,30] | 6g[17,26] | 6h[12,26] |
| B16 L1210 (R = i-C$_3$H$_7$) | | 4.0 ± 2.0 2.5 ± 0.7 | 3.7 ± 0.6 0.9 ± 0.6 | 6.0 ± 2.0 38 ± 0.3 | 1.1 ± 0.4 0.4 ± 0.1 | 2.2 ± 0.2 2.2 ± 0.2 | | 25.6 ± 12.5 47.1 ± 11.0 |
| | 7a[12,31] | 7b[12,26] | 7c[26,35] | 7d[12,31,32] | 7e[12,26] | 7f[12,26] | 7g[12,32] | 7h[12,32] |
| B16 L1210 (R = CH$_2$Ph) | | 14.0 ± 4.0 9.0 ± 5.0 | 2.5 ± 0.7 2.0 ± 1.0 | 27 ± 9 8.0 ± 4.0 | 2.4 ± 0.5 3.1 ± 0.1 | 2.0 ± 0.5 2.8 ± 0.4 | 2.5 ± 0.4 3.3 ± 0.1 | 2.4 ± 0.6 3.6 ± 2.1 |
| | 8a[11,12,24a] (Ph) | 8b (4-CH$_3$-C$_6$H$_4$) | 8c (4-NO$_2$-C$_6$H$_4$) | 8d (4-OCH$_3$-C$_6$H$_4$) | 8e (2-OH-3-OCH$_3$-C$_6$H$_3$) | 8f (2-OCH$_3$-3-OH-C$_6$H$_3$) | 8g (2,3-di-OCH$_3$-C$_6$H$_3$) | 8h (2,3,4-tri-OCH$_3$-C$_6$H$_2$) |
| B16 L1210 (R = Ph) (8a-h) | 7.0 ± 4.0 4.0 ± 2.0 | >100 >100 | 65.0 ± 7.0 65.0 ± 7.0 | 37.0 ± 6.0 55.0 ± 7.0 | 19.0 ± 2.0 6.0 ± 4.0 | 2.9 ± 0.4 2.8 ± 0.4 | 1.3 ± 0.1 2.9 ± 0.9 | 0.30 ± 0.03 0.36 ± 0.03 |

Core structure: 3,5-bis(arylidene)-N-substituted-piperidin-4-one with Ar substituents as shown for 8a–h.

It is worth noting that the compounds in the N—H series (4a-4 h) were relatively more potent for inhibiting the growth of L1210 cells than B16 cells. Compounds 4a-4c and 4e-4 h showed considerably lower $IC_{50}$ values ranging from 0.3 to 3.1 µM against L1210 cells. Compound 4h, possessing 3,4,5-trimethoxy substituted diarylidenyl groups, was equally potent against both B16 and L1210 cells with $IC_{50}$ values of 0.3 and 0.32 µM, respectively. Compound 4c, having an electron withdrawing nitro group at the para position in the diarylidenyl rings, displayed markedly higher potency against L1210 cells ($IC_{50}$=0.3 µM) and relatively moderate potency against B16 cells ($IC_{50}$=15 µM). Interestingly, DAP 4d, which has a para-methoxy substitution at the diarylidenyl units, was the least active in this series with $IC_{50}$ values of 43 and 35 µM for B16 and L1210 cells, respectively.

The N-methyl series was uniformly active against B16 and L1210 cells. Among the three para-monosubstituted analogs 5b, 5c and 5d, compound 5c, having electron withdrawing nitro substitution at the diarylidenyl groups, displayed significantly lower $IC_{50}$ value of 4.0 µM for B16 cells and even lower $IC_{50}$ value of 1.3 µM for L1210 cells. The other two monosubstituted analogs, 5b and 5d, showed moderate activity against both cell lines with $IC_{50}$ values of 41 and 23 µM for B16 and 35 and 62 µM for L1210 cells, respectively. The three compounds 5e, 5f, and 5g with 3,4-disubstitution pattern on the diarylidenyl units were equally potent against both B16 and L1210 cells with $IC_{50}$ values ranging from 1.3 to 2.1 µM for B16 and 0.8 to 1.9 µM for L1210 cells, respectively. The 3,4,5-trimethoxy substituted compound 5h emerged as the most cytotoxic in this series with $IC_{50}$ values of 0.31 and 0.37 µM for B16 and L1210 cells, respectively.

In the case of the N-isopropyl series, all compounds, except for the 3,4,5-trimethoxy substituted compound 6h, displayed remarkably lower $IC_{50}$ values ranging from 0.4 to 6.0 µM for both B16 and L1210 cells. Unlike its counterparts 4 h and 5 h, the 3,4,5-trimethoxy substituted compound 6h displayed modest cytotoxicity against B16 ($IC_{50}$ 25.6 µM) and L1210 ($IC_{50}$ 47 µM) cells. With an $IC_{50}$ value of 0.4 µM for L1210 cells, the 3,4-disubstituted compound 6e emerged as the most potent in this series. Compound 6e displayed significant potency even against B16 cells, albeit with a slightly higher $IC_{50}$ value of 1.1 µM.

The N-benzyl series exhibited good to excellent antiproliferative effects against B16 and L210 cells. With $IC_{50}$ values of 9.0 and 8.0 µM, para-methyl and para-methoxy substituted compounds 7b and 7d displayed good cytotoxicity against L1210 cells. These two compounds, however, were moderately active against B16 cells with $IC_{50}$ values of 14 and 27 µM, respectively. With $IC_{50}$ values of 2.4 and 3.6 µM for B16 and L1210 cell lines, respectively, the 3,4,5-trimethoxy substituted compound 7h exhibited almost 10-fold lower potency for B16 and L1210 cells than its counterparts 4 h and 5 h and 10-fold higher cytotoxic potency than its other counterpart 6 h.

In the N-phenyl series, all three para-monosubstituted compounds exhibited lower cytotoxicity against B16 and L1210 cells than all other analogs in this series. In fact, the para-methyl substituted compound 8b was inactive against both B16 and L1210 cells with $IC_{50}$ values of >100 µM. Among the three 3,4-disubstituted compounds 8e-g, 8f and 8g displayed significant cytotoxic activity against both B16 and L1210 cells. Compound 8e, which has a 3-hydroxy-4-methoxy substitution pattern was more cytotoxic against L1210 cells ($IC_{50}$=6.0 µM) than B16 cells ($IC_{50}$=19 µM). Consistent with DAP 4 h, 5 h, 7 h, and cyclohexanone 3, compound 8h, possessing the 3,45-trimethoxy substitution emerged as the most cytotoxic in the series with $IC_{50}$ values of 0.30 and 0.36 µM against B16 and L1210 cells, respectively.

It is worthy to note that DAP analogs 4a-8a, which contain unsubstituted diphenylidenyl groups, were particularly active against both B16 and L1210 cells. Compound 4a, belonging to the N—H-piperidone series, displayed an $IC_{50}$ value of 0.5 µM for L1210 cells, the lowest among the five analogs (4a-8a). Compound 8a, belonging to the N-phenylpiperidone series displayed an $IC_{50}$ value of 7.0 µM for the B16 cell line, the highest among the five analogs. On the other hand, the para-monosubstituted compounds (4b-8b, 4c-8c, and 4d-8d) were generally less potent than the other DAP analogs investigated in this study. The disubstituted analogs (4e-8e, 4f-8f, and 4g-8g) demonstrated roughly the same degree of cytotoxicity as the unsubstituted analogs (4a-8a). Compounds 4f-8f, having the 4-hydroxy-3-methoxy disubstitution pattern, similar to the substitution pattern on curcumin, showed consistently high cytotoxicity in both cell lines. A similar trend was apparent for the 3,4-dimethoxy substituted compounds 4g-8g suggesting that the hydroxyl group might not be crucial for activity. With $IC_{50}$ values close to 0.3 µM 3,4,5-trimethoxy substituted compounds 4h, 5 h, and 8 h are clearly the lead molecules. Interestingly, 2,6-bis(benzylidene)-4-phenylcyclohexanone analog, compound 3, possessing similar substitution pattern as compounds 4h, 5 h, and 8 h also exhibited significant cytotoxicity against B16 and L1210 cells with $IC_{50}$ values of 0.5 and 1.2 µM, respectively.[9] From these results, it is apparent that the 3,4,5-trimethoxy substitution in the diarylidenyl groups greatly enhances the cytotoxic potency, followed by two methoxy or methoxy and hydroxy substitution at 3 and 4 positions or no substitution. It also appears that the modification in the substitution on the piperidone-N atom is well tolerated; however, analogs 7 h and 8 h have the highest water solubility.

Four of the most potent 3,4,5-trimethoxy substituted DAP compounds 4h, 5 h, 7 h, and 8 h, were further evaluated for their antiproliferative activity against the human breast melanoma cell line, MDA-MB-435.[17] Following a 48 h exposure, all four compounds showed sub-µM $IC_{50}$ (concentration causing 50% reduction compared to vehicle-treated control) values, which correlated with the B16 and L1210 results. Compound 4h was the most potent with the lowest $IC_{50}$ value of 0.088 µM, followed by the novel N-phenyl analog 8 h (0.15 µM), 5 h (0.19 µM), and 7 h (0.76 µM). Because of its favorable aqueous solubility, DAP 8 h was selected over analog 4 h for further biological evaluation.

In an attempt to preliminarily probe the mechanism of action of analog 8 h, its ability to cause microtubule disruption in A-10 smooth muscle cells was studied.[17] At 30 µM it did not show any effect on the microtubules (data not shown), ruling out a potential tubulin-mediated mechanism of action. However, since the 4-phenylcyclohexanone compound 3, HO-3867 2, and other DAP analogs are known to inhibit the levels of active STAT3 the effect of DAP analog 8 h on STAT3 phosphorylation was examined. Analog 8 h efficiently inhibits the tyrosine (705) phosphorylation for activation of STAT3 in a dose, cell-density and time-dependent manner, in vitro, in cancer cells harboring constitutively active STAT3 (e.g. DU145, A549) (FIG. 1A). 8 h is more potent at inhibiting pSTAT3 in cells with persistent STAT3 activation, at concentrations >1 µM, than curcumin and stattic (FIG. 1B). It also blocked the STAT3-DNA binding activity at concentrations as low as 0.8 µM in DU145 nuclear extracts, and did so more efficiently than stattic (FIG. 1C). pls remove the refs[8c,18] (the line we are taking is that it does NOT bind to the DBD, in contrast to HO-3867). The inhibition of pSTAT3 by DAP 8 h persists for at least 24 h post treatment (FIG. 2A) and is selective for STAT3 over STAT1. STAT5a, and STAT5b which remain largely unaffected, as shown by both immunoblotting and an ELISA assay (FIG. 2B).

In confocal microscopy experiments in DU145 and MDA-MB-468 cells exposed to 8 h (5 µM) for 5 h, the compound's subcellular localization could be detected (FIG. 20A and FIG. 20B) by its blue fluorescence, upon UV excitation. 8 h penetrates the cellular membrane and remains localized in the cytoplasm. Under these conditions, the levels of nuclear STAT3 were decreased as evidenced from a significant reduction of the immunostaining of the protein in the DU145 nuclei, and instead accumulates in the cytoplasm (FIG. 20A). Similar results were obtained in A549 cells, treated for 18 h with 8 h, and stained for phosphorylated STAT3, with 8 h markedly decreasing the levels of the activated protein (FIG. 20C).

As shown above, through the selective tyrosine phosphorylation inhibition. 8 h effectively precludes the STAT3 translocation/accumulation to the nucleus, reduces the nuclear levels of the activated protein and blocks its DNA binding. As a result, 8 h downregulates the transcription of key STAT3 target genes involved in cell proliferation and apoptosis such as survivin and Bcl-2 (FIG. 3A). Ultimately it induces cell death via apoptosis as shown by cleaved-PARP induction in DU145 and A549 cells (FIG. 3B), which would account for its cytotoxic potency in these cell lines (FIG. 3C). DAP 8 h was also shown to be a potent inhibitor of pSTAT3 in cell lines highly resistant to the DNA-damaging chemotherapeutic agents cisplatin and oxaliplatin. The two cell lines were engineered to become multi-fold resistant to the two clinically-used platinum drugs (derived from the A2780 and HCT116 parental cell lines, respectively). 8 h efficiently inhibits the constitutively active STAT3 in the HCT116-oxaliplatin resistant cell line (FIG. 4A), but also the cytokine-inducible (IL-6) levels of pSTAT3 in the A2780-cisplatin resistant subline (FIG. 4B). In both cellular contexts, 8 h is more potent than all the other small-molecule STAT3 inhibitors tested. 8 h was again capable of inhibiting in A2780-cisplatin resistant cells, downstream STAT3 targets, such as the anti-apoptotic protein Bcl-xL, (FIG. 4C). As a result 8 h induces apoptosis as shown by the Annexin-V/Propidium iodide assay in these cells, when treated with the agent for 18 h (FIG. 4D). The cellular cleavage of PARP could also be detected by immunoblotting lysates of cells treated with 8 h for 1 h and left to recover for a extra 24 h (FIG. 4E).

DAP 8 h could radiosensitize DU145 cells, as determined by the clonogenic survival assay (FIG. 7A), and did so more efficiently than curcumin (based on the SRB growth inhibition assay) (FIG. 7B). Similarly, 8 h could chemosensitize DU145 cells to cisplatin, when the two agents were administered sequentially (8 h for 18 h followed by cisplatin for 1 h) at a fixed concentration ratio of 1:50 (FIG. 8A) achieving synergistic interactions (CI>1) for a number of concentrations, in the combination treatments (FIG. 8B). This was mirrored by the enhancement of apoptosis in the combinations as evidenced by an increase in the cellular protein levels of cleaved PARP and cleaved-caspase 3, as detected by immunoblotting (FIG. 8C). 8 h was able to chemosensitise DU145 cells to cisplatin b achieving higher levels of synergy and at a wider range of concentrations than stattic (FIG. 8D) and curcumin (FIG. 8E), both requiring considerably higher doses.

Synergistic interactions were also observed at a different drug schedule (non-fixed ratio), with DU145 cells acutely exposed to a single concentration of 8 h (5 µM) for 1 h, and subsequently treated with increasing doses of cisplatin for 1 h (FIG. 9A and FIG. 9B). Immunoblotting analysis confirmed that the dose of 5 µM 8 h was sufficient to inhibit pSTAT3 during the 1 h of treatment (FIG. 9C). The above observations were successfully reproduced in A549 cells for both drugs schedules; fixed ratio (FIG. 10A, FIG. 10B, FIG. 10C and FIG. 10E) and non-fixed ratio (FIG. 11A, FIG. 11B and FIG. 11C). Again, in the case of the fixed-ratio combination treatments, 8 h was more effective in enhancing cellular sensitivity to cisplatin, than stattic and curcumin (FIG. 10D and FIG. 10E). DAP 8 h was also capable of restoring cellular sensitivity to the highly oxaliplatin resistant HCT116 cells, in various drug schedules (fixed and non-fixed ratio combination treatments), achieving in many instances CI values <1 (FIGS. 12A-E and FIGS. 22A-C).

Figure 22A:
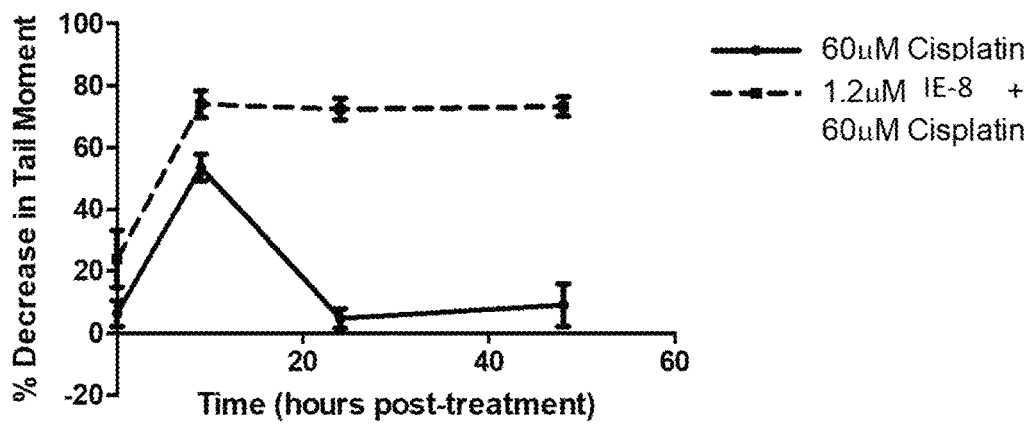
FIG. 22A shows that a pretreatment of DU145 cells with 1.2 µM IE-8 for 18 h, followed by treatment with cisplatin for 1 h, impairs the unhooking of the cisplatin-produced DNA ICLs. In cells treated with cisplatin only, DNA ICLs formation peaks at 9 h, and by 24 h, ICLs have mostly repaired ('unhooked'). However, in the combination treatments, DNA ICLs form as before, but they persist for up to 48 h.
Figure 22B:
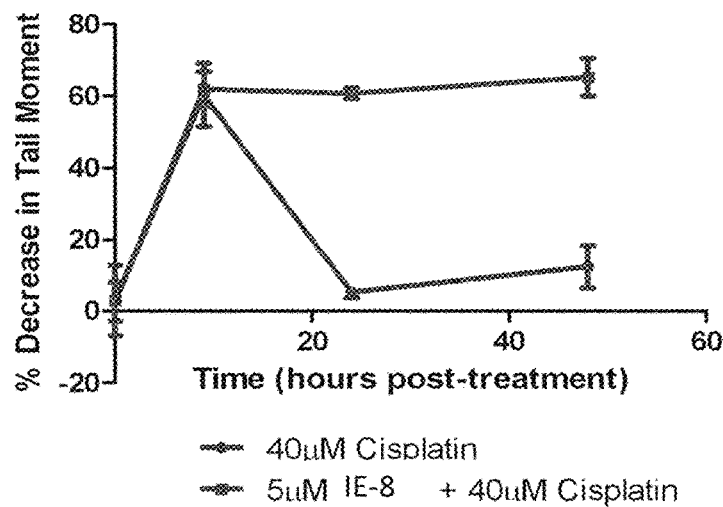
FIG. 22B shows that a pretreatment of DU145 cells with 1.2 µM IE-8 acutely for 1 h with 5 µM IE-8, followed by treatment with cisplatin for 1 h, impairs the unhooking of the cisplatin-produced DNA ICLs. In cells treated with cisplatin only, DNA ICLs formation peaks at 9 h, and by 24 h, ICLs have mostly repaired ('unhooked'). However, in the combination treatments, DNA ICLs form as before, but they persist for up to 48 h.
Figure 22C:
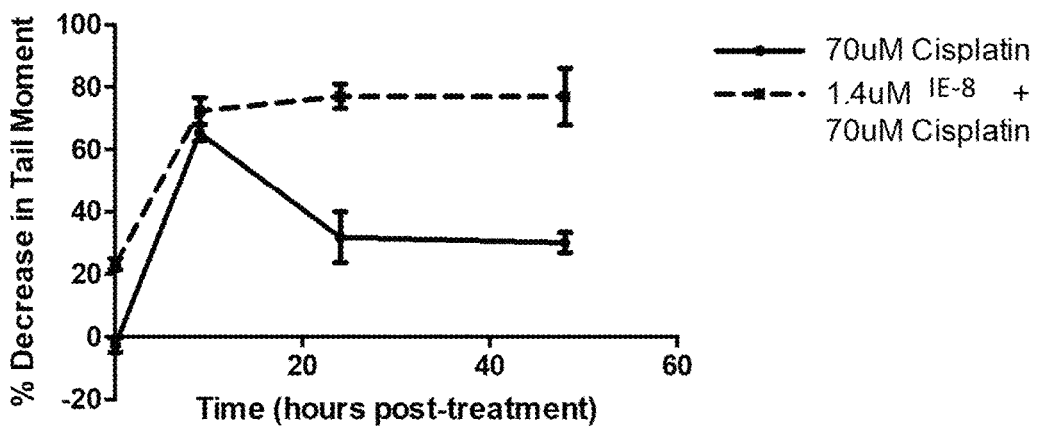
FIG. 22C shows that the same repair deficiency conferred by IE-8 was observed in A549 cells, pretreated with 1.4 µM IE-8 for 18 h, in which case cells were treated for 1 h with cisplatin and after 4 h, treated with 6 µM IE-8 for 1 h, and then left to recover in drug-free media.

A proposed mechanism of the observed chemosensitization to the DNA-damaging agents cisplatin and oxaliplatin is the STAT3 inhibition-mediated modulation of the repair of the DNA interstrand crosslinks (DNA ICLs) produced by these agents and thought to be the critical cytotoxic lesions. The modified single-cell gel electrophoresis (Comet) assay enables the monitoring of the induction and repair of DNA ICLs in intact cells. As shown in FIGS. 21A-C, 8 h, modulates the repair (i.e. 'unhooking') kinetics of the DNA ICLs without affecting their formation. Pretreatment with 8 h of DU145 (FIG. 22A) and A549 cells (FIG. 22B), impairs the 'unhooking' of the cisplatin-produced ICLs. The same is also observed in A2780-cisplatin resistant cells, treated with 8 h, 4 h post the acute (1 h) cisplatin treatment (FIG. 22C). DNA-damage response to cisplatin was enhanced by 8 h in combination treatments in DU145 cells, pretreated with 1.2 µM 8 h for 18 h and then with 60 µM cisplatin for 1 h, as assessed by the induction of γ-H2Ax, detected by immunofluorescence (FIG. 21A). The increase in the intensity and extent of nuclear staining for γ-H2Ax and the numerical increase of the detected foci (quantified by Cell Profiler—FIG. 21B) in the combination treatment is in agreement with the persistence of the DNA damage (and particularly the unresolved DNA ICLs) previously documented by the comet assay. The same effect on the induction of γ-H2Ax was observed in immunoblots of A549 cells, treated with 8 h and cisplatin alone, or with both agents in combination (FIG. 21C).

We subsequently investigated the effect of pSTAT3 inhibition on a number of key repair factors, known to be involved in DNA ICL repair. As shown in FIGS. 6A-B, 8h markedly downregulates the expression of BRCA1, FANCD2, EME1 and MUS81 at both mRNA (FIG. 6A) and protein (FIG. 6B) levels. This downregulation of the MUS81-EME11 endonuclease complex, which is known to be involved in the unhooking of ICLs by introducing incision at the ICL site, similarly to the XPF-ERCC1 endonuclease, provides a mechanistic rationale for the observed ICL repair defect, mediated by 8 h, and the resulting enhancement of cellular sensitivity to the ICL-producing drugs ciplatin and oxaliplatin.

Apart from being more potent in terms of its pSTAT3 inhibitory effect, 8 h is also more cytotoxic than the other tested inhibitors; HO-3867, atovaquone curcumin and stattic in HCT116-oxaliplatin resistant and A2780-cisplatin resistant cells. The inhibitors can be ranked in terms of their $IC_{50}$ values, in both cell lines, as follows: 8 h>HO-3867>stattic>atovaquone>curcumin. 8 h was found to be also cytotoxic in 3D multicellular tumor spheroid cultures, derived from the HCT116-oxaliplatin-resistant cells. Cytotoxicity was assessed by the 3D cell-titre Glo assay, after a 96 h exposure, and the $IC_{50}$ values were derived. Mirroring the superior activity of 8 h observed in the 2D monolayer cultures, the tested inhibitors' activity in spheroids, can be ranked as follows: 8 h (8.5 µM)>Atovaquone (16.5 µM)>HO-3867 (33 µM). The effects of the treatment with 8 h on the HCT116-oxaliplatin resistant spheroids' size can be seen in FIG. 24A. Immunoblotting confirmed the inhibition of pSTAT3 by 8 h. Additionally, 8 h was shown to induce apoptosis, as evidenced by the induction of cleaved PARP, in spheroids derived by A2780-cisplatin resistant cells, treated with the agent for 72 h (FIGS. 24A-C). Finally, 8 h was able to inhibit cell migration as shown by the wound healing assay in DU145 cells (FIG. 28). Treatment with 1 µM 8 h for 18 h, prior to the introduction of the wound, prevented its full closure for up to 60 h, as opposed to the untreated control where the wound was closed by 36 h, and the cells treated with a 5-fold higher concentration of stattic (FIGS. 1A-C).

In conclusion, the design, synthesis, and cytotoxicity evaluation of 40 DAP analogs provided insight into the structure-activity relationship for this class of compounds. From this study, a relatively water soluble, selective inhibitor of STAT3 phosphorylation and DNA binding, and lead cytotoxic agent 8 h was discovered. Para-Monosubstituted DAP analogs generally had low cytotoxic potency. The results also demonstrated that substitution of the N-atom on piperidone is well tolerated; however, the N-phenyl substitution, as demonstrated by 8 h, afforded a unique conformation that might contribute to the selectivity for and potency at inhibiting STAT3 phosphorylation and DNA binding, its water solubility, and endowing the molecule with fluorescent properties. With regard to the substitution pattern on the diarylidenyl groups, a clearer relationship emerged, with the 3,4,5-trimethoxy substitution to be the most preferred, over its 3,4-disubstituted or unsubstituted counterparts. Ultimately, with the results demonstrating unprecedented evidence on the potency and selectivity of DAP analogs, particularly 8 h, in inhibiting intracellular pSTAT3 levels, along with 8 h's ability to inhibit the growth of cancer cells, as well as sensitizing refractory cancer cells to radiation therapy and DNA damaging chemotherapeutic drugs, we conclude that it is crucial to further develop the DAP compounds as potential anticancer and/or as chemo and radio-sensitizing agents to increase the armamentanum for combating cancers.

Experimental

Solvents and organic reagents were purchased from Aldrich or Fisher, and were used without further purification. Melting points (mp) were performed using a Mel-temp instrument and are uncorrected. Infrared (IR) spectra were recorded using a Perkin Elmer Paragon 500 FT-IR instrument. $^1$H NMR spectra were obtained using a Varian Unity Inova 400 MHz instrument. Chemical shifts (δ) are reported at 20° C. in parts per million (ppm) downfield from internal tetramethylsilane ($Me_4Si$). High-resolution mass spectra (HRMS) and low-resolution mass spectra (LRMS) were provided by the Mass Spectrometry Laboratory. University of South Carolina. Columbia. TLC plates (silica gel (60 $F_{254}$) on aluminum) procured from Merck were used to monitor reactions. Visualization was achieved with UV light at 254 nm and/or 366 nm. $2$ vapor staining, or ninhydrin spray.

Method A. Sodium hydroxide solution (10% in water, 2.0 mL) was added drop wise to the solution of appropriate N-substituted-4-piperidinone (1.0 mmol) and the appropriate aryl aldehyde (2.0 mmol) in ethanol (5.0 mL) at room temperature. The reaction mixture was stirred at room temperature for 16 h. Upon completion of the reaction, the reaction mixture was filtered. The solid was washed with cold ethanol (1.0 mL) followed by water (5.0 mL) and dried in vacuum at 40-45° C.

Method B. The solution of the appropriate N-substituted-4-piperidinone (1.0 mmol) and appropriate aryl aldehyde (2.0 mmol) in glacial acetic acid (3.0 mL) was bubbled with dry hydrogen chloride gas for 20-25 min. The reaction mixture was stirred at room temperature for 16 h and filtered. The solid was washed with cold ethanol (2.0 mL) and then stirred in aqueous sodium carbonate (10%, 10 mL) for 15 minutes and filtered again. The separated solid was washed with water and dried in vacuum at 40-45° C.

3,5-Di(3-hydroxy-4-methoxylbenzyliden)-1-isopropylpiperidin-4-one (6e): (Method A) Yellow solid (110 mg, 34%), mp=165-168° C., $R_f$=0.42 [ethyl acetate:hexane:methanol (3:1:0.1)]; FT-IR (KBr): ν 3264, 3022, 2968, 2917, 2833, 2804, 1656, 1582, 1548, 1527, 1503, 1462, 1454, 1435, 1364, 1255, 1211, 1177, 1134, 1005, 935, 867, 800; $^1$H NMR (CDCl$_3$): δ 7.69 (s, 2H), 7.01 (d, J=4.0 Hz, 2H), 6.97 (dd, J=4.0, 8.0 Hz, 2H), 6.90 (d, J=8.0 Hz, 2H), 3.94 (s, 6H), 3.87 (s, 4H), 2.95 (m, 1H), 1.08 (d, J=4.0 Hz, 6H); LRMS (EI) m/z 409 (M$^+$, 100%).

3,5-Di(4-methylbenzylidene)-1-phenylpiperidin-4-one (8b): (Method A) Yellow solid (73 mg, 34%), mp=173-176° C., $R_f$=0.22 [ethyl acetate:hexane (1:9)]; FT-IR (KBr): ν 3020, 2913, 2872, 1668, 1597, 1573, 1498, 1458, 1354, 1239, 1177, 1042, 982, 817; $^1$H NMR (CDCl$_3$): δ 7.85 (s, 2H), 7.33 (d, J=7.7 Hz, 4H), 7.29 (d, J=7.7 Hz, 4H), 7.12 (t, J=7.7 Hz, 2H), 6.78 (t, J=7.7 Hz, 1H), 6.71 (d, J=7.7 Hz, 2H), 4.61 (s, 4H), 2.40 (s, 6H): $^{13}$C NMR (CDCl$_3$): δ 187.3, 149.0, 139.6, 137.5, 132.3, 132.2, 130.5, 129.6, 129.2, 120.1, 116.7, 51.5, 21.5; LRMS (EI) m/z 379 (M$^+$, 100%). HRMS (EI) calcd for $C_{27}H_{25}NO$ 379.1931, found 379.1936.

3,5-Di(4-nitrobenzylidene)-1-phenylpiperidin-4-one (8c): (Method B) Light brown solid (25 mg, 20%), mp=184-188° C. $R_f$=0.19 [ethyl acetate:hexane (2:3)]; FT-IR (KBr): ν 3044, 2929, 1680, 1667, 1613, 1595, 1514, 1493, 1460, 1342, 1260, 1195, 1107, 997, 852; $^1$H NMR (DMSO-d6): δ 8.30 (d, J=8.4 Hz, 4H), 7.81 (d, J=8.4 Hz, 4H), 7.79 (s, 2H), 7.06 (t, J=7.7 Hz, 2H), 6.68 (t, J=7.7 Hz, 1H), 6.56 (d, J=7.7 Hz, 2H), 4.72 (s, 4H)$^3$C NMR (DMSO-d6): δ 186.8, 148.4, 147.8, 141.3, 136.8, 135.2, 132.1, 129.7, 124.2, 120.0, 116.3, 50.5; LRMS (EI) m/z 441 (M$^+$, 100%). HRMS (EI) calcd for $C_{25}H_{19}N_3O_5$ 441.1322, found 441.1325.

3,5-Di(4-methoxybenzylidene)-1-phenylpiperidin-4-one (8d): (Method A) Yellow solid (20 mg, 8.5%), mp=152-155° C., $R_f$=0.21 [ethyl acetate:hexane (1:4)]; FT-IR (KBr): ν 3000, 2960, 2931, 2836, 1662, 1594, 1561, 1493, 1450, 1418, 1299, 1252, 1166, 1024, 975, 828; $^1$H NMR (CDCl$_3$): δ 7.83 (s, 2H), 7.39 (d, J=8.4 Hz, 4H), 7.13 (t, J=8.4 Hz, 2H), 6.97 (d, J=8.4 Hz, 4H), 6.79 (t, J=8.4 Hz, 1H), 6.73 (dd, J=8.4 Hz, 2H), 4.60 (s, 4H), 3.86 (s, 6H): $^{13}$C NMR (CDCl$_3$): δ 187.1, 160.4, 149.1, 137.1, 132.3, 131.2, 129.2, 127.8, 120.1, 116.8, 114.2, 55.4, 51.5; LRMS (EI) m/z 411 (M$^+$, 100%). HRMS (EI) calcd for $C_{27}H_{25}NO_3$ 411.1833, found 411.1834.

3,5-Di(3-hydroxy-4-methoxybenzylidene)-1-phenylpiperidin-4-one (8e): (Method B) Yellow solid (20 mg, 16%), mp=142-146° C., $R_f$=0.21 [ethyl acetate:hexane (2:3)]; FT-IR (KBr): ν 3410, 3288, 3020, 2962, 2839, 1649, 1573, 1509, 1440, 1211, 1126, 1016, 995, 866; $^1$H NMR (CDCl$_3$): δ 7.78 (s, 2H), 7.15 (t, J=7.7 Hz, 2H), 7.04 (s, 2H), 6.99 (d, J=8.4 Hz, 2H), 6.93 (d, J=8.4 Hz, 2H), 6.79 (t, J=8.4 Hz, 1H), 6.75 (d, J=8.4 Hz, 2H), 4.62 (s, 4H), 3.96 (s, 6H); $^{13}$C NMR (CDCl$_3$): δ 187.2, 149.0, 147.5, 145.5, 137.2, 131.6, 129.2, 128.7, 123.9, 120.0, 116.8, 116.2, 110.6, 56.0, 51.5; LRMS (EI) m/z 443 (M$^+$, 100%). HRMS (EI) calcd for C$_{27}$H$_{25}$NO$_5$ 443.1733, found 443.1733.

3,5-Di(4-hydroxy-3-methoxybenzylidene)-1-phenylpiperidin-4-one (8f): (Method B) Orange solid (80 mg, 64%), mp=139-143° C., $R_f$=0.29 [ethyl acetate:hexane (2:3)]; FT-IR (KBr): ν 3508, 3061, 2939, 2835, 1642, 1578, 1552, 1490, 1445, 1377, 1309, 1205, 1131, 1004, 933; $^1$H NMR (DMSO-d6): δ 7.64 (s, 2H), 7.09 (s, 2H), 7.05 (t, J=7.7 Hz, 2H), 7.01 (d, J=8.4 Hz, 2H), 6.89 (d, J=8.4 Hz, 2H), 6.66 (t, J=7.7 Hz, 1H), 6.62 (d, J=7.7 Hz, 2H), 4.68 (s, 4H), 3.81 (s, 6H); $^{13}$C NMR (DMSO-d6): δ 186.4, 149.0, 148.8, 148.0, 137.6, 130.9, 129.6, 126.5, 124.8, 119.5, 116.3, 116.2, 115.4, 56.1, 50.7; LRMS (EI) m/z 443 (M$^+$, 100%). HRMS (EI) calcd for C$_{27}$H$_{25}$NO$_5$ 443.1726. found 443.1733.

3,5-Di(3,4-dimethoxybenzylidene)-1-phenylpiperidin-4-one (8g): (Method B) Yellow solid (28 mg, 21%), mp=144-148° C., $R_f$=0.25 [ethyl acetate:hexane (3:7)]; FT-IR (KBr): ν 3020, 2935, 2865, 2837, 1662, 1591, 1573, 1509, 1499, 1467, 1446, 1374, 1352, 1316, 1273, 1243, 1209, 1136, 1017, 846, 811; $^1$H NMR (CDCl$_3$): δ 7.83 (s, 2H), 7.13 (t, J=7.7 Hz, 2H), 7.05 (d, J=8.4 Hz, 2H), 6.96 (s, 2H), 6.95 (d, J=8.4 Hz, 2H), 6.79 (t, J=7.7 Hz, 1H), 6.73 (d, J=7.7 Hz, 2H), 4.64 (s, 4H), 3.94 (s, 6H), 3.92 (s, 6H); $^{13}$C NMR (CDCl$_3$): δ 187.0, 150.1, 149.0, 148.9, 137.5, 131.4, 129.2, 128.1, 123.8, 120.1, 116.6, 113.7, 111.1, 56.0 (for both OCH$_3$ groups), 51.4; LRMS (EI) m/z 471 (M, 100%). HRMS (EI) calcd for C$_{29}$H$_{29}$NO$_5$ 471.2033, found 471.2046.

3,5-Di(3,4,5-trimethoxybenzylidene)-1-phenylpiperidin-4-one (8 h): (Method B) Yellow solid (100 mg, 33%), mp=134-136° C., $R_f$=0.55 [ethyl acetate:hexane (2:3)]; FT-IR (KBr): ν 3473, 3020, 2935, 2834, 1659, 1594, 1577, 1497, 1450, 1415, 1385, 1360, 1241, 1213, 1186, 1120, 1046, 1038, 996, 963, 835; $^1$H NMR (CDCl$_3$): δ 7.82 (s, 2H), 7.16 (t, J=8.0 Hz, 2H), 6.81 (t, J=8.0 Hz, 1H), 6.74 (d, J=8.0 Hz, 2H), 6.66 (s, 4H), 4.67 (s br, 4H), 3.93 (s, 6H), 3.91 (s, 12H); $^{13}$C NMR (CDCl$_3$): δ 186.9, 153.2, 148.7, 139.3, 137.9, 132.3, 130.6, 129.3, 120.2, 116.5, 107.9, 61.0, 56.3, 51.3; LRMS (EI) m/z 531 (M$^+$, 100%). HRMS (EI) calcd for C$_{31}$H$_{33}$NO$_7$ 531.2257. found 531.2254.

X-ray Diffraction Studies. Single crystal X-ray data for 5a and 8a were collected using a Bruker ApexII CCD diffractometer with Mo-Kα radiation (λ=0.71073 Å) with a fine focus sealed tube X-ray source with graphite monochromator. Single crystals were mounted on Mitegen micromesh mounts using a trace of mineral oil and cooled in-situ to 100(2) K for data collection. Frames were collected, reflections were indexed and processed, and the files scaled and corrected for absorption using APEX2.[36] The space groups were assigned and the structures were solved by direct methods using XPREP within the SHELXTL suite of programs[37] and refined by full matrix least squares against F$^2$ with all reflections using Shelxl20163[38] using the graphical interface Shelxle.[39] H atoms attached to carbon atoms were positioned geometrically and constrained to ride on their parent atoms, with carbon hydrogen bond distances of 0.95 Å for alkene and aromatic C—H, 0.99 and 0.98 Å for aliphatic CH$_2$ and CH$_3$ moieties, respectively. Methyl H atoms were allowed to rotate but not to tip to best fit the experimental electron density. U$_{iso}$(H) values were set to a multiple of U$_{eq}$(C) with 1.5 for CH$_3$, and 1.2 for C—H and CH$_2$ units, respectively. The structure of 5a is commensurately modulated with eight independent molecules in the asymmetric part of the unit cell (16 per unit cell). Conformations of the eight molecules are very similar. X-ray structural information for compounds 5a and 8a are given in cif format; CCDC 1545977 for 5a and CCDD 1545976 for 8a. These data can be obtained free of charge from The Cambridge Crystallographic Data Centre via www.ccdc.cam.ac.uk/data_request/cif.

Molecular Modeling Studies. Electrostatic surface potential, molecular dipole, HOMO, and LUMO were calculated using Gaussian 09[15] at the B3LYP level of theory with the 6-31G(d) basis set. WebMO[16] was the graphical interface used for preparing calculations and visualizing results.

Aqueous Solubility Assay. Aqueous solubility was measured with a modified version of the MultiScreen Solubility Filter Plate protocol (Millipore). This assay is based on the shake-flask equilibrium method and utilizes UV-Vis spectroscopy to quantify the unknown samples. The assay is conducted at room temperature at pH 7.4. Standard curves covering a range from 3.13-500 µM were generated for each compound using a 4:1 mixture of aqueous buffer (45 mM ethanolamine, 45 mM potassium dihydrogen phosphate 45 mM potassium acetate, pH 7.4) to acetonitrile. Each compound was dissolved in DMSO, and the final DMSO concentration was 5% (v/v). Each sample was analyzed by UV-Vis spectroscopy at 10 nm increments from 260-600 nm to determine the optimal wavelength for detection and construct standard curves. To measure the aqueous solubility of the DAP compounds, a 500 µM solution of each compound was prepared in aqueous buffer, mixed for 6 h, and briefly centrifuged to pellet any undissolved compound. A 4:1 mixture of supernatant to acetonitrile was added to a 96-well acrylic plate and analyzed by UV-Vis spectroscopy. Drug concentration in the supernatant was determined from the standard curve using the formula: aqueous solubility=A$_{max}$÷slope of standard curve×1.25 (multiplied by 1.25 to correct for acetonitrile dilution).

Cytotoxicity Studies. The MDA-MB-435, A10, B16, and L1210 cells were purchased from ATCC and maintained as previously described.[7,17] For the B16 and L1210 studies, the cells were subjected to a continuous 72 h exposure to the DAP analogs and the cytotoxicity determined using an MTT assay as described previously.[7,17a] The microtubule disrupting effects were evaluated in A-10 cells by indirect immunofluorescent techniques as previously described.[17] The cytotoxic potency of compounds 4h, 5 h, 7 h, and 8 h against MDA-MB-435 cells were determined as previously described using the sulforhodamine B (SRB) assay. Briefly, the cells were plated in 96-well plates at predetermined densities, allowed to adhere for 24 h, and then treated with vehicle (DMSO) or compounds for 48 hr. The cells were then fixed, stained with SRB dye, and cell densities determined by absorbance of SRB at 560 nm to construct concentration-response curves.[17] The IC$_{50}$ values were interpolated from these concentration-response curves and represent the mean of 4 independent experiments, with each concentration tested in triplicate.

Cell Lines and Culture Conditions (2D, 3D). DU145, MDA-MB-468. A549 cells and the A2780cis resistant cells were purchased from the European Collection of Authenticated Cell Cultures (ECACC) and cultured in the suitable culture medium, supplemented with 2 mM Glutamine and 10% Fetal Bovine Serum (FBS). HCT 116 cells were purchased from the American Type Culture Collection (ATCC) and the HCT116oxR cells were established by Ute Jungwirth at the Institute of Cancer Research, Medical University of Vienna. Austria. In the case of the resistant cells, 1 µM cisplatin and 10 µM oxaliplatin was added every 3 passages, to maintain resistance in the respective cell lines. All cells were grown and maintained as adherent monolayer cultures. For spheroid formation, cells were seeded at 2000 cells/well in super low cell attachment surface, 96-well microplates (Nuclon™ Sphera™, Thermofisher) and allowed to grow for 4 days, before any manipulation.

The cytotoxicity studies in spheroids were conducted using the CellTiter-Glo® 3D Cell viability assay (Promega) following the instructions of the manufacturer.

TransAM® STAT Family ELIS Assay. The Active Motif TransAM® STAT Family ELISA kit was utilized to study the specificity of 8 h for STAT3. 20 µg of whole cell extract was used and STAT activity was assessed according to the manufacturers protocol.

Electrophoretic Mobility Shift Assay. Nuclear extracts from DU145 and MDA-MB-468 cells were prepared using the Active Motif Nuclear Extract kit following the manufacturer's protocol, in the presence of protease inhibitor mix (1× Complete, Roche) and phosphatase inhibitor (1× phosSTOP, Roche). Protein concentrations were determined by the Bradford method, 20 µg of nuclear extracted protein were incubated with the indicated concentrations of 8 h and Stattic for 1 h prior to incubation for another hour with P-labeled double-stranded oligonucleotide containing the high-affinity sis-inducible element (hSIE) probe SIE (5'-AGCTTCAMTTCCCGTAAATCCCTA-3'; Eurofins MWG Operon) derived from the c-fos gene. Binding reactions contained 0.9 µg poly(dI-dC). Competition assays were performed by adding 100× excess cold SIE oligonucleotide (lane C) and non-specific competitor (lane M; FIRE; 5'-AGCGCCTCCCCGGCCGGGG-3'). The DNA-protein complexes were subjected to electrophoresis and resolved on a 5% non-denaturing polyacrylamide gel (30% acrylamide/Bis solution, Bio-Rad) in 0.5% TBE buffer containing 2.5% glycerol (pH 7.8) at 4° C. for 2 h. Once dried, the radioactive signal of the gel was visualized by exposure to Fuji medical X-ray film.

Immunoblotting. Whole cell lysates were prepared by incubation of harvested, trypsinised cells with CelLytic™ M lysis buffer (Sigma-Aldrich) supplemented with 1× protease and 1× phosphatase inhibitors (Roche). Protein quantification was carried out using a protein assay kit (Bio-Rad). 40 µg of the lysates were denatured by heating for 5 min at 95° C. in sample buffer containing 100 mM Tris-Cl (pH 6.8), 4% SDS, 10% 2-mercaptoethanol, 20% glycerol, and 0.02% bromophenol blue. Precision Plus Protein Dual colour standards (Bio-Rad) were used as a molecular weight reference. For the detection of STAT3, pSTAT3, a/0 tubulin, cleaved PARP, Bcl-2, Bcl-xL, FANCD2, BRCA1, EME1 and MUS81, proteins were separated on a NuPAGE 7% Tris-acetate gel (Life Technologies) and subsequently transferred to polyvinylidene difluoride membranes (Immobilon®-P transfer membrane; Millipore). Survivin and anti-phospho-histone H2AX proteins were resolved on a 12% Bis-Tris gel. Membranes were blocked for 1 h at ambient temperature in a blocking buffer containing 5% w/v Bovine Serum Albumin (BSA; Sigma-Aldrich) in 1×TBS 0.1% Tween-20. All proteins were identified by incubation in a 1:1000 dilution of the respective polyclonal antibodies (Cell signalling) in blocking buffer overnight at 4° C. and subsequent incubation for 1 h with an anti-rabbit or anti-mouse secondary antibody (Cell signalling) at a dilution of 1:1000. The α/β tubulin (1:2000; Cell Signaling) and the anti-phospho-histone H2AX Antibody (1:500; Millipore) were used in the denoted dilutions. Antibody binding was visualized by enhanced chemiluminescence (Amersham) on autoradiography film (Kodak-X-Omat). Alternatively Images were captured by the GelDoc-It Imaging System Fusion Fx7 (Vilber Lourmat, Germany).

Immunofluorescence staining. For STAT3, pSTAT3 staining, $2.5 \times 10^4$ cells/ml were plated on 13-mm glass cover slip (VWR) in 24 well plates, allowed to adhere and processed the next day. Cells were treated with 8 h for 18 h, and subsequently washed in ice cold PBS and fixed with 2% paraformaldehyde PFA (Alfa Aesar) for 10 min at room temperature, followed by permeabilization with PBS containing 0.5% Triton X-100 for 10 min. Cells were blocked in PBS 5% BSA for 1 h at ambient temperature. Respective proteins were identified by incubation for 4 h with anti-STAT3 and anti-pSTAT3 rabbit polyclonal antibodies (1:1000, Cell signalling) or anti-phospho-Histone H2A.X mouse monoclonal (1:500; Millipore) diluted in a PBS 1% BSA buffer. Cells were incubated with a secondary fluorescent conjugated antibody Alexa Fluor 488 (1:500; Life Technologies) for 2 h at RT. Nuclei were stained using propidium iodide (2 µg/ml; Sigma-Aldrich) and mounted on glass slides with mounting medium (Dako).

Confocal microscopy. Cell nuclei and protein levels were visualized by confocal microscopy (objective ×40, Leica TCS SP2). Nuclear images were acquired by sequential scanning using the LAS AF Lite programme. In the case of 8 h detection only, the blue fluorescent agent was excited with a UV-laser (364 nm) and detected using the DAPI filter. PI was excited with the 488 line of an argon-ion laser and detected at 642 nm. The fluorescence of 8 h was detected and imaged by z-stack acquisition using the Leica SP2 microscope software. In all cases the operating conditions were such that detectable signals of 8 h could not be obtained for cell samples not treated with drugs.

To quantify γ-H2AX foci from images obtained using the protocol above, the program CellProfiler was utilized. Each cell nucleus was identified and the number of foci within computationally counted. The number of foci was taken as an average from the first 30 cells measured with a detection threshold of 0.3.

Drug Combination studies. Sulforhodamine B (SRB) Cell Growth Inhibition Assay. The SRB assay was used to assess cell growth inhibition by 8 h alone and in combination with cisplatin. Cells were drug treated with 8 h at 700% confluency for 18 h or 1 h, media was replaced and cells were allowed to grow for 96 h. For combination studies drug treatments were sequential with 8 h applied first followed by cisplatin for 1 h. After 96 h, cells were fixed with ice cold 10% trichloroacetic acid and stained with 0.4% sulphorhodamine B in 1% acetic acid. After drying plates overnight at room temperature, SRB was resuspended with 10 mM Tris base at pH 10.5. Absorbance was read at 540 nm and results were normalized to untreated controls. For analysis of $GC_{50}$ values and statistical significance, non-linear regression analysis with a comparison of fits was performed with the GraphPad Prism 6.0 software.

MIT assay. Individual drug treatments and combinations were carried out as with the SRB assay. The MTT assay was carried out as previously (see Cytotoxicity studies sections) with the difference that it was completed in 96 h.

Combination Index Analysis:

The software Calcusyn was utilized for analysis of drug interactions using the Chou-Talalay combination index method (Chou, T.-C. Drug Combination Studies and Their Synergy Quantification Using the Chou-Talalay Method. *Cancer Res.* 70, 440-446 (2010).

The affected fractions were calculated from the SRB or MTT assay absorbance values and were registered to derive the respective CI values and isobolograms. A CI value of less than 1 indicates synergy.

Modified Single Cell Gel Electrophoresis (Comet) Assay. The comet assay was employed to study the induction and repair of cisplatin-induced DNA ICLs. Cells were treated in 6 well plates and harvested at four timepoints post cisplatin exposure: 0, 9, 24 and 48 h. The assay was performed as in (Spanswick, V. J., Hartley. J. M. & Hartley, J. A. Measurement of DNA Interstrand Crosslinking in Individual Cells Using the Single Cell Gel Electrophoresis (Comet) Assay. *Drug-DNA Interact. Protoc. Methods Mol. Biol.* 613, 267-282 (2010)). After visualization and quantification of the tail moment for 50 cells per sample using the Komet 6.0 Analysis software (Andor Technology) and a Nikon inverted microscope, the following formula was used to calculate the tail moment:

% Decrease in tail moment=[1−(TMdi−TMcu/Tci−TMcu)]×100

Where TMdi=tail moment of drug treated irradiated sample; TMcu=tail moment of untreated unirradiated control; TMci=tail moment of untreated irradiated control.

In the case of the study of the cisplatin DNA ICLs in the A2780-cisplatin resistant cell line, the 8 h, cisplatin and combination treated cells, along with the appropriate controls were treated in situ with MMS (1.5 mM) for 30 min, prior to harvesting. MMS was used in this instance as an inducer of random DNA strand breaks, in place of irradiation. All the downstream steps were performed exactly as before.

RT-PCR. After drug-treatment cells were harvested by trypsinisation followed by centrifugation. Cell pellets were washed in PBS before RNA extraction using the RNeasy Plus Mini-kit (Qiagen). 1 µg RNA was used for cDNA generation using the High Capacity cDNA Reverse Transcription Kit (Life Technologies). TaqMan Gene Expression Assays (Life Technologies) for FANCD2, BRCA1, EME1 and MUS81 were used to quantify changes in gene expression. Primer/probe mixes were diluted 1:10 with TaqMan 2× Universal PCR Mastermix (Life Technologies) and 50 ng cDNA per reaction used. PCR was performed using an Applied Biosystems 7500 RT-PCR machine with 10 minutes at 95° C. followed by 45 cycles of 95° C./60° C. for 15 seconds and 1 minute respectively. Fold change was calculated using the comparative CT method normalizing to GAPDH expression.

Annexin V/Propidium iodide Apoptosis/Cell death was assessed by flow cytometry using the FITC-conjugated annexin V protein (Affymetrix, eBioscience) and propidium iodide double staining. Cells were seeded in 24-well plates at densities between $7-10\times10^4$/per well and left to adhere overnight. The next day, they were exposed to increasing concentrations of 8 h for 24 h. After incubation cells were gently trypsinised, centrifuged (300 g) and resuspended in Annexin V/FITC (0.25 µg/ml) in binding buffer (10 mM HEPES/NaOH pH 7.4, 140 mM NaCl, 2.5 mM $CaCl_2$)) and incubated at 37° C. for 15 min. Cells were subsequently counterstained with the addition of PI (200 µg/ml) and analysed on a Millipore Guava easyCyte™ 8HT flow cytometer using the InCyte software. The derived data were analysed as dot plots and quantified using the FlowJo software (TreeStar).

REFERENCES (1) (a) Yu, H.; Jove, R. *Nat Rev Cancer* 2004, 4, 97; (b) Lu. Y.; Zhou, J.; Xu, C. *Cell Physiol. Biochem.* 2008, 21, 305; (c) Selvendiran, K.; Bratasz, A.; Tong, L.; Ignarro, L. J.; Kuppusamy, P. *Cell Cycle* 2008, 7, 81; (d) Yang, F.; Van Meter, T. E.; Buettner, R. *Mol. Cancer. Ther.* 2008, 7, 3519.

(2) (a) Darnell, J. E. Jr. *Science* 1997, 277, 1630; (b) Bromberg, J.; Darnell, J. E., Jr. *Oncogene* 2000, 19, 2468; (c) Bowman, T.; Garcia, R.; Turkson, J.; Jove, R. *Oncogene* 2000, 19, 2474; (d) Hirano, T.; Ishihara, K.; Hibi, N. *Oncogene* 2000, 19, 2548.

(3) (a) Johnston, P. A.; Grandis, J. R. *Mol. Interv.* 2011, 11, 18; (b) Selvendiran, K.; Koga, H.; Ueno, T. *Cancer Res.* 2006, 66, 4826; (c) Bharti, A. C.; Shishodia, S.; Reuben, J. M. *Blood* 2004, 103, 3175.

(4) (a) Chiba, T. *EC Cancer* 2016, 1.S1, S1. (b) Furtek, S. L.; Backos, D. S.; Matheson, C. J.; Reigan, P. Strategies and Approaches of Targeting STAT3 for Cancer Treatment. *ACS Chem. Biol.* 2016, 11, 308. (c) Chen, J.; Bai, L.; Bernard, D.; Nikolovska-Coleska, Z.; Gomez, C.; Zhang, J.; Yi, H.; Wang, S. *ACS Med. Chem. Lett.* 2010, 1, 85; (d) Xiang, M.; Kim, H.; Ho, V. T.; Walker, S. R.; Bar-Natan, M.; Anahtar, M.; Liu. S.; Toniolo, P. A.; Kroll, Y.; Jones, N.; Giaccone, Z. T.; Heppler, L. N.; Ye, D. Q.; Marineau, J. J.; Shaw, D.; Bradner, J. E.; Blonquist, T.; Neuberg, D.; Hetz, C.; Stone, R. M.; Soiffer, R. J.; Frank, D. A. *Blood* 2016, 128, 1845; (e) Zhang, Y.; Jin, Z.; Zhou, H.; Ou, X.; Xu, Y.; Li, H.; Liu, C.; Li, B. *Cancer Med.* 2016, 5, 1251.

(5) Imran, M.; Saeed, F.; Nadeem, M.; Arshad, M. U.; Ullah, A.; Suleria, H. A. *Crit. Rev. Food Sci. Nutr.* 2016 Nov. 22:0. [Epub ahead of print, DOI:10.1080/10408398.2016.1252711]

(6) Ingólfsson, H. I.; Thakur, P.; Herold, K. F.; Hobart, E. A.; Ramsey, N. B.; Periole, X.; de Jong, D. H.; Zwama. M.; Yilmaz, D.; Hall, K.; Maretzky. T.; Hemmings, H. C. Jr.; Blobel, C.; Marrink, S. J.; Koçer, A.; Sack, J. T.; Andersen, O. S. *ACS Chem. Biol.* 2014, 15, 1788.

(7) (a) Adams, B. K.; Ferstl, E. M.; Davis, M. C. *Bioorg. Med. Chem.* 2004, 12, 3871. (b) Pati, H. N.; Das, U.; Quail, J. W.; Kawase, M.; Sakagami, H.; Dimmock, J. R. *Eur. J. Med. Chem.* 2008, 43, 1; (c) Dimmock J. R.; Padmanilayam M. P.; Puthucode, R. N.; Nazarali, A. J.; Motaganahalli, N. L.; Zello, G. A.; Quail, J. W.; Oloo, E. O.; Kraatz, H-B.; Prisciak, J. S.; Allen, T. M.; Santos, C. L.; Balzarini, J.; De Clercq, E.; Manavathu, E. K. *J. Med. Chem.* 2001, 44, 586. (d) Gregory, M.; Dandavati. A.; Lee, M., Tzou, S.; Savagian, M.; Brien, K. A.; Satam, V.; Patil, P.; Lee, M. *Med. Chem. Res.* 2013, 22, 5588; (e) Adams, B. K.; Cai, J.; Armstrong, J. *Anticancer Drugs* 2005, 16, 263.

(8) (a) Selvendiran, K.; Liyue T.; Bratasz, A. *Mol. Cancer Ther.* 2010, 9, 1169; (b) B. J. Tiemey, G. A. McCann, D. E. Cohn, E. Eisenhauer, M. Sudhakar, P. Kuppusamy, K. Hideg, K. Selvendiran, *Cancer Biol. Ther.* 2012, 13, 766; (c) Rath, K. S.; Naidu, S. K.; Lata, P.; Bid, H. K.; Rivera, B. K.; McCann, G. A.; Tiemey. B. J.; Elnaggar, A. C.; Bravo, V.; Leone, G.; Houghton, P.; Hideg, K.; Kuppusamy, P.; Cohn, D. E.; Selvendiran, K. *Cancer Res.* 2014, 74, 2316. (d) Naidu, S.; Saini, U.; ElNaggar, A. C.; Bid, H. K.; Wanner, R.; Bixel, K.; Suarez, A. A.; Bolyard, C.; Kaur, B.; Goodfellow, P. J.; Kuppusamy, P.; Cohn, D.; Selvendiran, K. *Cancer Res.* 2015, 7S (15 Supplement), 1720.

(9) Davis, R.; Das, U.; Mackay, H.; Brown, T.; Mooberry, S L.; Dimmock, J. R.; Lee, M.; Pati. H. *Arch. Pharm. (Weinheim)* 2008, 341, 440.

(10) Weimbs, T.; Shillingford, J. 2017, Personal communication.

(11) Yuan, L.; Sumpter, B. G.; Abboud. K. A.; Castellano, R. K. *New J. Chem.* 2008, 32, 1924.
(12) (a) Almansour, A. I.; Kumar, R. S.; Arumugam, N.; Basiri, A.; Kia. Y.; Ali, M. A. *BioMed. Res. Int.* 2015, 1. (b) Almansour, A. I.; Kumar, R. S.; Beevi, F.; Shirazi, A. N.; Osman, H.; Ismail, R.; Choon, T. S.; Sullivan, B.; McCaffrey, K.; Nahhas, A.; et al., *Molecules* 2014, 19, 10033; (c) Huber, I.; Zupko, I.; Kovacs, I. J.; Minorics, R.; Gulyas-Fekete, G.; Maasz, G.; Perjesi, P. *Monatshefte fuer Chemie* 2015, 146, 973. (d) Larsson, R.; Linder, S. *Swed. Pat. Appl.* 2013, SE 2012000735 A1 20130420.
(13) Nesterov, V. N. *Acta Cryst. Section C* 2004, C60, o806.
(14) Krijnen, B.; Beverloo, H. B.; Verhoeven, J. W.; Reiss, C. A.; Goubitz, K.; Heijdenrijk, D. *J. Am. Chem. Soc.* 1989, 111, 4433.
(15) Frisch, M. J. Gaussian 09, Revision A. 1; Gaussian, Inc.; Wallingford CT, 2009.
(16) Schmidt. J. R., Polik, W. F. WebMO Enterprise, version 10.0. WebMO LLC; Holland. MI Available from http://www.webmo.net (accessed January 2015).
(17) (a) Lee, L.; Robb, L. M.; Lee, M.; Davis, R.; Mackay, H.; Chavda, S.; Babu, B.; O'Brien, E. L.; Risinger, A. L.; Mooberry, S. L.; Lee, M. *J. Med. Chem.* 2010, 53, 325. (b) Rae, J. M.; Creighton, C. J.; Meck, J. M.; Haddad, B. R.; Johnson, M. D. *Breast Cancer Res. Treat.* 2007, 104, 13.
(18) To be reported elsewhere.
(19) Wu, J.; Zhang, Y.; Cai, Y.; Wang, J.; Weng, B.; Tang, Q.; Chen, X. Pan, Z.; Liang, G.; Yang, S. *Bioorg. Med Chem.* 2013, 21, 3058.
(20) (a) Pati, H. N.; Das, U.; Quail, J. W.; Kawase, M.; Sakagami, H.; Dimmock, J. R. *Eur. J. Med. Chem.* 2008, 43, 1. (b) Jha, A.; Duffield, K. M. *Indian J. Chem., Section B* 2006, 45B, 2313.
(21) Tan, K-L.; Ali, A.; Du. Y.; Fu. H.; Jin, H-X.; Chin, T-M.; Khan, M.; Go, M-L. *J. Med Chem.* 2014, 57, 5904.
(22) Du, Z. Y.; Liu, R. R.; Shao, W. Y.; Mao, X. P.; Ma, L.; Gu, L. Q.; Huang, Z. S.; Chan, A. S. *Eur. J. Med Chem.* 2006, 41, 213.
(23) Das S.; Das, U.; Selvakumar, P.; Sharma. R. K.; Balzarini, J.; De Clercq, E.; Molnár, J.; Serly, J.; Baráth, Z.; Schatte, G.; Bandy, B.; Gorecki, D. K.; Dimmock, J. R. *ChemMedChem* 2009, 4, 1831.
(24) (a) Vatsadze, S. Z.; Manaenkova. M. A.; Sviridenkova, N. V.; Zyk, N. V.; Krut'ko, D. P.; Churakov, A. V.; Antipin, M. Y.; Howard, J. A. K, Lang, H. *Russian Chem. Bull.* 2006, 55, 1184; (b) Pati, H. N.; Das, U, D. S.; Bandy. B.; De Clercq, E.; Balzarini, J.; Kawase, M.; Sakagami, H.; Quail, J. W.; Stable, s J. P.; Dimmock, J. R. *Eur. J. Med Chem.* 2009, 44, 54.
(25) El-Subbagh H. I.; Abu-Zaid, S. M.; Mahran, M. A.; Badria, F. A.; Al-Obaid, A. M. *J. Med Chem.* 2000, 43, 2915.
(26) Commercially available.
(27) Youssef, K. M.; El-Sherbeny, M. A.; El-Shafie, F. S.; Farag, H. A.; Al-Deeb, O. A. Awadalla, S. A. *Arch. Pharm. (Weinheim)* 2004, 337, 42.
(28) Yadav, B.; Taurin, S.; Rosengren, R. J.; Schumacher, M.; Diederich, M.; Somers-Edgar, T. J.; Larsen, L. *Bioorg. Med Chem.* 2010, 18, 6701.
(29) (a) El-Kashef, H. S.; Geies, A. A.; Kamal El-Dean, A. M., Abdel-Hafez, A. A. *J. Chem. Tech. Biotech.* 1993, 57, 15. (b) Geies, A.; Abdel-Hafez, A. A.; Lancelot, J. C.; El-Kashef, H. S. *Bull. Chem. Soc. Japan* 1993, 66, 3716.
(30) Aly, K. 1 I.; Geies, A. A. *High Perform. Polym.* 1992, 4, 187.
(31) Karthikeyan, N. S.; Sathiyanarayanan, K. I.; Aravindan, P. G. *Bull. Korean Chem. Soc.* 2009, 30, 2555.
(32) (a) Buu-Hoi, N. P. *Bull. Soc. Chim. Fr.* 1964, 12, 3096. (b) Zhou, D-Y.; Zhang, K.; Conney, A. H.; Ding, N.; Cui, X-X.; Wang, H.; Verano, M.; Zhao, S.; Fan, Y-X.; Zheng, X.; Du, Z. Y. *Chem. Pharm. Bull.* 2013, 61, 1149.
(33) (a) Hossain, M.; Das, U.; Umemura. N.; Sakagami. H.; Balzarini, J.; Clercq, E. D.; Kawase, M.; Dimmock, J. R. *Bioorg. Med Chem.* 2016, 24, 2206; (b) Das, U.; Pati, H. N.; Baráth, Z.; Csonka, A.; Molnár, J.; Dimmock, J. R. *Bioorg. Med. Chem. Lett.* 2016, 26, 1319; (c) Dimmock, J. R.; Padmanilayam, M. P.; Puthucode, R. N.; Nazarali, A. J.; Motaganahalli, N. L.; Zello, G. A.; Quail, J. W.; Oloo, E. O.; Kraatz, H. B.; Prisciak, J. S.; Allen, T. M. *J. Med Chem.* 2001, 44, 586.
(34) Bharkavi, C.; Vivek Kumar, S.; Perumal, S. *Synlett* 2015, 26, 1665.
(35) Han, Z.-G.; Miao, C.-B.; Shi, F.; Ma, N.; Zhang, G.; Tu, S.-J. *J. Comb. Chem.* 2010, 12, 16.
(36) Apex2 v2009.7-0 or v2011.2-0, Saint V7.66A, Bruker AXS Inc.; Madison (Wis.), USA, 2009/2011
(37) (a) SHELXTL (Version 6.14) (2000-2003) Bruker Advanced X-ray Solutions, Bruker AXS Inc., Madison, Wisconsin; USA. (b) Sheldrick, G. M. *Acta Cryst.* 2008, A64, 112.
(38) Sheldrick G. M. Acta Cryst. 2015, C71, 3.
(39) Hübschle, C. B.; Sheldrick, G. M.; Dittrich, B. *J. Appl. Cryst.* 2011, 44, 1281.

In one embodiment, the invention is directed to the following items:

1. Novel achiral 3,5-diarylidenyl-N-substituted piperid-4-one (DAP) compounds depicted as general structure 1:

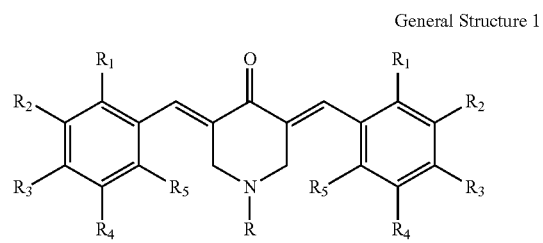

General Structure 1

R can preferably be a phenyl or an aromatic heterocycle, preferably phenyl, as depicted below. Examples of heterocycles can be a 6-membered pyrido, pyrimido, or triazino moiety; and 5-membered furano, thiopheno, pyrrolo, oxazolo, thiazolo, isoxazolo, or an isothiazolo moiety.

Examples of 6-membered R groups

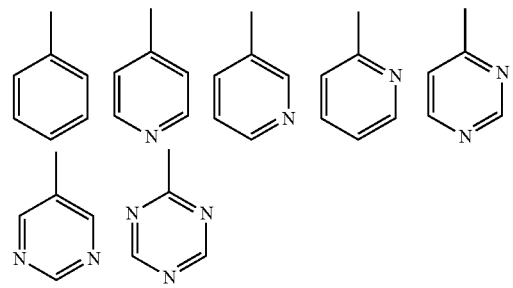

Examples of 5-membered heterocycles

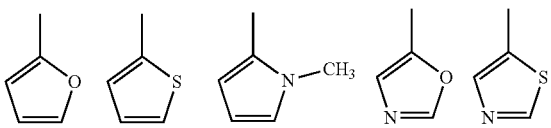

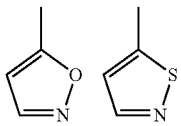

R can be substituted with hydrogen; between 1 to 5 low molecular weight alkyl (C1-C5) groups; between 1 to 5 low molecular weight alkyloxy groups; and between 1 to 5 nitrogen-containing substituents such as amino (—NH$_2$, —NHCH$_3$, —N(CH$_3$)$_2$, —NHCH$_2$CH$_3$, —N(CH$_2$CH$_3$)$_2$), hydroxylamino, nitro, and nitroso groups. The preferred substituent in R is hydrogen.

R$_1$ to R$^5$ can be the following:
(a) Hydrogen or short chain alkyl (C1-C5) groups, preferably hydrogen atoms or methyl groups. The alkyl groups may be straight chain or branched and include such groups as ethyl, propyl, butyl, and pentyl.
(b) Low molecular weight C1-C5 alkyloxy groups, preferably methoxy groups.
(c) Nitrogen-containing groups, such as amino (—NH$_2$, —NHCH$_3$, —N(CH$_3$)$_2$, —NHCH$_2$CH$_3$, —N(CH$_2$CH$_3$)$_2$), hydroxylamino, nitro, and nitroso groups, preferably nitro groups.
(d) Halogens, such as fluoro, chloro and bromo atoms.

2. A method of treatment of cancer responsive to a therapeutically effective amount of a compound depicted as general class I as described in embodiment 1.

3. A pharmaceutical composition consisting a compound depicted as general class I as described in embodiment 1.

4. The compounds of the invention described in embodiment 1 provide a method for selective and effective reduction of pSTAT3 levels in cancer cells. The compounds are potentially useful in lowering the levels of, survivin, Bcl-2, Bcl-xL in cells, while increasing the levels of cleaved-PARP, suggesting that the compounds selectively inhibit the STAT3 pathway and kill cells through apoptosis.

5. The composition of embodiment 3 wherein said compound is present in an amount to provide an effective dose of about 0.1 mg to about 100 mg/kg body weight.

6. The concept of using the compounds of this invention described in embodiment 1 for the treatment of diseases, including the treatment of cancer.

7. The concept of achieving enhanced anticancer activity by administering the compounds of this invention described in embodiment 1 in combination with other anticancer drugs or with other treatment modalities, such as radiation and surgery.

The invention claimed is:

1. A compound, comprising Formula I:

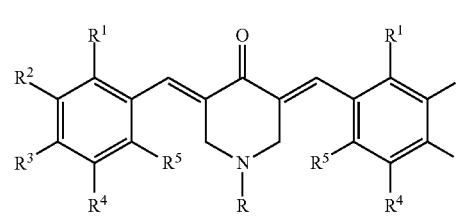

or a pharmaceutically acceptable salt, solvate, radiolabeled form, stereoisomeric form, racemic mixture, geometric isomer, and/or tautomer thereof, wherein:
R is —(C$_6$-C$_{14}$)aryl, which is unsubstituted or substituted with 1, 2, 3, 4, or 5 independently selected R$^6$ groups;
R$^6$ is selected from:
(a) —H, —(C$_1$-C$_6$)alkyl, —(C$_2$-C$_6$)alkenyl, —(C$_2$-C$_6$)alkynyl, —(C$_1$-C$_6$)alkoxy, and —(C$_3$-C$_5$)cycloalkyl; and
(b) -halo, —C(halo)$_3$, —CH(halo)$_2$, —CH$_2$(halo), —CN, —NO, —NO$_2$, —N$_3$, —OH, —SH, —N(R$^7$)$_2$, —NH(OH), —C(=O)R$^7$, —C(=O)OR$^7$, —OC(=O)R$^7$, —C(=O)N(R$^7$)$_2$, —N(R$^7$)C(=O)R$^7$, —N(R$^7$)C(=O)N(R$^7$)$_2$, —OC(=O)N(R$^7$)$_2$, and —N(R$^7$)C(=O)OR$^7$;

$R^1$, $R^2$, $R^4$, and $R^5$ are independently selected from:

(a) —H, —($C_1$-$C_6$)alkyl, —($C_2$-$C_6$)alkenyl, —($C_2$-$C_6$)alkynyl, and —($C_1$-$C_6$)alkoxy; and (b) -halo, —C(halo)$_3$, —CH(halo)$_2$, —CH$_2$(halo), —CN, —NO, —NO$_2$, —N$_3$, —OH, —SH, —N($R^7$)$_2$, —NH(OH), —C(=O)$R^7$, —C(=O)O$R^7$, —OC(=O)$R^7$, —C(=O)N($R^7$)$_2$, —N($R^7$)C(=O)$R^7$, —N($R^7$)C(=O)N($R^7$)$_2$, —OC(=O)N($R^7$)$_2$, and —N($R^7$)C(=O)O$R^7$;

$R^3$ is selected from the group consisting of:

(a) —($C_1$-$C_6$)alkyl, —($C_2$-$C_6$)alkenyl, —($C_2$-$C_6$)alkynyl, and —($C_1$-$C_6$)alkoxy; and (b) -halo, —C(halo)$_3$, —CH(halo)$_2$, —CH$_2$(halo), —CN, —NO, —NO$_2$, —N$_3$, —OH, —SH, —N($R^7$)$_2$, —NH(OH), —C(=O)$R^7$, —C(=O)O$R^7$, —OC(=O)$R^7$, —C(=O)N($R^7$)$_2$, —N($R^7$)C(=O)$R^7$, —N($R^7$)C(=O)N($R^7$)$_2$, —OC(=O)N($R^7$)$_2$, and —N($R^7$)C(=O)O$R^7$;

each $R^7$ is independently selected from the group consisting of —H, —($C_1$-$C_6$)alkyl, —($C_2$-$C_6$)alkenyl, and —($C_2$-$C_6$)alkynyl; and each halo is independently —F, —Cl, —Br, or —I.

2. The compound according to claim 1, wherein R is -phenyl.

3. The compound according to claim 1, wherein $R^1$, $R^2$, $R^4$ and $R^5$ are independently selected from the group consisting of —H, -halo, —($C_1$-$C_6$)alkyl, —($C_1$-$C_6$)alkoxy, —NO, —NO$_2$, —N($R^7$)$_2$, —NH(OH), and —OH, and wherein $R^3$ is selected from the group consisting of -halo, —($C_1$-$C_6$)alkyl, —($C_1$-$C_6$)alkoxy, —NO, —NO$_2$, —N($R^7$)$_2$, —NH(OH), and —OH.

4. The compound according to claim 1, wherein the $R^1$, $R^2$, $R^3$, $R^4$, or $R^5$ groups are selected to form the following substituents:

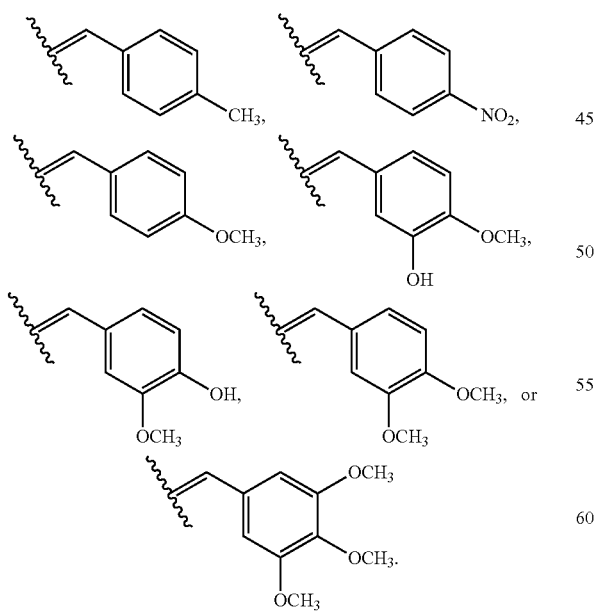

5. The compound of claim 1, wherein the compound is selected from the group consisting of:

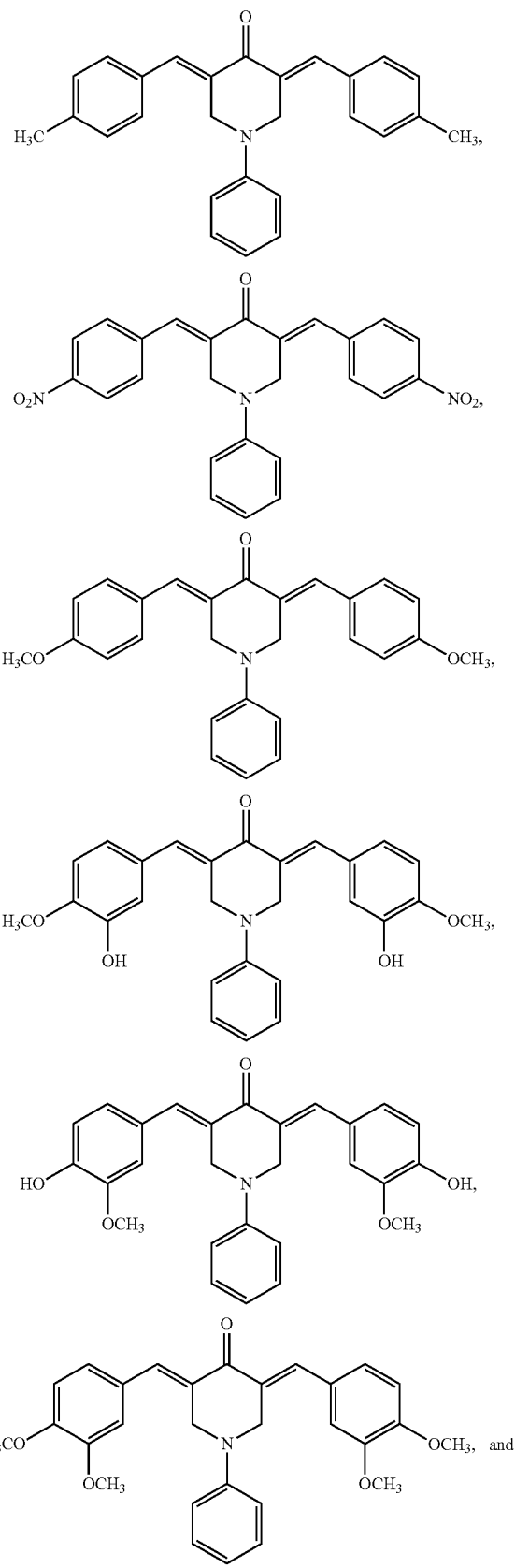

-continued

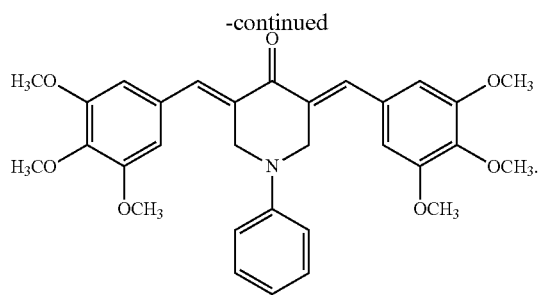

6. The compound according to claim 1, wherein the compound is achiral.

7. The compound according to claim 1, wherein the pharmaceutically acceptable salt, solvate, radiolabeled form, stereoisomeric form, racemic mixture, geometric isomer, and/or tautomer is a pharmaceutically acceptable salt.

8. A pharmaceutical composition, comprising:
   the compound of claim 1, or a pharmaceutically acceptable salt, solvate, radiolabeled form, stereoisomeric form, racemic mixture, geometric isomer, and/or tautomer thereof, and
   another therapeutic agent.

9. The pharmaceutical composition of claim 8, wherein the therapeutic agent is an anticancer drug.

10. The pharmaceutical composition of claim 9, wherein the anticancer drug is selected from the group consisting of paclitaxel, oxaliplatin, and cisplatin.

11. A method of preparing a pharmaceutical composition, comprising:
   admixing the compound of claim 1, or a pharmaceutically acceptable salt, solvate, radiolabeled form, stereoisomeric form, racemic mixture, geometric isomer, and/or tautomer thereof, with a pharmaceutically acceptable carrier.

12. A method of treating a disorder in a subject identified as in need of such treatment, comprising:
   administering to said subject in need thereof the compound of claim 1 or a pharmaceutically acceptable salt, solvate, radiolabeled form, stereoisomeric form, racemic mixture, geometric isomer, and/or tautomer thereof,
   wherein the disorder is selected from the group consisting of cancer, autoimmune disorders, inflammation disorders, and fibrotic disorders.

13. The method of claim 12, further comprising administering radiotherapy, immunotherapy and/or surgery to said subject.

14. The method of claim 12, further comprising administering to said subject at least one anticancer drug selected from the group consisting of taxanes, ruthenium-based compounds, and platinum-based compounds.

15. A method of inhibition of Stat3 pathway activity in a cell, comprising:
   administering to the cell in need thereof the compound of claim 1, or a pharmaceutically acceptable salt, solvate, radiolabeled form, stereoisomeric form, racemic mixture, geometric isomer, and/or tautomer thereof.

16. A fluorescent probe, comprising the compound of claim 1 or a pharmaceutically acceptable salt, solvate, radiolabeled form, stereoisomeric form, racemic mixture, geometric isomer, and/or tautomer thereof.

17. A process of preparing the compound of claim 1, or a pharmaceutically acceptable salt, solvate, radiolabeled form, stereoisomeric form, racemic mixture, geometric isomer, and/or tautomer thereof, wherein the process comprises:
   reacting an N-substituted-piperid-4-one with a substituted benzaldehyde,
   wherein the N-substituted-piperid-4-one is N-phenyl-piperid-4-one, and
   wherein the substituted benzaldehyde is selected from the group consisting of 4-methylbenzaldehyde, 4-nitrobenzaldehyde, 4-methoxybenzaldeyde, 3-hydroxy-4-methoxy-benzaldehyde, 4-hydroxy-3-methoxy-benzaldehyde, 3,4-dimethoxybenzaldehyde, and 3,4,5-trimethoxybenzaldehyde.

18. The compound of claim 1, wherein the compound comprises a stereoisomer, enantiomer, and/or diastereomer as the stereoisomeric form.

* * * * *